(12) United States Patent
Jin et al.

(10) Patent No.: US 11,135,262 B2
(45) Date of Patent: Oct. 5, 2021

(54) METHODS OF TREATING CERVICAL CANCER

(71) Applicant: GENEXINE, Inc., Seongnam-si (KR)

(72) Inventors: Hyun-Tak Jin, Seongnam-si (KR); Hye Seong Lim, Seongnam-si (KR); You Suk Suh, Seoul (KR); Eun Joo Nam, Seoul (KR)

(73) Assignee: GENEXINE, INC., Seongnam-si (KR)

( * ) Notice: Subject to any disclaimer, the term of this patent is extended or adjusted under 35 U.S.C. 154(b) by 252 days.

(21) Appl. No.: 15/503,997

(22) PCT Filed: Aug. 14, 2015

(86) PCT No.: PCT/IB2015/056214
§ 371 (c)(1),
(2) Date: Feb. 14, 2017

(87) PCT Pub. No.: WO2016/024255
PCT Pub. Date: Feb. 18, 2016

(65) Prior Publication Data
US 2017/0304385 A1    Oct. 26, 2017

Related U.S. Application Data

(60) Provisional application No. 62/038,134, filed on Aug. 15, 2014, provisional application No. 62/039,270, filed on Aug. 19, 2014.

(51) Int. Cl.
| | | |
|---|---|---|
| *A61K 38/02* | (2006.01) | |
| *A61K 47/68* | (2017.01) | |
| *A61K 39/00* | (2006.01) | |
| *A61K 38/00* | (2006.01) | |

(52) U.S. Cl.
CPC .......... *A61K 38/02* (2013.01); *A61K 39/0011* (2013.01); *A61K 47/6811* (2017.08); *A61K 38/00* (2013.01); *A61K 2039/53* (2013.01); *A61K 2039/572* (2013.01); *A61K 2039/585* (2013.01); *C07K 2319/02* (2013.01); *C12N 2710/20034* (2013.01); *C12N 2710/20071* (2013.01)

(58) Field of Classification Search
CPC . A61K 38/02; A61K 47/6811; A61K 39/0011
USPC ....................................................... 530/387.3
See application file for complete search history.

(56) References Cited

U.S. PATENT DOCUMENTS

| | | |
|---|---|---|
| 4,704,362 A | 11/1987 | Itakura et al. |
| 5,304,489 A | 4/1994 | Rosen |
| 5,741,957 A | 4/1998 | Deboer et al. |
| 5,849,992 A | 12/1998 | Meade et al. |
| 6,004,557 A | 12/1999 | Edwards et al. |
| 6,342,224 B1 | 1/2002 | Bruck et al. |
| 7,732,166 B2 | 6/2010 | Cheng |
| 8,137,674 B2 | 3/2012 | Sung et al. |
| 9,000,139 B2 | 4/2015 | Sung et al. |
| 9,399,665 B2 | 7/2016 | Sung et al. |
| 2007/0275003 A1 | 11/2007 | Cassetti et al. |
| 2010/0158930 A1 | 6/2010 | Zhu et al. |
| 2013/0195905 A1 | 8/2013 | Sung et al. |

FOREIGN PATENT DOCUMENTS

| | | |
|---|---|---|
| CN | 1679930 A | 10/2005 |
| EP | 1243655 A1 | 9/2002 |
| EP | 1757615 A1 | 2/2007 |
| JP | H10510989 A | 10/1998 |
| JP | 2001513986 A | 9/2001 |
| JP | 2009534027 A | 9/2009 |
| KR | 19980009278 A | 4/1998 |
| KR | 20030047667 A | 6/2003 |
| KR | 20050053732 A | 6/2005 |
| KR | 20090007333 A | 1/2009 |
| WO | WO-9619496 A1 | 6/1996 |
| WO | WO-0119408 A1 | 3/2001 |
| WO | WO-2004030636 A2 | 4/2004 |
| WO | WO-2007119896 A1 | 10/2007 |
| WO | WO-2009106362 A1 | 9/2009 |
| WO | WO-2011128247 A1 | 10/2011 |
| WO | WO-2012020871 A1 | 2/2012 |
| WO | WO 2013/092875 A1 | 6/2013 |
| WO | WO-2016024255 A1 | 2/2016 |

OTHER PUBLICATIONS

Bais, A.G., et al., "A Shift to a Peripheral Th2-type Cytokine Pattern During the Carcinogenesis of Cervical Cancer Becomes Manifest in CIN III Lesions," Journal of Clinical Pathology 58(10):1096-1100, BMJ Pub. Group, England (2005).

Baldassarre, H., et al., "Production of Transgenic Goats by Pronuclear Microinjection of in Vitro Produced Zygotes Derived From Oocytes Recovered by Laparoscopy," Theriogenology 59(3-4):831-839, Elsevier Science Inc., United States (2003).

Barnes, E., et al., "Novel Adenovirus-based Vaccines Induce Broad and Sustained T Cell Responses to HCV in Man," Science Translational Medicine 4(115):115ra1, American Association for the Advancement of Science, United States, 22 pages (2012).

Betts, M.R., et al., "Sensitive and Viable Identification of Antigen-specific CD8+ T Cells by a Flow Cytometric Assay for Degranulation," Journal of Immunological Methods 281(1-2):65-78, Elsevier B.V., Netherlands (2003).

Borysiewicz, L.K., et al., "A Recombinant Vaccinia Virus Encoding Human Papillomavirus Types 16 and 18, E6 and E7 Proteins as Immunotherapy for Cervical Cancer," The Lancet 347(9014):1523-1527, Lancet Publishing Group, England (1996).

(Continued)

*Primary Examiner* — Yan Xiao
(74) *Attorney, Agent, or Firm* — Sughrue Mion, PLLC

(57) ABSTRACT

This invention relates to the treatment of cervical tumor caused by human papillomavirus (HPV) infection. In particular, the invention provides methods for improving cervical tumor treatment and methods for treating cervical tumor caused by HPV infection using a polynucleotide encoding an E6/E7 fusion protein.

Figure 1A:
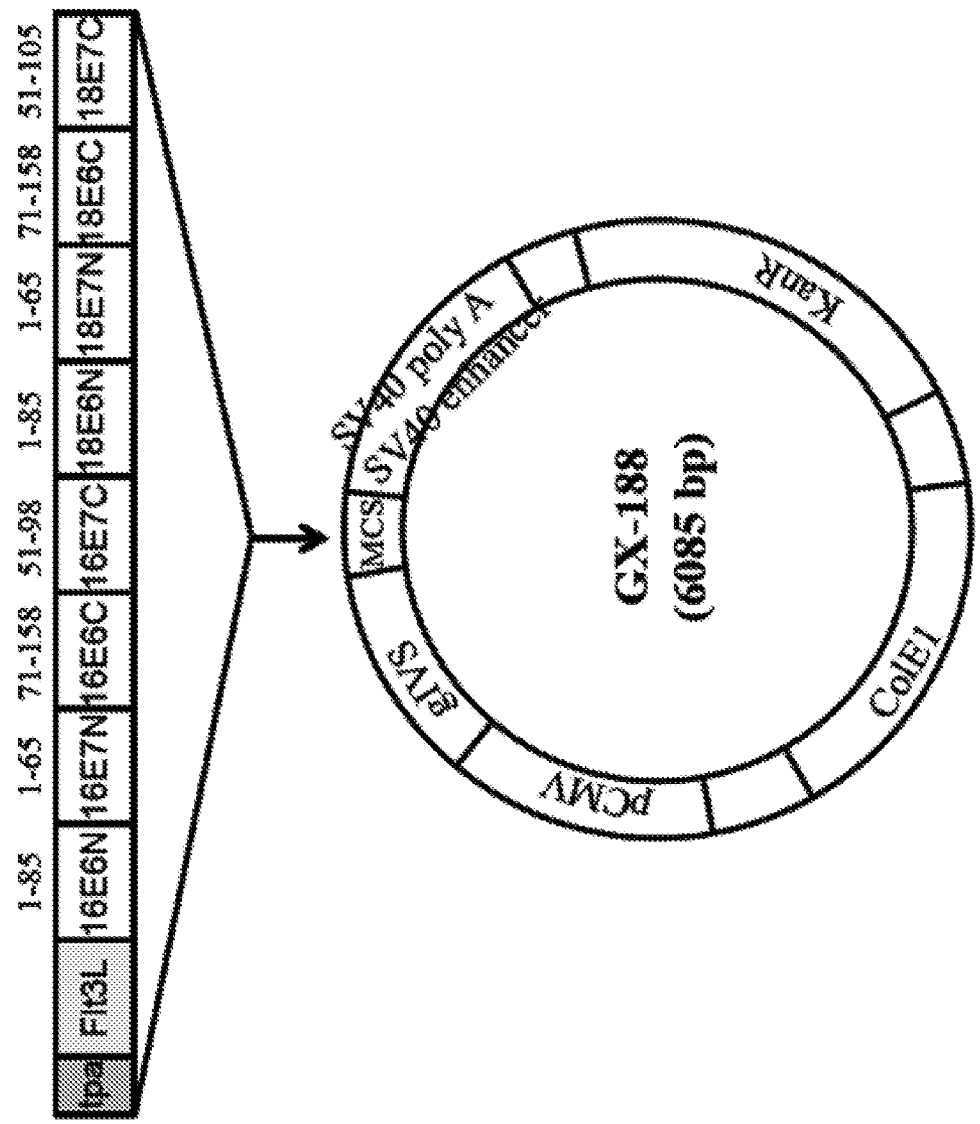

26 Claims, 28 Drawing Sheets
Specification includes a Sequence Listing.

(56) References Cited

OTHER PUBLICATIONS

Bourgault-Villada, I., et al., "Identification in Humans of HPV-16 E6 and E7 Protein Epitopes Recognized by Cytolytic T Lymphocytes in Association with HLA-B18 and Determination of the HLA-B18-specific Binding Motif," European Journal of Immunology 30(8):2281-2289, Wiley-VCH, Germany (2000).
Brinster, R.L., et al., "Expression of a Microinjected Immunoglobulin Gene in the Spleen of Transgenic Mice," Nature 306(5941):332-336, Macmillan Journals Ltd., England (1983).
Brinster, R.L., et al., "Factors Affecting the Efficiency of Introducing Foreign DNA into Mice by Microinjecting Eggs," Proceedings of the National Academy of Sciences USA 82(13):4438-4442, National Academy of Sciences, United States (1985).
Chen, H-W., et al., "Identification of HLA-A11—restricted CTL Epitopes Derived from HPV Type 18 Using DNA Immunization," Cancer Biology & Therapy 8(21):2025-2032, Taylor & Francis, United States (Nov. 1, 2009).
Clerici, M., et al., "Cytokine Production Patterns in Cervical Intraepithelial Neoplasia: Association With Human Papillomavirus Infection," Journal of the National Cancer Institute 89(3):245-250, Oxford University Press, United States (1997).
Cobrinik, D., et al., "The Retinoblastoma Protein and the Regulation of Cell Cycling," Trends in Biochemical Sciences 17:312-315, Elsevier Scientific Publishers, England (1992).
De Jong, A., et al., "Enhancement of Human Papillomavirus (HPV) Type 16 E6 and E7-specific T-cell Immunity in Healthy Volunteers Through Vaccination With TA-CIN, an HPV16 L2E7E6 Fusion Protein Vaccine," Vaccine 20(29-30):3456-3464, Elsevier Science, Netherlands (2002).
De Vos Van Steenwijk, P.J., et al., "A Placebo-controlled Randomized HPV16 Synthetic Long-peptide Vaccination Study in Women with High-grade Cervical Squamous Intraepithelial Lesions," Cancer Immunology, Immunotherapy 61(9):1485-1492, Springer Verlag, Germany (2012).
De Vos Van Steenwijk, P.J., et al., "Surgery Followed by Persistence of High-grade Squamous Intraepithelial Lesions is Associated with the Induction of a Dysfunctional HPV16-specific T-cell Response," Clinical Cancer Research 14(22):7188-7195, American Association of Cancer Research, United States (2008).
Deligeoroglou, E., et al., "HPV Infection: Immunological Aspects and Their Utility in Future Therapy," Infectious Diseases in Obstetrics and Gynecology 2013:540850, Hindawi Publishing, Egypt, 9 pages (Aug. 20, 2013).
Dochez, C., et al., "HPV Vaccines to Prevent Cervical Cancer and Genital Warts: an Update," Vaccine 32(14):1595-1601, Elsevier Science, Netherlands (Mar. 2014).
Einstein, M.H., et al., "Clinician's Guide to Human Papillomavirus Immunology: Knowns and Unknowns," The Lancet. Infectious Diseases 9(6):347-356, The Lancet Publishing Group, United States (2009).
English Language Abstract of Chinese Patent Publication No. CN1679930A, Chinese Patent Office, Espacenet Database (2005).
Evans, T.G., et al., "The Use of Flt3 Ligand as an Adjuvant for Hepatitis B Vaccination of Healthy Adults," Vaccine 21(3-4):322-329, Elsevier Science Ltd., England (2002).
Facchinetti, V., et al., "CD4+ T Cell Immunity Against the Human Papillomavirus-18 E6 Transforming Protein in Healthy Donors: Identification of Promiscuous Naturally Processed Epitopes," European Journal of Immunology 35(3):806-815, Wiley-VCH, Germany (2005).
Forman, D., et al., "Global Burden of Human Papillomavirus and Related Diseases," Vaccine 30(Suppl 5):F12-F23, Elsevier Ltd., England (Nov. 20, 2012).
Gallagher, K.M.E. and Man, S., "Identification of HLA-DR1- and HLA-DR15-restricted Human Papillomavirus Type 16 (HPV16) and HPV18 E6 Epitopes Recognized by CD4+ T Cells from Healthy Young Women," The Journal of General Virology 88(Pt 5):1470-1478, Society for General Microbiology, England (2007).
Garcia, F., et al., "ZYC101a for Treatment of High-Grade Cervical Intraepithelial Neoplasia: A Randomized Controlled Trial," Obstetrics and Gynecology 103(2):317-326, Lippincott Williams & Wilkins, United States (2004).
Gerdes, J., et al., "Cell Cycle Analysis of a Cell Proliferation-associated Human Nuclear Antigen Defined by the Monoclonal Antibody Ki-67," Journal of Immunology 133(4):1710-1715, American Association of Immunologists, United States (1984).
Hahn, H.S., et al., "Distribution of Maternal and Infant Human Papillomavirus: Risk Factors Associated With Vertical Transmission," European Journal of Obstetrics & Gynecology and Reproductive Biology 169(2):202-206, Elsevier Scientific Publishers, Ireland (2013).
International Search Report and Written Opinion for International Application No. PCT/IB2015/056214, Korean Intellectual Property Office, Republic of Korea, dated Oct. 16, 2015, 12 pages.
Kaech, S.M., et al., "Effector and Memory T-cell Differentiation: Implications for Vaccine Development," Nature Reviews. Immunology 2(4):251-262, Nature Pub. Group, England (2002).
Kather, A., et al., "Identification of a Naturally Processed HLA-A*0201 HPV18 E7 T Cell Epitope by Tumor Cell Mediated in Vitro Vaccination," International Journal of Cancer 104(3):345-353, Wiley-Liss, United States (2003).
Le, T.P., et al., "Safety, Tolerability and Humoral Immune Responses After Intramuscular Administration of a Malaria DNA Vaccine to Healthy Adult Volunteers," Vaccine 18(18):1893-1901, Elsevier Science Ltd., England (2000).
Liu, X., et al., "Structure of the Human *Papillomavirus* E7 Oncoprotein and Its Mechanism for Inactivation of the Retinoblastoma Tumor Suppressor," The Journal of Biological Chemistry 281(1):578-586, American Society for Biochemistry and Molecular Biology, Inc., United States (2006).
Malassagne, B., et al., "Hypodermin A, a New Inhibitor of Human Complement for the Prevention of Xenogeneic Hyperacute Rejection," Xenotransplantation 10(3):267-277, Blackwell Munksgaard, United Kingdom (2003).
Maraskovsky, E., et al., "In Vivo Generation of Human Dendritic Cell Subsets by Flt3 Ligand ," Blood 96(3):878-884, The American Society of Hematology, United States (2000).
McKnight, G.S., et al., "Expression of the Chicken Transferrin Gene in Transgenic Mice," Cell 34(2):335-341, MIT, United States (1983).
Mire-Sluis, A.R., et al., "Recommendations for the Design and Optimization of Immunoassays Used in the Detection of Host Antibodies Against Biotechnology Products," Journal of Immunological Methods 289(1-2):1-16, Elsevier B.V., Netherlands (2004).
Morishima, S., et al., "Identification of an HLA-A24-restricted Cytotoxic T Lymphocyte Epitope from Human Papillomavirus type-16 E6: The Combined Effects of Bortezomib and Interferon-gamma on the Presentation of a Cryptic Epitope," International Journal of Cancer 120(3):594-604, Wiley-Liss, United States (2007).
Moscicki, A-B., et al., "Updating the Natural History of Human Papillomavirus and Anogenital Cancers," Vaccine 30(5):F24-F33, Elsevier Science, Netherlands (2012).
Nakagawa, M., et al., "Different Methods of Identifying New Antigenic Epitopes of Human Papillomavirus Type 16 E6 and E7 Proteins," Clinical and Diagnostic Laboratory Immunology 11(5):889-896, American Society for Microbiology, United States (2004).
Nakagawa, M., et al., "HLA class I Binding Promiscuity of the CD8 T-cell Epitopes of Human Papillomavirus Type 16 E6 Protein," Journal of Virology 81(3):1412-1423, American Society for Microbiology, United States (2007).
Nakamura, Y., et al., "Codon Usage Tabulated from International DNA Sequence Databases: Status for the Year 2000," Nucleic Acids Research 28(1):292, Oxford University Press, United Kingdom (2000).
NCBI, "Codon Usage Database," accessed at http://www.kazusa.or.jp/codon/, accessed on Apr. 23, 2013, accessed on Mar. 10, 2017, 1 page.
Neumann, E., et al., "Gene Transfer into Mouse Lyoma Cells by Electroporation in High Electric Fields," The EMBO Journal 1(7):841-845, IRL Press Limited, England (1982).
Nonn, M., et al., "Dendritic Cell-based Tumor Vaccine for Cervical Cancer I: in Vitro Stimulation With Recombinant Protein-pulsed

(56) References Cited

OTHER PUBLICATIONS

Dendritic Cells Induces Specific T Cells to HPV16 E7 or HPV18 E7," Journal of Cancer Research and Clinical Oncology 129(9):511-520, Springer-Verlag, Germany (2003).
Öhlschläger, P., et al., "An Improved Rearranged Human Papillomavirus Type 16 E7 DNA Vaccine Candidate (HPV-16 E7SH) Induces an E7 Wildtype-Specific T cell Response," Vaccine 24:2880-2893, Elsevier Ltd, England (2006).
Pantaleo, G. and Harari, A., "Functional Signatures in Antiviral T-cell Immunity for Monitoring Virus-associated Diseases," Nature Reviews. Immunology 6(5):417-423, Nature Publishing Group, England (2006).
Park, K.S., et al., "Complete Protection Against a H5N2 Avian Influenza Virus by a DNA Vaccine Expressing a Fusion Protein of H1N1 HA and M2e," Vaccine 29(33):5481-5487, Elsevier Ltd., England (2011).
Parkin, D.M. and Bray, F., "Chapter 2: The Burden of HPV-related Cancers," Vaccine 24(S3):11-25, Elsevier Ltd., England (2006).
Peghini, B.C., et al., "Local Cytokine Profiles of Patients With Cervical Intraepithelial and Invasive Neoplasia," Human Immunology 73(9):920-926, Elsevier Inc., United States (2012).
Peng, S., et al., "Development of a DNA Vaccine Targeting Human Papillomavirus Type 16 Oncoprotein E6," Journal of Virology 78(16):8468-8476, American Society for Microbiology, United States (2004).
Ressing, M.E., et al., "Human CTL Epitopes Encoded by Human Papillomavirus Type 16 E6 and E7 Identified Through in Vivo and in Vitro Immunogenicity Studies of HLA-A*0201-binding peptides," The Journal of Immunology 154(11):5934-5943, American Association of Immunologists, United States (1995).
Ressing, M.E., et al., "Occasional Memory Cytotoxic T-Cell Responses of Patients with Human Papillomavirus Type 16—Positive Cervical Lesions Against a Human Leukocyte Antigen-A *0201-Restricted E7-Encoded Epitope," Cancer Research 56(3):582-588, American Association for Cancer Research, United States (1996).
Ridgway, A. A. G., et al., "Introduction of Vector into Host Cells," in Mammalian Expression Vectors, Chapter 24.2, Rodriguez and Denhardt, eds., pp. 470-472, Butterworths, Boston, Mass., United States (1988).
Ritchie, K.A., et al., "Allelic Exclusion and Control of Endogenous Immunoglobulin Gene Rearrangement in k Transgenic Mice," Nature 312(5994):517-520, Nature Publishing Group, England (1984).
Robl, J.M., et al., "Artificial Chromosome Vectors and Expression of Complex Proteins in Transgenic Animals," Theriogenology 59(1):107-113, Elsevier Science Inc., United States (2003).
Roederer, M., et al., "SPICE: Exploration and Analysis of Post-Cytometric Complex Multivariate Datasets," Cytometry A 79(2):167-174, Wiley-Liss, United States (2011).
Rudolf, M.P., et al., "Human T-Cell Responses to HLA-A-restricted High Binding Affinity Peptides of Human Papillomavirus Type 18 Proteins E6 and E7," Clinical Cancer Research 7(3 Suppl):788s-795s, The Association, United States (2001).
Rüther, U. and Müller-Hill, B., "Easy Identification of cDNA Clones," The EMBO Journal 2(10):1791-1794, IRL Press Ltd, England (1983).
Saade, F. and Petrovsky, N., "Technologies for Enhanced Efficacy of DNA Vaccines," Expert Review of Vaccines 11(2):189-209, Taylor & Francis, England (2012).
Sandoval-Montes, C. and Santos-Argumedo, L., "CD38 Is Expressed Selectively During the Activation of a Subset of Mature T Cells With Reduced Proliferation but Improved Potential to Produce Cytokines," Journal of Leukocyte Biology 77(4):513-521, Society for Leukocyte Biology, United States (2005).
Schiffman, M., et al., "Human Papillomavirus and Cervical Cancer," Lancet 370(9590):890-907, Elsevier, England (2007).
Schiffman, M.H., et al., "Epidemiologic Evidence Showing That Human Papillomavirus Infection Causes Most Cervical Intraepithelial Neoplasia," Journal of the National Cancer Institute 85(12):958-964, National Institutes of Health, United States (1993).

Seder, R.A., et al., "T-cell Quality in Memory and Protection: Implications for Vaccine Design," Nature Reviews. Immunology 8(4):247-258, Nature Publishing Group, England (2008).
Seo, S.H., et al., "Optimal Induction of HPV DNA Vaccine-induced CD8+ T cell Responses and Therapeutic Antitumor Effect by Antigen Engineering and Electroporation," Vaccine 27(42):5906-5912, Elsevier, The Netherlands (Aug. 3, 2009).
Shedlock, D.J., et al., "Ki-67 Staining for Determination of Rhesus Macaque T Cell Proliferative Responses Ex Vivo," Cytometry A 77(3):275-284, International Society for Advancement of Cytometry, United States (2010).
Smith, T.F. and Waterman, M.S., "Comparison of Biosequences," Advances in Applied Mathematics 2(4):482-489, Academic Press, Inc., United States (1981).
Soares, A., et al., "Novel Application of Ki67 to Quantify Antigen-specific in vitro Lymphoproliferation," Journal of Immunological Methods 362(1-2):43-50, Elsevier, Netherlands (2010).
Stauss, H.J., et al., "Induction of Cytotoxic T Lymphocytes with Peptides in Vitro: Identification of Candidate T-cell Epitopes in Human Papilloma Virus," Proceedings of the National Academy of Sciences U.S.A. 89(17):7871-7875, National Academy of Sciences, United States (1992).
Streeck, H., et al., "The Role of IFN-γ Elispot Assay in HIV Vaccine Research," Nature Protocols 4(4):461-469, Nature Publishing Group, England (2009).
Trimble, C.L., et al., "Naturally Occurring Systemic Immune Responses to HPV Antigens do not Predict Regression of CIN2/3," Cancer Immunology, Immunotherapy 59(5):799-803, Springer International, Germany (2010).
Urbani, S., et al., "Heterologous T Cell Immunity in Severe Hepatitis C Virus Infection," The Journal of Experimental Medicine 201(5):675-680, Rockefeller University Press, United States (2005).
Vasan, S., et al., "In Vivo Electroporation Enhances the Immunogenicity of an HIV-1 DNA Vaccine Candidate in Healthy Volunteers," PLoS One 6(5):e19252, Public Library of Science, United States, 10 pages (2011).
Von Knebel Doeberitz, M., et al., "Inhibition of Tumorigenicity of Cervical Cancer cells in Nude mice by HPV E6-E7 Anti-Sense RNA," International Journal of Cancer 51:831-834, Wiley-Liss, Inc, United States (1992).
Wagner, T.E., et al., "Microinjection of a Rabbit ß-Globin Gene into Zygotes and Its Subsequent Expression in Adult Mice and Their Offspring," Proceedings of the National Academy of Sciences USA 78(10):6376-6380, National Academy of Sciences, United States (1981).
Welters, M.J.P., et al., "Induction of Tumor-specific CD4+ and CD8+ T-cell Immunity in Cervical Cancer Patients by a Human Papillomavirus Type 16 E6 and E7 Long Peptides Vaccine," Clinical Cancer Research 14(1):178-187, American Association of Cancer Research, United States (2008).
Wherry, E.J. and Ahmed, R., "Memory CD8 T-cell Differentiation During Viral Infection," Journal of Virology 78(11):5535-5545, American Society for Microbiology, United States (2004).
Wherry, E.J., et al., "Lineage Relationship and Protective Immunity of Memory CD8 T Cell Subsets," Nature immunology 4(3):225-234, Nature Publishing Group, United States (2003).
Wherry, E.J., et al., "Low CD8 T-cell Proliferative Potential and High Viral Load Limit the Effectiveness of Therapeutic Vaccination," Journal of Virology 79(14):8960-8968, American Society for Microbiology, United States (2005).
Wherry, E.J., et al., "Molecular Signature of CD8$^+$T Cell Exhaustion During Chronic Viral Infection," Immunity 27(4):670-684, Elsevier Inc., United States (2007).
Wherry, E.J., et al., "Viral Persistence Alters CD8 T-cell Immunodominance and Tissue Distribution and Results in Distinct Stages of Functional Impairment," Journal of Virology 77(8):4911-4927, American Society for Microbiology, United States (2003).
Wigler, M., et al., "Biochemical Transfer of Single-Copy Eucaryotic Genes Using Total Cellular DNA as Donor," Cell 14(3):725-731, MIT, United States (1978).
Woo, Y.L., et al., "A Prospective Study on the Natural Course of Low-grade Squamous Intraepithelial Lesions and the Presence of

(56) References Cited

OTHER PUBLICATIONS

HPV16 E2-, E6- and E7-specific T-cell Responses," International Journal of Cancer 126(1):133-141, International Union against Cancer, United States (2010).

Yan, J., et al., "Cellular Immunity Induced by a Novel HPV18 DNA Vaccine Encoding an E6/E7 Fusion Consensus Protein in Mice and Rhesus Macaques," Vaccine 26(40):5210-5215, Elsevier Science, Netherlands (2008).

Yan, J., et al., "Induction of Antitumor Immunity in Vivo following Delivery of a Novel HPV-16 DNA Vaccine Encoding an E6/E7 Fusion Antigen," Vaccine 27(3):431-440, Elsevier Science, Netherlands (Jan. 14, 2009).

Yang, S-H., et al., "Correlation of Antiviral T-cell Responses With Suppression of Viral Rebound in Chronic Hepatitis B Carriers: A Proof-of-concept Study," Gene Therapy 13(14):1110-1117, Nature Publishing Group, England (2006).

Yugawa, T. and Kiyono, T., "Molecular Mechanisms of Cervical Carcinogenesis by High-risk Human Papillomaviruses: Novel Functions of E6 and E7 Oncoproteins," Reviews in Medical Virology 19(2):97-113, John Wiley & Sons, Ltd., England (2009).

Zajac A.J. and Harrington L.E., "Immune Response to Viruses: Cell-mediated Immunity," Encyclopedia of Virology 3(3):70-77, Elsevier Ltd., England (2008).

Zanier, K., et al., "Solution Structure Analysis of the HPV16 E6 Oncoprotein Reveals a Self-association Mechanism Required for E6-mediated Degradation of p53," Structure 20(4):604-617, Elsevier Ltd., United States (2012).

Zur Hausen, H., "Papillomavirus Infections—A Major Cause of Human Cancers," Biochimica et Biophysica Acta 1288:F55-F78, Elsevier Science B.V., Netherlands (1996).

Kim, T., et al., "Clearance of persistent HPV infection and cervical lesion by the therapeutic DNA vaccine in CIN3 patients," Nature Communications 5:1-14, Macmillan, United Kingdom (2014).

Supplementary European Search Report for EP Application No. EP 15832334, Munich, Germany, dated Mar. 8, 2018, 15 pages.

Clinical Trial Identifier NCT02411019 entitled "Safety and Efficacy of GX-188E DNA Therapeutic Vaccine Administered by Electroporation After Observation (GX-188E)," ClinicalTrials.gov, available at https://clinicaltrials.gov/ct2/show/NCT02411019, last accessed on Jul. 12, 2019, 4 pages.

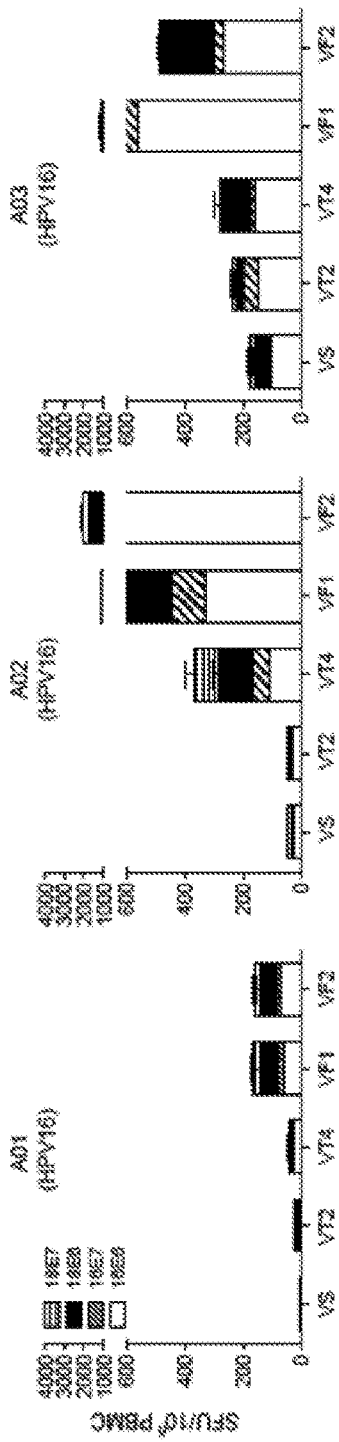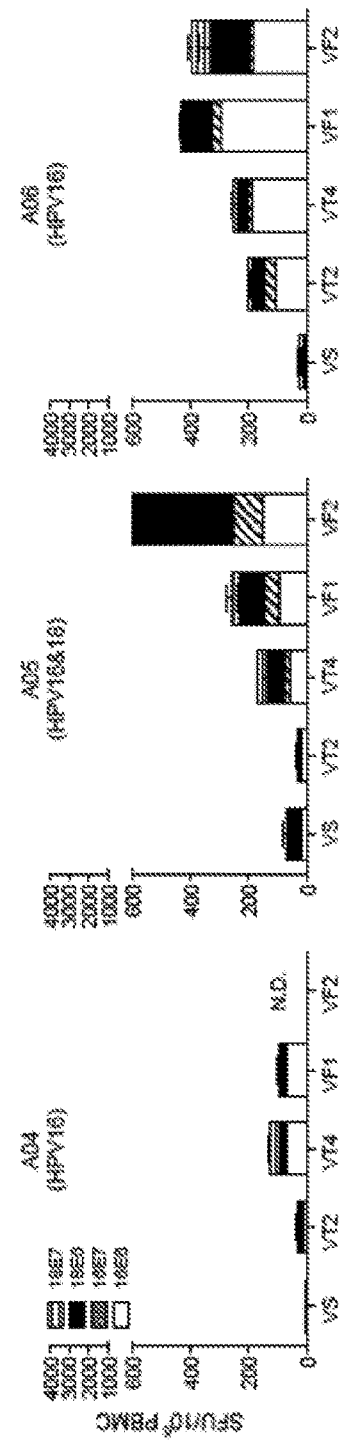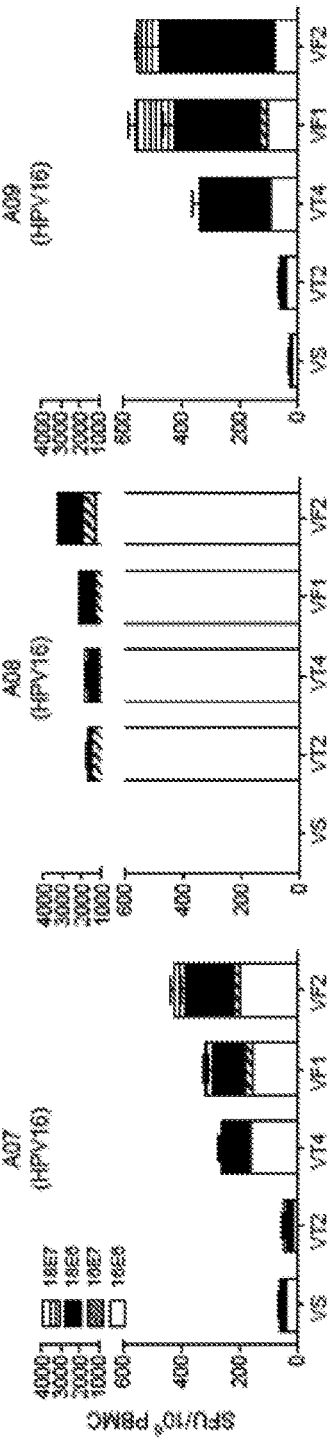

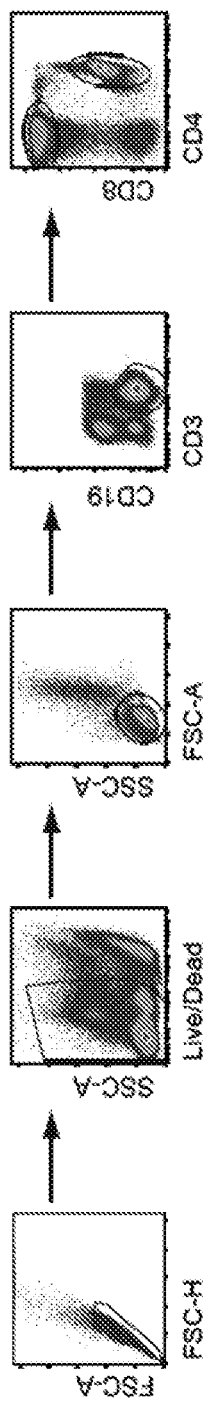
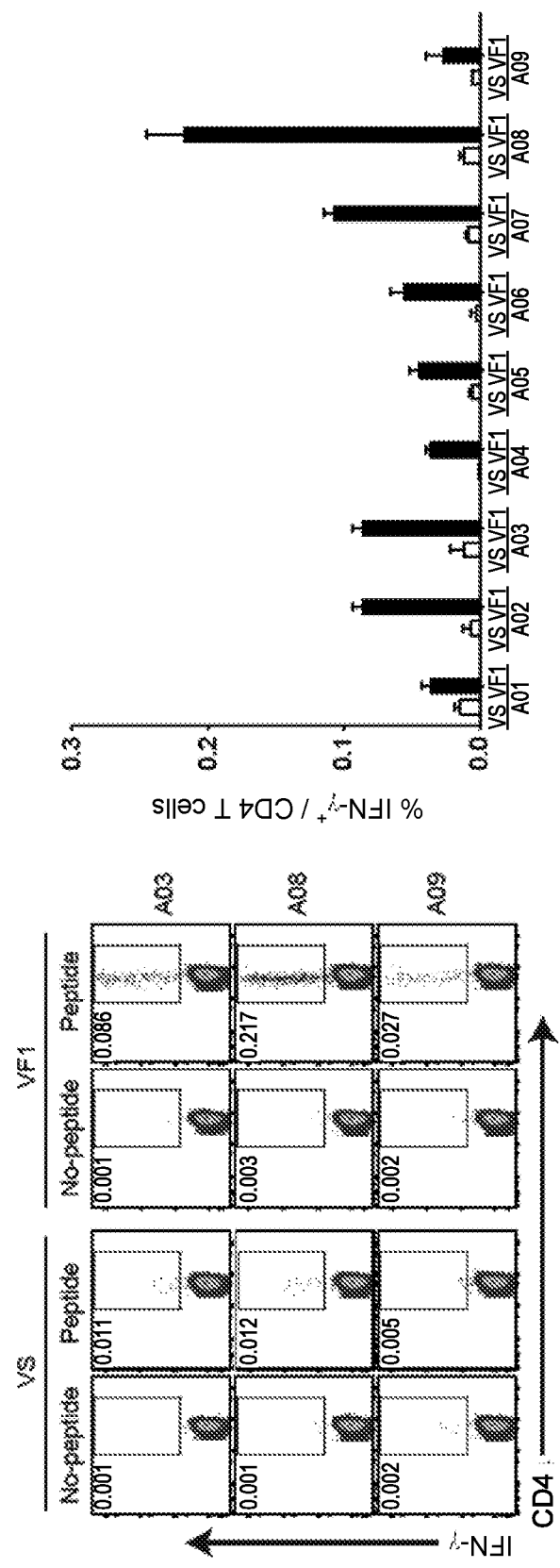
FIG. 4A
FIG. 4B
FIG. 4C

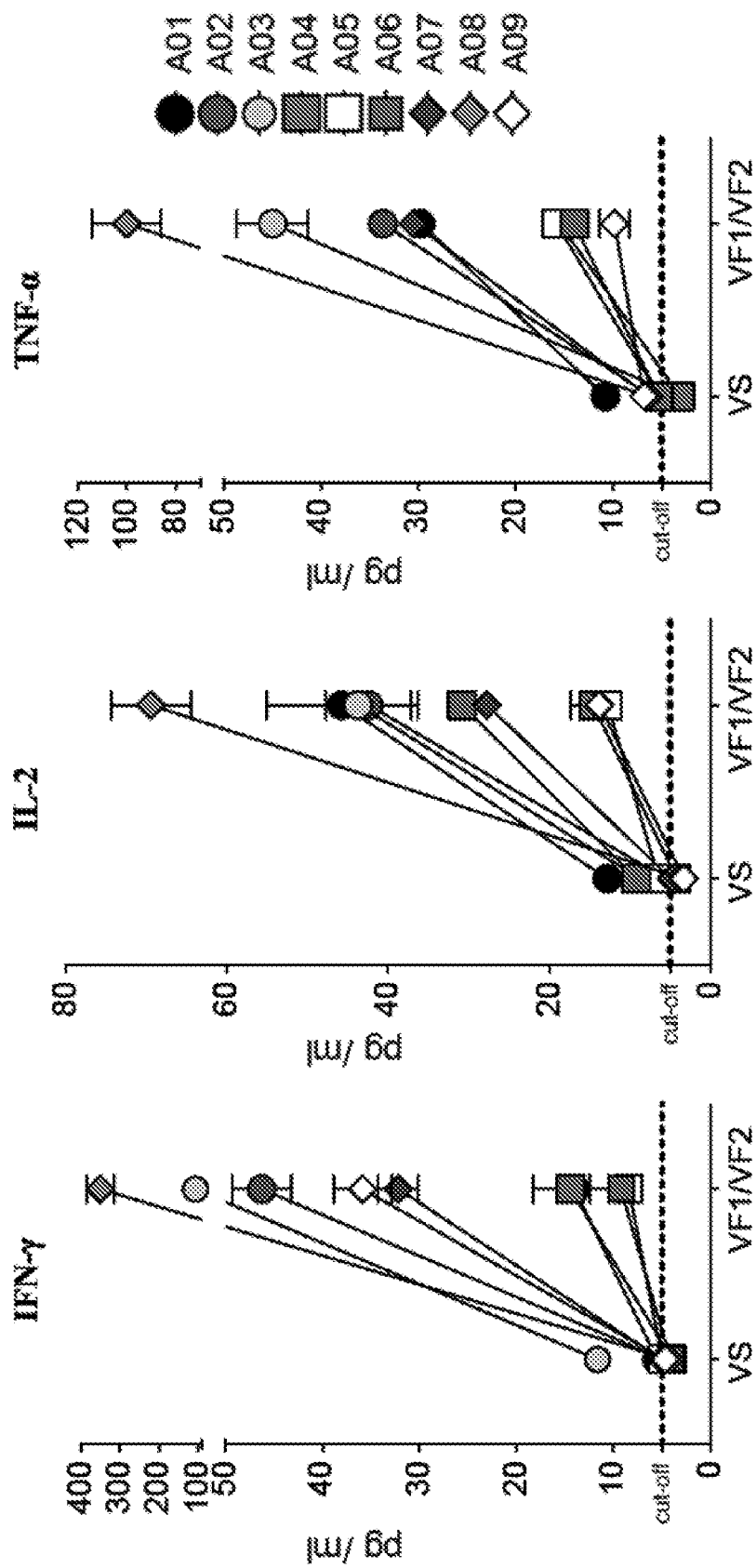

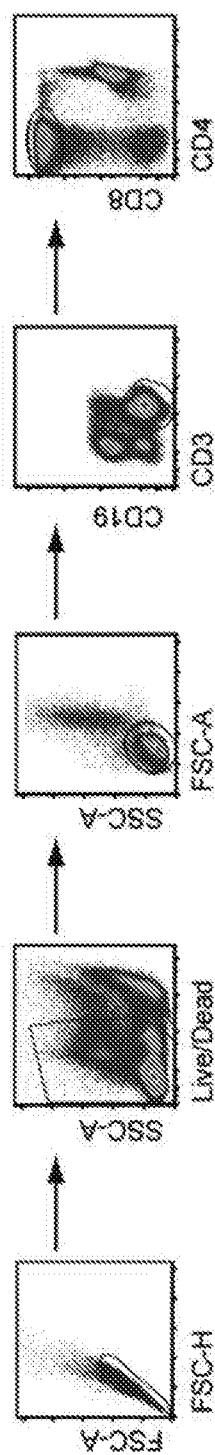
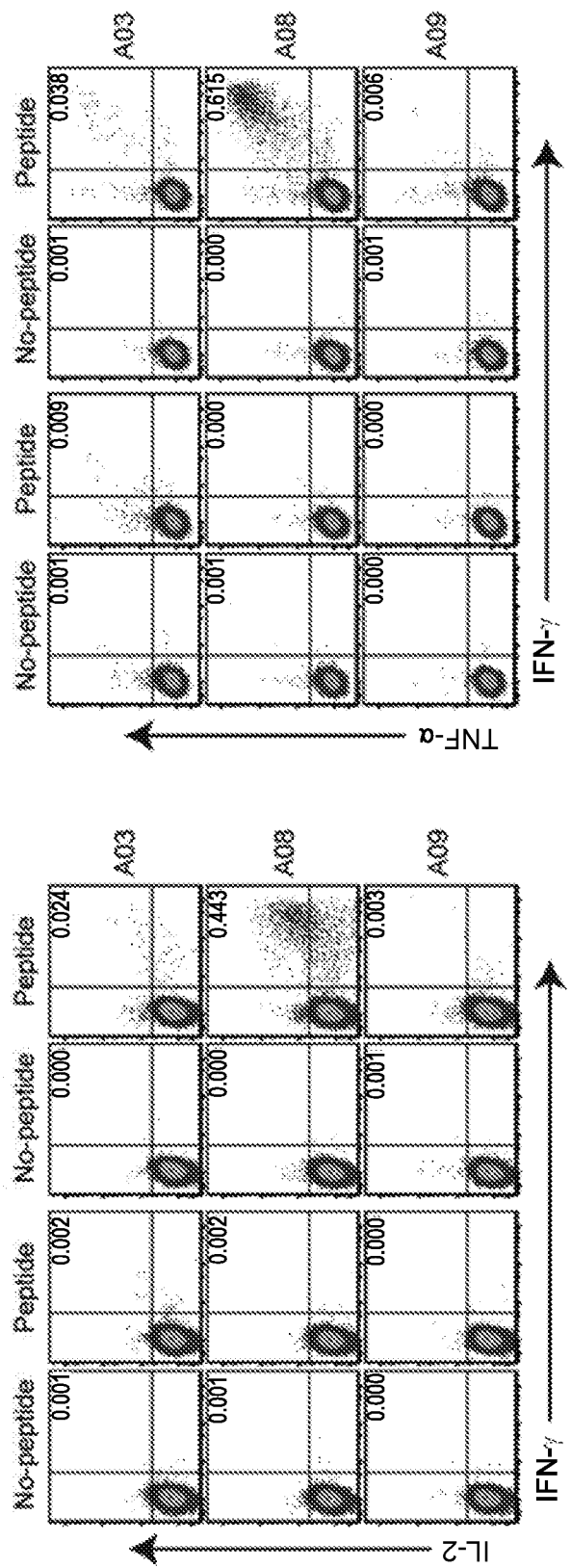
FIG. 7A
FIG. 7B
FIG. 7C

FIG. 8A
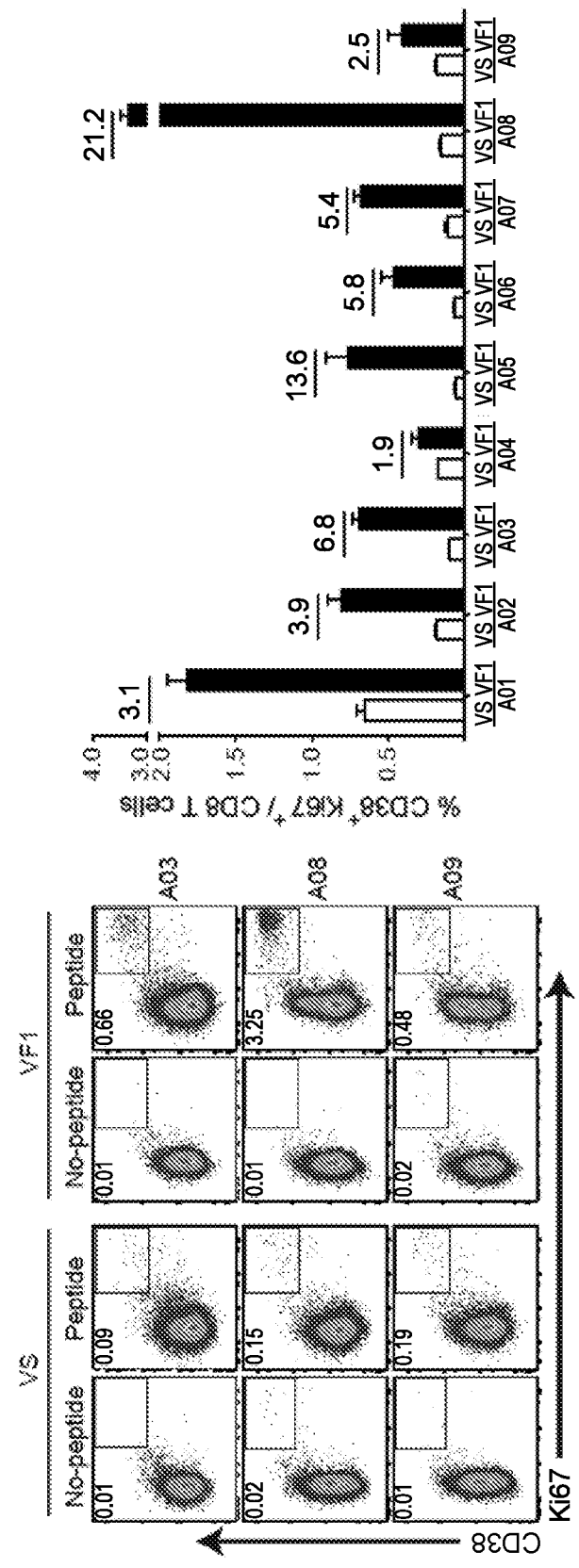
FIG. 8C
FIG. 8B

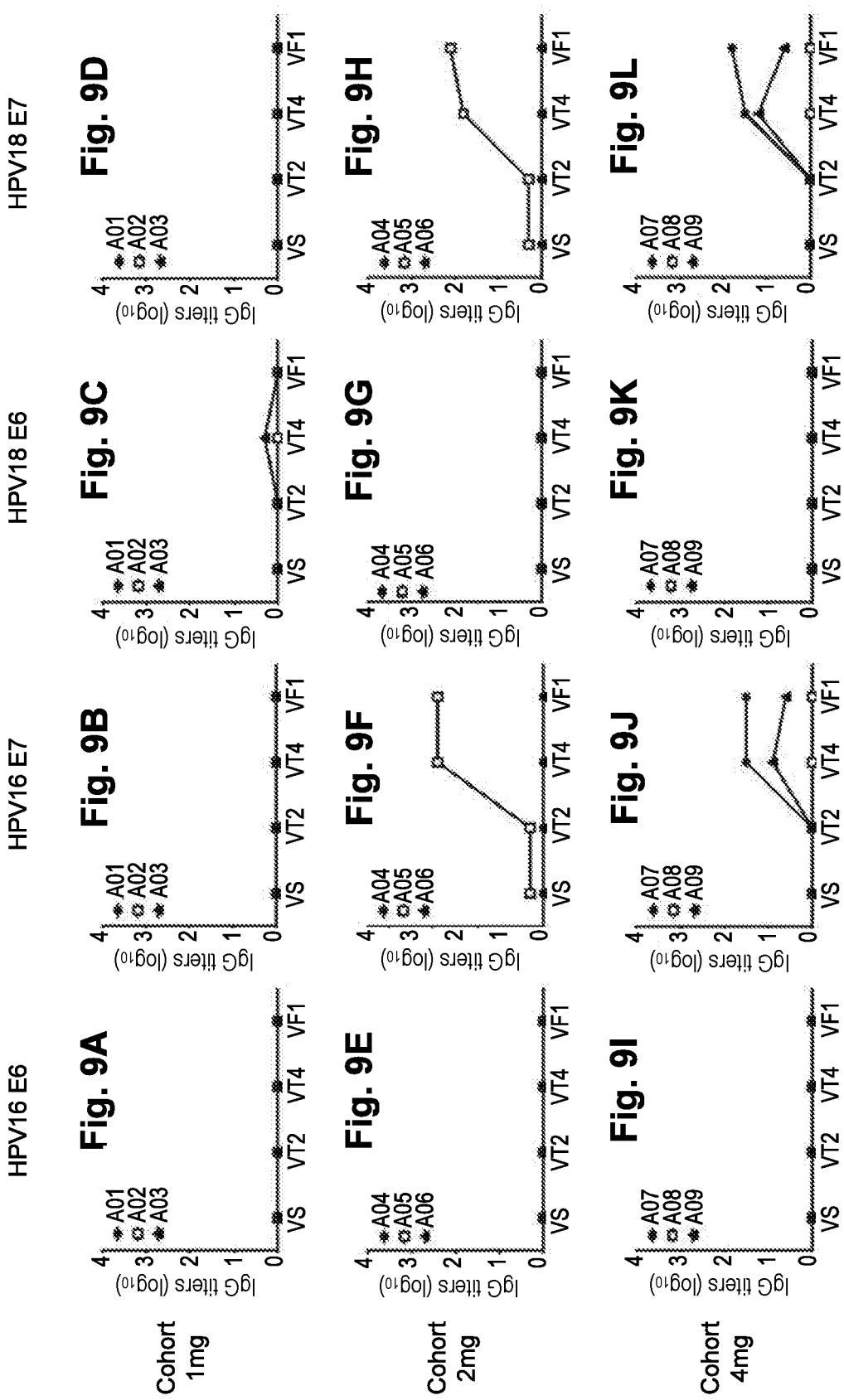

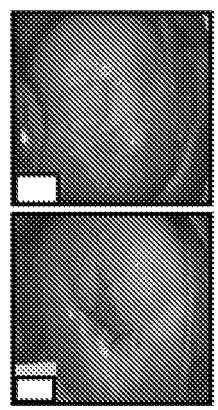 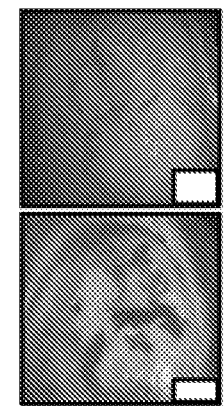
FIG. 10A
 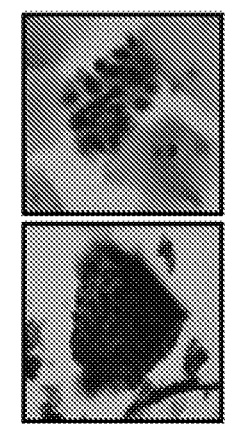
FIG. 10B
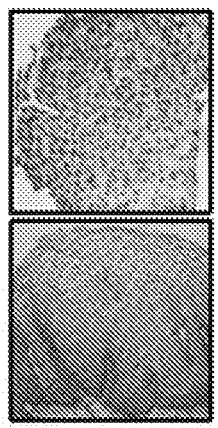 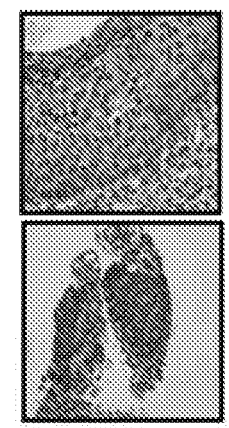
FIG. 10C

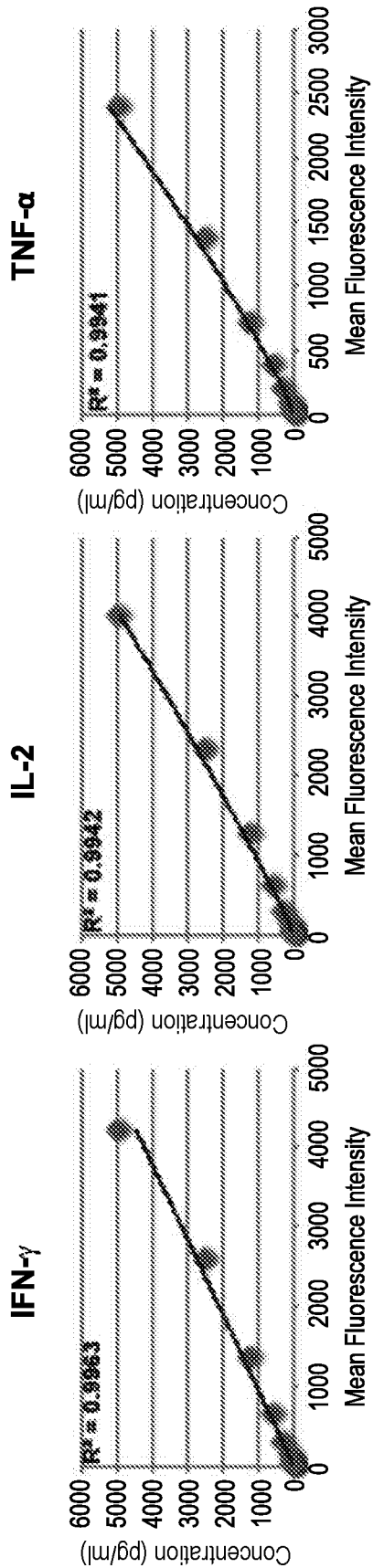
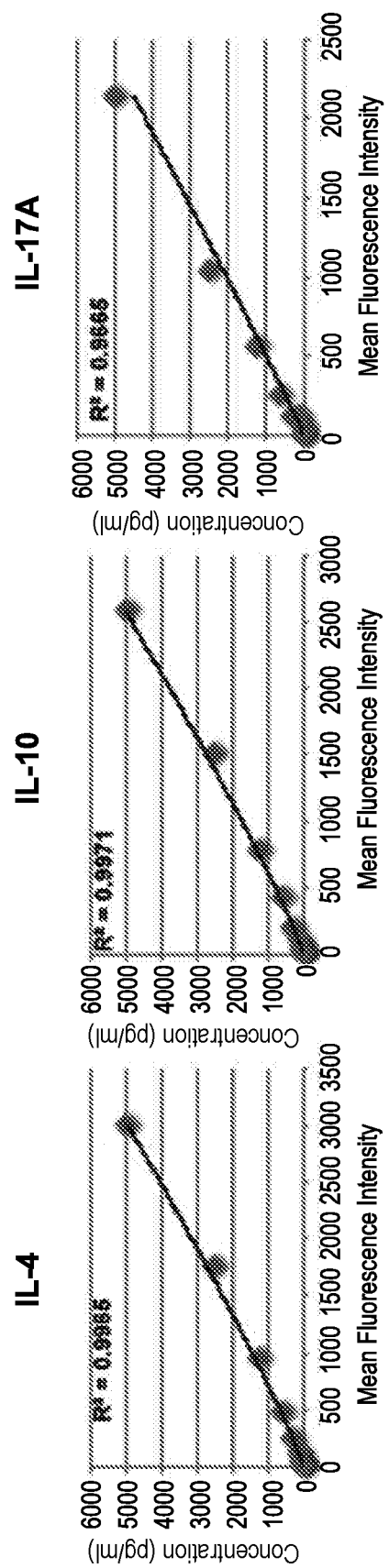
FIG. 12A  FIG. 12B  FIG. 12C
FIG. 12D  FIG. 12E  FIG. 12F

FIG. 14

| Lane | Category | Exp# | Description | tPA | FR3 | Seg1 | Seg2 | Seg3 | Seg4 | Seg5 | Seg6 | Seg7 | Seg8 |
|---|---|---|---|---|---|---|---|---|---|---|---|---|---|
| 1 Lane: A Mock control | Negative control | | pGX27 Vector only | | | | | | | | | | |
| 2 Lane: B GX-188 control | Positive Control | | GX-188E Natural SEQ. | tPA | FR3 | 1-85 16E6N | 1-65 16E7N | 71-158 16E6C | 51-98 16E7C | 1-85 18E6N | 1-65 18E7N | 71-158 18E6C | 51-105 18E7C |
| 3 Lane: C-1 E6 Mutant-1 | | EXP1 | HPV E6 mutant (Substitution: H21Q ... Y85H, V9CL) | tPA | FR3 | 1-85 16E6N | 1-65 16E7N | 71-158 16E6C | 51-98 16E7C | 1-85 18E6N | 1-65 18E7N | 71-158 18E6C | 51-105 18E7C |
| 4 Lane: C-2 Mutant-2 | | EXP2 | HPV E7 mutant (Substitution: M1?K, N2?S ... R77S, G85S) | tPA | FR3 | 1-85 16E6N | 1-65 16E7N | 71-158 16E6C | 51-98 16E7C | 1-85 18E6N | 1-65 18E7N | 71-158 18E6C | 51-105 18E7C |
| 5 Lane: D-1 Overlapping-1 | | EXP3 | Overlap(0/0) = 0+0+0+0 | tPA | FR3 | 1-78 16E6N | 1-58 16E7N | 79-158 16E6C | 59-98 16E7C | 1-85 18E6N | 1-65 18E7N | 71-158 18E6C | 51-105 18E7C |
| 6 Lane: D-2 Overlapping-2 | | EXP4 | Overlap(86/42) = 86+42+15+15 | tPA | FR3 | 1-130 16E6N | 1-85 16E7N | 45-158 16E6C | 44-98 16E7C | 1-85 18E6N | 1-65 18E7N | 71-158 18E6C | 51-105 18E7C |
| 7 Lane: E-1 Order-1 | | EXP5 | Shuffle(NC/NC) NCNCNCNC | tPA | FR3 | 1-85 16E6N | 51-98 16E7C | 1-65 16E7N | 71-158 16E6C | 1-85 18E6N | 1-65 18E7N | 71-158 18E6C | 51-105 18E7C |
| E-2 Order-2 | | EXP6 | CCNNCCNN | tPA | FR3 | 71-158 16E6C | 51-98 16E7C | 1-85 16E6N | 1-65 16E7N | 71-158 18E6C | 51-105 18E7C | 1-85 18E6N | 1-65 18E7N |

SEQUENCE LISTING

```
<160> NUMBER OF SEQ ID NOS: 116

<210> SEQ ID NO 1
<211> LENGTH: 477
<212> TYPE: DNA
<213> ORGANISM: Human papillomavirus 16
<220> FEATURE:
<221> NAME/KEY: misc_feature
<223> OTHER INFORMATION: E6 nucleotide sequence

<400> SEQUENCE: 1
atgcaccaaa agagaactgc aatgtttcag gacccacagg agcgacccag aaagttacca      60
catttatgca cagagctgca aacaactata catgatataa tattagaatg tgtgtactgc     120
aagcaacagt tactgcgacg tgaggtatat gactttgctt ttcgggattt atgcatagta     180
tatagagatg ggaatccata tgcagtgtgt gataaatgtt taaagtttta ttctaaaatt     240
agtgagtata gatattattg ttatagtgtg tatggaacaa cattagaaca gcaatacaac     300
aaaccgttgt gtgatttgtt aattaggtgt attaactgtc aaaagccact gtgtcctgaa     360
gaaaagcaaa gacatctgga caaaaagcaa agattccata atataagggg tcggtggacc     420
ggtcgatgta tgtcttgttg cagatcatca agaacacgta gagaaaccca gctgtaa       477

<210> SEQ ID NO 2
<211> LENGTH: 158
<212> TYPE: PRT
<213> ORGANISM: Human papillomavirus 16
<220> FEATURE:
```

```
<221> NAME/KEY: MISC_FEATURE
<223> OTHER INFORMATION: E6 protein

<400> SEQUENCE: 2

Met His Gln Lys Arg Thr Ala Met Phe Gln Asp Pro Gln Glu Arg Pro
1               5                   10                  15

Arg Lys Leu Pro His Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg Tyr Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 3
<211> LENGTH: 477
<212> TYPE: DNA
<213> ORGANISM: Human papillomavirus 18
<220> FEATURE:
<221> NAME/KEY: misc_feature
<223> OTHER INFORMATION: E6 nucleotide sequence

<400> SEQUENCE: 3
atggcgcgct ttgaggatcc aacacggcga ccctacaagc tacctgatct gtgcacggaa      60
ctgaacactt cactgcaaga catagaaata acctgtgtat attgcaagac agtattggaa     120
cttacagagg tatttgaatt tgcattcaaa gatttatttg tagtgtatag agacagtata     180
ccgcatgctg catgccataa atgtatagat ttctattcta gaattagaga attaagatat     240
tattcagact ctgtgtatgg agacacatta gaaaaactaa ctaacactgg ttatacaat      300 ttattaataa ggtgcctgcg gtgccagaaa ccgttgaatc cagcagaaaa acttagacac     360
cttaatgaaa aacgacgatt ccacaaaata gctgggcact atagaggcca gtgccattcg     420
tgctgcaacc gagcacgaca ggagagactc caacgacgca gagaaacaca agtataa        477

<210> SEQ ID NO 4
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: E6 protein

<400> SEQUENCE: 4

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30
```

Val Tyr Cys Lys Thr Val Leu Glu Leu Thr Glu Val Phe Glu Phe Ala
             35                  40                  45

Phe Lys Asp Leu Phe Val Val Tyr Arg Asp Ser Ile Pro His Ala Ala
 50                  55                  60

Cys His Lys Cys Ile Asp Phe Tyr Ser Arg Ile Arg Glu Leu Arg Tyr
 65                  70                  75                  80

Tyr Ser Asp Ser Val Tyr Gly Asp Thr Leu Glu Lys Leu Thr Asn Thr
                 85                  90                  95

Gly Leu Tyr Asn Leu Leu Ile Arg Cys Leu Arg Cys Gln Lys Pro Leu
             100                 105                 110

Asn Pro Ala Glu Lys Leu Arg His Leu Asn Glu Lys Arg Arg Phe His
             115                 120                 125

Lys Ile Ala Gly His Tyr Arg Gly Gln Cys His Ser Cys Cys Asn Arg
 130                 135                 140

Ala Arg Gln Glu Arg Leu Gln Arg Arg Arg Glu Thr Gln Val
145                 150                 155

<210> SEQ ID NO 5
<211> LENGTH: 297
<212> TYPE: DNA
<213> ORGANISM: Human papillomavirus 16
<220> FEATURE:
<221> NAME/KEY: misc_feature
<223> OTHER INFORMATION: E7 nucleotide sequence

<400> SEQUENCE: 5
atgcatggag atacacctac attgcatgaa tatatgttag atttgcaacc agagacaact      60
gatctctact gttatgagca attaaatgac agctcagagg aggaggatga aatagatggt     120
ccagctggac aagcgaaacc ggacagagcc cattacaata ttgtaacctt ttgttgcaag     180
tgtgactcta cgcttcggtt gtgcgtacaa agcacacacg tagacattcg tactttggaa     240
gacctgttaa tgggcacact aggaattgtg tgccccatct gttctcagaa accataa       297

<210> SEQ ID NO 6
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: E7 protein

<400> SEQUENCE: 6

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
             20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 7
<211> LENGTH: 318

```
<212> TYPE: DNA
<213> ORGANISM: Human papillomavirus 18
<220> FEATURE:
<221> NAME/KEY: misc_feature
<223> OTHER INFORMATION: E7 nucleotide sequence

<400> SEQUENCE: 7
atgtatggac ctaaggcaac attgcaagac attgtattgc atttagagcc tcaaaatgaa      60
attccggttg accttctatg tcacgagcaa ttaagcgact cagaggaaga aaacgatgaa     120
atagatggag ttaatcatca acatttacca gcccgacgag ccgaaccaca acgtcacaca     180
atgttgtgta tgtgttgtaa gtgtgaagcc agaattgagc tagtagtaga agctcagca      240 gacgaccttc gagcattcca gcagctgttt ctgagcaccc tgtcctttgt gtgtccgtgg     300
tgtgcatccc agcagtaa                                                   318

<210> SEQ ID NO 8
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: E7 protein

<400> SEQUENCE: 8

Met Tyr Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Ser Thr Leu Ser Phe
                85                  90                  95

Val Cys Pro Trp Cys Ala Ser Gln Gln
            100                 105

<210> SEQ ID NO 9
<211> LENGTH: 1737
<212> TYPE: DNA
<213> ORGANISM: Artificial Sequence
<220> FEATURE:
<223> OTHER INFORMATION: codon optimized sequence of GX-188 without
      FLT3L and signal peptide

<400> SEQUENCE: 9
atgcaccaga agagaaccgc catgttccag gaccctcagg agagacctag gaagctgcct      60
cacctgtgta cagagctcca gacaaccatc cacgacatca tcctggagtg cgtgtactgt     120
aagcagcagc tgctgagaag agaggtgtac gacttcgcct tcagagacct gtgcatcgtg     180
tacagagacg gcaacccttac gccgtgtgc gataagtgtc tgaagttcta ttccaaaatc     240
tccgaatata ggtacatgca cggcgacacc cctaccctgc acgagtacat gctggacctc     300
cagcctgaga ccacagacct gtactgctac gagcagctga acgacagctc tgaggaagag     360
gacgagattg acggacctgc tggccaggcc agcctgacag agccccacta caatatcgtg     420
acattctgtt gcaaatgcga ctccacactg gacagtgcc tgaagttcta cagcaagatc      480
```

-continued

```
tctgagtaca gatactactg ctactctgtg tacggcacca cactggagca gcagtacaac    540
aagcctctgt gcgacctcct gatccgctgc atcaactgcc agaagcctct gtgccctgag    600
gagaagcaga gacacctgga caagaagcag cggttccaca acatcagagg cagatggacc    660
ggcaggtgca tgtcctgctg tagatcctcc agaaccagac gggagaccca gctgcactac    720
aacatcgtga ccttctgctg caagtgcgac tctaccctga gactgtgcgt gcagtctacc    780
cacgtggaca tcagaaccct ggaggacctg ctgatgggca ccctgggcat cgtgtgccct    840
atctgctctc agaagcctat ggccaggttc gaggacccta ccagaagacc ctacaagctg    900
cctgacctgt gcaccgagct gaacacctct ctgcaagaca tcgagatcac ctgcgtgtac    960
tgcaagaccg tgctggagct gaccgaggtg ttcgagttcg ccttcaagga cctgttcgtg   1020
gtgtacagag acagcatccc tcacgctgcc tgccacaagt gcatcgactt ctattccagg   1080
atcagggagc tgcgctatta ctccgactct gtgatgtacg gccccaaggc caccctccag   1140
gacatcgtgc tgcacctgga gcctcagaac gagatccccg tggacctgct gtgccacgag   1200
cagctgtctg actctgaaga ggagaacgac gagatcgacg gcgtgaacca ccagcacctg   1260
cctgccagga gagctgaacc cagcggcat accatgctgt gtatgtgctt ctactctagg   1320
atcagagagc tgaggtacta ctctgactct gtgtacggcg acaccctgga gaagctgacc   1380
aacaccggcc tgtacaacct gctgatccgg tgcctgaggt gccagaagcc tctgaaccct   1440
gccgagaagc tgagacacct gaacgagaag agaagattcc acaagatcgc tggccactac   1500
agaggccagt gccactcttg ctgcaacaga gccagacagg agagactcca gcggagaagg   1560
gagacccagt ggccagaag agccgagcct cagagacaca ccatgctgtg catgtgctgc   1620
aagtgcgagg ccagaatcga gctggtggtg gagagctctg ccgacgacct gagagccttc   1680
cagcagctgt tcctgtctac cctgagcttc gtgtgcccct tggtgcgcct tcagcag     1737
```

<210> SEQ ID NO 10
<211> LENGTH: 579
<212> TYPE: PRT
<213> ORGANISM: Artificial Sequence
<220> FEATURE:
<223> OTHER INFORMATION: amino acid sequence of GX-188 without FLT3L and
      signal peptide

<400> SEQUENCE: 10

```
Met His Gln Lys Arg Thr Ala Met Phe Gln Asp Pro Gln Glu Arg Pro
1               5                   10                  15

Arg Lys Leu Pro His Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg Tyr Met His Gly Asp Thr Pro Thr Leu His Glu Tyr
                85                  90                  95

Met Leu Asp Leu Gln Pro Glu Thr Thr Asp Leu Tyr Cys Tyr Glu Gln
            100                 105                 110

Leu Asn Asp Ser Ser Glu Glu Glu Asp Glu Ile Asp Gly Pro Ala Gly
        115                 120                 125

Gln Ala Glu Pro Asp Arg Ala His Tyr Asn Ile Val Thr Phe Cys Cys
    130                 135                 140
```

```
Lys Cys Asp Ser Thr Leu Asp Lys Cys Leu Lys Phe Tyr Ser Lys Ile
145                 150                 155                 160

Ser Glu Tyr Arg Tyr Tyr Cys Tyr Ser Val Tyr Gly Thr Thr Leu Glu
            165                 170                 175

Gln Gln Tyr Asn Lys Pro Leu Cys Asp Leu Leu Ile Arg Cys Ile Asn
            180                 185                 190

Cys Gln Lys Pro Leu Cys Pro Glu Glu Lys Gln Arg His Leu Asp Lys
        195                 200                 205

Lys Gln Arg Phe His Asn Ile Arg Gly Arg Trp Thr Gly Arg Cys Met
        210                 215                 220

Ser Cys Cys Arg Ser Ser Arg Thr Arg Arg Glu Thr Gln Leu His Tyr
225                 230                 235                 240

Asn Ile Val Thr Phe Cys Cys Lys Cys Asp Ser Thr Leu Arg Leu Cys
                245                 250                 255

Val Gln Ser Thr His Val Asp Ile Arg Thr Leu Glu Asp Leu Leu Met
            260                 265                 270

Gly Thr Leu Gly Ile Val Cys Pro Ile Cys Ser Gln Lys Pro Met Ala
        275                 280                 285

Arg Phe Glu Asp Pro Thr Arg Arg Pro Tyr Lys Leu Pro Asp Leu Cys
290                 295                 300

Thr Glu Leu Asn Thr Ser Leu Gln Asp Ile Glu Ile Thr Cys Val Tyr
305                 310                 315                 320

Cys Lys Thr Val Leu Glu Leu Thr Glu Val Phe Glu Phe Ala Phe Lys
                325                 330                 335

Asp Leu Phe Val Val Tyr Arg Asp Ser Ile Pro His Ala Ala Cys His
            340                 345                 350

Lys Cys Ile Asp Phe Tyr Ser Arg Ile Arg Glu Leu Arg Tyr Tyr Ser
        355                 360                 365

Asp Ser Val Met Tyr Gly Pro Lys Ala Thr Leu Gln Asp Ile Val Leu
370                 375                 380

His Leu Glu Pro Gln Asn Glu Ile Pro Val Asp Leu Leu Cys His Glu
385                 390                 395                 400

Gln Leu Ser Asp Ser Glu Glu Asn Asp Glu Ile Asp Gly Val Asn
                405                 410                 415

His Gln His Leu Pro Ala Arg Arg Ala Glu Pro Gln Arg His Thr Met
            420                 425                 430

Leu Cys Met Cys Phe Tyr Ser Arg Ile Arg Glu Leu Arg Tyr Tyr Ser
        435                 440                 445

Asp Ser Val Tyr Gly Asp Thr Leu Glu Lys Leu Thr Asn Thr Gly Leu
450                 455                 460

Tyr Asn Leu Leu Ile Arg Cys Leu Arg Cys Gln Lys Pro Leu Asn Pro
465                 470                 475                 480

Ala Glu Lys Leu Arg His Leu Asn Glu Lys Arg Arg Phe His Lys Ile
                485                 490                 495

Ala Gly His Tyr Arg Gly Gln Cys His Ser Cys Cys Asn Arg Ala Arg
            500                 505                 510

Gln Glu Arg Leu Gln Arg Arg Glu Thr Gln Val Ala Arg Arg Ala
        515                 520                 525

Glu Pro Gln Arg His Thr Met Leu Cys Met Cys Cys Lys Cys Glu Ala
        530                 535                 540

Arg Ile Glu Leu Val Val Glu Ser Ser Ala Asp Asp Leu Arg Ala Phe
545                 550                 555                 560
```

```
        Gln Gln Leu Phe Leu Ser Thr Leu Ser Phe Val Cys Pro Trp Cys Ala
                        565                 570                 575

Ser Gln Gln

<210> SEQ ID NO 11
<211> LENGTH: 489
<212> TYPE: DNA
<213> ORGANISM: Artificial Sequence
<220> FEATURE:
<223> OTHER INFORMATION: Nucleotide sequence of FLT3L (fms-like
      tyrosine kinase-3 ligand)

<400> SEQUENCE: 11
atcacccagg actgctcctt ccaacacagc cccatctcct ccgacttcgc tgtcaaaatc    60
cgtgagctgt ctgactacct gcttcaagat tacccagtca ccgtggcctc caacctgcag   120
gacgaggagc tctgcggggg cctctggcgg ctggtcctgg cacagcgctg gatggagcgg   180
ctcaagactg tcgctgggtc caagatgcaa ggcttgctgg agcgcgtgaa cacggagata   240
cactttgtca ccaaatgtgc ctttcagccc cccccagct gtcttcgctt cgtccagacc    300
aacatctccc gcctcctgca ggagacctcc gagcagctgg tggcgctgaa gccctggatc   360
actcgccaga acttctcccg gtgcctggag ctgcagtgtc agcccgactc ctcaaccctg   420 ccaccccat ggagtccccg gcccctggag ccacagcccc gacagccccc gggcggcggc    480
agcggcgat                                                           489

<210> SEQ ID NO 12
<211> LENGTH: 163
<212> TYPE: PRT
<213> ORGANISM: Artificial Sequence
<220> FEATURE:
<223> OTHER INFORMATION: Amino acid sequence of FLT3L (fms-like
      tyrosine kinase-3 ligand)

<400> SEQUENCE: 12

Ile Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Gly Leu
        35                  40                  45

Trp Arg Leu Val Leu Ala Gln Arg Trp Met Glu Arg Leu Lys Thr Val
    50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
                85                  90                  95

Phe Val Gln Thr Asn Ile Ser Arg Leu Leu Gln Glu Thr Ser Glu Gln
            100                 105                 110

Leu Val Ala Leu Lys Pro Trp Ile Thr Arg Gln Asn Phe Ser Arg Cys
        115                 120                 125

Leu Glu Leu Gln Cys Gln Pro Asp Ser Ser Thr Leu Pro Pro Pro Trp
    130                 135                 140

Ser Pro Arg Pro Leu Glu Ala Thr Ala Pro Thr Ala Pro Gly Gly Gly
145                 150                 155                 160

Ser Gly Asp

<210> SEQ ID NO 13
```

<210> SEQ ID NO 13
<211> LENGTH: 69
<212> TYPE: DNA
<213> ORGANISM: Artificial Sequence
<220> FEATURE:
<223> OTHER INFORMATION: Signal peptide of tPA

<400> SEQUENCE: 13

```
atggatgcta tgaaacgggg cctgtgctgc gtgctgctcc tgtgcggcgc tgtgtttgtg    60
agccctagc                                                            69
```

<210> SEQ ID NO 14
<211> LENGTH: 23
<212> TYPE: PRT
<213> ORGANISM: Artificial Sequence
<220> FEATURE:
<223> OTHER INFORMATION: Signal peptide of tPA

<400> SEQUENCE: 14

```
Met Asp Ala Met Lys Arg Gly Leu Cys Cys Val Leu Leu Leu Cys Gly
1               5                   10                  15

Ala Val Phe Val Ser Pro Ser
            20
```

<210> SEQ ID NO 15
<211> LENGTH: 6085
<212> TYPE: DNA
<213> ORGANISM: Artificial Sequence
<220> FEATURE:
<223> OTHER INFORMATION: GX-188E

<400> SEQUENCE: 15

```
acgcgttgac attgattatt gactagttat taatagtaat caattacggg gtcattagtt    60
catagcccat atatggagtt ccgcgttaca taacttacgg taaatggccc gcctggctga   120
ccgcccaacg accccgccc attgacgtca ataatgacgt atgttcccat agtaacgcca   180
atagggactt tccattgacg tcaatgggtg gagtatttac ggtaaactgc ccacttggca   240
gtacatcaag tgtatcatat gccaagtacg ccccctattg acgtcaatga cggtaaatgg   300
cccgcctggc attatgccca gtacatgacc ttatgggact ttcctacttg gcagtacatc   360
tacgtattag tcatcgctat taccatggtg atgcggtttt ggcagtacat caatgggcgt   420
ggatagcggt ttgactcacg gggatttcca agtctccacc ccattgacgt caatgggagt   480
ttgttttggc accaaaatca acgggacttt ccaaaatgtc gtaacaactc cgccccattg   540
acgcaaatgg gcggtaggcg tgtacggtgg gaggtctata taagcagagc tctctggcta   600
actagagaac ccactgctta ctggcttatc gaaattaata cgactcacta gggagaccc   660 caagctggct agcgtgagtt tggggaccct tgattgttct tcttttcg ctattgtaaa   720 attcatgtta tatggagggg caaagttttt cagggtgttg tttagaacgg aagatgtcc   780 cttgtatcac catggaccct catgataatt tgtttctttt cactttctac tctgttgaca   840
accattgtct cctcttattt tcttttcatt ttctgtaact ttttcgttaa actttagctt   900
gcatttgtaa cgaatttta aattcacttt tgtttatttg tcagattgta agtactttct   960
ctaatcactt tttttcaag gcaatcaggg tatattat tgtacttcag cacagtttta  1020
gagaacaatt gttataatta aatgataagg tagaatattt ctgcatataa attctggctg  1080
gcgtggaaat attcttattg gtagaaacaa ctacatcctg gtcatcatcc tgcctttctc  1140
tttatggtta caatgataa cactgtttga gatgaggata aaatactctg agtccaaacc  1200
gggcccctct gctaaccatg ttcatgcctt cttctttttc ctacagctcc tgggcaacgt  1260
```

```
gctggttatt gtgctgtctc atcattttgg caaagaattg taatacgact cactataggg    1320
cgaattgaag cttggtaccg ccaccatgga tgctatgaaa cggggcctgt gctgcgtgct    1380
gctcctgtgc ggcgctgtgt ttgtgagccc tagcatcacc caggactgct ccttccaaca    1440
cagccccatc tcctccgact tcgctgtcaa aatccgtgag ctgtctgact acctgcttca    1500
agattaccca gtcaccgtgg cctccaacct gcaggacgag gagctctgcg ggggcctctg    1560
gcggctggtc ctggcacagc gctggatgga gcggctcaag actgtcgctg gtccaagat    1620
gcaaggcttg ctggagcgcg tgaacacgga gatacactt gtcaccaaat gtgcctttca    1680
gccccccccc agctgtcttc gcttcgtcca gaccaacatc tcccgcctcc tgcaggagac    1740
ctccgagcag ctggtggcgc tgaagccctg gatcactcgc cagaacttct cccggtgcct    1800
ggagctgcag tgtcagcccg actcctcaac cctgccaccc ccatggagtc cccggccct    1860
ggaggccaca gccccgacag ccccgggcgg cggcagcggc gatgctagca tgcaccagaa    1920
gagaaccgcc atgttccagg accctcagga gagacctagg aagctgcctc acctgtgtac    1980
agagctccag acaaccatcc acgacatcat cctggagtgc gtgtactgta agcagcagct    2040
gctgagaaga gaggtgtacg acttcgcctt cagagacctg tgcatcgtgt acagagacgg    2100
caaccccttac gccgtgtgcg ataagtgtct gaagttctat tccaaaatct ccgaatatag    2160
gtacatgcac ggcgacaccc ctaccctgca cgagtacatg ctggacctcc agcctgagac    2220
cacagacctg tactgctacg agcagctgaa cgacagctct gaggaagagg acgagattga    2280
cggacctgct ggccaggccg agcctgacag agcccactac aatatcgtga cattctgttg    2340
caaatgcgac tccacactgg acaagtgcct gaagttctac agcaagatct ctgagtacag    2400
atactactgc tactctgtgt acggcaccac actggagcag cagtacaaca agcctctgtg    2460
cgacctcctg atccgctgca tcaactgcca gaagcctctg tgccctgagg agaagcagag    2520
acacctggac aagaagcagc ggttccacaa catcagaggc agatggaccg gcaggtgcat    2580
gtcctgctgt agatcctcca gaaccagacg ggagacccag ctgcactaca acatcgtgac    2640
cttctgctgc aagtgcgact ctaccctgag actgtgcgtg cagtctaccc acgtggacat    2700
cagaaccctg gaggacctgc tgatgggcac cctgggcatc gtgtgcccta tctgctctca    2760
gaagcctatg gccaggttcg aggacctac cagaagaccc tacaagctgc ctgacctgtg    2820
caccgagctg aacacctctc tgcaagacat cgagatcacc tgcgtgtact gcaagaccgt    2880
gctggagctg accgaggtgt tcgagttcgc cttcaaggac ctgttcgtgg tgtacagaga    2940
cagcatccct cacgctgcct gccacaagtg catcgacttc tattccagga tcagggagct    3000
gcgctattac tccgactctg tgatgtacgg ccccaaggcc accctccagg acatcgtgct    3060
gcacctggag cctcagaacg agatccccgt ggacctgctg tgccacgagc agctgtctga    3120
ctctgaagag gagaacgacg agatcgacgg cgtgaaccac cagcacctgc ctgccaggag    3180
agctgaaccc cagcggcata ccatgctgtg tatgtgcttc tactctagga tcagagagct    3240
gaggtactac tctgactctg tgtacggcga caccctggag aagctgacca acaccggcct    3300
gtacaacctg ctgatccggt gcctgaggtg ccagaagcct ctgaaccctg ccgagaagct    3360
gagacacctg aacgagaaga aagattcca aagatcgct ggccactaca gggccagtg    3420
ccactcttgc tgcaacagag ccagacagga gagactccag cggagaaggg agacccaggt    3480
ggccagaaga gccgagcctc agagacacac catgctgtgc atgtgctgca agtgcgaggc    3540
cagaatcgag ctggtggtgg agagctctgc cgacgacctg agagccttcc agcagctgtt    3600
```

```
cctgtctacc ctgagcttcg tgtgcccttg gtgcgcctct cagcagtaat ctagagtcgg   3660
ggcggccggc cgcttcgagc agacatgata agatacattg atgagtttgg acaaaccaca   3720
actagaatgc agtgaaaaaa atgctttatt tgtgaaattt gtgatgctat tgctttattt   3780
gtaaccatta taagctgcaa taaacaagtt aacaacaaca attgcattca ttttatgttt   3840
caggttcagg gggaggtgtg ggaggttttt taaagcaagt aaaacctcta caaatgtggt   3900
aaaatcgata aggatctgaa cgatggagcg gagaatgggc ggaactgggc ggagttaggg   3960
gcgggatggg cggagttagg ggcgggacta tggttgctga ctaattgaga tgcatgcttt   4020
gcatacttct gcctgctggg gagcctgggg actttccaca cctggttgct gactaattga   4080
gatgcatgct ttgcatactt ctgcctgctg gggagcctgg ggactttcca cccctaact   4140
gacacacatt ccacagcgga tccgtcgact tcagaagaac tcgtcaagaa ggcgatagaa   4200
ggcgatgcgc cgcgaatcgg gagcggcgat accgtagagc acgaggaagc ggtcagccca   4260
ttcgccgcca agctcttcag caatatcacg ggtagccaac gctatgtcct gatagcggtc   4320
cgccacaccc agccggccac agtcgatgaa tccagaaaag cggccatttt ccaccatgat   4380
attcggcaag caggcatcgc catgggtcac gacgagatcc tcgccgtcgg gcatgctcgc   4440
cttgagcctg gcgaacagtt cggctggcgc gagcccctga tgctcttcgt ccagatcatc   4500
ctgatcgaca agaccggctt ccatccgagt acgtgctcgc tcgatgcgat gtttcgcttg   4560
gtggtcgaat gggcaggtag ccggatcaag cgtatgcagc cgccgcattg catcagccat   4620
gatggatact ttctcggcag gagcaaggtg agatgacagg agatcctgcc ccggcacttc   4680
gcccaatagc agccagtccc ttcccgcttc agtgacaacg tcgagcacag ctgcgcaagg   4740
aacgcccgtc gtggccagcc acgatagccg cgctgcctcg tcttgcagtt cattcagggc   4800
accggacagg tcggtcttga caaaaagaac cgggcgcccc tgcgctgaca gccggaacac   4860
ggcggcatca gagcagccga ttgtctgttg tgcccagtca tagccgaata gcctctccac   4920
ccaagcggcc ggagaacctg cgtgcaatcc atcttgttca atcatgcgaa acgatcctca   4980
tcctgtctct tgatcagatc ttgatcccct gcgccatcag atccttggcg caagaaagc   5040
catccagttt actttgcagg gcttcccaac cttaccagag ggcgccccag ctggcaattc   5100
cggttcgctt gctgtccata aaaccgccca gtctagctat cgccatgtaa gcccactgca   5160
agctacctgc tttctctttg cgcttgcgtt ttcccttgtc cagatagccc agtagctgac   5220
attcatccgg ggtcagcacc gtttctgcgg actggctttc tacgtgaaaa ggatctaggt   5280
gaagatcctt tttgataatc tcatgaccaa aatcccttaa cgtgagtttt cgttccactg   5340
agcgtcagac cccgtagaaa agatcaaagg atcttcttga gatccttttt ttctgcgcgt   5400
aatctgctgc ttgcaaacaa aaaaaccacc gctaccagcg gtggtttgtt tgccggatca   5460
agagctacca actctttttc cgaaggtaac tggcttcagc agagcgcaga taccaaatac   5520
tgttcttcta gtgtagccgt agttaggcca ccacttcaag aactctgtag caccgcctac   5580
atacctcgct ctgctaatcc tgttaccagt ggctgctgcc agtggcgata agtcgtgtct   5640
taccgggttg gactcaagac gatagttacc ggataaggcg cagcggtcgg gctgaacggg   5700
gggttcgtgc acacagccca gcttggagcg aacgacctac accgaactga gatacctaca   5760
gcgtgagcta tgagaaagcg ccacgcttcc cgaagggaga aaggcggaca ggtatccggt   5820
aagcggcagg gtcggaacag gagagcgcac gagggagctt ccagggggaa acgcccggta   5880
tctttatagt cctgtcgggt ttcgccacct ctgacttgag cgtcgatttt tgtgatgctc   5940
gtcagggggg cggagcctat ggaaaaacgc cagcaacgcg gcctttttac ggttcctggc   6000
```

```
cttttgctgg cctttgctc acatgttcgg gcccaatcga cccgggcgac ggccagtgaa    6060
ttgtaccgat gtacgggcca gatat                                        6085
```

<210> SEQ ID NO 16
<211> LENGTH: 12
<212> TYPE: PRT
<213> ORGANISM: Artificial Sequence
<220> FEATURE:
<223> OTHER INFORMATION: alpha-1 helix of E7 protein of HPV16 (position
      73-84)

<400> SEQUENCE: 16

His Val Asp Ile Arg Thr Leu Glu Asp Leu Leu Met
1               5                   10

<210> SEQ ID NO 17
<211> LENGTH: 8
<212> TYPE: PRT
<213> ORGANISM: Artificial Sequence
<220> FEATURE:
<223> OTHER INFORMATION: beta-2 sheet of E7 protein of HPV16 (position
      64-71)

<400> SEQUENCE: 17

Thr Leu Arg Leu Cys Val Gln Ser
1               5

<210> SEQ ID NO 18
<211> LENGTH: 11
<212> TYPE: PRT
<213> ORGANISM: Artificial Sequence
<220> FEATURE:
<223> OTHER INFORMATION: beta-1 sheet of E7 protein of HPV16 (position
      48-58)

<400> SEQUENCE: 18

Asp Arg Ala His Tyr Asn Ile Val Thr Phe Cys
1               5                   10

<210> SEQ ID NO 19
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91670.1 E6 Variant

<400> SEQUENCE: 19

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Arg Ser Ser Arg
        130                 135                 140

Thr Arg Arg Glu Thr Gln Leu
145                 150

<210> SEQ ID NO 20
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91673.1 E6 Variant

<400> SEQUENCE: 20

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Arg Ser Ser Arg
        130                 135                 140

Thr Arg Arg Glu Thr Gln Leu
145                 150

<210> SEQ ID NO 21
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91669.1 E6 Variant

<400> SEQUENCE: 21

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Lys Asn Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

```
Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 22
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91674.1 E6 Variant

<400> SEQUENCE: 22

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 23
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91680.1 E6 Variant

<400> SEQUENCE: 23

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80
```

```
Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 24
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91681.1

<400> SEQUENCE: 24

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 25
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91668.1 E6 Variant

<400> SEQUENCE: 25

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60
```

-continued

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 26
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91658.1 E6 Variant

<400> SEQUENCE: 26

Met Phe Gln Asp Pro Gln Glu Arg Pro Arg Lys Leu Pro Gln Leu Cys
 1               5                  10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 27
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91662.1 E6 Variant

<400> SEQUENCE: 27

Met Phe Gln Asp Pro Gln Glu Arg Pro Arg Lys Leu Pro Gln Leu Cys
 1               5                  10                  15

Thr Glu Leu Gln Thr Thr Ile His Glu Ile Ile Leu Glu Cys Val Tyr
                20                  25                  30

Cys Lys Gln Gln Leu Leu Arg Arg Glu Val Tyr Asp Phe Ala Phe Arg
            35                  40                  45

```
Asp Leu Cys Ile Val Tyr Arg Asp Gly Asn Pro Tyr Ala Val Cys Asp
 50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
                115                 120                 125

Arg Gly Arg Trp Thr Gly Arg Cys Met Ser Cys Arg Ser Ser Arg
130                 135                 140

Thr Arg Arg Glu Thr Gln Leu
145                 150

<210> SEQ ID NO 28
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91667.1 E6 Variant

<400> SEQUENCE: 28

Met Phe Gln Asp Pro Gln Glu Arg Pro Arg Lys Leu Pro Gln Leu Cys
 1               5                  10                  15

Thr Glu Leu Gln Thr Thr Ile His Glu Ile Ile Leu Glu Cys Val Tyr
                 20                  25                  30

Cys Lys Gln Gln Leu Leu Arg Arg Glu Val Tyr Asp Phe Ala Phe Arg
                 35                  40                  45

Asp Leu Cys Ile Val Tyr Arg Asp Gly Asn Pro Tyr Ala Val Cys Asp
 50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
                115                 120                 125

Arg Gly Arg Trp Thr Gly Arg Cys Met Ser Cys Arg Ser Ser Arg
130                 135                 140

Thr Arg Arg Glu Thr Gln Leu
145                 150

<210> SEQ ID NO 29
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91676.1 E6 Variant

<400> SEQUENCE: 29

Met Phe Gln Asp Pro Gln Glu Arg Pro Arg Lys Leu Pro Gln Leu Cys
 1               5                  10                  15

Thr Glu Leu Gln Thr Thr Ile His Glu Ile Ile Leu Glu Cys Val Tyr
                 20                  25                  30
```

Cys Lys Gln Gln Leu Leu Arg Arg Glu Val Tyr Asp Phe Ala Phe Arg
             35                  40                  45

Asp Leu Cys Ile Val Tyr Arg Asp Gly Asn Pro Tyr Ala Val Cys Asp
 50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
             85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
130                 135                 140

Thr Arg Arg Glu Thr Gln Leu
145                 150

<210> SEQ ID NO 30
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91671.1 E6 Variant

<400> SEQUENCE: 30

Met Phe Gln Asp Pro Gln Glu Arg Pro Arg Lys Leu Pro Gln Leu Cys
 1               5                  10                  15

Thr Glu Leu Gln Thr Thr Ile His Glu Ile Ile Leu Glu Cys Val Tyr
             20                  25                  30

Cys Lys Gln Gln Leu Leu Arg Arg Glu Val Tyr Asp Phe Ala Phe Arg
             35                  40                  45

Asp Leu Cys Ile Val Tyr Arg Asp Gly Asn Pro Tyr Ala Val Cys Asp
 50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
             85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
130                 135                 140

Thr Arg Arg Glu Thr Gln Leu
145                 150

<210> SEQ ID NO 31
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91656.1 E6 Variant

<400> SEQUENCE: 31

Met Phe Gln Asp Pro Gln Glu Arg Pro Gly Lys Leu Pro Gln Leu Cys
 1               5                  10                  15

```
Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 32
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91682.1 E6 Variant

<400> SEQUENCE: 32

Met Phe Gln Asp Pro Gln Glu Arg Pro Gly Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 33
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91657.1 E6 Variant

<400> SEQUENCE: 33
```

Met Phe Gln Asp Pro Gln Glu Arg Pro Gly Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 34
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91660.1 E6 Variant

<400> SEQUENCE: 34

Met Phe Gln Asp Pro Gln Glu Arg Pro Gly Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 35
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91677.1 E6 Variant

<400> SEQUENCE: 35

| Met | Phe | Gln | Asp | Pro | Gln | Glu | Arg | Pro | Thr | Lys | Leu | Pro | Asp | Leu | Cys |
|---|---|---|---|---|---|---|---|---|---|---|---|---|---|---|---|
| 1 | | | | 5 | | | | | 10 | | | | | 15 | |

| Thr | Glu | Leu | Gln | Thr | Thr | Ile | His | Asp | Ile | Ile | Leu | Glu | Cys | Val | Tyr |
|---|---|---|---|---|---|---|---|---|---|---|---|---|---|---|---|
| | | | 20 | | | | | 25 | | | | | 30 | | |

| Cys | Lys | Gln | Gln | Leu | Leu | Arg | Arg | Glu | Val | Tyr | Asp | Phe | Ala | Phe | Arg |
|---|---|---|---|---|---|---|---|---|---|---|---|---|---|---|---|
| | | | 35 | | | | | 40 | | | | | 45 | | |

| Asp | Leu | Cys | Ile | Val | Tyr | Arg | Asp | Gly | Asn | Pro | Tyr | Ala | Val | Cys | Asp |
|---|---|---|---|---|---|---|---|---|---|---|---|---|---|---|---|
| | 50 | | | | | 55 | | | | | 60 | | | | |

| Lys | Cys | Leu | Lys | Phe | Tyr | Ser | Lys | Ile | Ser | Glu | Tyr | Arg | Tyr | Tyr | Cys |
|---|---|---|---|---|---|---|---|---|---|---|---|---|---|---|---|
| 65 | | | | 70 | | | | | 75 | | | | | 80 | |

| Tyr | Ser | Leu | Tyr | Gly | Thr | Thr | Leu | Glu | Gln | Gln | Tyr | Asn | Lys | Pro | Leu |
|---|---|---|---|---|---|---|---|---|---|---|---|---|---|---|---|
| | | | | 85 | | | | | 90 | | | | | 95 | |

| Cys | Asp | Leu | Leu | Ile | Arg | Cys | Ile | Asn | Cys | Gln | Lys | Pro | Leu | Cys | Pro |
|---|---|---|---|---|---|---|---|---|---|---|---|---|---|---|---|
| | | | 100 | | | | | 105 | | | | | 110 | | |

| Glu | Glu | Lys | Gln | Arg | His | Leu | Asp | Lys | Lys | Gln | Arg | Phe | His | Asn | Ile |
|---|---|---|---|---|---|---|---|---|---|---|---|---|---|---|---|
| | | | 115 | | | | | 120 | | | | | 125 | | |

| Arg | Gly | Arg | Trp | Thr | Gly | Arg | Cys | Met | Ser | Cys | Cys | Arg | Ser | Ser | Arg |
|---|---|---|---|---|---|---|---|---|---|---|---|---|---|---|---|
| | 130 | | | | | 135 | | | | | 140 | | | | |

| Thr | Arg | Arg | Glu | Thr | Gln | Leu | | | | | | | | | |
|---|---|---|---|---|---|---|---|---|---|---|---|---|---|---|---|
| 145 | | | | | 150 | | | | | | | | | | |

<210> SEQ ID NO 36
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91678.1 E6 Variant

<400> SEQUENCE: 36

| Met | Phe | Gln | Asp | Pro | Gln | Glu | Arg | Pro | Thr | Lys | Leu | Pro | Asp | Leu | Cys |
|---|---|---|---|---|---|---|---|---|---|---|---|---|---|---|---|
| 1 | | | | 5 | | | | | 10 | | | | | 15 | |

| Thr | Glu | Leu | Gln | Thr | Thr | Ile | His | Asp | Ile | Ile | Leu | Glu | Cys | Val | Tyr |
|---|---|---|---|---|---|---|---|---|---|---|---|---|---|---|---|
| | | | 20 | | | | | 25 | | | | | 30 | | |

| Cys | Lys | Gln | Gln | Leu | Leu | Arg | Arg | Glu | Val | Tyr | Asp | Phe | Ala | Phe | Arg |
|---|---|---|---|---|---|---|---|---|---|---|---|---|---|---|---|
| | | | 35 | | | | | 40 | | | | | 45 | | |

| Asp | Leu | Cys | Ile | Val | Tyr | Arg | Asp | Gly | Asn | Pro | Tyr | Ala | Val | Cys | Asp |
|---|---|---|---|---|---|---|---|---|---|---|---|---|---|---|---|
| | 50 | | | | | 55 | | | | | 60 | | | | |

| Lys | Cys | Leu | Lys | Phe | Tyr | Ser | Lys | Ile | Ser | Glu | Tyr | Arg | Tyr | Tyr | Cys |
|---|---|---|---|---|---|---|---|---|---|---|---|---|---|---|---|
| 65 | | | | 70 | | | | | 75 | | | | | 80 | |

| Tyr | Ser | Leu | Tyr | Gly | Thr | Thr | Leu | Glu | Gln | Gln | Tyr | Asn | Lys | Pro | Leu |
|---|---|---|---|---|---|---|---|---|---|---|---|---|---|---|---|
| | | | | 85 | | | | | 90 | | | | | 95 | |

| Cys | Asp | Leu | Leu | Ile | Arg | Cys | Ile | Asn | Cys | Gln | Lys | Pro | Leu | Cys | Pro |
|---|---|---|---|---|---|---|---|---|---|---|---|---|---|---|---|
| | | | 100 | | | | | 105 | | | | | 110 | | |

| Glu | Glu | Lys | Gln | Arg | His | Leu | Asp | Lys | Lys | Gln | Arg | Phe | His | Asn | Ile |
|---|---|---|---|---|---|---|---|---|---|---|---|---|---|---|---|
| | | | 115 | | | | | 120 | | | | | 125 | | |

| Arg | Gly | Arg | Trp | Thr | Gly | Arg | Cys | Met | Ser | Cys | Cys | Arg | Ser | Ser | Arg |
|---|---|---|---|---|---|---|---|---|---|---|---|---|---|---|---|
| | 130 | | | | | 135 | | | | | 140 | | | | |

| Thr | Arg | Arg | Glu | Thr | Gln | Leu | | | | | | | | | |
|---|---|---|---|---|---|---|---|---|---|---|---|---|---|---|---|
| 145 | | | | | 150 | | | | | | | | | | |

<210> SEQ ID NO 37
<211> LENGTH: 151
<212> TYPE: PRT
<213> ORGANISM: Human papillomavirus 16

```
<220> FEATURE:
<221> NAME/KEY: MISC_FEATURE
<223> OTHER INFORMATION: AAA91672.1 E6 Variant

<400> SEQUENCE: 37

Met Phe Gln Asp Pro Gln Glu Arg Pro Thr Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Arg Ser Ser Arg
    130                 135                 140

Thr Arg Arg Glu Thr Gln Leu
145                 150

<210> SEQ ID NO 38
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91661.1 E6 Variant

<400> SEQUENCE: 38

Met Phe Gln Asp Pro Gln Glu Arg Pro Thr Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Arg Ser Ser Arg
    130                 135                 140

Thr Arg Arg Glu Thr Gln Leu
145                 150

<210> SEQ ID NO 39
```

-continued

```
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91664.1 E6 Variant

<400> SEQUENCE: 39

Met Phe Gln Asp Pro Gln Glu Arg Pro Ile Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 40
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91675.1 E6 Variant

<400> SEQUENCE: 40

Met Phe Gln Asp Pro Gln Glu Arg Pro Ile Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

<210> SEQ ID NO 41
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91665.1 E6 Variant

<400> SEQUENCE: 41

Met Phe Gln Asp Pro Gln Glu Arg Pro Ile Lys Leu Pro Asp Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 42
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91663.1 E6 Variant

<400> SEQUENCE: 42

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 43
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91659.1 E6 Variant

<400> SEQUENCE: 43

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 44
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91654.1 E6 Variant

<400> SEQUENCE: 44

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Arg Ser Arg
            130                 135                 140

Thr Arg Arg Glu Thr Gln Leu
145                 150

<210> SEQ ID NO 45
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91666.1 E6 Variant

<400> SEQUENCE: 45

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 46
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91679.1 E6 Variant

<400> SEQUENCE: 46

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

```
Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 47
<211> LENGTH: 151
<212> TYPE: PRT
<213> ORGANISM: Human papillomavirus 16
<220> FEATURE:
<221> NAME/KEY: MISC_FEATURE
<223> OTHER INFORMATION: AAA91655.1 E6 Variant

<400> SEQUENCE: 47

Met Phe Gln Asp Pro Gln Glu Arg Pro Arg Lys Leu Pro His Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg Tyr Tyr Cys
65                  70                  75                  80

Tyr Ser Val Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
        130                 135                 140

Thr Arg Arg Glu Thr Gln Leu
145                 150

<210> SEQ ID NO 48
<211> LENGTH: 147
<212> TYPE: PRT
<213> ORGANISM: Human papillomavirus 18
<220> FEATURE:
<221> NAME/KEY: MISC_FEATURE
<223> OTHER INFORMATION: AHZ96678.1 E6 Variant

<400> SEQUENCE: 48

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg Tyr
65                  70                  75                  80

Tyr Ser Asp Ser Val Tyr Gly Asp Thr Leu Glu Lys Leu Thr Asn Thr
                85                  90                  95
```

```
Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Lys Ile Ala Gly His Tyr Arg Gly Gln Cys His Ser Cys Cys Asn Arg
    130                 135                 140

Ala Arg Gln
145

<210> SEQ ID NO 49
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ABP99784.1 E6 Variant

<400> SEQUENCE: 49

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg Tyr
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Lys Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155

<210> SEQ ID NO 50
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: CAB53096.1 E6 Variant

<400> SEQUENCE: 50

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80
```

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Lys Ile Ala Gly His Tyr Arg Gly Gln Cys His Ser Cys Cys Asn Arg
    130                 135                 140

Ala Arg Gln Glu Arg Leu Gln Arg Arg Glu Thr Gln Val
145                 150                 155

<210> SEQ ID NO 51
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: AGU90327.1 E6 Variant

<400> SEQUENCE: 51

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Lys Ile Ala Gly His Tyr Arg Gly Gln Cys His Ser Cys Cys Asn Gln
    130                 135                 140

Ala Arg Gln Glu Arg Leu Gln Arg Arg Glu Thr Gln Val
145                 150                 155

<210> SEQ ID NO 52
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ADC35660.1 E6 Variant

<400> SEQUENCE: 52

Met Ala Arg Phe Glu Asp Pro Thr Arg Arg Pro Tyr Lys Val Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

```
Cys His Lys Cys Ile Asp Phe Tyr Ser Arg Ile Arg Glu Leu Arg His
 65                  70                  75                  80

Tyr Ser Asp Ser Val Tyr Gly Asp Thr Leu Glu Lys Leu Thr Asn Thr
                 85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
        130                 135                 140

Ala Arg Gln Glu Arg Leu Gln Arg Arg Glu Thr Gln Val
145                 150                 155
```

<210> SEQ ID NO 53
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: AHZ96677.1 E6 Variant

<400> SEQUENCE: 53

```
Met Ala Arg Phe Glu Asp Pro Thr Arg Arg Pro Tyr Lys Leu Pro Asp
 1               5                  10                  15

Leu Cys Thr Glu Leu Asn Thr Ser Leu Gln Asp Ile Glu Ile Thr Cys
                 20                  25                  30

Val Tyr Cys Lys Thr Val Leu Glu Leu Thr Glu Val Phe Glu Phe Ala
             35                  40                  45

Phe Lys Asp Leu Phe Val Val Tyr Arg Asp Ser Ile Pro His Ala Ala
         50                  55                  60

Cys His Lys Cys Ile Asp Phe Tyr Ser Arg Ile Arg Glu Leu Arg His
 65                  70                  75                  80

Tyr Ser Asp Ser Val Tyr Gly Asp Thr Leu Glu Lys Leu Thr Asn Thr
                 85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
        130                 135                 140

Ala Arg Gln Glu Arg Leu Gln Arg His Arg Glu Thr Gln Val
145                 150                 155
```

<210> SEQ ID NO 54
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ABP99736.1 E6 Variant

<400> SEQUENCE: 54

```
Met Ala Arg Phe Glu Asp Pro Thr Arg Arg Pro Tyr Lys Leu Pro Asp
 1               5                  10                  15

Leu Cys Thr Glu Leu Asn Thr Ser Leu Gln Asp Ile Glu Ile Thr Cys
                 20                  25                  30

Val Tyr Cys Lys Thr Val Leu Glu Leu Thr Gly Val Phe Glu Phe Ala
             35                  40                  45
```

```
Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
            130                 135                 140

Ala Arg Gln Glu Arg Leu Gln Arg Arg Arg Glu Thr Gln Val
145                 150                 155
```

<210> SEQ ID NO 55
<211> LENGTH: 158
<212> TYPE: PRT
<213> ORGANISM: Human papillomavirus 18
<220> FEATURE:
<221> NAME/KEY: MISC_FEATURE
<223> OTHER INFORMATION: ABP99704.1 E6 Variant

<400> SEQUENCE: 55

```
Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Asn Ile Ala Gly Arg Tyr Arg Gly Gln Cys His Ser Cys Cys Asn Arg
            130                 135                 140

Ala Arg Gln Glu Arg Leu Gln Arg Arg Arg Glu Thr Gln Val
145                 150                 155
```

<210> SEQ ID NO 56
<211> LENGTH: 90
<212> TYPE: PRT
<213> ORGANISM: Human papillomavirus 16
<220> FEATURE:
<221> NAME/KEY: MISC_FEATURE
<223> OTHER INFORMATION: ABL96587.1 E7 Variant

<400> SEQUENCE: 56

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
            20                  25                  30
```

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
     50                  55                  60

Leu Arg Leu Cys Val Arg Ser Thr His Val Asp Ile Arg Thr Leu Glu
 65                  70                  75                  80

Asp Leu Leu Met Gly Thr Leu Gly Ile Val
                 85                  90

<210> SEQ ID NO 57
<211> LENGTH: 90
<212> TYPE: PRT
<213> ORGANISM: Human papillomavirus 16
<220> FEATURE:
<221> NAME/KEY: MISC_FEATURE
<223> OTHER INFORMATION: ABL96591.1 E7 Variant

<400> SEQUENCE: 57

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Ser Asp Ser Ser
                 20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
     50                  55                  60

Leu Arg Leu Cys Val Gln Ser Thr His Val Asp Ile Cys Thr Leu Glu
 65                  70                  75                  80

Asp Leu Leu Met Gly Thr Leu Gly Ile Val
                 85                  90

<210> SEQ ID NO 58
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19726.1 E7 Variant

<400> SEQUENCE: 58

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                 20                  25                  30

Val Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
     50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro
                 85                  90

<210> SEQ ID NO 59
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19722.1 E7 Variant

<400> SEQUENCE: 59

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Val Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 60
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19752.1 E7 Variant

<400> SEQUENCE: 60

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Thr Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 61
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19732.1 E7 Variant

<400> SEQUENCE: 61

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Lys Asp Ser Ser
            20                  25                  30

Glu Glu Glu Asp Glu Val Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 62
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19762.1 E7 Variant

<400> SEQUENCE: 62

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Arg Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 63
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19668.1 E7 Variant

<400> SEQUENCE: 63

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Met Leu Glu
65                  70                  75                  80

Asp Leu Leu Met Gly Thr Leu Gly Ile Val Cys Pro
                85                  90

<210> SEQ ID NO 64
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19664.1 E7 Variant

<400> SEQUENCE: 64

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr

```
Leu Arg Leu Cys Val Gln Ser Thr His Val Asp Ile Arg Thr Leu Glu
65                  70                  75                  80

Asp Leu Leu Met Ser Thr Leu Gly Ile Val Cys Pro
                85                  90
```

<210> SEQ ID NO 65
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19766.1 E7 Variant

<400> SEQUENCE: 65

```
Met His Gly Asp Thr Pro Thr Leu His Glu Tyr Met Leu Asp Leu Gln
1               5                   10                  15

Pro Glu Thr Asn Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Phe Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90
```

<210> SEQ ID NO 66
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19756.1 E7 Variant

<400> SEQUENCE: 66

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Lys Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Ile Gly Thr Leu Gly Ile Val Cys Pro
                85                  90
```

<210> SEQ ID NO 67
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19680.1 E7 Variant

<400> SEQUENCE: 67

```
Met His Gly Asp Thr Pro Thr Leu His Glu Tyr Lys Leu Asp Leu Gln
1               5                   10                  15
```

```
Pro Glu Thr Thr Asp Leu Tyr Cys Tyr Glu Gln Leu Asn Asp Ser Ser
            20                  25                  30

Glu Glu Glu Asp Glu Ile Asp Gly Pro Thr Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 68
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19772.1 E7 Variant

<400> SEQUENCE: 68

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Asp Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Asp Thr Leu Gly Ile Val Cys Pro
                85                  90

<210> SEQ ID NO 69
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19696.1 E7 Variant

<400> SEQUENCE: 69

Met His Gly Asp Thr Pro Thr Leu His Glu Tyr Lys Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Lys Gly Thr Leu Gly Ile Val Cys Pro
                85                  90

<210> SEQ ID NO 70
<211> LENGTH: 92
<212> TYPE: PRT
<213> ORGANISM: Human papillomavirus 16
```

```
<220> FEATURE:
<221> NAME/KEY: MISC_FEATURE
<223> OTHER INFORMATION: AFJ19690.1 E7 Variant

<400> SEQUENCE: 70

Met His Gly Asp Thr Pro Thr Leu His Glu Tyr Met Leu Val Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Gly Leu Leu Met Gly Thr Leu Gly Ile Val Cys Pro
                85                  90

<210> SEQ ID NO 71
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19712.1 E7 Variant

<400> SEQUENCE: 71

Met His Gly Asp Thr Pro Thr Leu His Glu Tyr Lys Leu Asp Leu Gln
1               5                   10                  15

Pro Glu Thr Thr Asp Leu His Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Ile Thr Phe Cys Cys Arg Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 72
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AGO04504.1 E7 Variant

<400> SEQUENCE: 72

Met His Gly Asp Thr Pro Thr Leu His Glu Tyr Met Leu Gly Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Met Cys Asp Ser Thr
    50                  55                  60

Leu Arg Leu Cys Val Gln Ser Thr His Val Asp Ile Arg Thr Leu Glu
65                  70                  75                  80
```

-continued

```
Asp Leu Leu Met Gly Ala Leu Gly Ile Val Cys Pro
                85                  90

<210> SEQ ID NO 73
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19770.1 E7 Variant

<400> SEQUENCE: 73

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Tyr Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Gln Thr Leu Glu
65                  70                  75                  80

Asp Leu Leu Met Gly Ala Leu Gly Ile Val Cys Pro
                85                  90

<210> SEQ ID NO 74
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19520.2 E7 Variant

<400> SEQUENCE: 74

Met His Gly Asp Thr Pro Thr Leu His Lys Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Tyr Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Ser Thr Leu Gly Ile Val Cys Pro
                85                  90

<210> SEQ ID NO 75
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19708.1 E7 Variant

<400> SEQUENCE: 75

Met His Gly Asp Thr Pro Lys Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Gln Ala Gly Gln Ala Lys Pro Asp
```

```
                35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
65                  70                  75                  80

Gly Leu Leu Met Gly Thr Leu Gly Ile Val Cys Pro
                85                  90

<210> SEQ ID NO 76
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19674.1 E7 Variant

<400> SEQUENCE: 76

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Asn Ser
                20                  25                  30

Glu Glu Asp His Glu Ile Asp Gly Pro Asp Gly Gln Ala Glu Pro Asp
            35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 77
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AGO04498.1 E7 Variant

<400> SEQUENCE: 77

Met His Gly Asp Thr Ser Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Asn Val Thr Phe Cys Cys Lys Cys Asp Ser Thr
 50                  55                  60

Leu Arg Leu Cys Val Gln Ser Thr Leu Val Asp Ile Arg Thr Leu Glu
65                  70                  75                  80

Asp Met Leu Met Gly Thr Leu Gly Ile Val Ser Pro
                85                  90

<210> SEQ ID NO 78
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AGO04496.1 E7 Variant

<400> SEQUENCE: 78
```

Met His Gly Asp Thr Pro Thr Leu His Glu Tyr Val Leu Gly Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Val
        35                  40                  45

Arg Ala His Tyr Asn Ile Val Thr Phe Cys Cys Lys Cys Asp Ser Thr
50                  55                  60

Leu Arg Phe Cys Val Gln Ser Thr Arg Leu Asp Ile Arg Thr Leu Glu
65                  70                  75                  80

Asp Leu Leu Met Gly Thr Leu Gly Ile Val Cys Pro
                85                  90

<210> SEQ ID NO 79
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19684.1 E7 Variant

<400> SEQUENCE: 79

Met His Gly Asp Thr Pro Thr Leu His Glu Tyr Lys Leu Asp Leu Gln
1               5                   10                  15

Pro Glu Thr Thr Asp Leu Tyr Cys Tyr Glu His Leu Asn Asp Ser Ser
            20                  25                  30

Glu Glu Glu Asp Glu Ile Asp Cys Pro Ala Gly Gln Ala Glu Pro Asp
        35                  40                  45

Arg Ala His Tyr Lys Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Ile Leu Gly Ile Val Cys Pro
                85                  90

<210> SEQ ID NO 80
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19678.1 E7 Variant

<400> SEQUENCE: 80

Met His Gly Asp Thr Pro Thr Leu His Glu Tyr Lys Leu Asp Leu Gln
1               5                   10                  15

Pro Glu Thr Thr Asp Leu Cys Cys Tyr Glu Gln Leu Asn Asp Ser Ser
            20                  25                  30

Glu Glu Glu Asp Glu Ile Asp Gly Pro Thr Gly Gln Ala Glu Pro Asp
        35                  40                  45

Arg Ala His Tyr Thr Ile Val Thr Phe Cys Cys Met Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 81

```
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19698.1 E7 Variant

<400> SEQUENCE: 81

Met His Gly Asp Thr Pro Thr Leu His Glu Tyr Lys Leu Asp Leu Gln
1               5                   10                  15

Pro Glu Thr Thr Asp Leu Tyr Cys Tyr Glu Gln Leu Asn His Ser Ser
            20                  25                  30

Glu Gly Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Pro Arg Leu Cys Val Gln Ser Thr His Val Asp Ile Arg Thr Leu Glu
65                  70                  75                  80

Asp Leu Leu Met Asp Thr Leu Gly Ile Val Cys Pro
                85                  90

<210> SEQ ID NO 82
<211> LENGTH: 92
<212> TYPE: PRT
<213> ORGANISM: Human papillomavirus 16
<220> FEATURE:
<221> NAME/KEY: MISC_FEATURE
<223> OTHER INFORMATION: AFJ19746.1 E7 Variant

<400> SEQUENCE: 82

Met His Gly Asp Thr Pro Thr Leu His Glu Tyr Lys Leu Asp Leu Gln
1               5                   10                  15

Pro Glu Thr Thr Asp Leu Tyr Cys Asp Glu Gln Leu Asn His Ser Ser
            20                  25                  30

Glu Gly Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Pro Arg Leu Cys Val Gln Ser Thr His Val Asp Ile Arg Thr Leu Glu
65                  70                  75                  80

Asp Leu Leu Met Gly Thr Leu Gly Ile Val Cys Pro
                85                  90

<210> SEQ ID NO 83
<211> LENGTH: 93
<212> TYPE: PRT
<213> ORGANISM: Human papillomavirus 16
<220> FEATURE:
<221> NAME/KEY: MISC_FEATURE
<223> OTHER INFORMATION: AAF13395.1 E7 Variant

<400> SEQUENCE: 83

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Phe Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60
```

```
Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile
                 85                  90
```

<210> SEQ ID NO 84
<211> LENGTH: 95
<212> TYPE: PRT
<213> ORGANISM: Human papillomavirus 16
<220> FEATURE:
<221> NAME/KEY: MISC_FEATURE
<223> OTHER INFORMATION: AFU06654.1 E7 Variant

<400> SEQUENCE: 84

```
Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                 20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
         50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser
                 85                  90                  95
```

<210> SEQ ID NO 85
<211> LENGTH: 95
<212> TYPE: PRT
<213> ORGANISM: Human papillomavirus 16
<220> FEATURE:
<221> NAME/KEY: MISC_FEATURE
<223> OTHER INFORMATION: AFU06650.1 E7 Variant

<400> SEQUENCE: 85

```
Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Phe Asn Asp Ser Ser
                 20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
         50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser
                 85                  90                  95
```

<210> SEQ ID NO 86
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: AAB70738.1 E7 Variant

<400> SEQUENCE: 86

```
Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Phe Asn Asp Ser Ser
```

```
                    20                  25                  30

Glu Glu Glu Asp Glu Ile Asp Gly Pro Ala Gly Gln Ala Glu Pro Asp
                35                  40                  45

Arg Ala His Tyr Asn Ile Val Thr Phe Cys Cys Lys Cys Asp Ser Thr
            50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 87
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ACN22555.1 E7 Variant

<400> SEQUENCE: 87

Met His Gly Asp Thr Pro Thr Leu His Glu Tyr Met Leu Asp Val Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
                35                  40                  45

Arg Ala His Tyr Asn Ile Val Thr Phe Cys Cys Lys Cys Asp Ser Thr
            50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 88
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ABK32510.1 E7 Variant

<400> SEQUENCE: 88

Met His Gly Asp Thr Pro Thr Leu His Glu Tyr Met Leu Asp Leu Gln
1               5                   10                  15

Pro Glu Thr Ser Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
                35                  40                  45

Arg Ala His Tyr Asn Ile Val Thr Phe Cys Cys Lys Cys Asp Ser Thr
            50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```

<210> SEQ ID NO 89
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ABC54573.1 E7 Variant

<400> SEQUENCE: 89

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Ala Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 90
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ACN22554.1 E7 Variant

<400> SEQUENCE: 90

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Arg Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 91
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ABK32511.1 E7 Variant

<400> SEQUENCE: 91

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Lys Pro Asp

```
                35                  40                  45
Arg Ala His Tyr Asn Ile Val Thr Phe Cys Cys Lys Cys Asp Ser Thr
 50                  55                  60

Leu Arg Leu Cys Val Gln Ser Thr His Val Asp Ile Ser Thr Leu Glu
 65                  70                  75                  80

Asp Leu Leu Met Gly Thr Leu Gly Ile Val Cys Pro Ile Cys Ser Gln
                85                  90                  95

Lys Pro

<210> SEQ ID NO 92
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ACQ90216.1 E7 Variant

<400> SEQUENCE: 92

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Arg Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                85                  90                  95

Lys Pro

<210> SEQ ID NO 93
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: ADY75576.1 E7 Variant

<400> SEQUENCE: 93

Met His Gly Asp Thr Pro Thr Leu His Glu Tyr Met Leu Asp Leu Gln
 1               5                  10                  15

Pro Glu Thr Asn Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Phe Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                85                  90                  95

Lys Pro

<210> SEQ ID NO 94
<211> LENGTH: 98
<212> TYPE: PRT
```

<213> ORGANISM: Human papillomavirus 16
<220> FEATURE:
<221> NAME/KEY: MISC_FEATURE
<223> OTHER INFORMATION: AAM03025.1 E7 Variant

<400> SEQUENCE: 94

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Cys Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 95
<211> LENGTH: 98
<212> TYPE: PRT
<213> ORGANISM: Human papillomavirus 16
<220> FEATURE:
<221> NAME/KEY: MISC_FEATURE
<223> OTHER INFORMATION: AAL96634.1 E7 Variant

<400> SEQUENCE: 95

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Ser Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Trp Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 96
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: ABP99785.1 E7 Variant

<400> SEQUENCE: 96

Met Tyr Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met

```
                 50                  55                  60
Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Ser Thr Leu Ser Phe
                 85                  90                  95

Val Cys Pro Trp Cys Ala Ser Gln Gln
                100                 105
```

<210> SEQ ID NO 97
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: AGU90416.1 E7 Variant

<400> SEQUENCE: 97

```
Met Tyr Gly Pro Lys Ala Thr Leu Gln Asp Ile Val Leu His Leu Glu
 1               5                  10                  15

Pro Gln Asn Glu Ile Pro Val Asp Leu Leu Cys His Glu Gln Leu Ser
                 20                  25                  30

Asp Ser Glu Glu Glu Asn Asp Glu Ile Asp Gly Val Asn His Gln His
                 35                  40                  45

Leu Pro Ala Arg Arg Ala Glu Pro Gln Arg His Thr Met Leu Cys Met
                 50                  55                  60

Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Asn Thr Leu Ser Phe
                 85                  90                  95

Val Cys Pro Trp Cys Ala Ser Gln Gln
                100                 105
```

<210> SEQ ID NO 98
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: AGU90384.1 E7 Variant

<400> SEQUENCE: 98

```
Met Tyr Gly Pro Lys Ala Thr Leu Gln Asp Ile Val Leu His Leu Glu
 1               5                  10                  15

Pro Gln Asn Asp Ile Pro Val Asp Leu Leu Cys His Glu Gln Leu Ser
                 20                  25                  30

Asp Ser Glu Glu Glu Asn Asp Glu Ile Asp Gly Val Asn His Gln His
                 35                  40                  45

Leu Pro Ala Arg Arg Ala Glu Pro Gln Arg His Thr Met Leu Cys Met
                 50                  55                  60

Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Ser Thr Leu Ser Phe
                 85                  90                  95

Val Cys Pro Trp Cys Ala Ser Gln Gln
                100                 105
```

<210> SEQ ID NO 99
<211> LENGTH: 105
<212> TYPE: PRT

<213> ORGANISM: Human papillomavirus 18
<220> FEATURE:
<221> NAME/KEY: MISC_FEATURE
<223> OTHER INFORMATION: CAB53097.1 E7 Variant

<400> SEQUENCE: 99

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Lys Thr Leu Ser Phe
                85                  90                  95

Val Cys Pro Trp Cys Ala Ser Gln Gln
            100                 105

<210> SEQ ID NO 100
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: P06788.2 E7 Variant

<400> SEQUENCE: 100

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 101
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: CAB53098.1 E7 Variant

<400> SEQUENCE: 101

Met His Gly Pro Lys Ala Thr Leu Gln Asn Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

```
Leu Pro Ala Arg Arg Ala Glu Pro Gln Arg His Thr Met Leu Cys Met
        50                  55                  60

Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Lys Thr Leu Ser Phe
                85                  90                  95

Val Cys Pro Trp Cys Ala Ser Gln Gln
            100                 105

<210> SEQ ID NO 102
<211> LENGTH: 105
<212> TYPE: PRT
<213> ORGANISM: Human papillomavirus 18
<220> FEATURE:
<221> NAME/KEY: MISC_FEATURE
<223> OTHER INFORMATION: CAB53099.1 E7 Variant

<400> SEQUENCE: 102

Met His Gly Pro Lys Ala Thr Leu Gln Asp Ile Val Leu His Leu Glu
 1               5                  10                  15

Pro Gln Asn Glu Ile Pro Val Gly Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
        50                  55                  60

Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Lys Thr Leu Ser Phe
                85                  90                  95

Val Cys Pro Trp Cys Ala Ser Gln Gln
            100                 105

<210> SEQ ID NO 103
<211> LENGTH: 145
<212> TYPE: PRT
<213> ORGANISM: Human papillomavirus 18
<220> FEATURE:
<221> NAME/KEY: MISC_FEATURE
<223> OTHER INFORMATION: AGM34425.1 E6 Variant

<400> SEQUENCE: 103

Leu Pro Asp Leu Cys Thr Glu Leu Asn Thr Ser Leu Gln Asp Ile Glu
 1               5                  10                  15

Ile Thr Cys Val Tyr Cys Lys Thr Val Leu Glu Leu Thr Glu Val Phe
                20                  25                  30

Glu Phe Ala Phe Lys Asp Leu Phe Val Val Tyr Arg Asp Ser Ile Pro
            35                  40                  45

His Ala Ala Cys His Lys Cys Ile Asp Phe Tyr Ser Arg Ile Arg Glu
        50                  55                  60

Leu Arg Tyr Tyr Ser Asp Ser Val Tyr Gly Asp Thr Leu Glu Lys Leu
 65                  70                  75                  80

Thr Asn Thr Gly Leu Tyr Asn Leu Leu Ile Arg Cys Leu Arg Cys Gln
                85                  90                  95

Lys Pro Leu Asn Pro Ala Glu Lys Leu Arg His Leu Asn Glu Lys Arg
            100                 105                 110

Arg Phe His Lys Ile Ala Gly His Tyr Arg Gly Gln Cys His Ser Cys
        115                 120                 125
```

-continued

```
Cys Asn Arg Ala Arg Gln Glu Arg Leu Gln Arg Arg Glu Thr Gln
        130                 135                 140
Val
145

<210> SEQ ID NO 104
<211> LENGTH: 145
<212> TYPE: PRT
<213> ORGANISM: Human papillomavirus 18
<220> FEATURE:
<221> NAME/KEY: MISC_FEATURE
<223> OTHER INFORMATION: AGM34424.1 E6 Variant

<400> SEQUENCE: 104

Leu Pro Asp Leu Cys Thr Glu Leu Asn Thr Ser Leu Gln Asp Ile Glu
1               5                   10                  15

Ile Thr Cys Val Tyr Cys Lys Thr Val Leu Glu Leu Thr Glu Val Phe
            20                  25                  30

Glu Phe Ala Phe Lys Asp Leu Phe Val Val Tyr Arg Asp Ser Ile Pro
        35                  40                  45

His Ala Ala Cys His Lys Cys Ile Asp Phe Tyr Ser Arg Ile Arg Glu
    50                  55                  60

Leu Arg His Tyr Ser Asp Ser Val Tyr Gly Asp Thr Leu Glu Lys Leu
65                  70                  75                  80

Thr Asn Thr Gly Leu Tyr Asn Leu Leu Ile Arg Cys Leu Arg Cys Gln
                85                  90                  95

Lys Pro Leu Asn Pro Ala Glu Lys Leu Arg His Leu Asn Glu Lys Arg
            100                 105                 110

Arg Phe His Asn Ile Ala Gly His Tyr Arg Gly Gln Cys His Ser Cys
        115                 120                 125

Cys Asn Arg Ala Arg Gln Glu Arg Leu Gln Arg Arg Glu Thr Gln
    130                 135                 140
Val
145

<210> SEQ ID NO 105
<211> LENGTH: 6085
<212> TYPE: DNA
<213> ORGANISM: Artificial Sequence
<220> FEATURE:
<223> OTHER INFORMATION: C-1 mutant
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2186)
<223> OTHER INFORMATION: 16E6N (H21Q)
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2187)..(2381)
<223> OTHER INFORMATION: 16E7N
<220> FEATURE:
<221> NAME/KEY: misc_feature
<222> LOCATION: (2382)..(2645)
<223> OTHER INFORMATION: 16E6C (Y85H, V90L)
```

```
<220> FEATURE:
<221> NAME/KEY: misc_feature
<222> LOCATION: (2646)..(2789)
<223> OTHER INFORMATION: 16E7C
<220> FEATURE:
<221> NAME/KEY: misc_feature
<222> LOCATION: (2790)..(3671)
<223> OTHER INFORMATION: 18E6/E7

<400> SEQUENCE: 105
```

| | | | | | |
|---|---|---|---|---|---|
| taccgatgta | cgggccagat | atacgcgttg | acattgatta | ttgactagtt | attaatagta | 60 |
| atcaattacg | gggtcattag | ttcatagccc | atatatggag | ttccgcgtta | cataacttac | 120 |
| ggtaaatggc | ccgcctggct | gaccgcccaa | cgacccccgc | ccattgacgt | caataatgac | 180 |
| gtatgttccc | atagtaacgc | caatagggac | tttccattga | cgtcaatggg | tggagtattt | 240 |
| acggtaaact | gcccacttgg | cagtacatca | agtgtatcat | atgccaagta | cgccccctat | 300 |
| tgacgtcaat | gacggtaaat | ggcccgcctg | gcattatgcc | cagtacatga | ccttatggga | 360 |
| ctttcctact | tggcagtaca | tctacgtatt | agtcatcgct | attaccatgg | tgatgcggtt | 420 |
| ttggcagtac | atcaatgggc | gtggatagcg | gtttgactca | cggggatttc | caagtctcca | 480 |
| ccccattgac | gtcaatggga | gtttgttttg | gcaccaaaat | caacgggact | ttccaaaatg | 540 |
| tcgtaacaac | tccgccccat | tgacgcaaat | gggcggtagg | cgtgtacggt | gggaggtcta | 600 |
| tataagcaga | gctctctggc | taactagaga | acccactgct | tactggctta | tcgaaattaa | 660 |
| tacgactcac | tatagggaga | cccaagctgg | ctagcgtgag | tttggggacc | cttgattgtt | 720 |
| ctttcttttt | cgctattgta | aaattcatgt | tatatggagg | gggcaaagtt | ttcagggtgt | 780 |
| tgtttagaac | gggaagatgt | cccttgtatc | accatggacc | ctcatgataa | ttttgtttct | 840 |
| ttcactttct | actctgttga | caaccattgt | ctcctcttat | tttcttttca | ttttctgtaa | 900 |
| cttttttcgtt | aaactttagc | ttgcatttgt | aacgaatttt | taaattcact | tttgtttatt | 960 |
| tgtcagattg | taagtacttt | ctctaatcac | ttttttttca | aggcaatcag | ggtatattat | 1020 |
| attgtacttc | agcacagttt | tagagaacaa | ttgttataat | taaatgataa | ggtagaatat | 1080 |
| ttctgcatat | aaattctggc | tggcgtggaa | atattcttat | tggtagaaac | aactacatcc | 1140 |
| tggtcatcat | cctgcctttc | tctttatggt | tacaatgata | tacactgttt | gagatgagga | 1200 |
| taaaatactc | tgagtccaaa | ccgggcccct | ctgctaacca | tgttcatgcc | ttcttctttt | 1260 |
| tcctacagct | cctgggcaac | gtgctggtta | ttgtgctgtc | tcatcatttt | ggcaaagaat | 1320 |
| tgtaatacga | ctcactatag | ggcgaattga | agcttggtac | cgccaccatg | gatgctatga | 1380 |
| aacgggcct | gtgctgcgtg | ctgctcctgt | gcggcgctgt | gtttgtgagc | cctagcatca | 1440 |
| cccaggactg | ctccttccaa | cacagcccca | tctcctccga | cttcgctgtc | aaaatccgtg | 1500 |
| agctgtctga | ctacctgctt | caagattacc | cagtcaccgt | ggcctccaac | ctgcaggacg | 1560 |
| aggagctctg | cggggcctc | tggcggctgg | tcctggcaca | gcgctggatg | gagcggctca | 1620 |
| agactgtcgc | tggtccaag | atgcaaggct | gctggagcg | cgtgaacacg | gagatacact | 1680 |
| ttgtcaccaa | atgtgccttt | cagccccccc | ccagctgtct | tcgcttcgtc | cagaccaaca | 1740 |
| tctcccgcct | cctgcaggag | acctccgagc | agctggtggc | gctgaagccc | tggatcactc | 1800 |
| gccagaactt | ctcccggtgc | ctggagctgc | agtgtcagcc | cgactcctca | accctgccac | 1860 |
| ccccatggag | tccccggccc | ctggaggcca | cagccccgac | agccccgggc | ggcggcagcg | 1920 |
| gcgatgctag | catgcaccag | aagagaaccg | ccatgttcca | ggaccctcag | gagagaccta | 1980 |
| ggaagctgcc | tcagctgtgt | acagagctcc | agacaaccat | ccacgacatc | atcctggagt | 2040 |

```
gcgtgtactg taagcagcag ctgctgagaa gagaggtgta cgacttcgcc ttcagagacc    2100
tgtgcatcgt gtacagagac ggcaacccct acgccgtgtg cgataagtgt ctgaagttct    2160
attccaaaat ctccgaatat aggtacatgc acggcgacac ccctacgctg cacgagtaca    2220
tgctggacct ccagcctgag accacagacc tgtactgcta cgagcagctg aacgacagct    2280
ctgaggaaga ggacgagatt gacggacctg ctggccaggc cgagcctgac agagcccact    2340
acaatatcgt gacattctgt tgcaaatgcg actccacact ggacaagtgc ctgaagttct    2400
acagcaagat ctctgagtac agacactact gctactctct gtacggcacc acactggagc    2460
agcagtacaa caagcctctg tgcgacctcc tgatccgctg catcaactgc cagaagcctc    2520
tgtgccctga ggagaagcag agacacctgg acaagaagca gcggttccac aacatcagag    2580
gcagatggac cggcaggtgc atgtcctgct gtagatcctc cagaaccaga cgggagaccc    2640
agctgcacta caacatcgtg accttctgct gcaagtgcga ctctaccctg agactgtgcg    2700
tgcagtctac ccacgtggac atcagaaccc tggaggacct gctgatgggc acctgggca    2760
tcgtgtgccc tatctgctct cagaagccta tggccaggtt cgaggaccct accagaagac    2820
cctacaagct gcctgacctg tgcaccgagc tgaacacctc tctgcaagac atcgagatca    2880
cctgcgtgta ctgcaagacc gtgctggagc tgaccgaggt gttcgagttc gccttcaagg    2940
acctgttcgt ggtgtacaga gacagcatcc tcacgctgc ctgccacaag tgcatcgact    3000
tctattccag gatcagggag ctgcgctatt actccgactc tgtgatgtac ggccccaagg    3060
ccacccctcc aggacatcgtg ctgcacctgg agcctcagaa cgagatcccc gtggacctgc    3120
tgtgccacga gcagctgtct gactctgaag aggagaacga cgagatcgac ggcgtgaacc    3180
accagcacct gcctgccagg agagctgaac cccagcggca taccatgctg tgtatgtgct    3240
tctactctag gatcagagag ctgaggtact actctgactc tgtgtacggc gacaccctgg    3300
agaagctgac caacaccggc ctgtacaacc tgctgatccg gtgcctgagg tgccagaagc    3360
ctctgaaccc tgccgagaag ctgagacacc tgaacgagaa gaagattc cacaagatcg    3420
ctggccacta cagaggccag tgccactctt gctgcaacag agccagacag gagagactcc    3480
agcggagaag ggagacccag gtggccagaa gagccgagcc tcagagacac accatgctgt    3540
gcatgtgctg caagtgcgag gccagaatcg agctggtggt ggagagctct gccgacgacc    3600
tgagagcctt ccagcagctg ttcctgtcta ccctgagctt cgtgtgccct tggtgcgcct    3660
ctcagcagta atctagagtc ggggcggccg ccgcttcga gcagacatga taagatacat    3720
tgatgagttt ggacaaacca caactagaat gcagtgaaaa aaatgcttta tttgtgaaat    3780
ttgtgatgct attgctttat ttgtaaccat tataagctgc aataaacaag ttaacaacaa    3840
caattgcatt catttatgt tcaggttca ggggaggtg tgggaggttt tttaaagcaa    3900
gtaaacctc tacaaatgtg gtaaaatcga taaggatctg aacgatggag cggagaatgg    3960
gcggaactgg gcggagttag gggcgggatg ggcggagtta ggggcgggac tatggttgct    4020
gactaattga gatgcatgct ttgcatactt ctgcctgctg gggagcctgg ggactttcca    4080
cacctggttg ctgactaatt gagatgcatg ctttgcatac ttctgcctgc tggggagcct    4140
ggggactttc cacacccta ctgacacaca ttccacagcg gatccgtcga cttcagaaga    4200
actcgtcaag aaggcgatag aaggcgatgc gccgcgaatc gggagcggcg ataccgtaga    4260
gcacgaggaa gcggtcagcc cattcgccgc caagctcttc agcaatatca cgggtagcca    4320
acgctatgtc ctgatagcgg tccgccacac ccagccggcc acagtcgatg aatccagaaa    4380
agcggccatt ttccaccatg atattcggca agcaggcatc gccatgggtc acgacgagat    4440
```

-continued

```
cctcgccgtc gggcatgctc gccttgagcc tggcgaacag ttcggctggc gcgagcccct    4500
gatgctcttc gtccagatca tcctgatcga caagaccggc ttccatccga gtacgtgctc    4560
gctcgatgcg atgtttcgct tggtggtcga atgggcaggt agccggatca agcgtatgca    4620
gccgccgcat tgcatcagcc atgatggata ctttctcggc aggagcaagg tgagatgaca    4680
ggagatcctg ccccggcact tcgcccaata gcagccagtc ccttcccgct tcagtgacaa    4740
cgtcgagcac agctgcgcaa ggaacgcccg tcgtggccag ccacgatagc cgcgctgcct    4800
cgtcttgcag ttcattcagg gcaccggaca ggtcggtctt gacaaaaaga accgggcgcc    4860
cctgcgctga cagccggaac acggcggcat cagagcagcc gattgtctgt tgtgcccagt    4920
catagccgaa tagcctctcc acccaagcgg ccggagaacc tgcgtgcaat ccatcttgtt    4980
caatcatgcg aaacgatcct catcctgtct cttgatcaga tcttgatccc ctgcgccatc    5040
agatccttgg cggcaagaaa gccatccagt ttactttgca gggcttccca accttaccag    5100
agggcgcccc agctggcaat tccggttcgc ttgctgtcca taaaaccgcc cagtctagct    5160
atcgccatgt aagcccactg caagctacct gctttctctt tgcgcttgcg ttttcccttg    5220
tccagatagc ccagtagctg acattcatcc ggggtcagca ccgtttctgc ggactggctt    5280
tctacgtgaa aaggatctag gtgaagatcc ttttgataa  tctcatgacc aaaatccctt    5340
aacgtgagtt tcgttccac  tgagcgtcag accccgtaga aaagatcaaa ggatcttctt    5400
gagatccttt ttttctgcgc gtaatctgct gcttgcaaac aaaaaaacca ccgctaccag    5460
cggtggtttg tttgccggat caagagctac caactctttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagataccta cagcgtgagc tatgagaaag cgccacgctt cccgaaggga    5820
gaaaggcgga caggtatccg gtaagcggca gggtcggaac aggagagcgc acagggagc    5880
ttccaggggg aaacgcccgg tatctttata gtcctgtcgg gtttcgccac ctctgacttg    5940
agcgtcgatt tttgtgatgc tcgtcagggg ggcggagcct atggaaaaac gccagcaacg    6000
cggccttttt acgttcctg  gccttttgct ggccttttgc tcacatgttc gggcccaatc    6060
gacccgggcg acggccagtg aattg                                          6085
```

<210> SEQ ID NO 106
<211> LENGTH: 767
<212> TYPE: PRT
<213> ORGANISM: Artificial Sequence
<220> FEATURE:
<223> OTHER INFORMATION: C-1

<400> SEQUENCE: 106

```
Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60
```

```
Glu Glu Leu Cys Gly Gly Leu Trp Arg Leu Val Leu Ala Gln Arg Trp
 65                  70                  75                  80

Met Glu Arg Leu Lys Thr Val Ala Gly Ser Lys Met Gln Gly Leu Leu
                 85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Gly Ser Gly Asp Ala Ser Met His Gln Lys
                180                 185                 190

Arg Thr Ala Met Phe Gln Asp Pro Gln Glu Arg Pro Arg Lys Leu Pro
            195                 200                 205

Gln Leu Cys Thr Glu Leu Gln Thr Thr Ile His Asp Ile Ile Leu Glu
    210                 215                 220

Cys Val Tyr Cys Lys Gln Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
                245                 250                 255

Val Cys Asp Lys Cys Leu Lys Phe Tyr Ser Lys Ile Ser Glu Tyr Arg
                260                 265                 270

Tyr Met His Gly Asp Thr Pro Thr Leu His Glu Tyr Met Leu Asp Leu
            275                 280                 285

Gln Pro Glu Thr Thr Asp Leu Tyr Cys Tyr Glu Gln Leu Asn Asp Ser
    290                 295                 300

Ser Glu Glu Glu Asp Glu Ile Asp Gly Pro Ala Gly Gln Ala Glu Pro
305                 310                 315                 320

Asp Arg Ala His Tyr Asn Ile Val Thr Phe Cys Cys Lys Cys Asp Ser
                325                 330                 335

Thr Leu Asp Lys Cys Leu Lys Phe Tyr Ser Lys Ile Ser Glu Tyr Arg
                340                 345                 350

His Tyr Cys Tyr Ser Leu Tyr Gly Thr Thr Leu Glu Gln Gln Tyr Asn
            355                 360                 365

Lys Pro Leu Cys Asp Leu Leu Ile Arg Cys Ile Asn Cys Gln Lys Pro
    370                 375                 380

Leu Cys Pro Glu Glu Lys Gln Arg His Leu Asp Lys Lys Gln Arg Phe
385                 390                 395                 400

His Asn Ile Arg Gly Arg Trp Thr Gly Arg Cys Met Ser Cys Cys Arg
                405                 410                 415

Ser Ser Arg Thr Arg Arg Glu Thr Gln Leu His Tyr Asn Ile Val Thr
                420                 425                 430

Phe Cys Cys Lys Cys Asp Ser Thr Leu Arg Leu Cys Val Gln Ser Thr
            435                 440                 445

His Val Asp Ile Arg Thr Leu Glu Asp Leu Leu Met Gly Thr Leu Gly
    450                 455                 460

Ile Val Cys Pro Ile Cys Ser Gln Lys Pro Met Ala Arg Phe Glu Asp
465                 470                 475                 480

Pro Thr Arg Arg Pro Tyr Lys Leu Pro Asp Leu Cys Thr Glu Leu Asn
```

485                 490                 495
Thr Ser Leu Gln Asp Ile Glu Ile Thr Cys Val Tyr Cys Lys Thr Val
            500                 505                 510

Leu Glu Leu Thr Glu Val Phe Glu Phe Ala Phe Lys Asp Leu Phe Val
        515                 520                 525

Val Tyr Arg Asp Ser Ile Pro His Ala Ala Cys His Lys Cys Ile Asp
    530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
            565                 570                 575

Gln Asn Glu Ile Pro Val Asp Leu Leu Cys His Glu Gln Leu Ser Asp
        580                 585                 590

Ser Glu Glu Glu Asn Asp Glu Ile Asp Gly Val Asn His Gln His Leu
    595                 600                 605

Pro Ala Arg Arg Ala Glu Pro Gln Arg His Thr Met Leu Cys Met Cys
610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
            645                 650                 655

Ile Arg Cys Leu Arg Cys Gln Lys Pro Leu Asn Pro Ala Glu Lys Leu
        660                 665                 670

Arg His Leu Asn Glu Lys Arg Arg Phe His Lys Ile Ala Gly His Tyr
    675                 680                 685

Arg Gly Gln Cys His Ser Cys Cys Asn Arg Ala Arg Gln Glu Arg Leu
690                 695                 700

Gln Arg Arg Arg Glu Thr Gln Val Ala Arg Ala Glu Pro Gln Arg
705                 710                 715                 720

His Thr Met Leu Cys Met Cys Cys Lys Cys Glu Ala Arg Ile Glu Leu
            725                 730                 735

Val Val Glu Ser Ser Ala Asp Asp Leu Arg Ala Phe Gln Gln Leu Phe
        740                 745                 750

Leu Ser Thr Leu Ser Phe Val Cys Pro Trp Cys Ala Ser Gln Gln
    755                 760                 765

<210> SEQ ID NO 107
<211> LENGTH: 6085
<212> TYPE: DNA
<213> ORGANISM: Artificial Sequence
<220> FEATURE:
<223> OTHER INFORMATION: C-2 mutant
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2186)
<223> OTHER INFORMATION: 16E6N
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2187)..(2381)

```
<223> OTHER INFORMATION: 16E7N (M12K, N29S)
<220> FEATURE:
<221> NAME/KEY: misc_feature
<222> LOCATION: (2382)..(2645)
<223> OTHER INFORMATION: 16E6C
<220> FEATURE:
<221> NAME/KEY: misc_feature
<222> LOCATION: (2646)..(2789)
<223> OTHER INFORMATION: 16E7C (R77S, G85S)
<220> FEATURE:
<221> NAME/KEY: misc_feature
<222> LOCATION: (2790)..(3671)
<223> OTHER INFORMATION: 18E6/E7

<400> SEQUENCE: 107
taccgatgta cgggccagat atacgcgttg acattgatta ttgactagtt attaatagta      60
atcaattacg gggtcattag ttcatagccc atatatggag ttccgcgtta cataacttac    120
ggtaaatggc ccgcctggct gaccgcccaa cgacccccgc ccattgacgt caataatgac    180
gtatgttccc atagtaacgc caatagggac tttccattga cgtcaatggg tggagtattt    240
acggtaaact gcccacttgg cagtacatca agtgtatcat atgccaagta cgccccctat    300
tgacgtcaat gacggtaaat ggcccgcctg gcattatgcc cagtacatga ccttatggga    360
ctttcctact tggcagtaca tctacgtatt agtcatcgct attaccatgg tgatgcggtt    420
ttggcagtac atcaatgggc gtggatagcg gtttgactca cggggatttc caagtctcca    480
ccccattgac gtcaatggga gtttgttttg gcaccaaaat caacgggact ttccaaaatg    540
tcgtaacaac tccgccccat tgacgcaaat gggcggtagg cgtgtacggt gggaggtcta    600
tataagcaga gctctctggc taactagaga acccactgct tactggctta tcgaaattaa    660
tacgactcac tatagggaga cccaagctgg ctagcgtgag tttggggacc cttgattgtt    720
cttttctttt cgctattgta aaattcatgt tatatggagg ggcaaagtt tcagggtgt      780 tgtttagaac gggaagatgt cccttgtatc accatggacc ctcatgataa ttttgtttct    840
ttcactttct actctgttga caaccattgt ctcctcttat tttcttttca ttttctgtaa    900 cttttttcgtt aaactttagc ttgcatttgt aacgaatttt taaattcact tttgtttatt    960
tgtcagattg taagtacttt ctctaatcac ttttttttca aggcaatcag ggtatattat   1020
attgtacttc agcacagttt tagagaacaa ttgttataat taaatgataa ggtagaatat   1080
ttctgcatat aaattctggc tggcgtggaa atattcttat tggtagaaac aactacatcc   1140
tggtcatcat cctgccttc tctttatggt tacaatgata tacactgttt gagatgagga   1200
taaaatactc tgagtccaaa ccgggcccct ctgctaacca tgttcatgcc ttcttctttt   1260
tcctacagct cctgggcaac gtgctggtta ttgtgctgtc tcatcatttt ggcaaagaat   1320
tgtaatacga ctcactatag gcgaattga agcttggtac cgccaccatg atgctatga    1380 acgggggcct gtgctgcgtg ctgctcctgt gcggcgctgt gtttgtgagc cctagcatca   1440
cccaggactg ctccttccaa cacagccccc tctcctccga cttcgctgtc aaaatccgtg   1500
agctgtctga ctacctgctt caagattacc cagtcaccgt ggcctccaac ctgcaggacg   1560
aggagctctg cggggccctc tggcggctgg tcctggcaca gcgctggatg gagcggctca   1620
agactgtcgc tggtccaag atgcaaggct tgctggagcg cgtgaacacg gagatacact   1680
ttgtcaccaa atgtgccttt cagccccccc ccagctgtct tcgcttcgtc cagaccaaca   1740
tctcccgcct cctgcaggag acctccgagc tggtggtggc gctgaagccc tggatcactc   1800
gccagaactt ctcccggtgc ctggagctgc agtgtcagcc cgactcctca accctgccac   1860
ccccatggag tccccggccc ctggaggcca cagccccgac agccccgggc ggcggcagcg   1920
```

```
gcgatgctag catgcaccag aagagaaccg ccatgttcca ggaccctcag gagagaccta    1980
ggaagctgcc tcacctgtgt acagagctcc agacaaccat ccacgacatc atcctggagt    2040
gcgtgtactg taagcagcag ctgctgagaa gagaggtgta cgacttcgcc ttcagagacc    2100
tgtgcatcgt gtacagagac ggcaacccct tacgccgtgtg cgataagtgt ctgaagttct    2160
attccaaaat ctccgaatat aggtacatgc acggcgacac ccctaccctg cacgagtaca    2220
agctggacct ccagcctgag accacagacc tgtactgcta cgagcagctg tctgacagct    2280
ctgaggaaga ggacgagatt gacggacctg ctggccaggc cgagcctgac agagcccact    2340
acaatatcgt gacattctgt tgcaaatgcg actccacact ggacaagtgc ctgaagttct    2400
acagcaagat ctctgagtac agatactact gctactctgt gtacggcacc acactggagc    2460
agcagtacaa caagcctctg tgcgacctcc tgatccgctg catcaactgc cagaagcctc    2520
tgtgccctga ggagaagcag agacacctgg acaagaagca gcggttccac aacatcagag    2580
gcagatggac cggcaggtgc atgtcctgct gtagatcctc cagaaccaga cgggagaccc    2640
agctgcacta caacatcgtg accttctgct gcaagtgcga ctctaccctg agactgtgcg    2700
tgcagtctac ccacgtggac atcctcaccc tggaggacct gctgatgctc acctgggca    2760
tcgtgtgccc tatctgctct cagaagccta tggccaggtt cgaggaccct accagaagac    2820
cctacaagct gcctgacctg tgcaccagc tgaacacctc tctgcaagac atcgagatca    2880
cctgcgtgta ctgcaagacc gtgctggagc tgaccgaggt gttcgagttc gccttcaagg    2940
acctgttcgt ggtgtacaga gacagcatcc ctcacgctgc ctgccacaag tgcatcgact    3000
tctattccag gatcagggag ctgcgctatt actccgactc tgtgatgtac ggccccaagg    3060
ccaccctcca ggacatcgtg ctgcacctgg agcctcagaa cgagatcccc gtggacctgc    3120
tgtgccacga gcagctgtct gactctgaag aggagaacga cgagatcgac ggcgtgaacc    3180
accagcacct gcctgccagg agagctgaac cccagcggca taccatgctg tgtatgtgct    3240
tctactctag gatcagagag ctgaggtact actctgactc tgtgtacggc gacaccctgg    3300
agaagctgac caacaccggc ctgtacaacc tgctgatccg gtgcctgagg tgccagaagc    3360
ctctgaaccc tgccgagaag ctgagacacc tgaacgagaa gagaagattc cacaagatcg    3420
ctggccacta cagaggccag tgccactctt gctgcaacag agccagacag gagagactcc    3480
agcggagaag ggagacccag gtggccagaa gagccgagcc tcagagacac accatgctgt    3540
gcatgtgctg caagtgcgag gccagaatcg agctggtggt ggagagctct gccgacgacc    3600
tgagagcctt ccagcagctg ttcctgtcta ccctgagctt cgtgtgccct tggtgcgcct    3660
ctcagcagta atctagagtc ggggcggccg gccgcttcga gcagacatga taagatacat    3720
tgatgagttt ggacaaacca caactagaat gcagtgaaaa aatgctttta tttgtgaaat    3780
ttgtgatgct attgctttat ttgtaaccat tataagctgc aataaacaag ttaacaacaa    3840
caattgcatt cattttatgt ttcaggttca ggggaggtg tgggaggttt tttaaagcaa    3900
gtaaacctc tacaaatgtg gtaaaatcga taaggatctg aacgatggag cggagaatgg    3960
gcggaactgg gcggagttag gggcgggatg gcggagtta ggggcgggac tatggttgct    4020
gactaattga gatgcatgct ttgcatactt ctgcctgctg gggagcctgg ggactttcca    4080
cacctggttg ctgactaatt gagatgcatg ctttgcatac ttctgcctgc tggggagcct    4140
ggggactttc cacacccta ctgacacaca ttccacagcg gatccgtcga cttcagaaga    4200
actcgtcaag aaggcgatag aaggcgatgc gccgcgaatc gggagcggcg ataccgtaga    4260
```

```
gcacgaggaa gcggtcagcc cattcgccgc caagctcttc agcaatatca cgggtagcca      4320
acgctatgtc ctgatagcgg tccgccacac ccagccggcc acagtcgatg aatccagaaa      4380
agcggccatt ttccaccatg atattcggca agcaggcatc gccatgggtc acgacgagat      4440
cctcgccgtc gggcatgctc gccttgagcc tggcgaacag ttcggctggc gcgagcccct      4500
gatgctcttc gtccagatca tcctgatcga caagaccggc ttccatccga gtacgtgctc      4560
gctcgatgcg atgtttcgct ggtggtcga atgggcaggt agccggatca agcgtatgca      4620
gccgccgcat tgcatcagcc atgatggata ctttctcggc aggagcaagg tgagatgaca      4680
ggagatcctg ccccggcact cgcccaata gcagccagtc ccttcccgct tcagtgacaa      4740
cgtcgagcac agctgcgcaa ggaacgcccg tcgtggccag ccacgatagc cgcgctgcct      4800
cgtcttgcag ttcattcagg gcaccggaca ggtcggtctt gacaaaaaga ccgggcgcc       4860 cctgcgctga cagccggaac acggcggcat cagagcagcc gattgtctgt tgtgcccagt      4920
catagccgaa tagcctctcc acccaagcgg ccggagaacc tgcgtgcaat ccatcttgtt      4980
caatcatgcg aaacgatcct catcctgtct cttgatcaga tcttgatccc ctgcgccatc      5040
agatccttgg cggcaagaaa gccatccagt ttactttgca gggcttccca accttaccag      5100
agggcgcccc agctggcaat tccggttcgc ttgctgtcca taaaaccgcc cagtctagct      5160
atcgccatgt aagcccactg caagctacct gctttctctt tgcgcttgcg ttttcccttg      5220
tccagatagc ccagtagctg acattcatcc ggggtcagca ccgttctgc ggactggctt       5280 tctacgtgaa aaggatctag gtgaagatcc ttttgataa tctcatgacc aaaatcccctt     5340 aacgtgagtt ttcgttccac tgagcgtcag accccgtaga aaagatcaaa ggatcttctt      5400
gagatccttt ttttctgcgc gtaatctgct gcttgcaaac aaaaaaacca ccgctaccag      5460
cggtggtttg tttgccggat caagagctac caactctttt tccgaaggta actggcttca      5520
gcagagcgca gataccaaat actgttcttc tagtgtagcc gtagttaggc caccacttca      5580
agaactctgt agcaccgcct acatacctcg ctctgctaat cctgttacca gtggctgctg      5640
ccagtggcga taagtcgtgt cttaccgggt tggactcaag acgatagtta ccggataagg      5700
cgcagcggtc gggctgaacg gggggttcgt gcacacagcc cagcttggag cgaacgacct      5760
acaccgaact gagataccta cagcgtgagc tatgagaaag cgccacgctt cccgaaggga      5820
gaaaggcgga caggtatccg gtaagcggca gggtcggaac aggagagcgc acgagggagc      5880
ttccaggggg aaacgcccgg tatctttata gtcctgtcgg gtttcgccac ctctgacttg      5940
agcgtcgatt tttgtgatgc tcgtcagggg ggcggagcct atggaaaaac gccagcaacg      6000
cggccttttt acggttcctg gccttttgct ggccttttgc tcacatgttc gggcccaatc      6060
gacccgggcg acggccagtg aattg                                            6085
```

<210> SEQ ID NO 108
<211> LENGTH: 767
<212> TYPE: PRT
<213> ORGANISM: Artificial Sequence
<220> FEATURE:
<223> OTHER INFORMATION: C-2

<400> SEQUENCE: 108

Met Asp Ala Met Lys Arg Gly Leu Cys Cys Val Leu Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp

-continued

```
            35                  40                  45
Tyr Leu Leu Gln Asp Tyr Pro Val Thr Val Ala Ser Asn Leu Gln Asp
 50                  55                  60
Glu Glu Leu Cys Gly Gly Leu Trp Arg Leu Val Leu Ala Gln Arg Trp
 65                  70                  75                  80
Met Glu Arg Leu Lys Thr Val Ala Gly Ser Lys Met Gln Gly Leu Leu
                 85                  90                  95
Glu Arg Val Asn Thr Glu Ile His Phe Val Thr Lys Cys Ala Phe Gln
                100                 105                 110
Pro Pro Pro Ser Cys Leu Arg Phe Val Gln Thr Asn Ile Ser Arg Leu
                115                 120                 125
Leu Gln Glu Thr Ser Glu Gln Leu Val Ala Leu Lys Pro Trp Ile Thr
            130                 135                 140
Arg Gln Asn Phe Ser Arg Cys Leu Glu Leu Gln Cys Gln Pro Asp Ser
145                 150                 155                 160
Ser Thr Leu Pro Pro Pro Trp Ser Pro Arg Pro Leu Glu Ala Thr Ala
                    165                 170                 175
Pro Thr Ala Pro Gly Gly Gly Ser Gly Asp Ala Ser Met His Gln Lys
                180                 185                 190
Arg Thr Ala Met Phe Gln Asp Pro Gln Glu Arg Pro Arg Lys Leu Pro
                195                 200                 205
His Leu Cys Thr Glu Leu Gln Thr Thr Ile His Asp Ile Ile Leu Glu
            210                 215                 220
Cys Val Tyr Cys Lys Gln Gln Leu Leu Arg Arg Glu Val Tyr Asp Phe
225                 230                 235                 240
Ala Phe Arg Asp Leu Cys Ile Val Tyr Arg Asp Gly Asn Pro Tyr Ala
                    245                 250                 255
Val Cys Asp Lys Cys Leu Lys Phe Tyr Ser Lys Ile Ser Glu Tyr Arg
                260                 265                 270
Tyr Met His Gly Asp Thr Pro Thr Leu His Glu Tyr Lys Leu Asp Leu
            275                 280                 285
Gln Pro Glu Thr Thr Asp Leu Tyr Cys Tyr Glu Gln Leu Ser Asp Ser
        290                 295                 300
Ser Glu Glu Glu Asp Glu Ile Asp Gly Pro Ala Gly Gln Ala Glu Pro
305                 310                 315                 320
Asp Arg Ala His Tyr Asn Ile Val Thr Phe Cys Cys Lys Cys Asp Ser
                325                 330                 335
Thr Leu Asp Lys Cys Leu Lys Phe Tyr Ser Lys Ile Ser Glu Tyr Arg
                340                 345                 350
Tyr Tyr Cys Tyr Ser Val Tyr Gly Thr Thr Leu Glu Gln Gln Tyr Asn
            355                 360                 365
Lys Pro Leu Cys Asp Leu Leu Ile Arg Cys Ile Asn Cys Gln Lys Pro
        370                 375                 380
Leu Cys Pro Glu Glu Lys Gln Arg His Leu Asp Lys Lys Gln Arg Phe
385                 390                 395                 400
His Asn Ile Arg Gly Arg Trp Thr Gly Arg Cys Met Ser Cys Cys Arg
                    405                 410                 415
Ser Ser Arg Thr Arg Arg Glu Thr Gln Leu His Tyr Asn Ile Val Thr
                420                 425                 430
Phe Cys Cys Lys Cys Asp Ser Thr Leu Arg Leu Cys Val Gln Ser Thr
            435                 440                 445
His Val Asp Ile Leu Thr Leu Glu Asp Leu Leu Met Leu Thr Leu Gly
        450                 455                 460
```

Ile Val Cys Pro Ile Cys Ser Gln Lys Pro Met Ala Arg Phe Glu Asp
465                 470                 475                 480

Pro Thr Arg Arg Pro Tyr Lys Leu Pro Asp Leu Cys Thr Glu Leu Asn
            485                 490                 495

Thr Ser Leu Gln Asp Ile Glu Ile Thr Cys Val Tyr Cys Lys Thr Val
        500                 505                 510

Leu Glu Leu Thr Glu Val Phe Glu Phe Ala Phe Lys Asp Leu Phe Val
            515                 520                 525

Val Tyr Arg Asp Ser Ile Pro His Ala Ala Cys His Lys Cys Ile Asp
        530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
            565                 570                 575

Gln Asn Glu Ile Pro Val Asp Leu Leu Cys His Glu Gln Leu Ser Asp
            580                 585                 590

Ser Glu Glu Glu Asn Asp Glu Ile Asp Gly Val Asn His Gln His Leu
            595                 600                 605

Pro Ala Arg Arg Ala Glu Pro Gln Arg His Thr Met Leu Cys Met Cys
            610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
            645                 650                 655

Ile Arg Cys Leu Arg Cys Gln Lys Pro Leu Asn Pro Ala Glu Lys Leu
            660                 665                 670

Arg His Leu Asn Glu Lys Arg Arg Phe His Lys Ile Ala Gly His Tyr
            675                 680                 685

Arg Gly Gln Cys His Ser Cys Cys Asn Arg Ala Arg Gln Glu Arg Leu
            690                 695                 700

Gln Arg Arg Arg Glu Thr Gln Val Ala Arg Arg Ala Glu Pro Gln Arg
705                 710                 715                 720

His Thr Met Leu Cys Met Cys Cys Lys Cys Glu Ala Arg Ile Glu Leu
            725                 730                 735

Val Val Glu Ser Ser Ala Asp Asp Leu Arg Ala Phe Gln Gln Leu Phe
            740                 745                 750

Leu Ser Thr Leu Ser Phe Val Cys Pro Trp Cys Ala Ser Gln Gln
            755                 760                 765

```
<210> SEQ ID NO 109
<211> LENGTH: 5995
<212> TYPE: DNA
<213> ORGANISM: Artificial Sequence
<220> FEATURE:
<223> OTHER INFORMATION: D-1 (overlapping-1)
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2165)
<223> OTHER INFORMATION: 16E6N (1-78aa)
<220> FEATURE:
<221> NAME/KEY: misc_feature
```

```
<222> LOCATION: (2166)..(2339)
<223> OTHER INFORMATION: 16E7N (1-58aa)
<220> FEATURE:
<221> NAME/KEY: misc_feature
<222> LOCATION: (2340)..(2579)
<223> OTHER INFORMATION: 16E6C (79-158aa)
<220> FEATURE:
<221> NAME/KEY: misc_feature
<222> LOCATION: (2580)..(2699)
<223> OTHER INFORMATION: 16E7C (59-98aa)
<220> FEATURE:
<221> NAME/KEY: misc_feature
<222> LOCATION: (2700)..(3581)
<223> OTHER INFORMATION: 18E6/E7

<400> SEQUENCE: 109
```

| | | | | | |
|---|---|---|---|---|---|
| taccgatgta | cgggccagat | atacgcgttg | acattgatta | ttgactagtt | attaatagta | 60 |
| atcaattacg | gggtcattag | ttcatagccc | atatatggag | ttccgcgtta | cataacttac | 120 |
| ggtaaatggc | ccgcctggct | gaccgcccaa | cgaccccgc | ccattgacgt | caataatgac | 180 |
| gtatgttccc | atagtaacgc | caatagggac | tttccattga | cgtcaatggg | tggagtattt | 240 |
| acggtaaact | gcccacttgg | cagtacatca | agtgtatcat | atgccaagta | cgccccctat | 300 |
| tgacgtcaat | gacggtaaat | ggcccgcctg | gcattatgcc | cagtacatga | ccttatggga | 360 |
| ctttcctact | tggcagtaca | tctacgtatt | agtcatcgct | attaccatgg | tgatgcggtt | 420 |
| ttggcagtac | atcaatgggc | gtggatagcg | gtttgactca | cggggatttc | caagtctcca | 480 |
| ccccattgac | gtcaatggga | gtttgttttg | gcaccaaaat | caacgggact | ttccaaaatg | 540 |
| tcgtaacaac | tccgccccat | tgacgcaaat | gggcggtagg | cgtgtacggt | gggaggtcta | 600 |
| tataagcaga | gctctctggc | taactagaga | acccactgct | tactggctta | tcgaaattaa | 660 |
| tacgactcac | tatagggaga | cccaagctgg | ctagcgtgag | tttggggacc | cttgattgtt | 720 |
| ctttcttttt | cgctattgta | aaattcatgt | tatatggagg | gggcaaagtt | ttcagggtgt | 780 |
| tgtttagaac | gggaagatgt | cccttgtatc | accatggacc | ctcatgataa | ttttgtttct | 840 |
| ttcactttct | actctgttga | caaccattgt | ctcctcttat | tttcttttca | ttttctgtaa | 900 |
| cttttcgtt | aaactttagc | ttgcatttgt | aacgaatttt | taaattcact | tttgtttatt | 960 |
| tgtcagattg | taagtacttt | ctctaatcac | ttttttttca | aggcaatcag | ggtatattat | 1020 |
| attgtacttc | agcacagttt | tagagaacaa | ttgttataat | taaatgataa | ggtagaatat | 1080 |
| ttctgcatat | aaattctggc | tggcgtggaa | atattcttat | tggtagaaac | aactacatcc | 1140 |
| tggtcatcat | cctgcctttc | tctttatggt | tacaatgata | tacactgttt | gagatgagga | 1200 |
| taaaatactc | tgagtccaaa | ccgggcccct | ctgctaacca | tgttcatgcc | ttcttctttt | 1260 |
| tcctacagct | cctgggcaac | gtgctggtta | ttgtgctgtc | tcatcatttt | ggcaaagaat | 1320 |
| tgtaatacga | ctcactatag | ggcgaattga | agcttggtac | cgccaccatg | gatgctatga | 1380 |
| aacggggcct | gtgctgcgtg | ctgctcctgt | gcggcgctgt | gtttgtgagc | cctagcatca | 1440 |
| cccaggactg | ctccttccaa | cacagcccca | tctcctccga | cttcgctgtc | aaaatccgtg | 1500 |
| agctgtctga | ctacctgctt | caagattacc | cagtcaccgt | ggcctccaac | ctgcaggacg | 1560 |
| aggagctctg | cggggcctc | tggcggctgg | tcctggcaca | gcgctggatg | gagcggctca | 1620 |
| agactgtcgc | tgggtccaag | atgcaaggct | tgctggagcg | cgtgaacacg | gagatacact | 1680 |
| tgtcaccaa | atgtgccttt | cagccccccc | ccagctgtct | tcgcttcgtc | cagaccaaca | 1740 |
| tctcccgcct | cctgcaggag | acctccgagc | agctggtggc | gctgaagccc | tggatcactc | 1800 |
| gccagaactt | ctcccggtgc | ctggagctgc | agtgtcagcc | cgactcctca | accctgccac | 1860 |

```
ccccatggag tccccggccc ctggaggcca cagccccgac agccccgggc ggcggcagcg    1920
gcgatgctag catgcaccag aagagaaccg ccatgttcca ggaccctcag gagagaccta    1980
ggaagctgcc tcacctgtgt acagagctcc agacaaccat ccacgacatc atcctggagt    2040
gcgtgtactg taagcagcag ctgctgagaa gagaggtgta cgacttcgcc ttcagagacc    2100
tgtgcatcgt gtacagagac ggcaacccct tacgccgtgtg cgataagtgt ctgaagttct    2160
attccatgca cggcgacacc cctaccctgc acgagtacat gctggacctc cagcctgaga    2220
ccacagacct gtactgctac gagcagctga cgacagctc tgaggaagag gacgagattg    2280
acggacctgc tggccaggcc gagcctgaca gagcccacta caatatcgtg acattctgta    2340
agatctctga gtacagatac tactgctact ctgtgtacgg caccacactg gagcagcagt    2400
acaacaagcc tctgtgcgac ctcctgatcc gctgcatcaa ctgccagaag cctctgtgcc    2460
ctgaggagaa gcagagacac ctggacaaga agcagcggtt ccacaacatc agaggcagat    2520
ggaccggcag gtgcatgtcc tgctgtagat cctccagaac cagacgggag acccagctgt    2580
gcaagtgcga ctctacccctg agactgtgcg tgcagtctac ccacgtggac atcagaaccc    2640
tggaggacct gctgatgggc acccctgggca tcgtgtgccc tatctgctct cagaagccta    2700
tggccaggtt cgaggaccct accagaagac cctacaagct gcctgacctg tgcaccgagc    2760
tgaacacctc tctgcaagac atcgagatca cctgcgtgta ctgcaagacc gtgctggagc    2820
tgaccgaggt gttcgagttc gccttcaagg acctgttcgt ggtgtacaga cagcatcc    2880
ctcacgctgc ctgccacaag tgcatcgact ctattccag gatcagggag ctgcgctatt    2940
actccgactc tgtgatgtac ggccccaagg ccaccctcca ggacatcgtg ctgcacctgg    3000
agcctcagaa cgagatcccc gtggacctgc tgtgccacga gcagctgtct gactctgaag    3060
aggagaacga cgagatcgac ggcgtgaacc accagcacct gcctgccagg agagctgaac    3120
cccagcggca taccatgctg tgtatgtgct tctactctag gatcagagag ctgaggtact    3180
actctgactc tgtgtacggc gacaccctgg agaagctgac caacaccggc ctgtacaacc    3240
tgctgatccg gtgcctgagg tgccagaagc ctctgaaccc tgccgagaag ctgagacacc    3300
tgaacgagaa gagaagattc cacaagatcg ctggccacta cagaggccag tgccactctt    3360
gctgcaacag agccagacag gagagactcc agcggagaag ggagacccag gtggccagaa    3420
gagccgagcc tcagagacac accatgctgt gcatgtgctg caagtgcgag gccagaatcg    3480
agctggtggt ggagagctct gccgacgacc tgagagcctt ccagcagctg ttcctgtcta    3540
ccctgagctt cgtgtgccct tggtgcgcct ctcagcagta atctagagtc ggggcggccg    3600
gccgcttcga gcagacatga taagatacat tgatgagttt ggacaaacca caactagaat    3660
gcagtgaaaa aaatgcttta tttgtgaaat ttgtgatgct attgctttat ttgtaaccat    3720
tataagctgc aataaacaag ttaacaacaa caattgcatt catttatgt ttcaggttca    3780
gggggaggtg tgggaggttt tttaaagcaa gtaaaacctc tacaaatgtg gtaaaatcga    3840
taaggatctg aacgatggag cggagaatgg gcggaactgg gcggagttag gggcgggatg    3900
ggcggagtta ggggcgggac tatggttgct gactaattga gatgcatgct ttgcatactt    3960
ctgcctgctg gggagcctgg ggactttcca cacctggttg ctgactaatt gagatgcatg    4020
cttttgcatac ttctgcctgc tggggagcct ggggactttc cacaccctaa ctgacacaca    4080
ttccacagcg gatccgtcga cttcagaaga actcgtcaag aaggcgatag aaggcgatgc    4140
gccgcgaatc gggagcggcg ataccgtaga gcacaggaa gcggtcagcc cattcgccgc    4200
caagctcttc agcaatatca cgggtagcca acgctatgtc ctgatagcgg tccgccacac    4260
```

```
ccagccggcc acagtcgatg aatccagaaa agcggccatt ttccaccatg atattcggca    4320
agcaggcatc gccatgggtc acgacgagat cctcgccgtc gggcatgctc gccttgagcc    4380
tggcgaacag ttcggctggc gcgagcccct gatgctcttc gtccagatca tcctgatcga    4440
caagaccggc ttcatccgga gtacgtgctc gctcgatgcg atgtttcgct ggtggtcga    4500 atgggcaggt agccggatca agcgtatgca gccgccgcat tgcatcagcc atgatggata    4560 cttctcggc aggagcaagg tgagatgaca ggagatcctg ccccggcact cgcccaata    4620 gcagccagtc ccttcccgct tcagtgacaa cgtcgagcac agctgcgcaa ggaacgcccg    4680
tcgtggccag ccacgatagc cgcgctgcct cgtcttgcag ttcattcagg caccggaca    4740 ggtcggtctt gacaaaaaga accgggcgcc cctgcgctga cagccggaac acggcggcat    4800
cagagcagcc gattgtctgt tgtgcccagt catagccgaa tagcctctcc acccaagcgg    4860
ccggagaacc tgcgtgcaat ccatcttgtt caatcatgcg aaacgatcct catcctgtct    4920
cttgatcaga tcttgatccc ctgcgccatc agatccttgg cggcaagaaa gccatccagt    4980
ttactttgca gggcttccca accttaccag agggcgcccc agctggcaat tccggttcgc    5040
ttgctgtcca taaaaccgcc cagtctagct atcgccatgt aagcccactg caagctacct    5100
gctttctctt tgcgcttgcg ttttcccttg tccagatagc ccagtagctg acattcatcc    5160
ggggtcagca ccgtttctgc ggactggctt tctacgtgaa aaggatctag gtgaagatcc    5220
tttttgataa tctcatgacc aaaatccctt aacgtgagtt ttcgttccac tgagcgtcag    5280
accccgtaga aaagatcaaa ggatcttctt gagatccttt ttttctgcgc gtaatctgct    5340
gcttgcaaac aaaaaaacca ccgctaccag cggtggtttg tttgccggat caagagctac    5400
caactctttt tccgaaggta actggcttca gcagagcgca gataccaaat actgttcttc    5460
tagtgtagcc gtagttaggc caccacttca agaactctgt agcaccgcct acatacctcg    5520
ctctgctaat cctgttacca gtggctgctg ccagtggcga taagtcgtgt cttaccgggt    5580
tggactcaag acgatagtta ccggataagg cgcagcggtc gggctgaacg gggggttcgt    5640
gcacacagcc cagcttggag cgaacgacct acaccgaact gagataccta cagcgtgagc    5700
tatgagaaag cgccacgctt cccgaaggga gaaaggcgga caggtatccg gtaagcggca    5760
gggtcggaac aggagagcgc acgagggagc ttccaggggg aaacgcccgg tatctttata    5820
gtcctgtcgg gtttcgccac ctctgacttg agcgtcgatt tttgtgatgc tcgtcagggg    5880
ggcggagcct atggaaaaac gccagcaacg cggccttttt acggttcctg gccttttgct    5940
ggccttttgc tcacatgttc gggcccaatc gacccgggcg acggccagtg aattg    5995
```

<210> SEQ ID NO 110
<211> LENGTH: 737
<212> TYPE: PRT
<213> ORGANISM: Artificial Sequence
<220> FEATURE:
<223> OTHER INFORMATION: D-1

<400> SEQUENCE: 110

```
Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
                20                  25                  30

Ser Pro Ile Ser Ser Asp Phe Ala Val Lys Ile Arg Glu Leu Ser Asp
            35                  40                  45

Tyr Leu Leu Gln Asp Tyr Pro Val Thr Val Ala Ser Asn Leu Gln Asp
```

```
            50                  55                  60
Glu Glu Leu Cys Gly Gly Leu Trp Arg Leu Val Leu Ala Gln Arg Trp
 65                  70                  75                  80

Met Glu Arg Leu Lys Thr Val Ala Gly Ser Lys Met Gln Gly Leu Leu
                 85                  90                  95

Glu Arg Val Asn Thr Glu Ile His Phe Val Thr Lys Cys Ala Phe Gln
                100                 105                 110

Pro Pro Pro Ser Cys Leu Arg Phe Val Gln Thr Asn Ile Ser Arg Leu
                115                 120                 125

Leu Gln Glu Thr Ser Glu Gln Leu Val Ala Leu Lys Pro Trp Ile Thr
                130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Gly Ser Gly Asp Ala Ser Met His Gln Lys
                180                 185                 190

Arg Thr Ala Met Phe Gln Asp Pro Gln Glu Arg Pro Arg Lys Leu Pro
                195                 200                 205

His Leu Cys Thr Glu Leu Gln Thr Thr Ile His Asp Ile Ile Leu Glu
                210                 215                 220

Cys Val Tyr Cys Lys Gln Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
                245                 250                 255

Val Cys Asp Lys Cys Leu Lys Phe Tyr Ser Met His Gly Asp Thr Pro
                260                 265                 270

Thr Leu His Glu Tyr Met Leu Asp Leu Gln Pro Glu Thr Thr Asp Leu
                275                 280                 285

Tyr Cys Tyr Glu Gln Leu Asn Asp Ser Ser Glu Glu Glu Asp Glu Ile
                290                 295                 300

Asp Gly Pro Ala Gly Gln Ala Glu Pro Asp Arg Ala His Tyr Asn Ile
305                 310                 315                 320

Val Thr Phe Cys Lys Ile Ser Glu Tyr Arg Tyr Tyr Cys Tyr Ser Val
                325                 330                 335

Tyr Gly Thr Thr Leu Glu Gln Gln Tyr Asn Lys Pro Leu Cys Asp Leu
                340                 345                 350

Leu Ile Arg Cys Ile Asn Cys Gln Lys Pro Leu Cys Pro Glu Glu Lys
                355                 360                 365

Gln Arg His Leu Asp Lys Lys Gln Arg Phe His Asn Ile Arg Gly Arg
370                 375                 380

Trp Thr Gly Arg Cys Met Ser Cys Cys Arg Ser Ser Arg Thr Arg Arg
385                 390                 395                 400

Glu Thr Gln Leu Cys Lys Cys Asp Ser Thr Leu Arg Leu Cys Val Gln
                405                 410                 415

Ser Thr His Val Asp Ile Arg Thr Leu Glu Asp Leu Leu Met Gly Thr
                420                 425                 430

Leu Gly Ile Val Cys Pro Ile Cys Ser Gln Lys Pro Met Ala Arg Phe
                435                 440                 445

Glu Asp Pro Thr Arg Arg Pro Tyr Lys Leu Pro Asp Leu Cys Thr Glu
                450                 455                 460

Leu Asn Thr Ser Leu Gln Asp Ile Glu Ile Thr Cys Val Tyr Cys Lys
465                 470                 475                 480
```

```
Thr Val Leu Glu Leu Thr Glu Val Phe Glu Phe Ala Phe Lys Asp Leu
            485                 490                 495
Phe Val Val Tyr Arg Asp Ser Ile Pro His Ala Ala Cys His Lys Cys
            500                 505                 510
Ile Asp Phe Tyr Ser Arg Ile Arg Glu Leu Arg Tyr Tyr Ser Asp Ser
            515                 520                 525
Val Met Tyr Gly Pro Lys Ala Thr Leu Gln Asp Ile Val Leu His Leu
            530                 535                 540
Glu Pro Gln Asn Glu Ile Pro Val Asp Leu Leu Cys His Glu Gln Leu
545                 550                 555                 560
Ser Asp Ser Glu Glu Glu Asn Asp Glu Ile Asp Gly Val Asn His Gln
            565                 570                 575
His Leu Pro Ala Arg Arg Ala Glu Pro Gln Arg His Thr Met Leu Cys
            580                 585                 590
Met Cys Phe Tyr Ser Arg Ile Arg Glu Leu Arg Tyr Tyr Ser Asp Ser
            595                 600                 605
Val Tyr Gly Asp Thr Leu Glu Lys Leu Thr Asn Thr Gly Leu Tyr Asn
            610                 615                 620
Leu Leu Ile Arg Cys Leu Arg Cys Gln Lys Pro Leu Asn Pro Ala Glu
625                 630                 635                 640
Lys Leu Arg His Leu Asn Glu Lys Arg Arg Phe His Lys Ile Ala Gly
            645                 650                 655
His Tyr Arg Gly Gln Cys His Ser Cys Cys Asn Arg Ala Arg Gln Glu
            660                 665                 670
Arg Leu Gln Arg Arg Arg Glu Thr Gln Val Ala Arg Ala Glu Pro
            675                 680                 685
Gln Arg His Thr Met Leu Cys Met Cys Cys Lys Cys Glu Ala Arg Ile
            690                 695                 700
Glu Leu Val Val Glu Ser Ser Ala Asp Asp Leu Arg Ala Phe Gln Gln
705                 710                 715                 720
Leu Phe Leu Ser Thr Leu Ser Phe Val Cys Pro Trp Cys Ala Ser Gln
            725                 730                 735
Gln

<210> SEQ ID NO 111
<211> LENGTH: 6379
<212> TYPE: DNA
<213> ORGANISM: Artificial Sequence
<220> FEATURE:
<223> OTHER INFORMATION: D-2 (overlapping-2)
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2321)
<223> OTHER INFORMATION: 16E6N (1-130aa)
<220> FEATURE:
<221> NAME/KEY: misc_feature
<222> LOCATION: (1932)..(3083)
<223> OTHER INFORMATION: 16E6/E7
<220> FEATURE:
<221> NAME/KEY: misc_feature
<222> LOCATION: (2322)..(2576)
<223> OTHER INFORMATION: 16E7N (1-85aa)
<220> FEATURE:
```

```
<221> NAME/KEY: misc_feature
<222> LOCATION: (2577)..(2918)
<223> OTHER INFORMATION: 16E6C (45-158aa)
<220> FEATURE:
<221> NAME/KEY: misc_feature
<222> LOCATION: (2919)..(3083)
<223> OTHER INFORMATION: 16E7C (44-98aa)
<220> FEATURE:
<221> NAME/KEY: misc_feature
<222> LOCATION: (3084)..(3965)
<223> OTHER INFORMATION: 18E6/E7

<400> SEQUENCE: 111
taccgatgta cgggccagat atacgcgttg acattgatta ttgactagtt attaatagta      60
atcaattacg gggtcattag ttcatagccc atatatggag ttccgcgtta cataacttac     120
ggtaaatggc ccgcctggct gaccgcccaa cgacccccgc ccattgacgt caataatgac     180
gtatgttccc atagtaacgc caatagggac tttccattga cgtcaatggg tggagtattt     240
acggtaaact gcccacttgg cagtacatca agtgtatcat atgccaagta cgccccctat     300
tgacgtcaat gacggtaaat ggcccgcctg gcattatgcc cagtacatga ccttatggga     360
ctttcctact tggcagtaca tctacgtatt agtcatcgct attaccatgg tgatgcggtt     420
ttggcagtac atcaatgggc gtggatagcg gtttgactca cggggatttc caagtctcca     480
ccccattgac gtcaatggga gtttgttttg gcaccaaaat caacgggact ttccaaaatg     540
tcgtaacaac tccgccccat tgacgcaaat gggcggtagg cgtgtacggt gggaggtcta     600
tataagcaga gctctctggc taactagaga acccactgct tactggctta tcgaaattaa     660
tacgactcac tatagggaga cccaagctgg ctagcgtgag tttggggacc cttgattgtt     720
ctttcttttt cgctattgta aaattcatgt tatatggagg gggcaaagtt tcagggtgt      780
tgtttagaac gggaagatgt cccttgtatc accatggacc tcatgataaa ttttgtttct     840
ttcactttct actctgttga caaccattgt ctcctcttat tttcttttca ttttctgtaa     900
cttttcgtt aaactttagc ttgcatttgt aacgaatttt taaattcact tttgtttatt     960
tgtcagattg taagtacttt ctctaatcac tttttttca aggcaatcag ggtatattat    1020
attgtacttc agcacagttt tagagaacaa ttgttataat taaatgataa ggtagaatat    1080
ttctgcatat aaattctggc tggcgtggaa atattcttat tggtagaaac aactacatcc    1140
tggtcatcat cctgcctttc tctttatggt tacaatgata tacactgttt gagatgagga    1200
taaaatactc tgagtccaaa ccgggcccct ctgctaacca tgttcatgcc ttcttctttt    1260
tcctacagct cctgggcaac gtgctggtta ttgtgctgtc tcatcatttt ggcaaagaat    1320
tgtaatacga ctcactatag gcgaattga agcttggtac cgccaccatg gatgctatga     1380
aacgggccct gtgctgcgtg ctgctcctgt gcggcgctgt gtttgtgagc cctagcatca    1440
cccaggactg ctccttccaa cacagcccca tctcctccga cttcgctgtc aaaatccgtg    1500
agctgtctga ctacctgctt caagattacc cagtcaccgt ggcctccaac ctgcaggacg    1560
aggagctctg cggggcctc tggcggctgg tcctggcaca gcgctggatg gagcggctca    1620
agactgtcgc tgggtccaag atgcaaggct tgctggagcg cgtgaacacg gagatacact    1680
ttgtcaccaa atgtgccttt cagccccccc ccagctgtct tcgcttcgtc cagaccaaca    1740
tctcccgcct cctgcaggag acctccgagc agctggtggc gctgaagccc tggatcactc    1800
gccagaactt ctccggtgc ctggagctgc agtgtcagcc cgactcctca accctgccac    1860
ccccatggag tccccggccc ctggaggcca cagccccgac agccccgggc ggcggcagcg    1920
gcgatgctag catgcaccag aagagaaccg ccatgttcca ggaccctcag gagagaccta    1980
```

-continued

```
ggaagctgcc tcacctgtgt acagagctcc agacaaccat ccacgacatc atcctggagt    2040
gcgtgtactg taagcagcag ctgctgagaa gagaggtgta cgacttcgcc ttcagagacc    2100
tgtgcatcgt gtacagagac ggcaacccct tacgccgtgt cgataagtgt ctgaagttct    2160
attccaagat ctctgagtac agatactact gctactctgt gtacggcacc acactggagc    2220
agcagtacaa caagcctctg tgcgacctcc tgatccgctg catcaactgc cagaagcctc    2280
tgtgccctga ggagaagcag agacacctgg acaagaagca gatgcacggc gacacccta    2340
ccctgcacga gtacatgctg gacctccagc tgagaccaca gacctgtac tgctacgagc    2400
agctgaacga cagctctgag gaagaggacg agattgacgg acctgctggc caggccgagc    2460
ctgacagagc ccactacaat atcgtgacat ctgttgcaa gtgcgactct accctgagac    2520
tgtgcgtgca gtctacccac gtggacatca gaaccctgga ggacctgctg atgggcctga    2580
gaagagaggt gtacgacttc gccttcagag acctgtgcat cgtgtacaga cacggcaacc    2640
cttacgccgt gtgcgataag tgtctgaagt tctattccaa gatctctgag tacagatact    2700
actgctactc tgtgtacggc accacactgg agcagcagta caacaagcct ctgtgcgacc    2760
tcctgatccg ctgcatcaac tgccagaagc ctctgtgccc tgaggagaag cagagacacc    2820
tggacaagaa gcagcggttc cacaacatca gaggcagatg gaccggcagg tgcatgtcct    2880
gctgtagatc ctccagaacc agacgggaga cccagctgca ggccgagcct gacagagccc    2940
actacaatat cgtgacattc tgttgcaagt gcgactctac cctgagactg tgcgtgcagt    3000
ctacccacgt ggacatcaga accctggagg acctgctgat gggcaccctg gcatcgtgt    3060
gccctatctg ctctcagaag cctatggcca ggttcgagga cccctaccaga gaccctaca    3120
agctgcctga cctgtgcacc gagctgaaca cctctctgca agacatcgag atcacctgcg    3180
tgtactgcaa gaccgtgctg gagctgaccg aggtgttcga gttcgccttc aaggacctgt    3240
tcgtggtgta cagagacagc atccctcacg ctgcctgcca aagtgcatc gacttctatt    3300
ccaggatcag ggagctgcgc tattactccg actctgtgat gtacggcccc aaggccaccc    3360
tccaggacat cgtgctgcac ctggagcctc agaacgagat ccccgtggac ctgctgtgcc    3420
acgagcagct gtctgactct gaagaggaga cgacgagat cgacggcgtg aaccaccagc    3480
acctgcctgc caggagagct gaaccccagc ggcataccat gctgtgtatg tgcttctact    3540
ctaggatcag agagctgagg tactactctg actctgtgta cggcgacacc ctggagaagc    3600
tgaccaacac cggcctgtac aacctgctga tccggtgcct gaggtgccag aagcctctga    3660
accctgccga gaagctgaga cacctgaacg agaagagaag attccacaag atcgctggcc    3720
actacagagg ccagtgccac tcttgctgca cagagccag acaggagaga ctccagcgga    3780
gaagggagac ccaggtggcc agaagagccg agcctcagag acacaccatg ctgtgcatgt    3840
gctgcaagtg cgaggccaga atcgagctgg tggtggagag ctctgccgac gacctgagag    3900
ccttccagca gctgttcctg tctaccctga gcttcgtgtg cccttggtgc gcctctcagc    3960
agtaatctag agtcggggcg gccggccgct tcgagcagac atgataagat acattgatga    4020
gtttggacaa accacaacta gaatgcagtg aaaaaaatgc tttatttgtg aaatttgtga    4080
tgctattgct ttatttgtaa ccattataag ctgcaataaa caagttaaca acaacaattg    4140
cattcatttt atgtttcagg ttcaggggga ggtgtgggag gttttttaaa gcaagtaaaa    4200
cctctacaaa tgtggtaaaa tcgataagga tctgaacgat ggagcggaga atgggcggaa    4260
ctgggcggag ttaggggcgg gatgggcgga gttaggggcg ggactatggt tgctgactaa    4320
```

```
ttgagatgca tgctttgcat acttctgcct gctggggagc ctggggactt ccacacctg    4380
gttgctgact aattgagatg catgctttgc atacttctgc ctgctgggga gcctggggac    4440
tttccacacc ctaactgaca cacattccac agcggatccg tcgacttcag aagaactcgt    4500
caagaaggcg atagaaggcg atgcgccgcg aatcggagcg gcgataccg tagagcacga    4560
ggaagcggtc agcccattcg ccgccaagct cttcagcaat atcacgggta gccaacgcta    4620
tgtcctgata gcggtccgcc acacccagcc ggccacagtc gatgaatcca gaaaagcggc    4680
cattttccac catgatattc ggcaagcagg catcgccatg ggtcacgacg agatcctcgc    4740
cgtcgggcat gctcgccttg agcctggcga acagttcggc tggcgcgagc ccctgatgct    4800
cttcgtccag atcatcctga tcgacaagac cggcttccat ccgagtacgt gctcgctcga    4860
tgcgatgttt cgcttggtgg tcgaatgggc aggtagccgg atcaagcgta tgcagccgcc    4920
gcattgcatc agccatgatg gatactttct cggcaggagc aaggtgagat gacaggagat    4980
cctgccccgg cacttcgccc aatagcagcc agtcccttcc cgcttcagtg acaacgtcga    5040
gcacagctgc gcaaggaacg cccgtcgtgg ccagccacga tagccgcgct gcctcgtctt    5100
gcagttcatt cagggcaccg gacaggtcgg tcttgacaaa aagaaccggg cgcccctgcg    5160
ctgacagccg gaacacggcg gcatcagagc agccgattgt ctgttgtgcc cagtcatagc    5220
cgaatagcct ctccacccaa gcggccgag aacctgcgtg caatccatct tgttcaatca    5280
tgcgaaacga tcctcatcct gtctcttgat cagatcttga tccctgcgc catcagatcc    5340
ttggcggcaa gaaagccatc cagtttactt tgcagggctt cccaacctta ccagagggcg    5400
ccccagctgg caattccggt tcgcttgctg tccataaaac cgcccagtct agctatcgcc    5460
atgtaagccc actgcaagct acctgctttc tctttgcgct tgcgttttcc cttgtccaga    5520
tagcccagta gctgacattc atccggggtc agcaccgttt ctgcggactg gctttctacg    5580
tgaaaaggat ctaggtgaag atccttttg ataatctcat gaccaaaatc ccttaacgtg    5640
agttttcgtt ccactgagcg tcagaccccg tagaaaagat caaggatct tcttgagatc    5700
ctttttttct gcgcgtaatc tgctgcttgc aaacaaaaaa accaccgcta ccagcggtgg    5760
tttgtttgcc ggatcaagag ctaccaactc tttttccgaa ggtaactggc ttcagcagag    5820
cgcagatacc aaatactgtt cttctagtgt agccgtagtt aggccaccac ttcaagaact    5880
ctgtagcacc gcctacatac ctcgctctgc taatcctgtt accagtggct gctgccagtg    5940
gcgataagtc gtgtcttacc gggttggact caagacgata gttaccggat aaggcgcagc    6000
ggtcgggctg aacggggggt tcgtgcacac agcccagctt ggagcgaacg acctacaccg    6060
aactgagata cctacagcgt gagctatgag aaagcgccac gcttcccgaa gggagaaagg    6120
cggacaggta tccggtaagc ggcagggtcg aacaggaga gcgcacgagg gagcttccag    6180
ggggaaacgc ctggtatctt tatagtcctg tcgggtttcg ccacctctga cttgagcgtc    6240
gatttttgtg atgctcgtca ggggggcgga gcctatggaa aaacgccagc aacgcggcct    6300
ttttacggtt cctggccttt tgctggcctt ttgctcacat gttcgggccc aatcgacccg    6360
ggcgacggcc agtgaattg                                                6379
```

<210> SEQ ID NO 112
<211> LENGTH: 865
<212> TYPE: PRT
<213> ORGANISM: Artificial Sequence
<220> FEATURE:
<223> OTHER INFORMATION: D-2

<400> SEQUENCE: 112

-continued

```
Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
            35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
                100                 105                 110

Pro Pro Pro Ser Cys Leu Arg Phe Val Gln Thr Asn Ile Ser Arg Leu
            115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Ser Gly Asp Ala Ser Met His Gln Lys
            180                 185                 190

Arg Thr Ala Met Phe Gln Asp Pro Gln Glu Arg Pro Arg Lys Leu Pro
                195                 200                 205

His Leu Cys Thr Glu Leu Gln Thr Thr Ile His Asp Ile Ile Leu Glu
    210                 215                 220

Cys Val Tyr Cys Lys Gln Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
            245                 250                 255

Val Cys Asp Lys Cys Leu Lys Phe Tyr Ser Lys Ile Ser Glu Tyr Arg
            260                 265                 270

Tyr Tyr Cys Tyr Ser Val Tyr Gly Thr Thr Leu Glu Gln Gln Tyr Asn
    275                 280                 285

Lys Pro Leu Cys Asp Leu Leu Ile Arg Cys Ile Asn Cys Gln Lys Pro
    290                 295                 300

Leu Cys Pro Glu Glu Lys Gln Arg His Leu Asp Lys Lys Gln Met His
305                 310                 315                 320

Gly Asp Thr Pro Thr Leu His Glu Tyr Met Leu Asp Leu Gln Pro Glu
                325                 330                 335

Thr Thr Asp Leu Tyr Cys Tyr Glu Gln Leu Asn Asp Ser Ser Glu Glu
            340                 345                 350

Glu Asp Glu Ile Asp Gly Pro Ala Gly Gln Ala Glu Pro Asp Arg Ala
    355                 360                 365

His Tyr Asn Ile Val Thr Phe Cys Cys Lys Cys Asp Ser Thr Leu Arg
    370                 375                 380

Leu Cys Val Gln Ser Thr His Val Asp Ile Arg Thr Leu Glu Asp Leu
385                 390                 395                 400

Leu Met Gly Leu Arg Arg Glu Val Tyr Asp Phe Ala Phe Arg Asp Leu
                405                 410                 415
```

-continued

```
Cys Ile Val Tyr Arg Asp Gly Asn Pro Tyr Ala Val Cys Asp Lys Cys
            420                 425                 430

Leu Lys Phe Tyr Ser Lys Ile Ser Glu Tyr Arg Tyr Tyr Cys Tyr Ser
            435                 440                 445

Val Tyr Gly Thr Thr Leu Glu Gln Gln Tyr Asn Lys Pro Leu Cys Asp
            450                 455                 460

Leu Leu Ile Arg Cys Ile Asn Cys Gln Lys Pro Leu Cys Pro Glu Glu
465                 470                 475                 480

Lys Gln Arg His Leu Asp Lys Lys Gln Arg Phe His Asn Ile Arg Gly
                    485                 490                 495

Arg Trp Thr Gly Arg Cys Met Ser Cys Cys Arg Ser Ser Arg Thr Arg
            500                 505                 510

Arg Glu Thr Gln Leu Gln Ala Glu Pro Asp Arg Ala His Tyr Asn Ile
            515                 520                 525

Val Thr Phe Cys Cys Lys Cys Asp Ser Thr Leu Arg Leu Cys Val Gln
            530                 535                 540

Ser Thr His Val Asp Ile Arg Thr Leu Glu Asp Leu Leu Met Gly Thr
545                 550                 555                 560

Leu Gly Ile Val Cys Pro Ile Cys Ser Gln Lys Pro Met Ala Arg Phe
                    565                 570                 575

Glu Asp Pro Thr Arg Arg Pro Tyr Lys Leu Pro Asp Leu Cys Thr Glu
            580                 585                 590

Leu Asn Thr Ser Leu Gln Asp Ile Glu Ile Thr Cys Val Tyr Cys Lys
            595                 600                 605

Thr Val Leu Glu Leu Thr Glu Val Phe Glu Phe Ala Phe Lys Asp Leu
610                 615                 620

Phe Val Val Tyr Arg Asp Ser Ile Pro His Ala Ala Cys His Lys Cys
625                 630                 635                 640

Ile Asp Phe Tyr Ser Arg Ile Arg Glu Leu Arg Tyr Tyr Ser Asp Ser
                    645                 650                 655

Val Met Tyr Gly Pro Lys Ala Thr Leu Gln Asp Ile Val Leu His Leu
            660                 665                 670

Glu Pro Gln Asn Glu Ile Pro Val Asp Leu Leu Cys His Glu Gln Leu
            675                 680                 685

Ser Asp Ser Glu Glu Glu Asn Asp Glu Ile Asp Gly Val Asn His Gln
            690                 695                 700

His Leu Pro Ala Arg Arg Ala Glu Pro Gln Arg His Thr Met Leu Cys
705                 710                 715                 720

Met Cys Phe Tyr Ser Arg Ile Arg Glu Leu Arg Tyr Tyr Ser Asp Ser
                    725                 730                 735

Val Tyr Gly Asp Thr Leu Glu Lys Leu Thr Asn Thr Gly Leu Tyr Asn
            740                 745                 750

Leu Leu Ile Arg Cys Leu Arg Cys Gln Lys Pro Leu Asn Pro Ala Glu
            755                 760                 765

Lys Leu Arg His Leu Asn Glu Lys Arg Arg Phe His Lys Ile Ala Gly
            770                 775                 780

His Tyr Arg Gly Gln Cys His Ser Cys Cys Asn Arg Ala Arg Gln Glu
785                 790                 795                 800

Arg Leu Gln Arg Arg Arg Glu Thr Gln Val Ala Arg Ala Glu Pro
                    805                 810                 815

Gln Arg His Thr Met Leu Cys Met Cys Cys Lys Cys Glu Ala Arg Ile
            820                 825                 830

Glu Leu Val Val Glu Ser Ser Ala Asp Asp Leu Arg Ala Phe Gln Gln
```

```
                835                 840                 845
Leu Phe Leu Ser Thr Leu Ser Phe Val Cys Pro Trp Cys Ala Ser Gln
    850                 855                 860

Gln
865
```

<210> SEQ ID NO 113
<211> LENGTH: 6085
<212> TYPE: DNA
<213> ORGANISM: Artificial Sequence
<220> FEATURE:
<223> OTHER INFORMATION: E-1 (Order-1)
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2186)
<223> OTHER INFORMATION: 16E6N
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2187)..(2330)
<223> OTHER INFORMATION: 16E7C
<220> FEATURE:
<221> NAME/KEY: misc_feature
<222> LOCATION: (2331)..(2525)
<223> OTHER INFORMATION: 16E7N
<220> FEATURE:
<221> NAME/KEY: misc_feature
<222> LOCATION: (2526)..(2789)
<223> OTHER INFORMATION: 16E6C
<220> FEATURE:
<221> NAME/KEY: misc_feature
<222> LOCATION: (2790)..(3671)
<223> OTHER INFORMATION: 18E6/E7

<400> SEQUENCE: 113

```
taccgatgta cgggccagat atacgcgttg acattgatta ttgactagtt attaatagta    60
atcaattacg gggtcattag ttcatagccc atatatggag ttccgcgtta cataacttac   120
ggtaaatggc ccgcctggct gaccgcccaa cgacccccgc ccattgacgt caataatgac   180
gtatgttccc atagtaacgc caatagggac tttccattga cgtcaatggg tggagtattt   240
acggtaaact gcccacttgg cagtacatca agtgtatcat atgccaagta cgccccctat   300
tgacgtcaat gacggtaaat ggcccgcctg gcattatgcc cagtacatga ccttatggga   360
ctttcctact tggcagtaca tctacgtatt agtcatcgct attaccatgg tgatgcggtt   420
ttggcagtac atcaatgggc gtggatagcg gtttgactca cggggatttc caagtctcca   480
ccccattgac gtcaatggga gtttgttttg caccaaaatc aacgggactt tccaaaatg    540
tcgtaacaac tccgccccat tgacgcaaat gggcggtagg cgtgtacggt gggaggtcta   600
tataagcaga gctctctggc taactagaga acccactgct tactggctta tcgaaattaa   660
tacgactcac tatagggaga cccaagctgg ctagcgtgag tttggggacc cttgattgtt   720
ctttcttttt cgctattgta aaattcatgt tatatggagg gggcaaagtt ttcagggtgt   780
tgtttagaac gggaagatgt cccttgtatc accatggacc ctcatgataa ttttgttttct  840
ttcactttct actctgttga caaccattgt ctcctcttat tttcttttca ttttctgtaa   900
```

```
cttttccgtt aaactttagc ttgcatttgt aacgaattct taaattcact tttgtttatt      960
tgtcagattg taagtacttt ctctaatcac ttttttttca aggcaatcag ggtatattat     1020
attgtacttc agcacagttt tagagaacaa ttgttataat taaatgataa ggtagaatat     1080
ttctgcatat aaattctggc tggcgtggaa atattcttat tggtagaaac aactacatcc     1140
tggtcatcat cctgcctttc tctttatggt tacaatgata tacactgttt gagatgagga     1200
taaaatactc tgagtccaaa ccgggcccct ctgctaacca tgttcatgcc ttcttctttt     1260
tcctacagct cctgggcaac gtgctggtta ttgtgctgtc tcatcatttt ggcaaagaat     1320
tgtaatacga ctcactatag ggcgaattga agcttggtac cgccaccatg gatgctatga     1380
aacggggcct gtgctgcgtg ctgctcctgt gcggcgctgt gtttgtgagc cctagcatca     1440
cccaggactg ctccttccaa cacagcccca tctcctccga cttcgctgtc aaaatccgtg     1500
agctgtctga ctacctgctt caagattacc cagtcaccgt ggcctccaac ctgcaggacg     1560
aggagctctg cggggggcctc tggcggctgg tcctggcaca gcgctggatg gagcggctca     1620
agactgtcgc tgggtccaag atgcaaggct tgctggagcg cgtgaacacg gagatacact     1680
ttgtcaccaa atgtgccttt cagccccccc ccagctgtct tcgcttcgtc cagaccaaca     1740
tctcccgcct cctgcaggag acctccgagc agctggtggc gctgaagccc tggatcactc     1800
gccagaactt ctccggtgc ctggagctgc agtgtcagcc cgactcctca accctgccac     1860
ccccatggag tccccggccc ctggaggcca cagccccgac agcccgggc ggcggcagcg     1920 gcgatgctag catgcaccag aagagaaccg ccatgttcca ggaccctcag gagagaccta     1980
ggaagctgcc tcacctgtgt acagagctcc agacaaccat ccacgacatc atcctggagt     2040
gcgtgtactg taagcagcag ctgctgagaa gagaggtgta cgacttcgcc ttcagagacc     2100
tgtgcatcgt gtacagagac ggcaacccct tacgccgtgtg cgataagtgt ctgaagttct     2160
attccaaaat ctccgaatat aggtaccact acaacatcgt gaccttctgc tgcaagtgcg     2220
actctaccct gagactgtgc gtgcagtcta cccacgtgga catcagaacc ctggaggacc     2280
tgctgatggg caccctgggc atcgtgtgcc ctatctgctc tcagaagcct atgcacggcg     2340
acacccctac cctgcacgag tacatgctgg acctccagcc tgagaccaca gacctgtact     2400
gctacgagca gctgaacgac agctctgagg aagaggacga gattgacgga cctgctggcc     2460
aggccgagcc tgacagagcc cactacaata tcgtgacatt ctgttgcaaa tgcgactcca     2520
cactggacaa gtgcctgaag ttctacagca agatctctga gtacagatac tactgctact     2580
ctgtgtacgg caccacactg gagcagcagt acaacaagcc tctgtgcgac ctcctgatcc     2640
gctgcatcaa ctgccagaag cctctgtgcc ctgaggagaa gcagagacac ctggacaaga     2700
agcagcggtt ccacaacatc agaggcagat ggaccggcag gtgcatgtcc tgctgtagat     2760
cctccagaac cagacgggag acccagctga tggccaggtt cgaggaccct accagaagac     2820
cctacaagct gcctgacctg tgcaccgagc tgaacacctc tctgcaagac atcgagatca     2880
cctgcgtgta ctgcaagacc gtgctggagc tgaccgaggt gttcgagttc gccttcaagg     2940
acctgttcgt ggtgtacaga gacagcatcc ctcacgctgc ctgccacaag tgcatcgact     3000
tctattccag gatcagggag ctgcgctatt actccgactc tgtgatgtac ggccccaagg     3060 ccacccctcca ggacatcgtg ctgcacctgg agcctcagaa cgagatcccc gtggacctgc     3120
tgtgccacga gcagctgtct gactctgaag aggagaacga cgagatcgac ggcgtgaacc     3180
accagcacct gcctgccagg agagctgaac cccagcggca taccatgctg tgtatgtgct     3240
```

-continued

```
tctactctag gatcagagag ctgaggtact actctgactc tgtgtacggc gacaccctgg    3300
agaagctgac caacaccggc ctgtacaacc tgctgatccg gtgcctgagg tgccagaagc    3360
ctctgaaccc tgccgagaag ctgagacacc tgaacgagaa gagaagattc cacaagatcg    3420
ctggccacta cagaggccag tgccactctt gctgcaacag agccagacag agagagactcc   3480
agcggagaag ggagacccag gtggccagaa gagccgagcc tcagagacac accatgctgt    3540
gcatgtgctg caagtgcgag gccagaatcg agctggtggt ggagagctct gccgacgacc    3600
tgagagcctt ccagcagctg ttcctgtcta ccctgagctt cgtgtgccct tggtgcgcct    3660
ctcagcagta atctagagtc ggggcggccg gccgcttcga gcagacatga taagatacat    3720
tgatgagttt ggacaaacca aactagaat gcagtgaaaa aaatgcttta tttgtgaaat    3780
ttgtgatgct attgctttat tgtaaccat tataagctgc aataaacaag ttaacaacaa    3840
caattgcatt cattttatgt ttcaggttca gggggaggtg tgggaggttt tttaaagcaa    3900
gtaaacctc tacaaatgtg gtaaaatcga taaggatctg aacgatggag cggagaatgg    3960
gcggaactgg gcggagttag gggcgggatg ggcggagtta ggggcgggac tatggttgct    4020
gactaattga gatgcatgct ttgcatactt ctgcctgctg gggagcctgg ggactttcca    4080
cacctggttg ctgactaatt gagatgcatg cttttgcatac ttctgcctgc tggggagcct    4140
ggggactttc cacaccctaa ctgacacaca ttccacagcg gatccgtcga cttcagaaga    4200
actcgtcaag aaggcgatag aaggcgatgc gccgcgaatc gggagcggcg ataccgtaga    4260
gcacgaggaa gcggtcagcc cattcgccgc caagctcttc agcaatatca cgggtagcca    4320
acgctatgtc ctgatagcgg tccgccacac ccagccggcc acagtcgatg aatccagaaa    4380
agcggccatt ttccaccatg atattcggca agcaggcatc gccatgggtc acgacgagat    4440
cctcgccgtc gggcatgctc gccttgagcc tggcgaacag ttcggctggc gcgagcccct    4500
gatgctcttc gtccagatca tcctgatcga caagaccggc ttccatccga gtacgtgctc    4560
gctcgatgcg atgtttcgct tggtggtcga atgggcaggt agccggatca agcgtatgca    4620
gccgccgcat tgcatcagcc atgatggata cttttctcggc aggagcaagg tgagatgaca    4680
ggagatcctg ccccggcact tcgcccaata gcagccagtc ccttcccgct tcagtgacaa    4740
cgtcgagcac agctgcgcaa ggaacgcccg tcgtggccag ccacgatagc cgcgctgcct    4800
cgtcttgcag ttcattcagg gcaccggaca ggtcggtctt gacaaaaaga accgggcgcc    4860
cctgcgctga cagccggaac acggcggcat cagagcagcc gattgtctgt tgtgcccagt    4920
catagccgaa tagcctctcc acccaagcgg ccggagaacc tgcgtgcaat ccatcttgtt    4980
caatcatgcg aaacgatcct catcctgtct cttgatcaga tcttgatccc ctgcgccatc    5040
agatccttgg cggcaagaaa gccatccagt ttactttgca gggcttccca accttaccag    5100
agggcgcccc agctggcaat tccggttcgc ttgctgtcca taaaaccgcc cagtctagct    5160
atcgccatgt aagcccactg caagctacct gctttctctt gcgcttgcg ttttcccttg    5220
tccagatagc ccagtagctg acattcatcc ggggtcagca ccgtttctgc ggactggctt    5280
tctacgtgaa aaggatctag gtgaagatcc ttttttgataa tctcatgacc aaaatccctt    5340
aacgtgagtt ttcgttccac tgagcgtcag accccgtaga aaagatcaaa ggatcttctt    5400
gagatccttt ttttctgcgc gtaatctgct gcttgcaaac aaaaaaacca ccgctaccag    5460
cggtggtttg tttgccggat caagagctac caactctttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
```

-continued

```
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagataccta cagcgtgagc tatgagaaag cgccacgctt cccgaaggga    5820
gaaaggcgga caggtatccg gtaagcggca gggtcggaac aggagagcgc acgagggagc    5880
ttccaggggg aaacgcccgg tatctttata gtcctgtcgg gtttcgccac ctctgacttg    5940
agcgtcgatt tttgtgatgc tcgtcagggg ggcggagcct atggaaaaac gccagcaacg    6000 cggcctttttt acggttcctg gccttttgct ggccttttgc tcacatgttc gggcccaatc    6060
gacccgggcg acggccagtg aattg                                          6085
```

<210> SEQ ID NO 114
<211> LENGTH: 767
<212> TYPE: PRT
<213> ORGANISM: Artificial Sequence
<220> FEATURE:
<223> OTHER INFORMATION: E-1

<400> SEQUENCE: 114

```
Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Gly Ser Gly Asp Ala Ser Met His Gln Lys
            180                 185                 190

Arg Thr Ala Met Phe Gln Asp Pro Gln Glu Arg Pro Arg Lys Leu Pro
        195                 200                 205

His Leu Cys Thr Glu Leu Gln Thr Thr Ile His Asp Ile Ile Leu Glu
    210                 215                 220

Cys Val Tyr Cys Lys Gln Gln Leu Leu Arg Arg Glu Val Tyr Asp Phe
225                 230                 235                 240

Ala Phe Arg Asp Leu Cys Ile Val Tyr Arg Asp Gly Asn Pro Tyr Ala
                245                 250                 255

Val Cys Asp Lys Cys Leu Lys Phe Tyr Ser Lys Ile Ser Glu Tyr Arg
            260                 265                 270

Tyr His Tyr Asn Ile Val Thr Phe Cys Cys Lys Cys Asp Ser Thr Leu
```

```
            275                 280                 285
Arg Leu Cys Val Gln Ser Thr His Val Asp Ile Arg Thr Leu Glu Asp
290                 295                 300

Leu Leu Met Gly Thr Leu Gly Ile Val Cys Pro Ile Cys Ser Gln Lys
305                 310                 315                 320

Pro Met His Gly Asp Thr Pro Thr Leu His Glu Tyr Met Leu Asp Leu
                    325                 330                 335

Gln Pro Glu Thr Thr Asp Leu Tyr Cys Tyr Glu Gln Leu Asn Asp Ser
                340                 345                 350

Ser Glu Glu Glu Asp Glu Ile Asp Gly Pro Ala Gly Gln Ala Glu Pro
            355                 360                 365

Asp Arg Ala His Tyr Asn Ile Val Thr Phe Cys Cys Lys Cys Asp Ser
370                 375                 380

Thr Leu Asp Lys Cys Leu Lys Phe Tyr Ser Lys Ile Ser Glu Tyr Arg
385                 390                 395                 400

Tyr Tyr Cys Tyr Ser Val Tyr Gly Thr Thr Leu Glu Gln Gln Tyr Asn
                    405                 410                 415

Lys Pro Leu Cys Asp Leu Leu Ile Arg Cys Ile Asn Cys Gln Lys Pro
                420                 425                 430

Leu Cys Pro Glu Glu Lys Gln Arg His Leu Asp Lys Lys Gln Arg Phe
            435                 440                 445

His Asn Ile Arg Gly Arg Trp Thr Gly Arg Cys Met Ser Cys Cys Arg
450                 455                 460

Ser Ser Arg Thr Arg Arg Glu Thr Gln Leu Met Ala Arg Phe Glu Asp
465                 470                 475                 480

Pro Thr Arg Arg Pro Tyr Lys Leu Pro Asp Leu Cys Thr Glu Leu Asn
                    485                 490                 495

Thr Ser Leu Gln Asp Ile Glu Ile Thr Cys Val Tyr Cys Lys Thr Val
                500                 505                 510

Leu Glu Leu Thr Glu Val Phe Glu Phe Ala Phe Lys Asp Leu Phe Val
            515                 520                 525

Val Tyr Arg Asp Ser Ile Pro His Ala Ala Cys His Lys Cys Ile Asp
530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
                    565                 570                 575

Gln Asn Glu Ile Pro Val Asp Leu Leu Cys His Glu Gln Leu Ser Asp
                580                 585                 590

Ser Glu Glu Glu Asn Asp Glu Ile Asp Gly Val Asn His Gln His Leu
            595                 600                 605

Pro Ala Arg Arg Ala Glu Pro Gln Arg His Thr Met Leu Cys Met Cys
610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
                    645                 650                 655

Ile Arg Cys Leu Arg Cys Gln Lys Pro Leu Asn Pro Ala Glu Lys Leu
                660                 665                 670

Arg His Leu Asn Glu Lys Arg Arg Phe His Lys Ile Ala Gly His Tyr
            675                 680                 685

Arg Gly Gln Cys His Ser Cys Cys Asn Arg Ala Arg Gln Glu Arg Leu
690                 695                 700
```

```
Gln Arg Arg Arg Glu Thr Gln Val Ala Arg Arg Ala Glu Pro Gln Arg
705                 710                 715                 720

His Thr Met Leu Cys Met Cys Cys Lys Cys Glu Ala Arg Ile Glu Leu
                725                 730                 735

Val Val Glu Ser Ser Ala Asp Asp Leu Arg Ala Phe Gln Gln Leu Phe
            740                 745                 750

Leu Ser Thr Leu Ser Phe Val Cys Pro Trp Cys Ala Ser Gln Gln
        755                 760                 765
```

```
<210> SEQ ID NO 115
<211> LENGTH: 6085
<212> TYPE: DNA
<213> ORGANISM: Artificial Sequence
<220> FEATURE:
<223> OTHER INFORMATION: E-2 (Order-2)
<220> FEATURE:
<221> NAME/KEY: misc_feature
<222> LOCATION: (1368)..(1433)
<223> OTHER INFORMATION: encodes tPA
<220> FEATURE:
<221> NAME/KEY: misc_feature
<222> LOCATION: (1434)..(1925)
<223> OTHER INFORMATION: encodes FLT3L
<220> FEATURE:
<221> NAME/KEY: misc_feature
<222> LOCATION: (1932)..(2195)
<223> OTHER INFORMATION: 16E6C
<220> FEATURE:
<221> NAME/KEY: misc_feature
<222> LOCATION: (1932)..(2789)
<223> OTHER INFORMATION: 16E6/E7
<220> FEATURE:
<221> NAME/KEY: misc_feature
<222> LOCATION: (2196)..(2339)
<223> OTHER INFORMATION: 16E7C
<220> FEATURE:
<221> NAME/KEY: misc_feature
<222> LOCATION: (2340)..(2594)
<223> OTHER INFORMATION: 16E6N
<220> FEATURE:
<221> NAME/KEY: misc_feature
<222> LOCATION: (2595)..(2789)
<223> OTHER INFORMATION: 16E7N
<220> FEATURE:
<221> NAME/KEY: misc_feature
<222> LOCATION: (2790)..(3671)
<223> OTHER INFORMATION: 18E6/E7

<400> SEQUENCE: 115
taccgatgta cgggccagat atacgcgttg acattgatta ttgactagtt attaatagta    60
atcaattacg gggtcattag ttcatagccc atatatggag ttccgcgtta cataacttac   120
ggtaaatggc ccgcctggct gaccgcccaa cgacccccgc ccattgacgt caataatgac   180
gtatgttccc atagtaacgc caatagggac tttccattga cgtcaatggg tggagtattt   240
acggtaaact gcccacttgg cagtacatca agtgtatcat atgccaagta cgccccctat   300
tgacgtcaat gacggtaaat ggcccgcctg gcattatgcc cagtacatga ccttatggga   360
ctttcctact tggcagtaca tctacgtatt agtcatcgct attaccatgg tgatgcggtt   420
ttggcagtac atcaatgggc gtggatagcg gtttgactca cggggatttc caagtctcca   480
ccccattgac gtcaatggga gtttgttttg gcaccaaaat caacgggact ttccaaaatg   540
tcgtaacaac tccgccccat tgacgcaaat gggcggtagg cgtgtacggt gggaggtcta   600
tataagcaga gctctctggc taactagaga acccactgct tactggctta tcgaaattaa   660
tacgactcac tatagggaga cccaagctgg ctagcgtgag tttggggacc cttgattgtt   720
```

|                                                                          |      |
| ------------------------------------------------------------------------ | ---- |
| ctttcttttt cgctattgta aaattcatgt tatatggagg gggcaaagtt ttcagggtgt          | 780  |
| tgtttagaac gggaagatgt cccttgtatc accatggacc ctcatgataa ttttgtttct          | 840  |
| ttcactttct actctgttga caaccattgt ctcctcttat tttcttttca ttttctgtaa          | 900  |
| cttttcgtt aaactttagc ttgcatttgt aacgaatttt taaattcact tttgtttatt           | 960  |
| tgtcagattg taagtacttt ctctaatcac ttttttttca aggcaatcag ggtatattat          | 1020 |
| attgtacttc agcacagttt tagagaacaa ttgttataat taaatgataa ggtagaaatt          | 1080 |
| ttctgcatat aaattctggc tggcgtggaa atattcttat tggtagaaac aactacatcc          | 1140 |
| tggtcatcat cctgccttc tctttatggt tacaatgata tacactgttt gagatgagga           | 1200 |
| taaaatactc tgagtccaaa ccgggcccct ctgctaacca tgttcatgcc ttcttctttt          | 1260 |
| tcctacagct cctgggcaac gtgctggtta ttgtgctgtc tcatcatttt ggcaaagaat          | 1320 |
| tgtaatacga ctcactatag ggcgaattga agcttggtac cgccaccatg gatgctatga          | 1380 |
| aacgggcct gtgctgcgtg ctgctcctgt gcggcgctgt gtttgtgagc cctagcatca           | 1440 |
| cccaggactg ctccttccaa cacagcccca tctcctccga cttcgctgtc aaaatccgtg          | 1500 |
| agctgtctga ctacctgctt caagattacc cagtcaccgt ggcctccaac ctgcaggacg          | 1560 |
| aggagctctg cggggcctc tggcggctgg tcctggcaca gcgctggatg gagcggctca           | 1620 |
| agactgtcgc tgggtccaag atgcaaggct tgctggagcg cgtgaacacg agatacact           | 1680 |
| ttgtcaccaa atgtgccttt cagccccccc ccagctgtct tcgcttcgtc cagaccaaca          | 1740 |
| tctcccgcct cctgcaggag acctccgagc agctggtggc gctgaagccc tggatcactc          | 1800 |
| gccagaactt ctcccggtgc ctggagctgc agtgtcagcc cgactcctca accctgccac          | 1860 |
| ccccatggag tccccggccc ctggaggcca cagccccgac agccccgggc ggcggcagcg          | 1920 |
| gcgatgctag cgacaagtgc ctgaagttct acagcaagat ctctgagtac agatactact          | 1980 |
| gctactctgt gtacggcacc acactggagc agcagtacaa caagcctctg tgcgacctcc          | 2040 |
| tgatccgctg catcaactgc cagaagcctc tgtgccctga ggagaagcag agacacctgg          | 2100 |
| acaagaagca gcggttccac aacatcagag gcagatggac cggcaggtgc atgtcctgct          | 2160 |
| gtagatcctc cagaaccaga cgggagaccc agctgcacta acatcgtga accttctgct           | 2220 |
| gcaagtgcga ctctacccta agactgtgcg tgcagtctac ccacgtggac atcagaaccc          | 2280 |
| tggaggacct gctgatgggc accctgggca tcgtgtgccc tatctgctct cagaagccta          | 2340 |
| tgcaccagaa gagaaccgcc atgttccagg accctcagga gagacctagg aagctgcctc          | 2400 |
| acctgtgtac agagctccag acaaccatcc acgacatcat cctggagtgc gtgtactgta          | 2460 |
| agcagcagct gctgagaaga gaggtgtacg acttcgcctt cagagacctg tgcatcgtgt          | 2520 |
| acagagacgg caaccttac gccgtgtgcg ataagtgtct gaagttctat tccaaaatct           | 2580 |
| ccgaatatag gtacatgcac ggcgacaccc ctaccctgca cgagtacatg ctggacctcc          | 2640 |
| agcctgagac cacagacctg tactgctacg agcagctgaa cgacagctct gaggaagagg          | 2700 |
| acgagattga cggacctgct ggccaggccg agcctgacag agcccactac aatatcgtga          | 2760 |
| cattctgttg caaatgcgac tccacactga tggccaggtt cgaggaccct accagaagac          | 2820 |
| cctacaagct gcctgacctg tgcaccgagc tgaacacctc tctgcaagac atcgagatca          | 2880 |
| cctgcgtgta ctgcaagacc gtgctggagc tgaccgaggt gttcgagttc gccttcaagg          | 2940 |
| acctgttcgt ggtgtacaga gacagcatcc tcacgctgc ctgccacaag tgcatcgact           | 3000 |
| tctattccag gatcagggag ctgcgctatt actccgactc tgtgatgtac ggccccaagg          | 3060 |
| ccaccctcca ggacatcgtg ctgcacctgg agcctcagaa cgagatcccc gtggacctgc          | 3120 |

```
tgtgccacga gcagctgtct gactctgaag aggagaacga cgagatcgac ggcgtgaacc    3180
accagcacct gcctgccagg agagctgaac cccagcggca taccatgctg tgtatgtgct    3240
tctactctag gatcagagag ctgaggtact actctgactc tgtgtacggc gacaccctgg    3300
agaagctgac caacaccggc ctgtacaacc tgctgatccg gtgcctgagg tgccagaagc    3360
ctctgaaccc tgccgagaag ctgagacacc tgaacgagaa gagaagattc cacaagatcg    3420
ctggccacta cagaggccag tgccactctt gctgcaacag agccagacag agagagactcc   3480 agcggagaag ggagacccag gtggccagaa gagccgagcc tcagagacac accatgctgt    3540
gcatgtgctg caagtgcgag gccagaatcg agctggtggt ggagagctct gccgacgacc    3600
tgagagcctt ccagcagctg ttcctgtcta ccctgagctt cgtgtgccct tggtgcgcct    3660
ctcagcagta atctagagtc ggggcggccg gccgcttcga gcagacatga taagatacat    3720
tgatgagttt ggacaaacca aactagaat gcagtgaaaa aaatgcttta tttgtgaaat     3780
ttgtgatgct attgctttat ttgtaaccat tataagctgc aataaacaag ttaacaacaa    3840
caattgcatt cattttatgt ttcaggttca ggggagggtg tgggaggttt tttaaagcaa    3900 gtaaacctc tacaaatgtg gtaaaatcga taaggatctg aacgatggag cggagaatgg    3960
gcggaactgg gcggagttag gggcgggatg ggcggagtta ggggcgggac tatggttgct    4020
gactaattga gatgcatgct ttgcatactt ctgcctgctg gggagcctgg ggactttcca    4080
cacctggttg ctgactaatt gagatgcatg cttttgcatac ttctgcctgc tggggagcct    4140
ggggactttc cacaccctaa ctgacacaca ttccacagcg gatccgtcga cttcagaaga    4200
actcgtcaag aaggcgatag aaggcgatgc gccgcgaatc gggagcggcg ataccgtaga    4260
gcacgaggaa gcggtcagcc cattcgccgc caagctcttc agcaatatca cgggtagcca    4320
acgctatgtc ctgatagcgg tccgccacac ccagccggcc acagtcgatg aatccagaaa    4380
agcggccatt ttccaccatg atattcggca agcaggcatc gccatgggtc acgacgagat    4440
cctcgccgtc gggcatgctc gccttgagcc tggcgaacag ttcggctggc gcgagcccct    4500
gatgctcttc gtccagatca tcctgatcga caagaccggc ttccatccga gtacgtgctc    4560
gctcgatgcg atgtttcgct tggtggtcga atgggcaggt agccggatca agcgtatgca    4620
gccgccgcat tgcatcagcc atgatggata ctttctcggc aggagcaagg tgagatgaca    4680
ggagatcctg ccccggcact cgcccaata gcagccagtc ccttcccgct tcagtgacaa    4740
cgtcgagcac agctgcgcaa ggaacgcccg tcgtggccag ccacgatagc cgcgctgcct    4800
cgtcttgcag ttcattcagg gcaccggaca ggtcggtctt gacaaaaaga accgggcgcc    4860
cctgcgctga cagccggaac acggcggcat cagagcagcc gattgtctgt tgtgcccagt    4920
catagccgaa tagcctctcc acccaagcgg ccggagaacc tgcgtgcaat ccatcttgtt    4980
caatcatgcg aaacgatcct catcctgtct cttgatcaga tcttgatccc ctgcgccatc    5040
agatccttgg cggcaagaaa gccatccagt ttactttgca gggcttccca accttaccag    5100
agggcgcccc agctggcaat tccggttcgc ttgctgtcca taaaaccgcc cagtctagct    5160
atcgccatgt aagcccactg caagctacct gctttctctt tgcgcttgcg ttttcccttg    5220
tccagatagc ccagtagctg acattcatcc ggggtcagca ccgtttctgc ggactggctt    5280
tctacgtgaa aaggatctag gtgaagatcc ttttttgataa tctcatgacc aaaatccctt    5340
aacgtgagtt ttcgttccac tgagcgtcag accccgtaga aaagatcaaa ggatcttctt    5400
gagatccttt ttttctgcgc gtaatctgct gcttgcaaac aaaaaaacca ccgctaccag    5460
```

```
cggtggtttg tttgccggat caagagctac caactcttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagataccta cagcgtgagc tatgagaaag cgccacgctt cccgaaggga    5820
gaaaggcgga caggtatccg gtaagcggca gggtcggaac aggagagcgc acgagggagc    5880
ttccaggggg aaacgcccgg tatctttata gtcctgtcgg gtttcgccac ctctgacttg    5940
agcgtcgatt tttgtgatgc tcgtcagggg ggcggagcct atggaaaaac gccagcaacg    6000
cggccttttt acggttcctg gccttttgct ggccttttgc tcacatgttc gggcccaatc    6060
gacccgggcg acggccagtg aattg                                          6085
```

<210> SEQ ID NO 116
<211> LENGTH: 767
<212> TYPE: PRT
<213> ORGANISM: Artificial Sequence
<220> FEATURE:
<223> OTHER INFORMATION: E-2

<400> SEQUENCE: 116

```
Met Asp Ala Met Lys Arg Gly Leu Cys Cys Val Leu Leu Cys Gly
1               5                   10                  15

Ala Val Phe Val Ser Pro Ser Ile Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Gly Gly Ser Gly Asp Ala Ser Asp Lys Cys Leu
            180                 185                 190

Lys Phe Tyr Ser Lys Ile Ser Glu Tyr Arg Tyr Cys Tyr Ser Val
        195                 200                 205

Tyr Gly Thr Thr Leu Glu Gln Gln Tyr Asn Lys Pro Leu Cys Asp Leu
    210                 215                 220

Leu Ile Arg Cys Ile Asn Cys Gln Lys Pro Leu Cys Pro Glu Glu Lys
225                 230                 235                 240

Gln Arg His Leu Asp Lys Lys Gln Arg Phe His Asn Ile Arg Gly Arg
                245                 250                 255
```

```
Trp Thr Gly Arg Cys Met Ser Cys Cys Arg Ser Ser Arg Thr Arg Arg
            260                 265                 270

Glu Thr Gln Leu His Tyr Asn Ile Val Thr Phe Cys Cys Lys Cys Asp
            275                 280                 285

Ser Thr Leu Arg Leu Cys Val Gln Ser Thr His Val Asp Ile Arg Thr
            290                 295                 300

Leu Glu Asp Leu Leu Met Gly Thr Leu Gly Ile Val Cys Pro Ile Cys
305                 310                 315                 320

Ser Gln Lys Pro Met His Gln Lys Arg Thr Ala Met Phe Gln Asp Pro
                325                 330                 335

Gln Glu Arg Pro Arg Lys Leu Pro His Leu Cys Thr Glu Leu Gln Thr
            340                 345                 350

Thr Ile His Asp Ile Ile Leu Glu Cys Val Tyr Cys Lys Gln Gln Leu
            355                 360                 365

Leu Arg Arg Glu Val Tyr Asp Phe Ala Phe Arg Asp Leu Cys Ile Val
    370                 375                 380

Tyr Arg Asp Gly Asn Pro Tyr Ala Val Cys Asp Lys Cys Leu Lys Phe
385                 390                 395                 400

Tyr Ser Lys Ile Ser Glu Tyr Arg Tyr Met His Gly Asp Thr Pro Thr
                405                 410                 415

Leu His Glu Tyr Met Leu Asp Leu Gln Pro Glu Thr Thr Asp Leu Tyr
            420                 425                 430

Cys Tyr Glu Gln Leu Asn Asp Ser Ser Glu Glu Glu Asp Glu Ile Asp
            435                 440                 445

Gly Pro Ala Gly Gln Ala Glu Pro Asp Arg Ala His Tyr Asn Ile Val
    450                 455                 460

Thr Phe Cys Cys Lys Cys Asp Ser Thr Leu Met Ala Arg Phe Glu Asp
465                 470                 475                 480

Pro Thr Arg Arg Pro Tyr Lys Leu Pro Asp Leu Cys Thr Glu Leu Asn
                485                 490                 495

Thr Ser Leu Gln Asp Ile Glu Ile Thr Cys Val Tyr Cys Lys Thr Val
            500                 505                 510

Leu Glu Leu Thr Glu Val Phe Glu Phe Ala Phe Lys Asp Leu Phe Val
            515                 520                 525

Val Tyr Arg Asp Ser Ile Pro His Ala Ala Cys His Lys Cys Ile Asp
    530                 535                 540

Phe Tyr Ser Arg Ile Arg Glu Leu Arg Tyr Tyr Ser Asp Ser Val Met
545                 550                 555                 560

Tyr Gly Pro Lys Ala Thr Leu Gln Asp Ile Val Leu His Leu Glu Pro
                565                 570                 575

Gln Asn Glu Ile Pro Val Asp Leu Leu Cys His Glu Gln Leu Ser Asp
            580                 585                 590

Ser Glu Glu Glu Asn Asp Glu Ile Asp Gly Val Asn His Gln His Leu
            595                 600                 605

Pro Ala Arg Arg Ala Glu Pro Gln Arg His Thr Met Leu Cys Met Cys
    610                 615                 620

Phe Tyr Ser Arg Ile Arg Glu Leu Arg Tyr Tyr Ser Asp Ser Val Tyr
625                 630                 635                 640

Gly Asp Thr Leu Glu Lys Leu Thr Asn Thr Gly Leu Tyr Asn Leu Leu
                645                 650                 655

Ile Arg Cys Leu Arg Cys Gln Lys Pro Leu Asn Pro Ala Glu Lys Leu
            660                 665                 670
```

-continued

```
Arg His Leu Asn Glu Lys Arg Arg Phe His Lys Ile Ala Gly His Tyr
        675                 680                 685

Arg Gly Gln Cys His Ser Cys Cys Asn Arg Ala Arg Gln Glu Arg Leu
    690                 695                 700

Gln Arg Arg Glu Thr Gln Val Ala Arg Arg Ala Glu Pro Gln Arg
705                 710                 715                 720

His Thr Met Leu Cys Met Cys Cys Lys Cys Glu Ala Arg Ile Glu Leu
                725                 730                 735

Val Val Glu Ser Ser Ala Asp Asp Leu Arg Ala Phe Gln Gln Leu Phe
            740                 745                 750

Leu Ser Thr Leu Ser Phe Val Cys Pro Trp Cys Ala Ser Gln Gln
        755                 760                 765
```

METHODS OF TREATING CERVICAL CANCER

REFERENCE TO SEQUENCE LISTING SUBMITTED ELECTRONICALLY

The content of the electronically submitted sequence listing (Name: 2629_0030003_SequenceListing.txt; Size: 220,742 bytes; and Date of Creation: Feb. 14, 2017) was originally submitted in the International Application No. PCT/M2015/056214 and is incorporated herein by reference in its entirety.

BACKGROUND OF THE INVENTION

Field of Invention

This invention relates to the treatment of cervical tumor caused by human papillomavirus (HPV) infection. In particular, the invention provides methods for improving cervical tumor treatment and methods for treating cervical tumor caused by HPV infection.

Persistent viral infection often induces functional inactivation of virus-specific CD8 T cells, impairing their capacity to proliferate, produce immune-stimulatory cytokines, and lyse virally infected cells (Wherry, E. J. and Ahmed, R., *Journal of Virology* 78:5535-5545, 2004). Cervical cancer is one of the leading causes of cancer death in women worldwide (Einstein, M. H., et al. *The Lancet infectious diseases* 9:347-356 (2009); Parkin, D. M. and Bray, F., *Vaccine* 24(3S):11-25, 2007), and about 75% of its cases are caused by persistent infection with the most common high-risk human papillomavirus (HPV) types, namely HPV16 and HPV18 (Schiffman, M., et al., *Lancet* 370:890-907, 2007; Forman, D., et al., *Vaccine* 30(5S):F12-23, 2012). HPV persistence is usually associated with the lack of demonstrable HPV-specific T-cell immunity, and the virus-specific T cells found in pre-malignant and malignant patients are reported to be generally dysfunctional and sometimes even suppressive (de Vos van Steenwijk, P. J., et al., *Clinical cancer research: an official journal of the American Association for Cancer Research* 14:7188-7195, 2008; Trimble, C. L., *Cancer immunology, immunotherapy: CII* 59:799-803, 2010). These findings suggest that the functional impairment of virus-specific T cells might be associated with the emergence of HPV-induced cervical cancer.

Cervical cancer arises via a course of high-risk HPV infection, viral persistence, clonal expansion and differentiation of persistently infected cells to a pre-malignant lesion, and their gradual transformation into invasive cancer (Schiffman, M., et al., *Lancet* 370:890-907, 2007). The pre-malignant cervical intraepithelial neoplasia 2 and 3 (CIN2 and 3), in particular those positive for HPV16, are considered as high-grade lesions that have approximately a 30% chance of developing into invasive cancer (Moscicki, A. B., et al., *Vaccine* 30(5S):F24-33, 2012). Therefore, there is urgent need for an effective therapeutic vaccine that can prevent severe complication of persistent HPV infection and eradicate HPV-related neoplasia.

HPV E6 and E7 act as viral oncoproteins by binding and promoting degradation of tumor suppressor proteins, p53 and retinoblastoma (pRb), respectively (Yugawa, T. and Kiyono, T., *Reviews in medical virology* 19:97-113, 2009). These viral oncoproteins are an ideal set of targets for a therapeutic vaccine against CIN2/3 and cervical cancer not only because these proteins induce tumorigenesis but they are also constitutively expressed in HPV-infected pre-malignant and malignant cells (Yugawa, T. and Kiyono, T., *Reviews in medical virology* 19:97-113, 2009). Since the regression of cervical lesions is associated with the presence of a cellular, but not humoral, immune response (Deligeoroglou, E., et al., *Infectious diseases in obstetrics and gynecology* 2013:540850, 2013; Woo, Y. L., et al., *International journal of cancer Journal international du cancer* 126:133-141, 2010), a therapeutic vaccine capable of selectively inducing robust E6/E7-specific T-cell immunity is highly desirable.

BRIEF SUMMARY OF THE INVENTION

The present invention is directed to a method for identifying a subject who does not require a surgery for removal of a cervical tumor comprising administering an effective amount of a polynucleotide encoding a fusion protein to the subject, wherein the subject exhibits an increased cellular immune response after the administration, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18. In specific embodiments, the method described herein further comprises measuring the increased cellular immune response of the subject after administration. In some embodiments, the method described herein further comprised instructing a healthcare provider to measure the increased cellular immune response of the subject after administration.

Also disclosed is a method of treating cervical tumor without a surgery comprising administering a polynucleotide encoding a fusion protein which comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18, wherein the fusion protein does not bind to pRb or does not form a dimer with an E7 protein of HPV16 or HPV18, wherein the subject exhibits an increased cellular immune response after the administration, wherein the cellular immune response is increased at least 2 fold after the administration, and wherein the cervical tumor is removed from the subject without a surgery.

Further disclosed is a method of treating cervical tumor comprising (a) identifying a subject who does not exhibit an increased cellular immune response after administration of a polynucleotide encoding a fusion protein and (b) determining the subject to be suitable for surgery to remove the cervical tumor, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is method of treating cervical tumor in a subject in need thereof comprising (a) identifying a subject who does not exhibit an increased cellular immune response after administration of a polynucleotide encoding a fusion protein and (b) instructing a healthcare provider to perform a surgery on the subject to remove the cervical tumor, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Also provided is a method of treating cervical tumor in a subject in need thereof comprising (a) administering a polynucleotide encoding a fusion protein to a subject in need thereof, (b) identifying the subject who does not exhibit an increased cellular immune response after administration of the fusion protein and (c) determining the subject to be suitable for surgery to remove the cervical tumor, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18. In some embodiments, identifying the subject comprises measuring the increased cellular immune response.

Also disclosed is a method of treating cervical tumor in a subject in need thereof comprising administering a polynucleotide encoding a fusion protein to a population of subjects, where each of the subjects carries human leucocyte antigens (HLA)-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is a method of treating cervical tumor in a subject comprising (a) identifying a subject who carries HLA-A02 and (b) administering a polynucleotide encoding a fusion protein which comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Also disclosed is a method of improving cervical tumor treatment comprising (a) administering a polynucleotide encoding a fusion protein to a population of subjects, each of the subjects carries human leucocyte antigens (HLA)-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is a method of improving cervical tumor treatment comprising (a) identifying a subject who carries HLA-A02 and (b) administering to the subject a polynucleotide encoding a fusion protein which comprises two or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Some embodiments disclose a method of improving cervical tumor treatment comprising (a) submitting a blood sample obtained from a subject in need thereof to identify the HLA type and (b) administering a polynucleotide encoding a fusion protein to the subject who carries HLA-A02, wherein the fusion protein comprises three or more amino acid sequences selected from:

(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18. In some embodiments, the subject exhibits an increased cellular immune response after the administration.

Also disclosed is a method of treating cervical tumor comprising (a) administering a first dose of a polynucleotide encoding a fusion protein to a subject in need thereof and (b) further administering to the subject a second dose of the polynucleotide if the subject exhibits increased cellular immune response after administration of the first dose, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is a method of treating cervical tumor comprising (a) administering a first dose of a polynucleotide encoding a fusion protein to a subject in need thereof, (b) measuring cellular immune response after the administration, and (c) administering a second dose of the polynucleotide to the subject who exhibits an increased cellular immune response after administration of the first dose, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18. Also disclosed is the method described herein, further comprising measuring the cellular immune response after administration of the second dose. Further disclosed is the method described herein, further comprising administering a third dose of the polynucleotide.

Certain embodiments disclose a method of treating cervical tumor comprising (a) administering a first dose and a second dose of a polynucleotide encoding a fusion protein to a subject in need thereof and (b) further administering to the subject a third dose of the polynucleotide if the subject exhibits increased cellular immune response after administration of the first dose or the second dose, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is a method of treating cervical tumor comprising (a) administering a first dose and a second dose of a polynucleotide encoding a fusion protein to a subject in need thereof, (b) measuring cellular immune response after the administration of the first dose or the second dose, and (c) administering to the subject a third dose of the polynucleotide if the subject exhibits an increased cellular immune response after administration of the first or second dose, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is a method of increasing systemic HPV-specific poly-functional CD8 T cell response in a subject in need thereof comprising administering a polynucleotide encoding a fusion protein which comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18, wherein the fusion protein does not bind to pRb or does not form a dimer with an E7 protein of HPV16 or HPV18, and wherein the poly-functional CD8 T cell response comprises increased expression of IFN-γ, IL-2, TNF-α, or any combination thereof.

Further disclosed is a pharmaceutical kit comprising a pharmaceutical composition which comprises a polynucleotide encoding a fusion protein and instructions to perform a surgery to remove a cervical tumor if the cellular immune response after administration of an effective amount of the pharmaceutical composition is not increased, wherein the fusion protein comprises three or more amino acid sequences selected from:
(1) an N-terminal portion of an E6 protein of HPV16,
(2) a C-terminal portion of an E6 protein of HPV16, (3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Also disclosed is a pharmaceutical kit comprising a pharmaceutical composition which comprises a polynucleotide encoding a fusion protein and instructions to administer an effective amount of the pharmaceutical composition to a subject who shows an increased number of polyfunctional T cells after administration of an initial amount of the polynucleotide, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is a pharmaceutical kit comprising a pharmaceutical composition which comprises a polynucleotide encoding a fusion protein and instructions to administer an effective amount of the pharmaceutical composition to a subject who carries HLA-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Also disclosed is a pharmaceutical kit comprising a pharmaceutical composition which comprises a polynucleotide encoding a fusion protein and instructions to administer an effective amount of the pharmaceutical composition to a subject who shows an increased number of polyfunctional T cells after administration of an initial amount of the polynucleotide, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

Further disclosed is a pharmaceutical kit comprising a pharmaceutical composition which comprises a polynucleotide encoding a fusion protein and instructions to discontinue further administration of the pharmaceutical composition if a single dose or two doses of the pharmaceutical composition to a subject does not exhibit an increased cellular immune response, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18.

EMBODIMENTS

Embodiment (E) 1

A method for identifying a subject who does not require a surgery for removal of a cervical tumor comprising administering an effective amount of a polynucleotide encoding a fusion protein to the subject, wherein the subject exhibits an increased cellular immune response after the administration, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E2

The method of embodiment E1, further comprising measuring the increased cellular immune response of the subject after administration.

E3

The method of embodiment E1, further comprising instructing a healthcare provider to measure the increased cellular immune response of the subject after administration.

E4

A method of treating a cervical tumor without a surgery comprising administering a polynucleotide encoding a fusion protein which comprises three or more amino acid sequences selected from:
(1) an N-terminal portion of an E6 protein of HPV16,
(2) a C-terminal portion of an E6 protein of HPV16, (3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18, wherein the fusion protein does not bind to pRb or does not form a dimer with an E7 protein of HPV16 or HPV18, wherein the subject exhibits an increased cellular immune response after the administration, wherein the cellular immune response is increased at least 2 fold after the administration, and wherein the cervical tumor is removed from the subject without a surgery.

E5

A method of treating a cervical tumor comprising (a) identifying a subject who does not exhibit an increased cellular immune response after administration of a polynucleotide encoding a fusion protein and (b) determining the subject to be suitable for surgery to remove the cervical tumor, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E6

A method of treating a cervical tumor in a subject in need thereof comprising (a) identifying a subject who does not exhibit an increased cellular immune response after administration of a polynucleotide encoding a fusion protein and (b) instructing a healthcare provider to perform a surgery on the subject remove the cervical tumor, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E7

A method of treating a cervical tumor in a subject in need thereof comprising (a) administering a polynucleotide encoding a fusion protein to a subject in need thereof, (b) identifying the subject who does not exhibit an increased cellular immune response after administration of the fusion protein and (c) determining the subject to be suitable for surgery to remove the cervical tumor, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E8

The method of any one of embodiment E5 to E7, wherein identifying the subject comprises measuring the increased cellular immune response.

E9

A method of treating a cervical tumor in a population of subjects in need thereof comprising administering a polynucleotide encoding a fusion protein to the population of subjects, wherein each of the subjects carries human leucocyte antigens (HLA)-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E10

A method of treating a cervical tumor in a subject in need thereof comprising (a) identifying a subject who carries HLA-A02 and (b) administering to the subject a polynucleotide encoding a fusion protein which comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E11

A method of improving cervical tumor treatment comprising administering a polynucleotide encoding a fusion protein to a population of subjects, wherein each of the subjects carries human leucocyte antigens (HLA)-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E12

A method of improving cervical tumor treatment comprising (a) identifying a subject who carries HLA-A02 and (b) administering to the subject a polynucleotide encoding a fusion protein which comprises two or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E13

A method of improving cervical tumor treatment comprising (a) submitting a blood sample obtained from a subject in need thereof to identify the HLA type and (b) administering a polynucleotide encoding a fusion protein to the subject who carries HLA-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E14

The method of any one of embodiment E9 to E13, wherein the subject exhibits an increased cellular immune response after the administration.

E15

A method of treating cervical tumor comprising (a) administering a first dose of a polynucleotide encoding a fusion protein to a subject in need thereof and (b) further administering a second dose of the polynucleotide to the subject who exhibits increased cellular immune response after administration of the first dose, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E16

A method of treating cervical tumor comprising (a) administering a first dose of a polynucleotide encoding a fusion protein to a subject in need thereof, (b) measuring cellular immune response after the administration, and (c) administering a second dose of the polynucleotide to the subject who exhibits an increased cellular immune response after administration of the first dose, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E17

The method of embodiment E15 or E16, further comprising measuring the cellular immune response after administration of the second dose.

E18

The method of any one of embodiment E15 to E17, further comprising administering a third dose of the polynucleotide.

E19

A method of treating cervical tumor comprising (a) administering a first dose and a second dose of a polynucleotide encoding a fusion protein to a subject in need thereof and (b) further administering to the subject a third dose of the polynucleotide to the subject who exhibits increased cellular immune response after administration of the first dose or the second dose, wherein the fusion protein comprises three or more amino acid sequences selected from:
(1) an N-terminal portion of an E6 protein of HPV16,
(2) a C-terminal portion of an E6 protein of HPV16, (3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E20

A method of treating cervical tumor comprising (a) administering a first dose and a second dose of a polynucleotide encoding a fusion protein to a subject in need thereof, (b) measuring cellular immune response after the administration of the first dose or the second dose, and (c) administering to the subject a third dose of the polynucleotide if the subject exhibits an increased cellular immune response after administration of the first or second dose, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E21

The method of any one of embodiment E15 to E20, wherein the first dose is at least about 0.5 mg, at least about 1 mg, at least about 1.5 mg, at least about 2 mg, at least about 2.5 mg, at least about 3 mg, at least about 3.5 mg, at least about 4 mg, at least about 4.5 mg, or at least about 5 mg.

E22

The method of any one of embodiment E15 to E21, wherein the second dose is at least about 0.5 mg, at least about 1 mg, at least about 1.5 mg, at least about 2 mg, at least about 2.5 mg, at least about 3 mg, at least about 3.5 mg, at least about 4 mg, at least about 4.5 mg, or at least about 5 mg.

E23

The method of any one of embodiment E18 to E22, wherein the first dose and the second dose are identical or different.

E24

The method of any one of embodiment E18 to E23, wherein the third dose is at least about 0.5 mg, at least about 1 mg, at least about 1.5 mg, at least about 2 mg, at least about 2.5 mg, at least about 3 mg, at least about 3.5 mg, at least about 4 mg, at least about 4.5 mg, or at least about 5 mg.

E25

The method of any one of embodiment E18 to E24, wherein the first dose, the second dose, and the third dose are identical.

E26

The method of any one of embodiment E18 to E24, wherein the first dose, the second dose, and the third dose are different.

E27

The method of any one of embodiment E15 to E26, wherein the first dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg and the second dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg.

E28

The method of any one of embodiment E18 to E27, wherein the third dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg.

E29

The method of any one of embodiment E15 to E28, wherein the first dose is about 1 mg to about 4 mg and the second dose is about 1 mg to about 4 mg.

E30

The method of any one of embodiment E18 to E29, wherein the third dose is about 1 mg to about 4 mg.

E31

The method of embodiment E30, wherein the first dose is about 1 mg, the second dose is about 1 mg, and the third dose is about 1 mg. E

E32

The method of embodiment E30, wherein the first dose is about 2 mg, the second dose is about 2 mg, and the third dose is about 2 mg.

E33

The method of embodiment E30, wherein the first dose is about 4 mg, the second dose is about 4 mg, and the third dose is about 4 mg.

E34

The method of any one of embodiment E1 to E8 and E14 to E33, wherein the increased cellular immune response is increased CD8 T cell response, increased CD4 T cell response, increased cytokine secretion, or any combination thereof.

E35

The method of any one of embodiment E1 to E8 and E14 to E34, wherein the increased cellular immune response is increased number of poly-functional T cells.

E36

The method of any one of embodiment E1 to E8 and E14 to E35, wherein the poly-functional T cells exhibit at least three, at least four, or at least five markers selected from IFN-γ, IL-2, TNF-α, MIP-β, and CD107a/b when measured by flow cytometry.

E37

The method of embodiment E35 or E36, wherein the number of the poly-functional T cells is increased at least about 5%, at least about 6%, at least about 7%, at least about 8%, at least about 9%, at least about 10%, at least about 15%, at least about 20%, or at least about 30% higher than the number of the poly-functional T cells prior to the administration of the polynucleotide.

E38

The method of embodiment E34, wherein the increased CD8 T cell response comprises increased expression of IFN-γ, IL-2, TNF-α, MIP-β, CD107a/b, or any combinations thereof.

E39

The method of embodiment E34, wherein the increased CD8 T cell response comprises increased CD38+ Ki67+ CD8 T cells.

E40

The method of embodiment E39, wherein the increased CD8 T cell response is at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, at least about 15 fold, at least about 16 fold, at least about 17 fold, at least about 18 fold, at least about 19 fold, at least about 20 fold, at least about 21 fold, at least about 22 fold, at least about 23 fold, at least about 24 fold, or at least about 25 fold increase in the number of CD38+ Ki67+ CD8 T cells.

E41

The method of any one of embodiment E34 to E40, wherein the increased CD8 T cell response is measured by a flow cytometry.

E42

The method of any one of embodiment E34 to E41, wherein the increased CD4 T cell response comprises increased IFN-γ+ CD4 cells.

E43

The method of any one of embodiment E34 to E42, wherein the increased CD4 T cell response is at least about 1.5, 2.0, 2.5, 3.0, 3.5, or 4.0 fold increase in the number of IFN-γ+ CD4 cells.

E44

The method of any one of embodiment E34 to E43, wherein the increased cellular immune response comprises increased HPV16 and HPV18 E6 and E7 specific IFN-γ response.

E45

The method of embodiment E44, wherein the IFN-γ response is measured by IFN-γ ELISPOT assay.

E46

The method of any one of embodiment E34 to E45, wherein the increased cytokine expression comprises increased expression of IFN-γ, IL-2, TNF-α, or any combination thereof.

E47

The method of embodiment E46, wherein the IFN-γ expression is increased at least 5 fold, at least 10 fold, at least 20 fold, at least 30 fold, at least 40 fold, at least 45 fold, at least 50 fold relative to the level prior to the administration.

E48

The method of embodiment E46, wherein the IL-2 expression is increased at least 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, or at least about 15 fold relative to the level prior to the administration.

E49

The method of embodiment E46, wherein the TNF-α expression is increased at least about 2 fold, at least about 3 fold, at least about 4 fold, at least about 5 fold, at least about 10 fold, at least about 15 fold, at least about 16 fold, at least about 17 fold, at least about 18 fold, at least about 19 fold, at least about 20 fold, at least about 21 fold, at least about 22 fold, at least about 23 fold, at least about 24 fold, or at least about 25 fold relative to the level prior to the administration.

E50

The method of any one of embodiment E1 to E49, wherein IL-4 or IL-17a expression is not increased after the administration.

E51

The method of any one of embodiment E15 to E50, wherein the second dose is administered at least about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks after the first dose.

E52

The method of any one of embodiment E18 to E51, wherein the third dose is administered at least about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks after the second dose.

E53

The method of any one of embodiment E1 to E52, wherein the polynucleotide is administered by electroporation.

E54

The method of any one of embodiment E1 to E53, wherein the cervical tumor is a benign tumor or a malignant tumor.

E55

The method of any one of embodiment E1 to E54, wherein the cervical tumor is squamous cell carcinoma (SCC), adenocarcinoma, adenosquamous carcinoma, small cell carcinoma, neuroendocrine tumor (NET), glassy cell carcinoma, villoglandular adenocarcinoma (VGA), non-carcinoma malignancies, melanoma, lymphoma, or cervical intraepithelial neoplasia (CIN).

E56

The method of any one of embodiment E1 to E55, wherein the cervical tumor is CIN1, CIN2, CIN3, or cervical cancer.

E57

A method of increasing systemic HPV-specific polyfunctional CD8 T cell response in a subject in need thereof comprising administering a polynucleotide encoding a fusion protein which comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18, wherein the fusion protein does not bind to pRb or does not form a dimer with an E7 protein of HPV16 or HPV18, and wherein the poly-functional CD8 T cell response comprises increased expression of IFN-γ, IL-2, TNF-α, or any combination thereof.

E58

The method of embodiment E57, wherein the administration comprises at least two doses or three doses.

E59

The method of embodiment E57 or E58, wherein the IFN-γ expression is increased at least 5 fold, at least about 10 fold, at least about 20 fold, at least about 30 fold, at least about 40 fold, at least about 45 fold, at least about 50 fold relative to the level prior to the administration.

E60

The method of any one of embodiment E57 to E59, wherein the IL-2 expression is increased at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, or at least about 15 fold relative to the level prior to the administration.

E61

The method of any one of embodiment E57 to E60, wherein the TNF-α expression is increased at least about 2 fold, at least about 3 fold, at least about 4 fold, at least about 5 fold, at least about 10 fold, at least about 15 fold, at least about 16 fold, at least about 17 fold, at least about 18 fold, at least about 19 fold, at least about 20 fold, at least about 21 fold, at least about 22 fold, at least about 23 fold, at least about 24 fold, or at least about 25 fold relative to the level prior to the administration.

E62

The method of any one of embodiment E57 to E61, wherein IL-4 or IL-17a expression is not increased after the administration.

E63

A pharmaceutical kit comprising a pharmaceutical composition which comprises a polynucleotide encoding a fusion protein and instructions to perform a surgery to remove a cervical tumor if the cellular immune response after administration of an effective amount of the pharmaceutical composition is not increased, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E64

A pharmaceutical kit comprising a pharmaceutical composition which comprises a polynucleotide encoding a fusion protein and instructions to administer an effective amount of the pharmaceutical composition to a subject who shows an increased number of poly-functional T cells after administration of an initial amount of the polynucleotide, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E65

A pharmaceutical kit comprising a pharmaceutical composition which comprises a polynucleotide encoding a fusion protein and instructions to administer an effective amount of the pharmaceutical composition to a subject who carries HLA-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E66

The kit of any one of embodiment E63 to E65, wherein the effective amount is at least 1 mg, 2 mg, 3 mg, 4 mg, 5 mg, or 6 mg.

E67

A pharmaceutical kit comprising a pharmaceutical composition which comprises a polynucleotide encoding a fusion protein and instructions to discontinue further administration of the pharmaceutical composition if a single dose or two doses of the pharmaceutical composition to a subject does not exhibit an increased cellular immune response, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV 18 and wherein the fusion protein does not bind to pRb or does not form a dimer with an E7 protein of HPV16 or HPV18.

E68

The kit of embodiment E67, wherein the single dose is at least about 0.5 mg, 1 mg, 1.5 mg, 2 mg, 2.5 mg, 3 mg, 3.5 mg, 4 mg, 4.5 mg, or 5 mg.

E69

The kit of embodiment E67 or E68, wherein the two doses comprises a first dose and a second dose, wherein the first dose is at least about 0.5 mg, 1 mg, 1.5 mg, 2 mg, 2.5 mg, 3 mg, 3.5 mg, 4 mg, 4.5 mg, or 5 mg and the second dose is at least about 0.5 mg, 1 mg, 1.5 mg, 2 mg, 2.5 mg, 3 mg, 3.5 mg, 4 mg, 4.5 mg, or 5 mg.

E70

The kit of any one of embodiment E67 to E69, wherein the first dose and the second dose are identical.

E71

The kit of any one of embodiment E67 to E69, wherein the first dose and the second dose are different.

E72

The kit of any one of embodiment E67 to E71, wherein the first dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg and the second dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg.

E73

The kit of any one of embodiment E67 to E71, wherein the first dose is about 1 mg to 4 mg and the second dose is about 1 mg to about 4 mg.

E74

The kit of embodiment E73, wherein the first dose is about 1 mg and the second dose is about 1 mg.

E75

The kit of embodiment E73, wherein the first dose is about 2 mg and the second dose is about 2 mg.

E76

The kit of embodiment E73, wherein the first dose is about 4 mg and the second dose is about 4 mg.

E77

The method of any one of embodiment E1 to E62 or the kit of any one of embodiment E63 to E76, wherein the fusion protein comprises at least four, at least five, at least six, at least seven or eight amino acid sequences selected from
(1) an N-terminal portion of an E6 protein of HPV16,
(2) a C-terminal portion of an E6 protein of HPV16,
(3) an N-terminal portion of an E7 protein of HPV16, (4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18.

E78

The method of any one of embodiment E1 to E62 and 77 or the kit of any one of embodiment E63 to E77, wherein the fusion protein comprises the same number of the epitopes that are contained in the naturally occurring E6 protein of HPV16, the naturally occurring E6 protein of HPV18, the naturally occurring E7 protein of HPV18 and the naturally occurring E7 protein of HPV18, or more epitopes than the epitopes contained in the naturally occurring E6 protein of HPV16, the naturally occurring E6 protein of HPV18, the naturally occurring E7 protein of HPV18 and the naturally occurring E7 protein of HPV18.

E79

The method of any one of embodiment E1 to E62 and E77 and E78 or the kit of any one of embodiment E63 to E78, wherein each of the N-terminal portion of an E6 protein of HPV16, the C-terminal portion of an E6 protein of HPV16, an N-terminal portion of an E6 protein of HPV18, and the C-terminal portion of an E6 protein of HPV18 does not comprise the complete E6-associated protein (E6AP) binding site.

E80

The method or the kit of embodiment E79, wherein the complete E6AP binding site comprises amino acids 35 to 136 corresponding to SEQ ID NO: 2 (E6 HPV16) or amino acids 30 to 131 corresponding to SEQ ID NO: 4 (E6 HPV18).

E81

The method of any one of embodiment E1 to E62 and E77 to E80 or the kit of any one of embodiment E63 to E76 and E77 to E80, wherein each of the N-terminal portion of an E7 protein of HPV16, the C-terminal portion of an E7 protein of HPV16, an N-terminal portion of an E7 protein of HPV18, and the C-terminal portion of an E7 protein of HPV18 does not comprise the complete CR2 domain or the complete CR3 domain.

E82

The method or the kit of embodiment E81, wherein the complete CR2 domain and the CR3 domain are amino acids 18 to 98 corresponding to SEQ ID NO: 6 (E7 HPV16) or amino acids 21 to 105 corresponding to SEQ ID NO: 8 (E7 HPV18).

E83

The method of any one of embodiment E1 to E62 and E77 to E82 and the kit of any one of embodiment E63 to E76 and E77 to E82, wherein the N terminal portion of an E6 protein of HPV16 comprises an amino acid sequence at least 80%, at least 85%, at least 90%, at least 95%, at least 96%, at least 97%, at least 98%, at least 99%, or 100% identical to the N terminal sequence of SEQ ID NO: 2 (16E6Na-b), wherein a is an amino acid selected from amino acid residue 1 or 2 corresponding to SEQ ID NO: 2 and b is an amino acid selected from amino acid residues 35 to 135 corresponding to SEQ ID NO: 2 and wherein the C-terminal portion of an E6 protein of HPV16 comprises an amino acid sequence at least 80%, at least 85%, at least 90%, at least 95%, at least 96%, at least 97%, at least 98%, at least 99%, or 100% identical to the C-terminal sequence of SEQ ID NO: 2 (16E6Cc-d), wherein c is an amino acid selected from amino acid residues equal to or higher than 36 and amino acid residues equal to or lower than amino acid b+1 corresponding to SEQ ID NO: 2 and d is an amino acid selected from amino acid residue 157 or 158 corresponding to SEQ ID NO: 2

E84

The method or the kit of embodiment E83, wherein b is an amino acid selected from amino acid residues 35 to 39, 57 to 62, 69 to 85, 87 to 88, 98 to 99, 107, 109, 114, and 135 corresponding to SEQ ID NO: 2.

E85

The method or the kit of embodiment E83 or E84, wherein b is amino acid residue 35 and c is an amino acid residue 36; b is amino acid residue 36 and c is amino acid residue 36 or 37; b is amino acid residue 37 and c is amino acid residue 36, 37, or 38; b is amino acid residue 38 and c is amino acid residue 36, 37, 38, or 39; b is amino acid residue 39 and c is amino acid residue 36, 37, 38, 39, or 40; b is amino acid residue 57 and c is an amino acid selected from amino acid residue 36 to 58; b is amino acid residue 58 and c is an amino acid selected from amino acid residues 36 to 59; b is amino acid residue 59 and c is an amino acid selected from amino acid residues 36 to 60; b is amino acid residue 60 and c is an amino acid selected from amino acid residues 36 to 61; b is amino acid residue 61 and c is an amino acid selected from amino acid residues 36 to 62; b is amino acid residue 62 and c is an amino acid selected from amino acid residues 36 to 63; b is amino acid residue 69 and c is an amino acid selected from amino acid residues 36 to 70; b is amino acid residue 70 and c is an amino acid selected from amino acid residues 36 to 71; b is amino acid residue 71 and c is an amino acid selected from amino acid residues 36 to 72; b is amino acid residue 72 and c is an amino acid selected from amino acid residues 36 to 73; b is amino acid residue 73 and c is an amino acid selected from amino acid residues 36 to 74; b is amino acid residue 74 and c is an amino acid selected from amino acid residues 36 to 75; b is amino acid residue 75 and c is an amino acid selected from amino acid residues 36 to 76; b is amino acid residue 76 and c is an amino acid selected from amino acid residues 36 to 77; b is amino acid residue 77 and c is an amino acid selected from amino acid residues 36 to 78; b is amino acid residue 78 and c is an amino acid selected from amino acid residues 36 to 79; b is amino acid residue 79 and c is an amino acid selected from amino acid residues 36 to 80; b is amino acid residue 80 and c is an amino acid selected from amino acid residues 36 to 81; b is amino acid residue 81 and c is an amino acid selected from amino acid residues 36 to 82; b is amino acid residue 82 and c is an amino acid selected from amino acid residues 36 to 83; b is amino acid residue 83 and c is an amino acid selected from amino acid residues 36 to 84; b is amino acid residue 84 and c is an amino acid selected from amino acid residues 36 to 85; b is amino acid residue 85 and c is an amino acid selected from amino acid residues 36 to 86; b is amino acid residue 87 and c is an amino acid selected from amino acid residues 36 to 88; b is amino acid residue 88 and c is an amino acid selected from amino acid residues 36 to 89; b is amino acid residue 98 and c is an amino acid selected from amino acid residues 36 to 99; b is amino acid residue 99 and c is an amino acid selected from amino acid residues 36 to 100; b is amino acid residue 107 and c is an amino acid selected from amino acid residues 36 to 108; b is amino acid residue 109 and c is an amino acid selected from amino acid residues 36 to 110; b is amino acid residue 114 and c is an amino acid selected from amino acid residues 36 to 115; or b is amino acid residue 135 and c is an amino acid selected from amino acid residues 36 to 136 corresponding to SEQ ID NO: 2.

E86

The method of any one of embodiment E1 to E62 and E77 to E85 and the kit of any one of embodiment E63 to E85, wherein the N-terminal portion of an E6 protein of HPV18 comprises an amino acid sequence at least 80%, at least 85%, at least 90%, at least 95%, at least 96%, at least 97%, at least 98%, at least 99%, or 100% identical to the N-terminal sequence of SEQ ID NO: 4 (18E6Ni-j), wherein i is an amino acid selected from amino acid residue 1 or 2 corresponding to SEQ ID NO: 4 and j is an amino acid selected from amino acid residues 30 to 130 corresponding to SEQ ID NO: 4 and wherein the C-terminal portion of an E6 protein of HPV18 comprises an amino acid sequence at least 80%, at least 85%, at least 90%, at least 95%, at least 96%, at least 97%, at least 98%, at least 99%, or 100% identical to the C-terminal sequence of SEQ ID NO: 4 (18E6Ck-l), wherein k is an amino acid selected from amino acid residues equal to or higher than 31 and amino acid residues equal to or lower than j+1 corresponding to SEQ ID NO: 4 and l is an amino acid selected from amino acid residue 157 or 158 corresponding to SEQ ID NO: 4.

E87

The method or the kit of embodiment E85, wherein j is an amino acid selected from amino acid residues 30 to 34, 52 to 57, 64 to 80, 82 to 83, 93, 94, 102, 104, 109, and 130 corresponding to SEQ ID NO: 4.

E88

The method or the kit of embodiment E86 or E87, wherein j is amino acid residue 30 and k is an amino acid residue 31; j is amino acid residue 31 and k is amino acid residue 31 or 32; j is amino acid residue 32 and k is amino acid residue 31, 32, or 33; j is amino acid residue 33 and k is amino acid residue 31, 32, 33, or 34; j is amino acid residue 34 and k is amino acid residue 31, 32, 33, 34 or 35; j is amino acid residue 52 and k is an amino acid selected from amino acid residue 31 to 53; j is amino acid residue 53 and k is an amino acid selected from amino acid residue 31 to 54; j is amino acid residue 54 and k is an amino acid selected from amino acid residues 31 to 55; j is amino acid residue 55 and k is an amino acid selected from amino acid residues 31 to 56; j is amino acid residue 56 and k is an amino acid selected from amino acid residues 31 to 57; j is amino acid residue 57 and k is an amino acid selected from amino acid residues 31 to 58 j is amino acid residue 64 and k is an amino acid selected from amino acid residues 31 to 65; j is amino acid residue 65 and k is an amino acid selected from amino acid residues 31 to 66; j is amino acid residue 66 and k is an amino acid selected from amino acid residues 31 to 67; j is amino acid residue 67 and k is an amino acid selected from amino acid residues 31 to 68; j is amino acid residue 68 and k is an amino acid selected from amino acid residues 31 to 69; j is amino acid residue 69 and k is an amino acid selected from amino acid residues 31 to 70; j is amino acid residue 70 and k is an amino acid selected from amino acid residues 31 to 71; j is amino acid residue 71 and k is an amino acid selected from amino acid residues 31 to 72; j is amino acid residue 72 and k is an amino acid selected from amino acid residues 31 to 73; j is amino acid residue 73 and k is an amino acid selected from amino acid residues 31 to 74; j is amino acid residue 74 and k is an amino acid selected from amino acid residues 31 to 75; j is amino acid residue 75 and k is an amino acid selected from amino acid residues 31 to 76; j is amino acid residue 76 and k is an amino acid selected from amino acid residues 31 to 77; j is amino acid residue 77 and k is an amino acid selected from amino acid residues 31 to 78; j is amino acid residue 78 and k is an amino acid selected from amino acid residues 31 to 79; j is amino acid residue 79 and k is an amino acid selected from amino acid residues 31 to 80; j is amino acid residue 80 and k is an amino acid selected from amino acid residues 31 to 81; j is amino acid residue 82 and k is an amino acid selected from amino acid residues 31 to 83; j is amino acid residue 83 and k is an amino acid selected from amino acid residues 31 to 84; j is amino acid residue 93 and k is an amino acid selected from amino acid residues 31 to 94; j is amino acid residue 94 and k is an amino acid selected from amino acid residues 31 to 95; j is amino acid residue 102 and k is an amino acid selected from amino acid residues 31 to 103; j is amino acid residue 104 and k is an amino acid selected from amino acid residues 31 to 105; j is amino acid residue 109 and k is an amino acid selected from amino acid residues 31 to 110; or j is amino acid residue 130 and k is an amino acid selected from amino acid residues 31 to 131 corresponding to SEQ ID NO: 4.

E89

The method of any one of embodiment E1 to E62 and E77 to E88 and the kit of any one of EM 63 to 88, wherein the N-terminal portion of an E7 protein of HPV16 comprises an amino acid sequence at least 80%, at least 85%, at least 90%, at least 95%, at least 96%, at least 97%, at least 98%, at least 99%, or 100% identical to the N terminal sequence of SEQ ID NO: 6 (16E7Ne-f), wherein e is an amino acid selected from amino acid residue 1 or 2 corresponding to SEQ ID NO: 6 and f is an amino acid selected from amino acid residues 18 to 97 corresponding to SEQ ID NO: 6 and wherein the C-terminal portion of an E7 protein of HPV16 comprises an amino acid sequence at least 80%, at least 85%, at least 90%, at least 95%, at least 96%, at least 97%, at least 98%, at least 99%, or 100% identical to the C-terminal sequence of SEQ ID NO: 6 (16E7Cg-h), wherein g is an amino acid selected from amino acid residues equal to or higher than 19 and amino acid residues equal to or lower than f+1 corresponding to SEQ ID NO: 6 and h is an amino acid selected from amino acid residue 97 or 98 corresponding to SEQ ID NO: 6.

E 90

The method or the kit of embodiment E89, wherein f is an amino acid selected from amino acid residues 18 to 39 and 44 to 97 corresponding to SEQ ID NO: 6.

E 91

The method or the kit of embodiment E89 or E90, wherein f is an amino acid residue selected from 18 to 39 corresponding to SEQ ID NO: 6 and g is an amino acid selected from amino acid residues equal to or higher than 19 and amino acid residues equal to or lower than f+1 corresponding to SEQ ID NO: 6 or wherein f is an amino acid residue selected from amino acid residues 44 to 97 corresponding to SEQ ID NO: 6 and g is an amino acid selected from amino acid residues equal to or higher than 45 and amino acid residues equal to or lower than amino acid f+1 corresponding to SEQ ID NO: 6.

E92

The method of any one of embodiment E1 to E62 and E77 to E91 and the kit of any one of embodiment E63 to E91, wherein the N-terminal portion of an E7 protein of HPV18 comprises an amino acid sequence at least 80%, at least 85%, at least 90%, at least 95%, at least 96%, at least 97%, at least 98%, at least 99%, or 100% identical to the N-terminal sequence of SEQ ID NO: 8 (18E7 Nm-n), wherein m is an amino acid selected from amino acid residue 1 or 2 corresponding to SEQ ID NO: 8 and n is an amino acid selected from amino acid residues 21 to 104 corresponding to SEQ ID NO: 8 and wherein the C-terminal portion of an E7 protein of HPV18 comprises an amino acid sequence at least 80%, at least 85%, at least 90%, at least 95%, at least 96%, at least 97%, at least 98%, at least 99%, or 100% identical to the C-terminal sequence of SEQ ID NO: 8 (18E7Co-p), wherein o is an amino acid selected from amino acid residues equal to or higher than 22 and amino acid residues equal to or lower than n+1 corresponding to SEQ ID NO: 8 and p is an amino acid selected from amino acid residue 104 or 105 corresponding to SEQ ID NO: 8.

E93

The method or the kit of embodiment E92, wherein n is an amino acid selected from amino acid residues 21 to 42 and 47 to 104 corresponding to SEQ ID NO: 8.

E94

The method or the kit of embodiment E92 or E93, wherein n is an amino acid residue selected from 21 to 41 and o is an amino acid selected from amino acid residues equal to or higher than 22 and amino acid residues equal to or lower than n+1 or wherein n is an amino acid residue selected from amino acid residues 47 to 104 and o is an amino acid selected from amino acid residues equal to or higher than 48 and amino acid residues equal to or lower than n+1 corresponding to SEQ ID NO: 8.

E95

The method of any one of embodiment E1 to E62 and E77 to E94 or the kit of any one of embodiment E63 to E94, wherein the fusion protein does not comprise the naturally occurring, full length E6 protein of HPV16, the naturally occurring, full length E7 protein of HPV16, the naturally occurring, full length E6 protein of HPV18, and the naturally occurring, full length E7 protein of HPV18.

E96

The method or the kit of embodiment E95, wherein the fusion protein comprises, from N terminus to C terminus, (i) 16E6Na-b-16E7Ne-f-16E6Cc-d-16E7Cg-h-18E6Ni-j-18E7 Nm-n-18E6Ck-l-18E7Co-p; (ii) 18E6Ni-j-18E7 Nm-n-18E6Ck-l-18E7Co-p-16E6Na-b-16E7Ne-f-16E6Cc-d-16E7Cg-h; (iii) 16E7Ne-f-16E6Na-b-16E7Cg-h-16E6Cc-d-18E7 Nm-n-18E6Ni-j-18E7Co-p-18E6Ck-l; (iv) 18E7 Nm-n-18E6Ni-j-18E7Co-p-18E6Ck-l-16E7Ne-f-16E6Na-b-16E7Cg-h-16E6Cc-d; (v) 18E6Ni-j-16E7Ne-f-16E6Cc-d-18E6Ck-l-18E7 Nm-n-16E6Na-b-18E7Co-p-16E7Cg-h; (vi) 16E6Na-b-18E6Ni-j-18E7Co-p-16E6Cc-d-16E7Ne-f-18E7 Nm-n-16E7Cg-h-18E6Ck-l; (vii) 18E7 Nm-n-16E6Na-b-18E7Co-p-16E7Cg-h-16E7Ne-f-18E6Ni-j 16E6Cc-d-18E6Ck-l; or (viii) 16E7Ne-f-18E6Ni-j-16E7Cg-h-18E7Co-p-18E7 Nm-n-16E6Na-b-18E6Ck-l-16E6Cc-d.

E97

The method or the kit of embodiment E96, wherein the fusion protein comprises, from N terminus to C terminus, 16E6Na-b-16E7Ne-f-16E6Cc-d-16E7Cg-h-18E6Ni-j-18E7 Nm-n-18E6Ck-l-18E7Co-p, a is amino acid residue 1 of SEQ ID NO: 2, b is amino acid residue 85 of SEQ ID NO: 2, c is amino acid residue 71 of SEQ ID NO: 2, d is amino acid residue 158 of SEQ ID NO: 2, e is amino acid residue 1 of SEQ ID NO: 6, f is amino acid residue 65 of SEQ ID NO: 6, g is amino acid residue 51 of SEQ ID NO: 6, h is amino acid residue 98 of SEQ ID NO: 6, i is amino acid residue 1 of SEQ ID NO: 4, j is amino acid residue 85 of SEQ ID NO: 4, k is amino acid residue 71 of SEQ ID NO: 4, l is amino acid residue 158 of SEQ ID NO: 4, m is amino acid residue 1 of SEQ ID NO: 8, n is amino acid residue 65 of SEQ ID NO: 8, o is amino acid residue 51 of SEQ ID NO: 8, and p is amino acid residue 105 of SEQ ID NO: 8.

E98

The method and the kit of embodiment E95, wherein the fusion protein comprises an amino acid sequence at least at least 80%, at least 85%, at least 90%, at least 95%, at least 96%, at least 97%, at least 98%, at least 99%, or 100% identical to SEQ ID NO: 10.

E99

The method or the kit of any one of embodiment E95 to E98, wherein the polynucleotide is codon-optimized for human expression.

E100

The method or the kit of any one of embodiment E95 to E99, wherein the polynucleotide comprises a nucleotide sequence at least at least 80%, at least 85%, at least 90%, at least 95%, at least 96%, at least 97%, at least 98%, at least 99%, or 100% identical to SEQ ID NO: 9.

E101

The method of any one of embodiment E1 to E62 and E77 to E100 or the kit of any one of embodiment E63 to E100, wherein the polynucleotide further comprises a nucleic acid sequence encoding a heterologous polypeptide.

E102

The method or the kit of embodiment E101, wherein the heterologous polypeptide comprises an Fms-related tyrosine kinase 3 ligand ("FLT3L") or a portion thereof.

E103

The method or the kit of embodiment E102, wherein the FLT3L or a portion thereof comprises an extracellular domain of FLT3L.

E104

The method or the kit of embodiment E102 or E103, wherein the FLT3L or a portion thereof comprises an amino acid sequence at least 80%, at least 85%, at least 90%, at least 95%, at least 96%, at least 97%, at least 98%, at least 99%, or 100% identical to SEQ ID NO: 12.

E105

The method or the kit of any one of embodiment E101 to E104, wherein the nucleic acid sequence encoding a heterologous polypeptide comprises a nucleic acid sequence at least 80%, at least 85%, at least 90%, at least 95%, at least 96%, at least 97%, at least 98%, at least 99%, or 100% identical to SEQ ID NO: 11.

E106

The method of any one of embodiment E1 to E62 and E77 to E105 or the kit of any one of embodiment E63 to E105, wherein the polynucleotide further comprises a nucleotide sequence encoding a signal peptide.

E107

The method or the kit of embodiment E106, wherein the signal peptide is selected from a signal peptide of tissue plasminogen activator (tPA), a signal peptide of Herpes Simplex Virus Glycoprotein D (HSV gDs), a signal peptide of a growth hormone, and any combinations thereof.

E108

The method or the kit of embodiment E106, wherein the signal peptide is a signal peptide of tPA.

E109

The method or the kit of embodiment E108, wherein the signal peptide comprises an amino acid sequence at least 80%, at least 85%, at least 90%, at least 95%, at least 96%, at least 97%, at least 98%, at least 99%, or 100% identical to SEQ ID NO: 14.

E110

The method or the kit of embodiment E109, wherein the nucleotide sequence encoding the signal peptide comprises a nucleic acid sequence at least 80%, at least 85%, at least 90%, at least 95%, at least 96%, at least 97%, at least 98%, at least 99%, or 100% identical to SEQ ID NO: 13.

E111

The method of any one of embodiment E1 to E62 and E77 to E110 or the kit of any one of embodiment E77 to E110, wherein the polynucleotide is a vector.

E112

The method or the kit of embodiment E111, wherein the vector is a plasmid.

E113

The method or the kit of embodiment E112, wherein the plasmid further comprises an SV40 polyA sequence, an SV40 enhancer, pCMV promoter, gIVS or any combination thereof.

E114

The method or the kit of embodiment E113, wherein the plasmid further comprises an SV40 polyA sequence, an SV40 enhancer, ColE1, pCMV promoter, and gIVS.

E115

The method of any one of embodiment E1 to E62 and E77 to E114 or the kit of any one of embodiment E77 to E114, wherein the polynucleotide is a DNA or RNA.

E116

The method of any one of embodiment E1 to E62 and E77 to E115 or the kit of any one of embodiment E77 to E115, wherein the polynucleotide is a DNA vaccine.

E117

A method of making a polynucleotide encoding a fusion protein, which is effective in treating or preventing a cervical tumor caused by human papillomavirus infection comprising (i) constructing a polynucleotide that encodes a fusion protein comprising at least three amino acid sequences selected from:
 (1) an N-terminal portion of an E6 protein of HPV16,
 (2) a C-terminal portion of an E6 protein of HPV16,
 (3) an N-terminal portion of an E7 protein of HPV16,
 (4) a C-terminal portion of an E7 protein of HPV16,
 (5) an N-terminal portion of an E6 protein of HPV18,
 (6) a C-terminal portion of an E6 protein of HPV18,
 (7) an N-terminal portion of an E7 protein of HPV18, and
 (8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18, and (ii) transfecting the polynucleotide in a host cell.

E118

The method of Embodiment E117, wherein the fusion protein does not comprise a complete E6 associated protein (AP) binding site.

E119

A method of making a polynucleotide encoding a fusion protein, which is effective in treating or preventing a cervical tumor caused by human papillomavirus infection comprising (i) constructing a polynucleotide that encodes a fusion protein comprising:
 (1) an N-terminal portion of an E6 protein of HPV16,
 (2) a C-terminal portion of an E6 protein of HPV16, (3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18, wherein the fusion protein does not bind to pRb or does not form a dimer with an E7 protein of HPV16 or HPV18, and wherein the fusion protein comprises at least all epitopes for immunogenicity contained in the naturally occurring E6 protein of HPV16 and HPV18 and the naturally occurring E7 protein of HPV16 and HPV18 and (ii) transfecting the polynucleotide in a host cell, wherein the fusion protein is expressed.

E120

A method of removing a P53 binding site and a pRb binding site in a fusion protein comprising the sequence of an E6 protein of HPV16, the sequence of an E7 protein of HPV16, the sequence of an E6 protein of HPV18, and the sequence of an E7 protein of HPV18, while comprising at least all of the epitopes for immunogenicity contained in the naturally occurring E6 protein of HPV16, the naturally occurring E7 protein of HPV16, the naturally occurring E6 protein of HPV18, and the naturally occurring E7 protein of HPV18 comprising (i) constructing a polynucleotide that encodes a fusion protein comprising:
  (1) an N-terminal portion of an E6 protein of HPV16,
  (2) a C-terminal portion of an E6 protein of HPV16,
  (3) an N-terminal portion of an E7 protein of HPV16,
  (4) a C-terminal portion of an E7 protein of HPV16,
  (5) an N-terminal portion of an E6 protein of HPV18,
  (6) a C-terminal portion of an E6 protein of HPV18,
  (7) an N-terminal portion of an E7 protein of HPV18, and
  (8) a C-terminal portion of an E7 protein of HPV18,
    wherein
(a) the E6 protein of HPV16 is split at the C-terminal end of amino acids 35 to 135 corresponding to SEQ ID NO: 2 into the N-terminal portion of the E6 protein of HPV16 (16E6Na-b) and the C-terminal portion of the E6 protein of HPV16 (16E6Cc-d), which when aligned together, comprise all of the sequences of the E6 protein of HPV16 and an optional overlapping sequence;
(b) the E7 protein of HPV16 is split at the C-terminal end of amino acids 18 to 97 corresponding to SEQ ID NO: 6 into the N-terminal portion of the E7 protein of HPV16 (16E7Ne-f) and the C-terminal portion of the E7 protein of HPV16 (16E7g-h), which when aligned together, comprise all of the sequences of the E7 protein of HPV16 and an optional overlapping sequence;
(c) the E6 protein of HPV18 is split at the C-terminal end of amino acids 30 to 130 corresponding to SEQ ID NO: 6 into the N-terminal portion of the E6 protein of HPV18 (18E6Ni-j) and the C-terminal portion of the E6 protein of HPV18 (18E6Nk-l), which when aligned together, comprise all of the sequences of the E6 protein of HPV18 and an optional overlapping sequence; and
(d) the E7 protein of HPV18 is split at the C-terminal end of amino acids 21 to 104 corresponding to SEQ ID NO: 8 into the N-terminal portion of the E7 protein of HPV18 (18E7 Nm-n) and the C-terminal portion of the E7 protein of HPV18 (18E7Co-p), which when aligned together, comprise all of the sequences of the E7 protein of HPV18 and an optional overlapping sequence;
(ii) transfecting the polynucleotide in a host cell.

E121

The method of Embodiment E120, wherein the overlapping sequence for the E6 protein of HPV16 in (a) comprises at least one amino acids, at least two amino acids, at least three amino acids, at least four amino acids, at least five amino acids, at least 10 amino acids, at least 15 amino acids, or at least 20 amino acids; the overlapping sequence for the E7 protein of HPV16 in (b) comprises at least one amino acids, at least two amino acids, at least three amino acids, at least four amino acids, at least five amino acids, at least 10 amino acids, at least 15 amino acids, or at least 20 amino acids; the overlapping sequence for the E6 protein of HPV18 in (c) comprises at least 1, 2, 5, 10, 15, 20, 25, 30, 35, or 40 amino acids; or the overlapping sequence for the E7 protein of HPV18 in (d) comprises at least 1, 2, 5, 10, 15, 20, 25, 30, 35, or 40 amino acids.

E122

A method of preventing a formation of a homodimer of an E6 protein of HPV16 and/or HPV18 and/or an E7 protein of HPV16 and/or HPV18 in a fusion protein comprising the sequence of an E6 protein of HPV16, the sequence of an E7 protein of HPV16, the sequence of an E6 protein of HPV18, and the sequence of an E7 protein of HPV18, while comprising all of the epitopes for immunogenicity of the E6 protein of HPV16, the E7 protein of HPV16, the E6 protein of HPV18, and the E7 protein of HPV18 comprising (i) constructing a polynucleotide that encodes a fusion protein comprising
  (1) an N-terminal portion of an E6 protein of HPV16,
  (2) a C-terminal portion of an E6 protein of HPV16,
  (3) an N-terminal portion of an E7 protein of HPV16,
  (4) a C-terminal portion of an E7 protein of HPV16,
  (5) an N-terminal portion of an E6 protein of HPV18,
  (6) a C-terminal portion of an E6 protein of HPV18,
  (7) an N-terminal portion of an E7 protein of HPV18, and
  (8) a C-terminal portion of an E7 protein of HPV18,
    wherein
(a) the E6 protein of HPV16 is split at the C-terminal end of amino acids 37 to 72 corresponding to SEQ ID NO: 2 into the N-terminal portion of the E6 protein of HPV16 (16E6Na-b) and the C-terminal portion of the E6 protein of HPV16 (16E6Cc-d), which when aligned together, comprise all of the sequences of the E6 protein of HPV16 and an optional overlapping sequence;
(b) the E7 protein of HPV16 is split at the C-terminal end of amino acids 44 to 97 corresponding to SEQ ID NO: 6 into the N-terminal portion of the E7 protein of HPV16 (16E7Ne-f) and the C-terminal portion of the E7 protein of HPV16 (16E7g-h), which when aligned together, comprise all of the sequences of the E7 protein of HPV16 and an optional overlapping sequence;
(c) the E6 protein of HPV18 is split at the C-terminal end of amino acids 32 to 67 corresponding to SEQ ID NO: 4 into the N-terminal portion of the E6 protein of HPV18 (18E6Ni-j) and the C-terminal portion of the E6 protein of HPV18 (18E6Nk-l), which when aligned together, comprise all of the sequences of the E6 protein of HPV18 and an optional overlapping sequence; and
(d) the E7 protein of HPV18 is split at the C-terminal end of amino acids 47 to 104 corresponding to SEQ ID NO: 8 into the N-terminal portion of the E7 protein of HPV18 (18E7 Nm-n) and the C-terminal portion of the E7 protein of HPV18 (18E7Co-p), which when aligned together, comprise all of the sequences of the E7 protein of HPV18 and an optional overlapping sequence;
(ii) transfecting the polynucleotide in a host cell.

E123

The method of Embodiment 122, wherein the overlapping sequence for the E6 protein of HPV16 in (a) comprises at least 1, 2, 5, 10, 15, 20, 25, 30, 35, or 40 amino acids; the overlapping sequence for the E7 protein of HPV16 in (b) comprises at least 1, 2, 5, 10, 15, 20, 25, 30, 35, or 40 amino acids; the overlapping sequence for the E6 protein of HPV18 in (c) comprises at least 1, 2, 5, 10, 15, 20, 25, 30, 35, or 40 amino acids; or the overlapping sequence for the E7 protein of HPV18 in (d) comprises at least 1, 2, 5, 10, 15, 20, 25, 30, 35, or 40 amino acids.

E124

The method of any one of Embodiments 117 to 123, wherein the fusion protein is not SEQ ID NO: 10.

DESCRIPTION OF THE DRAWINGS/FIGURES

Figure 1B:
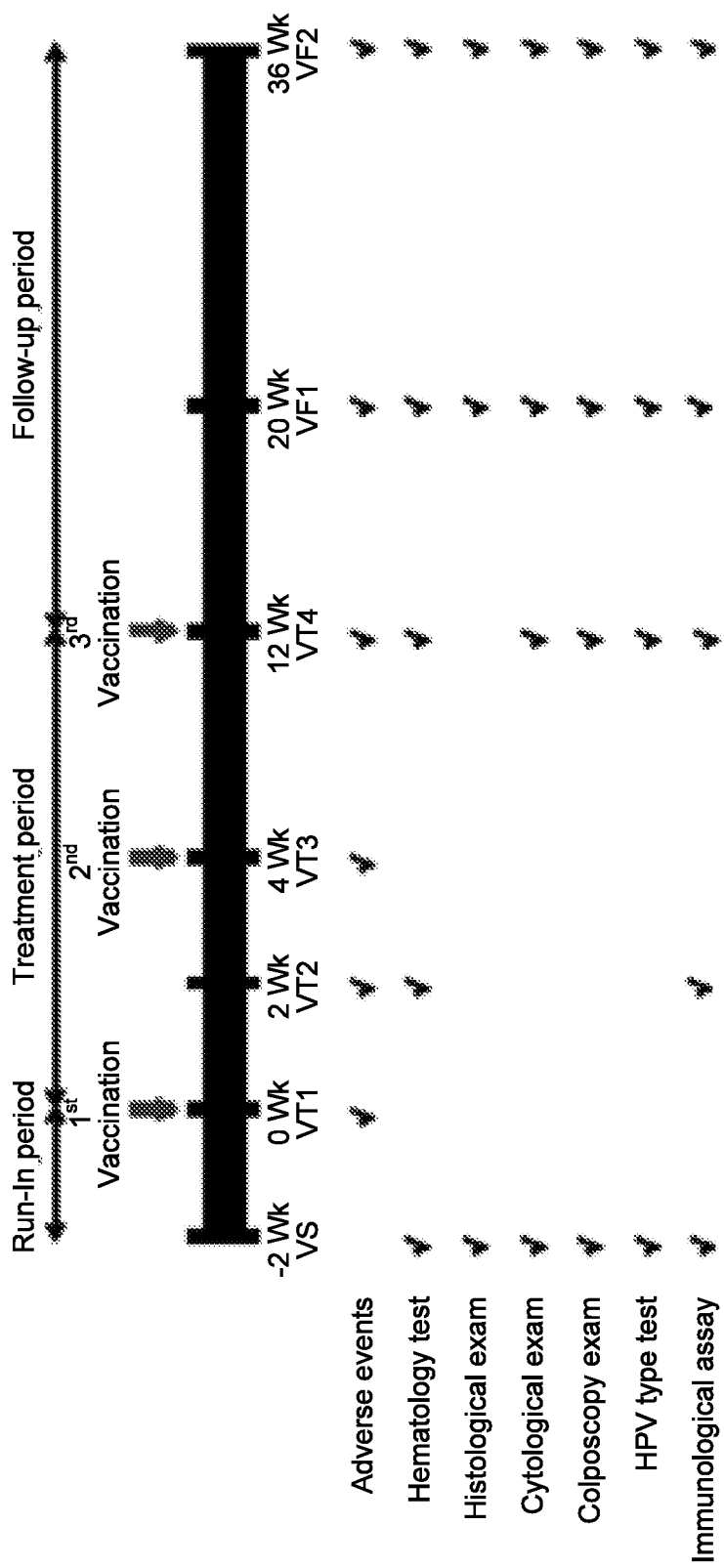

FIG. 1A illustrates a diagram of therapeutic molecule (e.g., HPV E6/E7 DNA therapeutic vaccine, designated GX-188). FIG. 1A shows the GX-188 vaccine constructed by inserting shuffled overlapping N- and C-terminal domains of E6 and E7 genes of HPV16 and HPV18 types into the pGX27 vector. The E6 and E7 domains are preceded by the secretory signal sequence of tissue plasminogen activator (tPA) and the extracellular domain of Fms-like tyrosine kinase-3 ligand (FLT3L). The inserted viral domains are abbreviated according to the HPV strain, the gene, and the domain; e.g., 16E6N represents N-terminal domain of HPV16 E6. Other abbreviation used: MCS, multi-cloning site; SV40 poly A, Simian virus 40 late polyadenylation sequence; SV40 enhancer, Simian virus 40 enhancer; KanR, Kanamycin resistance gene; ColE1, ColE1-type bacterial origin of replication; pCMV, Cytomegalovirus early enhancer/promoter; gIVS, rabbit β-globin intervening sequence. The numbers above each gene segment indicates the corresponding amino acid sequence. FIG. 1B shows a schematic outline of the clinical trial. The clinical trial had three periods: Screening of the recruited patients, treatment by 3 injections of the vaccine, and follow-up monitoring of the patients. Patients made visits for screening (VS), treatment (VT), and follow-up monitoring (VF) to the clinic during these three periods at the indicated time points to be examined and/or to receive vaccination.

Figure 2A:
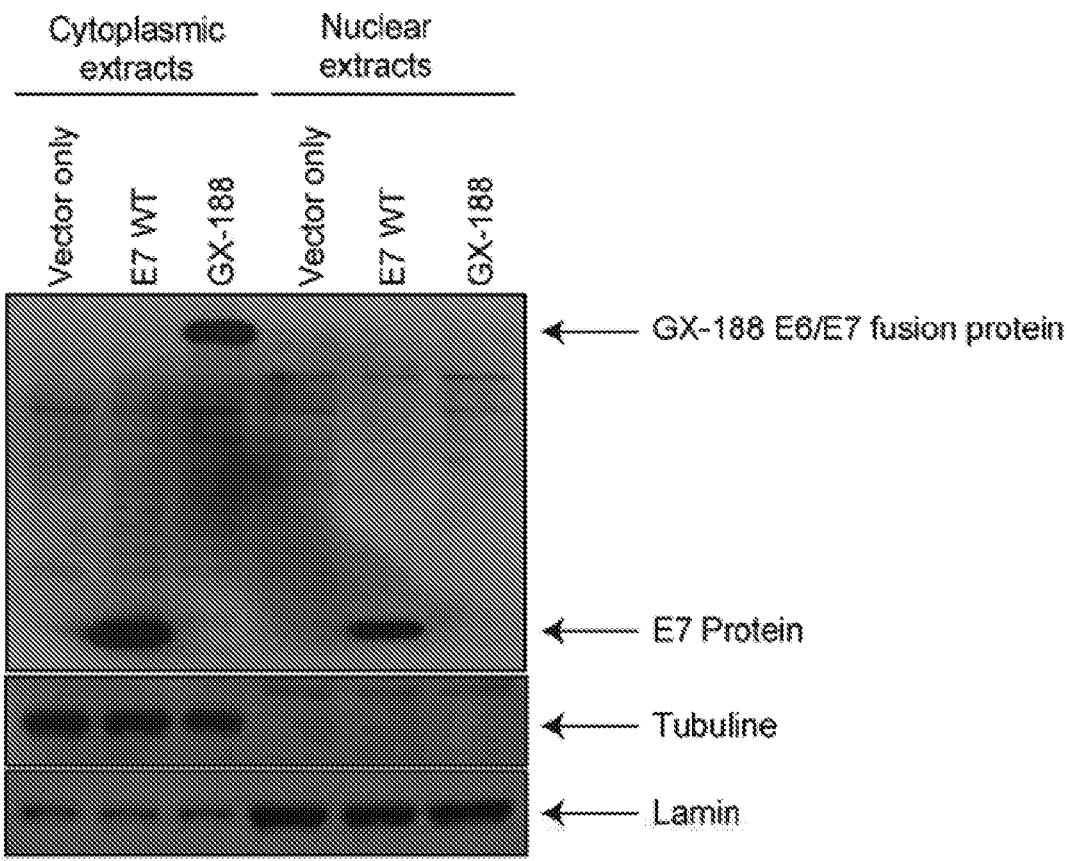
Figure 2B:
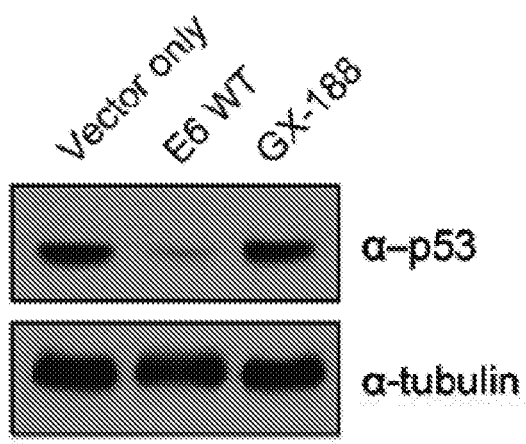
Figure 2C:
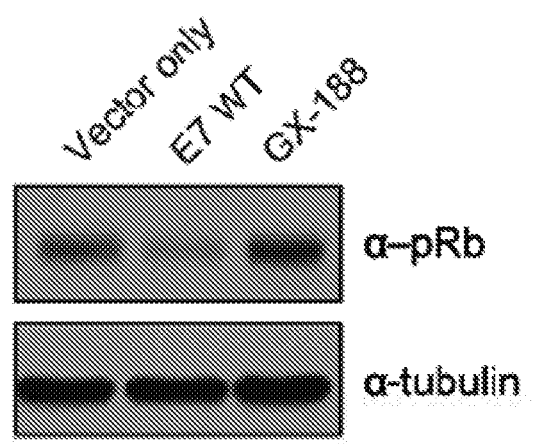

FIG. 2A-2C shows subcellular localization of GX-188 E6/E7 fusion protein and its effect on degradation of cellular p53 and pRb proteins. 293T cells were transfected with pGX27 control vector, GX-188, or pGX27 inserted with wild type E6 or E7 genes. Twenty-four hours post transfection, cell lysates were prepared and protein expressions were analyzed by immunoblotting. FIG. 2A shows the cells resuspended in lysis buffer A (10 mM HEPES, pH 7.9, 10 mM KCl, 0.2 mM EDTA, 1 mM DTT, 0.25 mM PMSF, and proteinase inhibitor cocktail), and the supernatants of extracts were collected as cytoplasmic extracts. The pellet was resuspended in buffer B (20 mM HEPES, pH 7.9, 420 mM NaCl, 2 mM EDTA, 1 mM DTT, 1 0.25 mM PMSF, and PIC), and their supernatants after pelleting were collected as nuclear extracts. The purity of the fractions was tested by Western blotting for tubulin and lamin to define the cytoplasmic and nuclear fractions, respectively. FIGS. 2B and 2C show the cells resuspended in lysis buffer (20 mM HEPES, pH 7.4, 150 mM NaCl, 5 mM EDTA, 10% glycerol, 0.5% Triton X-100, 1 mM DTT, 1 mM PMSF, 1 mM NaF, 1 mM Na3Vo4, and PIC). The supernatants were collected as whole-cell lysates. FIG. 2B shows the analysis for the expression level of cellular p53 protein. FIG. 2C shows the analysis for the expression level of cellular pRb protein.

FIGS. 3A-3I show that vaccination with GX-188 by electroporation induced significant HPV16 and HPV18 E6/E7-specific IFN-γ responses. Patients' peripheral blood mononuclear cells (PBMCs) were harvested and cryopreserved before (VS), during (VT2, VT4), and after (VF1, VF2) vaccination with GX-188 in all patients. The number of HPV16/18 E6- and E7-specific IFN-γ secreting cells in PBMCs was determined individually by IFN-γ ELISPOT assays described herein after stimulation with HPV16 or HPV18 E6 and E7 peptide pools for 48 hours at indicated time points. Shown are the average spot-forming units (SFU) per $10^6$ PBMCs in triplicate wells against each antigen after subtracting the background number of spots which was 5.7±2.2 (mean±s.d.). FIG. 3A shows the results of administration of 1 mg GX-188 in patient A01. The percentage of E6-specific response in total number of spots in patient A01 was 76.6% at VF1. FIG. 3B shows the results of administration of 1 mg GX-188 in A02. The percentage of E6-specific response in total number of spots in patient A02 was 69.3% at VF1. FIG. 3C shows the results of administration of 1 mg GX-188 in patient A03. The percentage of E6-specific response in total number of spots in patient A03 was 88.9% at VF1. FIG. 3D shows the results of administration of 2 mg GX-188 in patient A04. The percentage of E6-specific response in total number of spots in patient A04 was 89.2% at VF1. FIG. 3E shows the results of administration of 2 mg GX-188 in A05. The percentage of E6-specific response in total number of spots in patient A05 was 69.1% at VF1. FIG. 3F shows the results of administration of 2 mg GX-188 in A06. The percentage of E6-specific response in total number of spots in patient A06 was 89.4% at VF1. FIG. 3G shows the results of administration of 4 mg GX-188 in patient A07. The percentage of E6-specific response in total number of spots in patient A07 was 84.2% at VF1. FIG. 3H shows the results of administration of 4 mg GX-188 in patient A08. The percentage of E6-specific response in total number of spots in patient A08 was 75.1% at VF1. FIG. 3I shows the results of administration of 4 mg GX-188 in patient A09. The percentage of E6-specific response in total number of spots in patient A09 was 70.1% at VF1. The HPV types found in each patient are indicated in the parentheses. N.D; not determined.

Figures 4D, 4E:
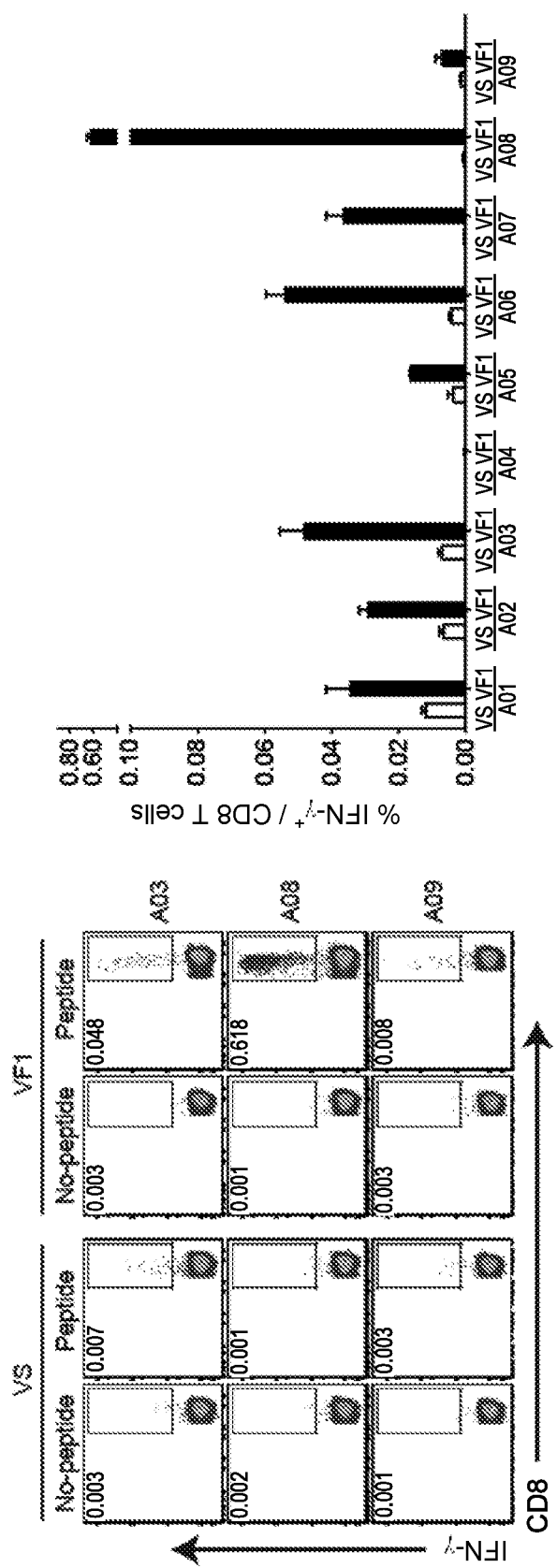

FIGS. 4A-4E shows that GX-188 vaccination elicited a significant increase in the frequency of HPV16-specific IFN-γ+ CD4 and/or CD8 T cells. Cryopreserved PBMCs of patients harvested before (VS) and after (VF1) GX-188 vaccination were stimulated with a combined mixture of HPV16 E6 and E7 peptide pools for 13 hours. The frequency of HPV16-specific IFN-γ+ CD4 and CD8 T cells was determined by intracellular cytokine staining followed by multicolor flow cytometry analysis. FIG. 4A shows gating strategy to determine the IFN-γ-producing CD4 and CD8 T cells by flow cytometry. FIG. 4B shows the representative plots of the frequencies of CD4 producing IFN-γ before (VS) and after (VF1) vaccination. FIG. 4B shows the summary graph of FIG. 4B plots. FIG. 4D shows the representative plots of the frequencies of CD8 producing IFN-γ before (VS) and after (VF1) vaccination. FIG. 4E shows the summary graph of FIG. 4D plots. Data shown in the graphs of FIGS. 4C and 4E represent the average of two independent experiments, with duplicate in each experiment, and error bars represent s.d. The background values were determined by the response of the medium only as a control and were 0.004±0.002% for CD4 and 0.003±0.002 for CD8 T cells (mean±s.d.).

Figures 5D, 5E, 5F:
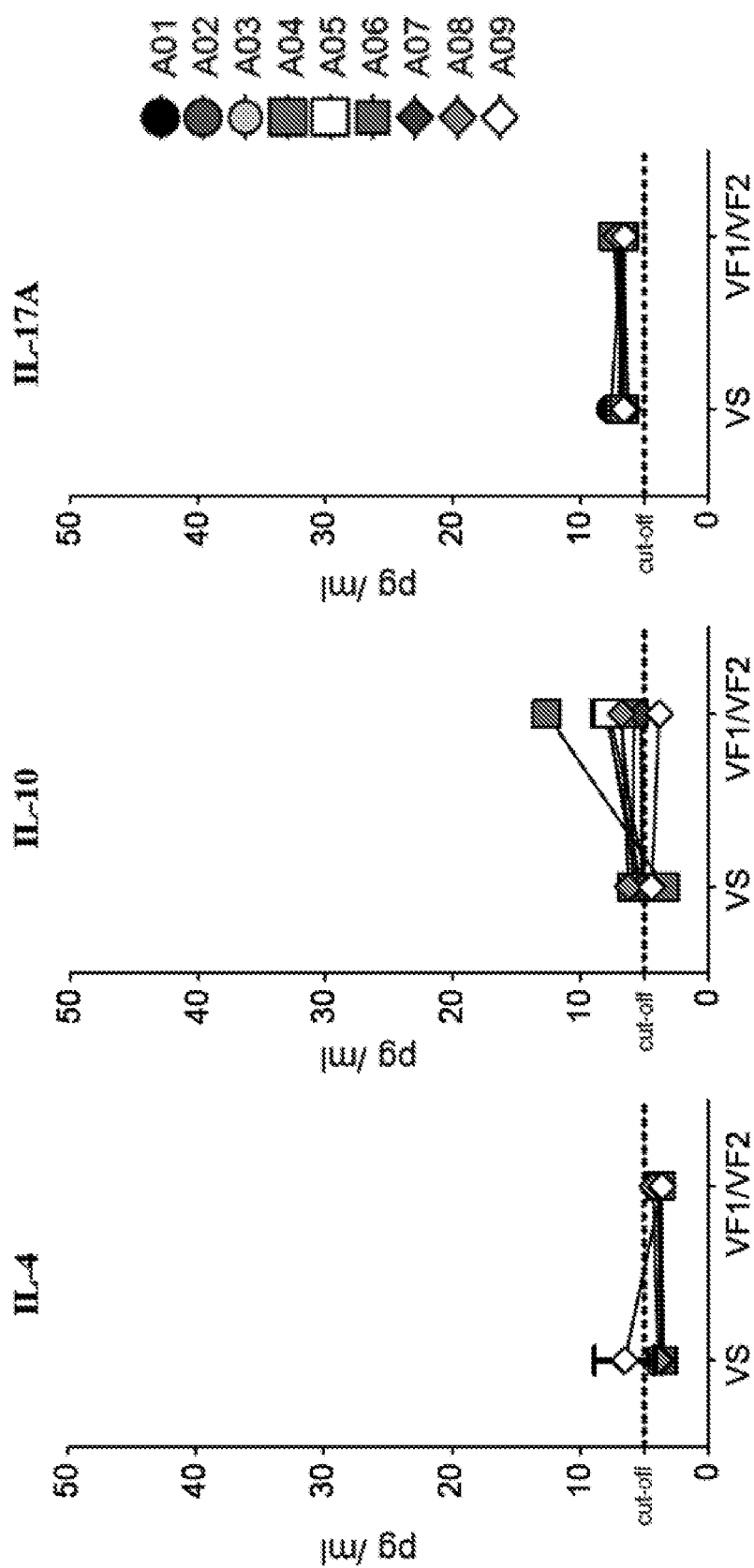

FIGS. 5A-5F show that GX-188 immunization generated HPV16-specific Th1, but not Th2 or Th17 response. Cryopreserved PBMCs from patients before (VS) and after (VF1+VF2) vaccination were stimulated with a mixture of HPV16 E6 and E7 peptide pools for 48 hours. Pooled PBMCs at VF1 and VF2 were used for all patients except for patient A04 in whom VF1 cells were used, as she received surgery before VF2. The indicated cytokines in supernatants of cultures were quantified using Th1/Th2/Th17 cytometric bead array kit. Shown are mean±s.d. of duplicate. The horizontal dashed lines indicate the cut-off level determined by standard curve of each cytokine. FIG. 5A shows the level of IFN-γ measured after GX-188 immunization. The mean value of the medium alone as a background (mean±s.d. pg ml$^{-1}$) was 4.19±0.41. FIG. 5B shows the level of IL-2 measured after GX-188 immunization. The mean value of the medium alone as a background (mean±s.d. pg ml$^{-1}$) was 5.11±0.63. FIG. 5C shows the level of TNF-α measured after GX-188 immunization. The mean value of the medium alone as a background (mean±s.d. pg ml$^{-1}$) was 5.58±0.88. FIG. 5D shows the level of IL-4 measured after GX-188 immunization. The mean value of the medium alone as a background (mean±s.d. pg ml$^{-1}$) was 3.3±0.24. FIG. 5E shows the level of IL-10 measured after GX-188 immunization. The mean value of the medium alone as a background (mean±s.d. pg ml$^{-1}$) was 5.01±0.64 for IL-10 (E). FIG. 5E shows the level of IL-17A measured after GX-188 immunization. The mean value of the medium alone as a background (mean±s.d. pg ml$^{-1}$) was 5.45±0.28.

Figure 6A:
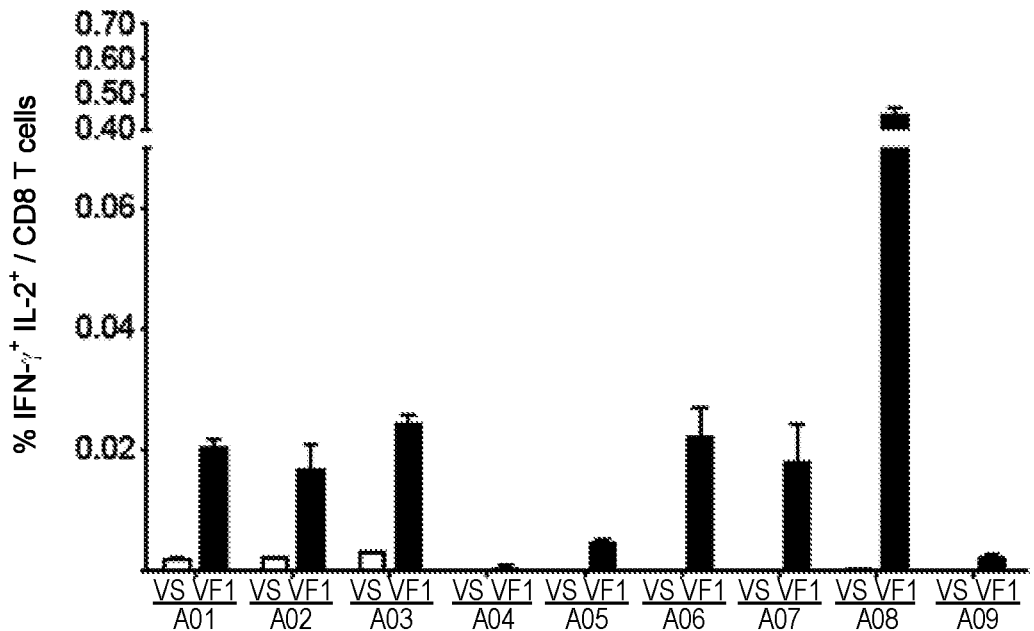
Figure 6B:
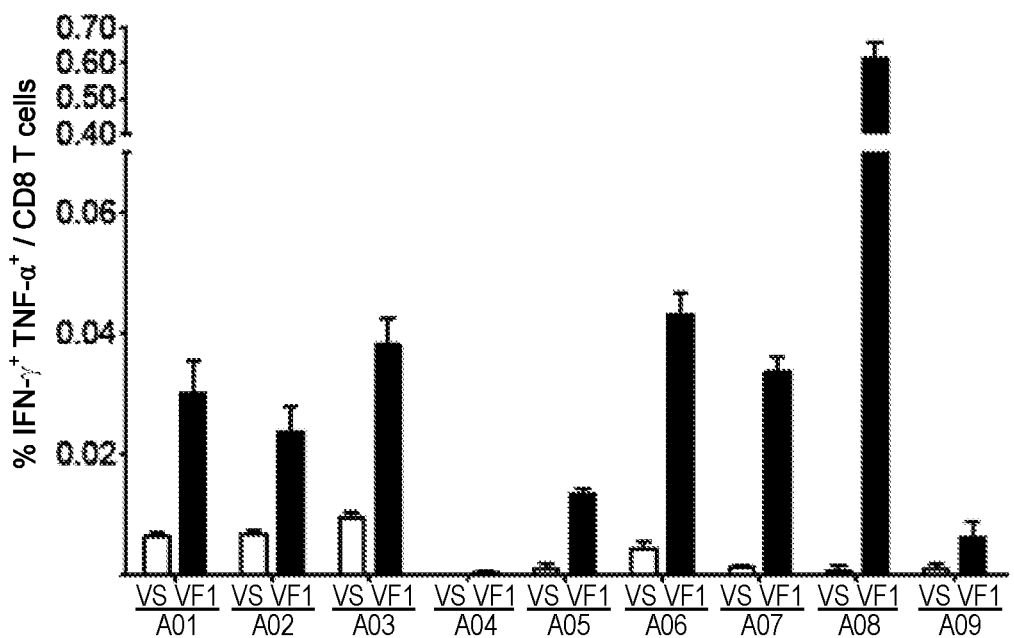
Figure 6C:
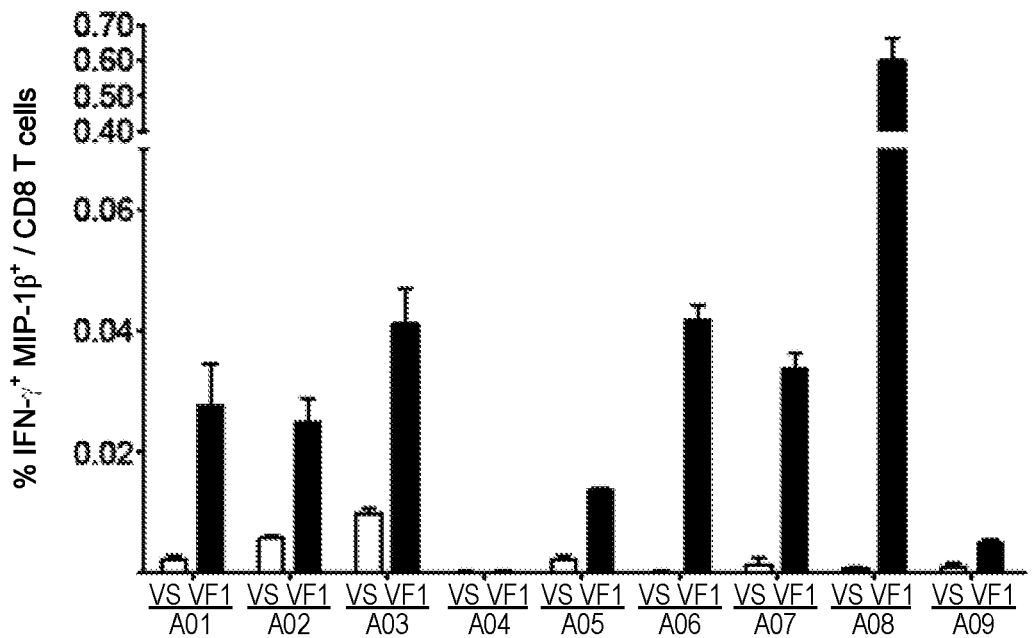
Figure 6D:
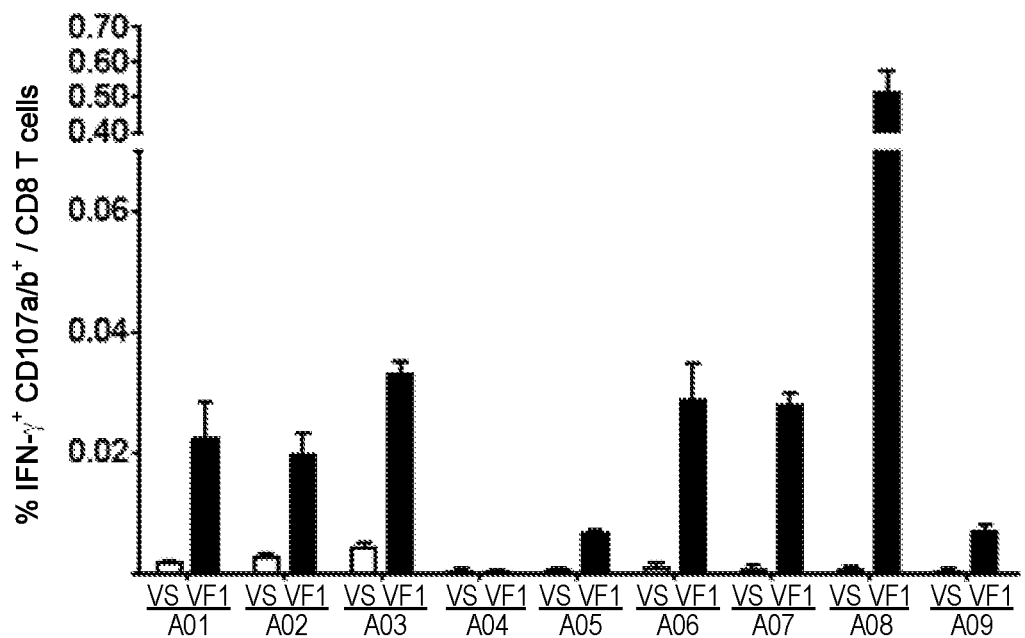
Figure 6E:
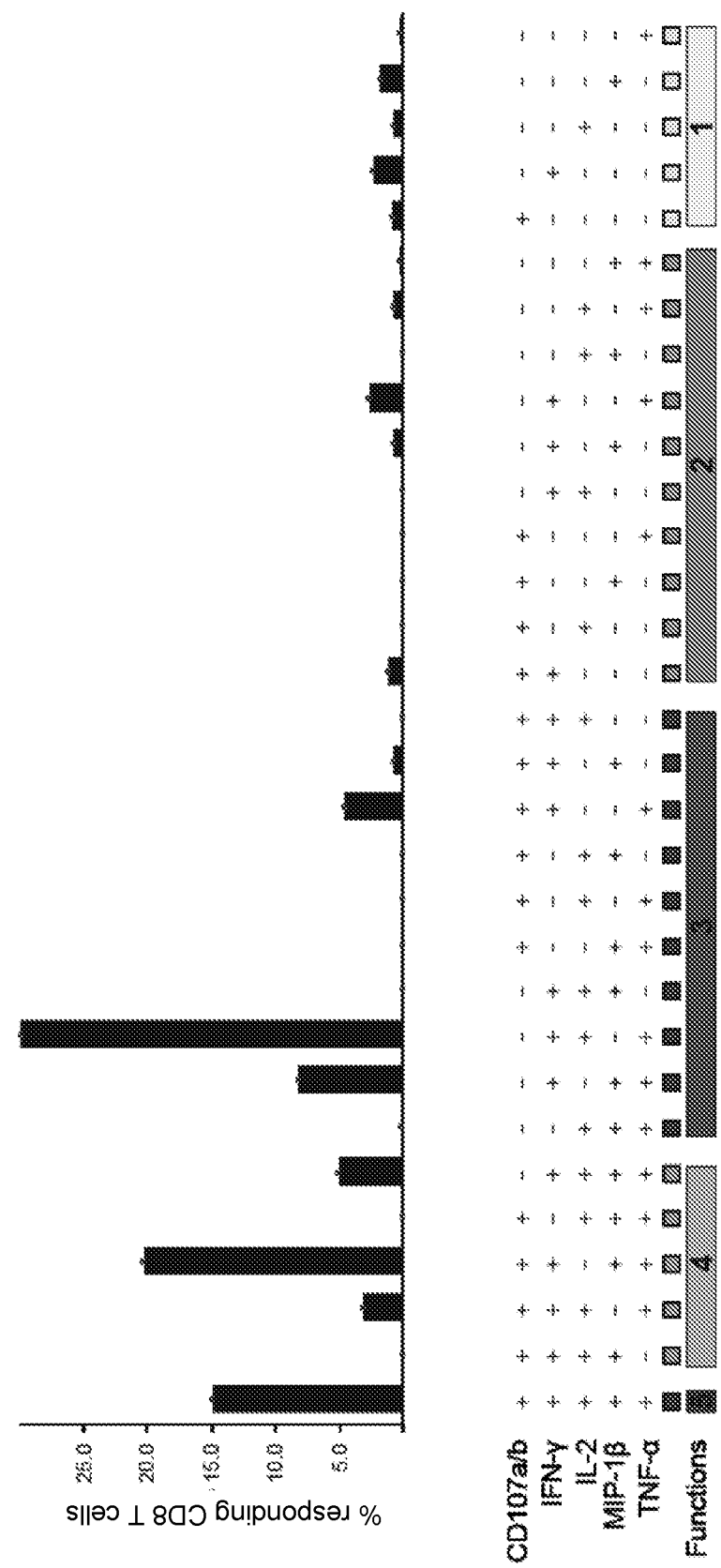
Figure 6F:
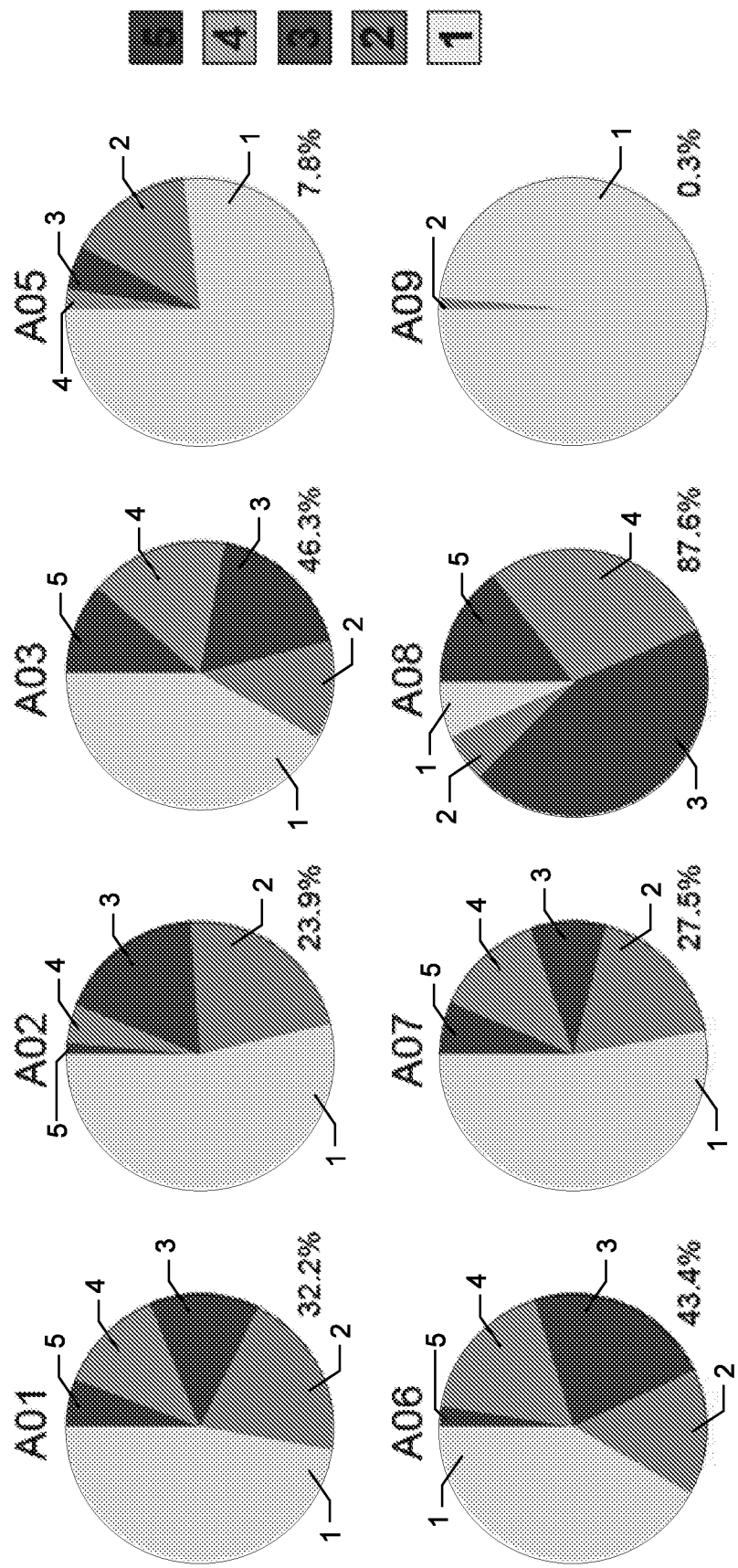

FIGS. 6A-6F shows that GX-188 vaccination induced the polyfunctionality of HPV16-specific CD8 T cells. Patients' PBMCs were stimulated at before (VS) and after (VF1) vaccination as described in FIGS. 4A-4E and then analyzed with multi-color flow cytometry to detect HPV16-specific expression of IL-2, IFN-γ, TNF-α, MIP-1β, and the cytotoxic degranulating marker, CD107a/b. FIG. 6A shows the summary graphs of the frequencies of IFN-γ$^+$ CD8 T cells co-expressing IL-2 on gated CD8 T cells; FIG. 6B shows the summary graphs of the frequencies of IFN-γ$^+$ CD8 T cells co-expressing TNF-α; FIG. 6C shows the summary graphs of the frequencies of IFN-γ$^+$ CD8 T cells co-expressing MIP-1β; FIG. 6D shows the summary graphs of the frequencies of IFN-γ$^+$ CD8 T cells co-expressing CD107a/b. FIG. 6E shows a representative graph of A08 patient's polyfunctional responses to HPV16 E6/E7 peptides subsequent to Boolean gating after vaccination (VF1). The five functions, CD107a/b, IFN-γ, IL-2, MIP-1β, and TNF-α are listed along x-axis with each of their respective 31 possible combinations. The five horizontal bars below x-axis depict the populations of five, four, three, two or one functional responses. FIG. 6F shows each pie chart representing the relative frequency of HPV16 E6/E7-specific CD8 T cells with each combination of the 5 functional responses post vaccination (VF1). The numbers to the bottom right of each pie chart indicate the percentage of HPV16-specific CD8 T cells that produce 3 or more functional molecules. The polyfunctional profile of A04 patient was not available because of too low frequency of the responding CD8 T cells for analysis. Data shown in the graphs represent the average of two independent experiments, with duplicate in each experiment, and error bars represent s.d. The background values were determined by the response of the medium only and were 0.0008±0.001% for IFN-γ$^+$ IL-2$^+$, 0.0016±0.0014% for IFN-γ$^+$ TNF-α$^+$, 0.0015±0.0019% for IFN-γ$^+$ MIP-1β$^+$, and 0.0009±0.0012% for IFN-γ$^+$ IL-2$^+$ CD8 T cells (mean±s.d.)

Figure 7E:
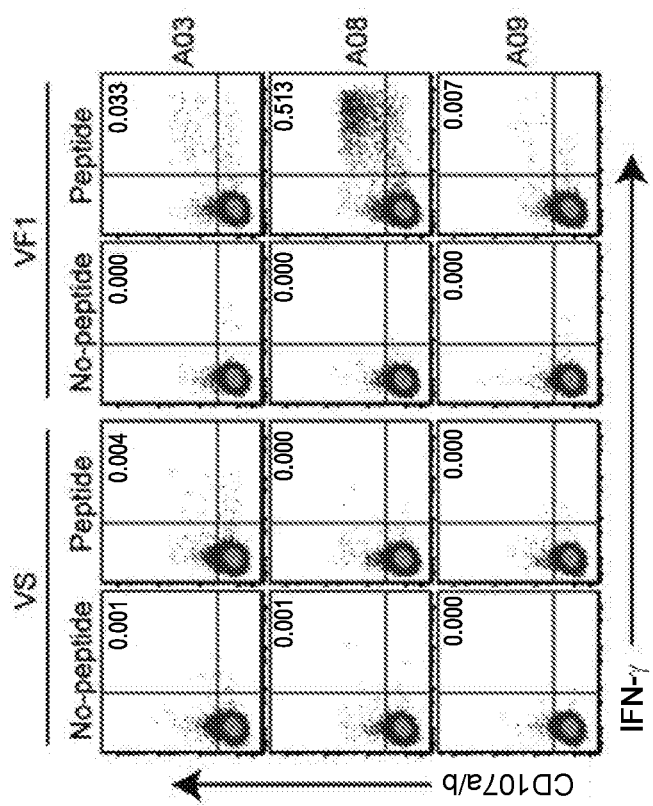
Figure 7D:
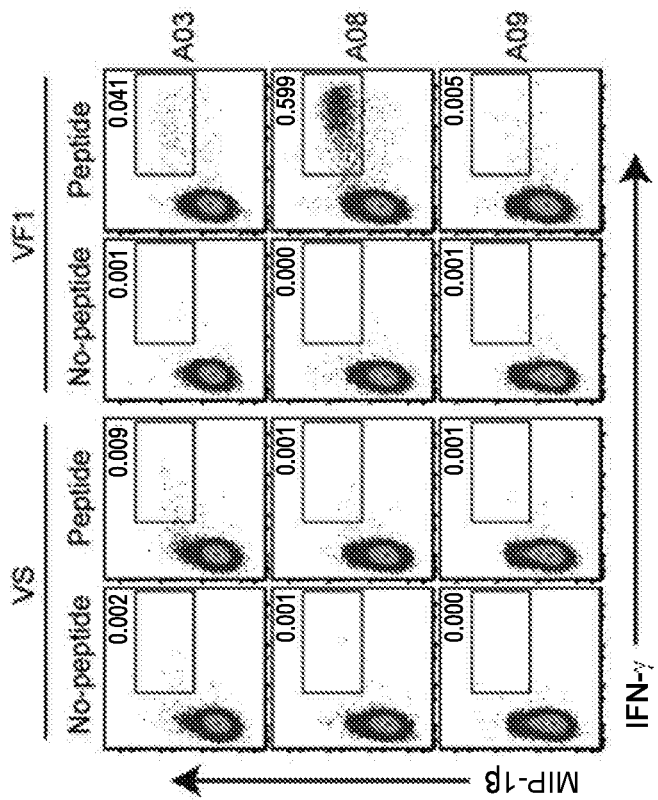

FIG. 7A-7E illustrates that GX-188 vaccination strongly induced the polyfunctionality of HPV16 specific CD8 T cells. Cryopreserved PBMCs of patients harvested before (VS) and after (VF1) GX-188 vaccination were stimulated with a combined mixture of HPV16 E6 and E7 peptide pools for 13 hours, and then analyzed with multi-color flow cytometry to detect HPV16-specific expression of IL-2, IFN-γ, TNF-α, MIP-1β, and CD107a/b. FIG. 7A shows gating strategy to determine the functional molecules-producing CD8 T cells by flow cytometry. FIG. 7B shows the representative plots of the frequencies of IFN-γ$^+$ CD8 T cells co-expressing IL-2 on gated CD8 T cells; FIG. 7C shows the representative plots of the frequencies of IFN-γ$^+$ CD8 T cells co-expressing TNF-α; FIG. 7D shows the representative plots of the frequencies of IFN-γ$^+$ CD8 T cells co-expressing MIP-1β; and FIG. 7E shows the representative plots of the frequencies of IFN-γ$^+$ CD8 T cells co-expressing CD107a/b. The numbers of plots indicate the frequency of responding population on gated CD8 T cells FIGS. 8A-8C show that GX-188 vaccination induced proliferation of HPV16-specific CD8 T cells. Patients' PBMCs were stimulated at before (VS) and after (VF1) vaccination and analyzed by flow cytometry as described below to examine the expression of CD38 and Ki67 on virus-specific CD8 T cells. FIG. 8A shows gating strategy to determine the expression Ki67 and CD38 on CD8 T cells by flow cytometry. FIG. 8B shows the representative plots of the frequency of proliferating CD38$^+$ Ki67$^+$ CD8 T cells. Data shown in FIG. 8C represent the average of duplicate, and error bars represent s.d. The cells shown in FIG. 8B are gated on CD8 T cells. The numbers in FIG. 8C indicate fold increase post vaccination. The background value was determined by the response of the medium only control, which was 0.011±0.015% for CD38$^+$ Ki67$^+$ CD8 T cells (mean±s.d.).

FIGS. 9A-9L show IgG titer to HPV16/18 E6 and E7 proteins following GX-188 vaccination. Plasma IgG antibody titers against the recombinant E6 and E7 proteins of HPV16 and HPV18 were measured for each patient at a range of dilution by ELISA. FIG. 9A shows the HPV16 E6 IgG titer results for each vaccine dose group after administration of 1 mg of GX-188 at the time before immunization (VS) and after immunization (VT2, VT4, and VF); FIG. 9B shows the HPV16 E7 IgG titer results; FIG. 9C shows the HPV18 E6 IgG titer results; and FIG. 9D shows the HPV18 E7 IgG titer results. FIG. 9E shows the HPV16 E6 IgG titer results for each vaccine dose group after administration of 2 mg of GX 188 at the time before immunization (VS) and after immunization (VT2, VT4, and VF); FIG. 9F shows the HPV16 E7 IgG titer results; FIG. 9G shows the HPV18 E6 IgG titer results; and FIG. 9H shows the HPV18 E7 IgG titer results. FIG. 9I shows the HPV16 E6 IgG titer results for each vaccine dose group after administration of 4 mg of GX-188 at the time before immunization (VS) and after immunization (VT2, VT4, and VF); FIG. 9J shows the HPV16 E7 IgG titer results; FIG. 9K shows the HPV18 E6 IgG titer results; and FIG. 9L shows the HPV18 E7 IgG titer results. Data are represented as dilution fold of samples showing positivity which was considered if the average optical density of a sample was greater than negative cut-off values (0.173 for HPV16 E6, 0.213 for HPV16 E7, 0.214 for HPV18 E6, and 0.227 for HPV18 E7). As patient's plasma was tested in a well coated with irrelevant recombinant erythropoietin (EPO), optical density of all samples was below negative cut-off value.

FIGS. 10A-10C illustrates that GX-188 vaccination led to clearance of cervical lesions as determined by colposcopy, cytology, and histology. FIG. 10A shows photographs of cervical colposcopy from a representative responder (A05) and a non-responder (A09) patient before (VS) and after (VF2) GX-188 immunization. In FIG. 10A, patient A05 at VS exhibited dense acetowhite epithelium with coarse punctuation in transformation zone, but at VF2 showed reduced intermediate acetowhite epithelium without punctuation; patient A09 at VS and VF2 displayed dense acetowhite epithelium with rolled margin and coarse punctuation in transformation zone. FIG. 10B shows photographs of endocervical cytology from a representative responder (A05) and a non-responder (A09) patient before (VS) and after (VF2) GX-188 immunization. In FIG. 10B, patient A05 at VS exhibited high-grade squamous intraepithelial lesion (HSIL) with enlarged nuclear size and hyperchromasia (×400), but at VF2 showed only normochromic epithelium with no intraepithelial lesion (ML) (×400); patient A09 at VS and VF2 displayed HSIL variable nuclear size and hyperchromasia (×400). FIG. 10C shows photographs of histology from a representative responder (A05) and a non-responder (A09) patient before (VS) and after (VF2) GX-188 immunization. In FIG. 10C, patient A05 at VS was diagnosed as CIN3 with full thickness of the epithelium, and with mitoses visible in the upper layer (×400), but at VF2 displayed normal squamous epithelium without atypical neoplastic cells (×200); patient A09 at VS and VF2 was diagnosed as CIN3 with thick and abnormal epithelium and the presence of keratinized cells with nuclear atypical in the upper layer (×200).

Figure 11A:
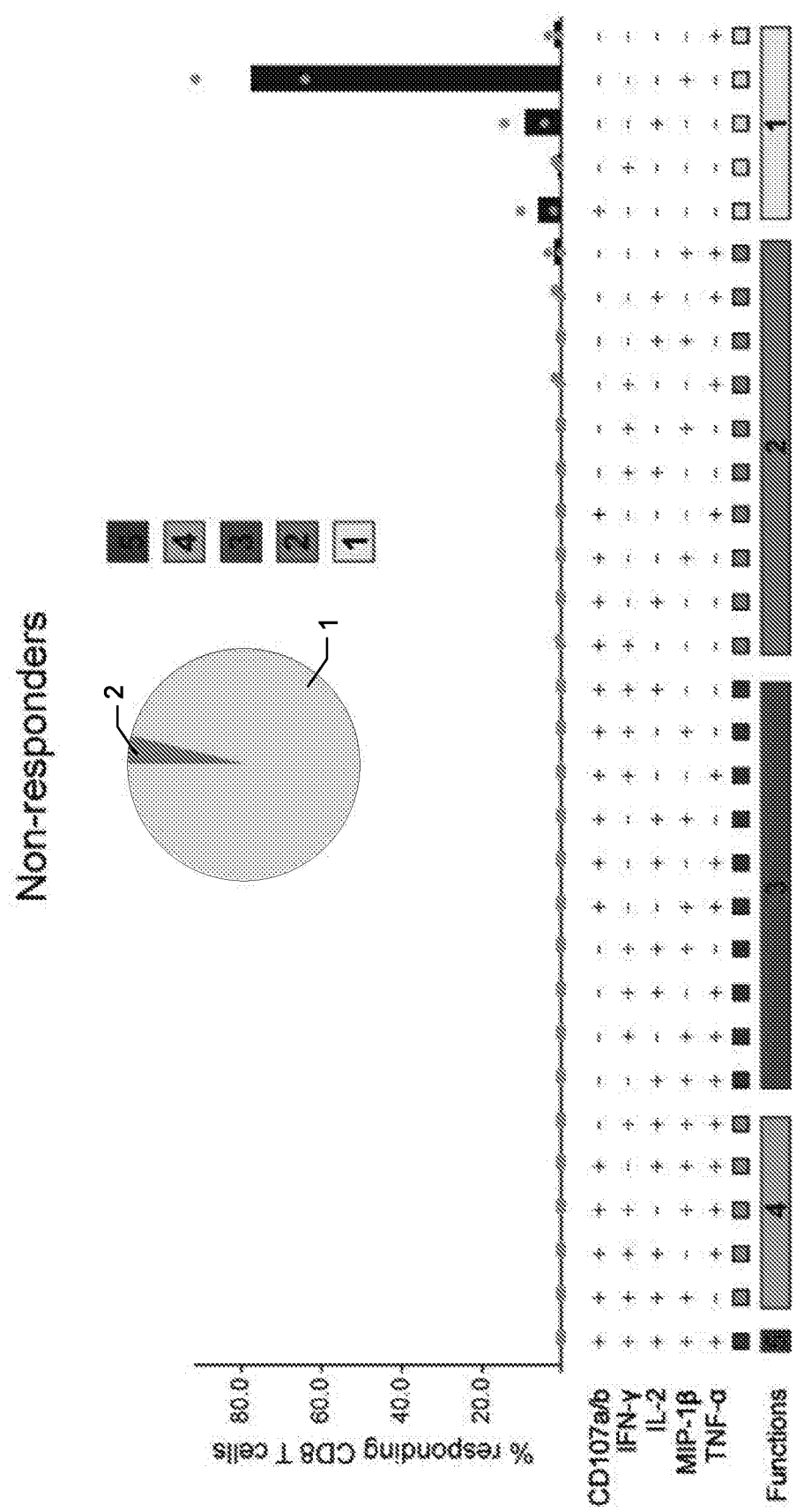
Figure 11B:
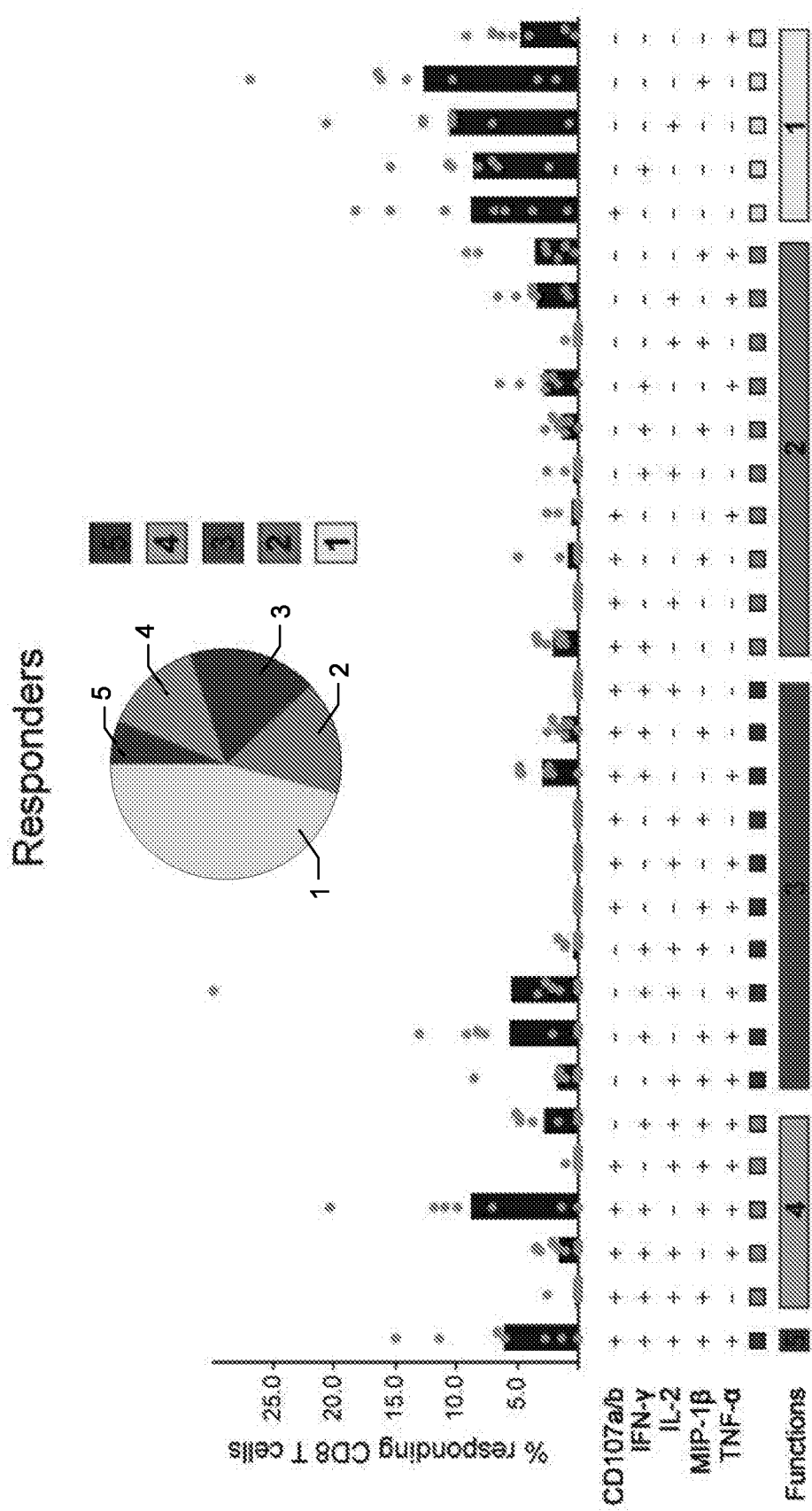

FIGS. 11A-11B show a polyfunctional assay of HPV-specific T cells in the non-responders and responders of GX-188 vaccination. The frequency of HPV16-specific IL-2, IFN-γ-, TNFα-, MIP-1β-, or CD107a/b-producing CD8 T cells was measured 20 weeks (VF1) after vaccination using Boolean gating. Patients are grouped into non-responders (A04 and A09) and responders (A01, A02, A03, A05, A06, A07 and A08) according to clinical and virological outcomes. FIG. 11A shows the non-responders' polyfunctional CD8 T-cell responses to HPV16 E6/E7 peptides post GX-188 vaccination are presented as a graph. In the graph, black bars represent mean response, and dots correspond to the response from a single subject. The each of the possible functional combination of cytokines is listed along the x-axis. The five horizontal bars of different colors below x-axis depict the populations of five, four, three, two or one functional response. FIG. 11B shows the responders' polyfunctional CD8 T-cell responses to HPV16 E6/E7 peptides post GX-188 vaccination presented as a pie chart. The pie chart represents the relative frequency of HPV16 E6/E7 specific CD8 T cells with each combination of the five functional responses.

FIGS. 12A-12F illustrate Th1/Th2/Th17 cytokine standard generated by cytometric bead array. To ensure a valid analysis of protein below 10 pg ml$^{-1}$ (the default outlined limit for quantification), human Th1/Th2/Th17 cytokine standards were reconstituted in 50 L1 assay diluent, and the standards were constructed from 5-5,000 pg ml$^{-1}$ (dilution rate; 1:1, 1:2, 1:4, 1:8, 1:16, 1:32, 1:64, 1:128, 1:256, 1:512, and 1:1028). Cytokine standard curves were generated after sample acquiring using power fit and $R^2 > 0.96$ for all cytokines. The concentration for each cytokine in cell supernatants was determined by interpolation from the corresponding standard curve. FIG. 12A shows IFN-γ measurement; FIG. 12B shows IL-2 measurement; FIG. 12C shows TNF-α measurement; FIG. 12D shows IL-4 measurement; FIG. 12E shows IL-10 measurement; and FIG. 12F shows IL-17A measurement.

Figure 13A:
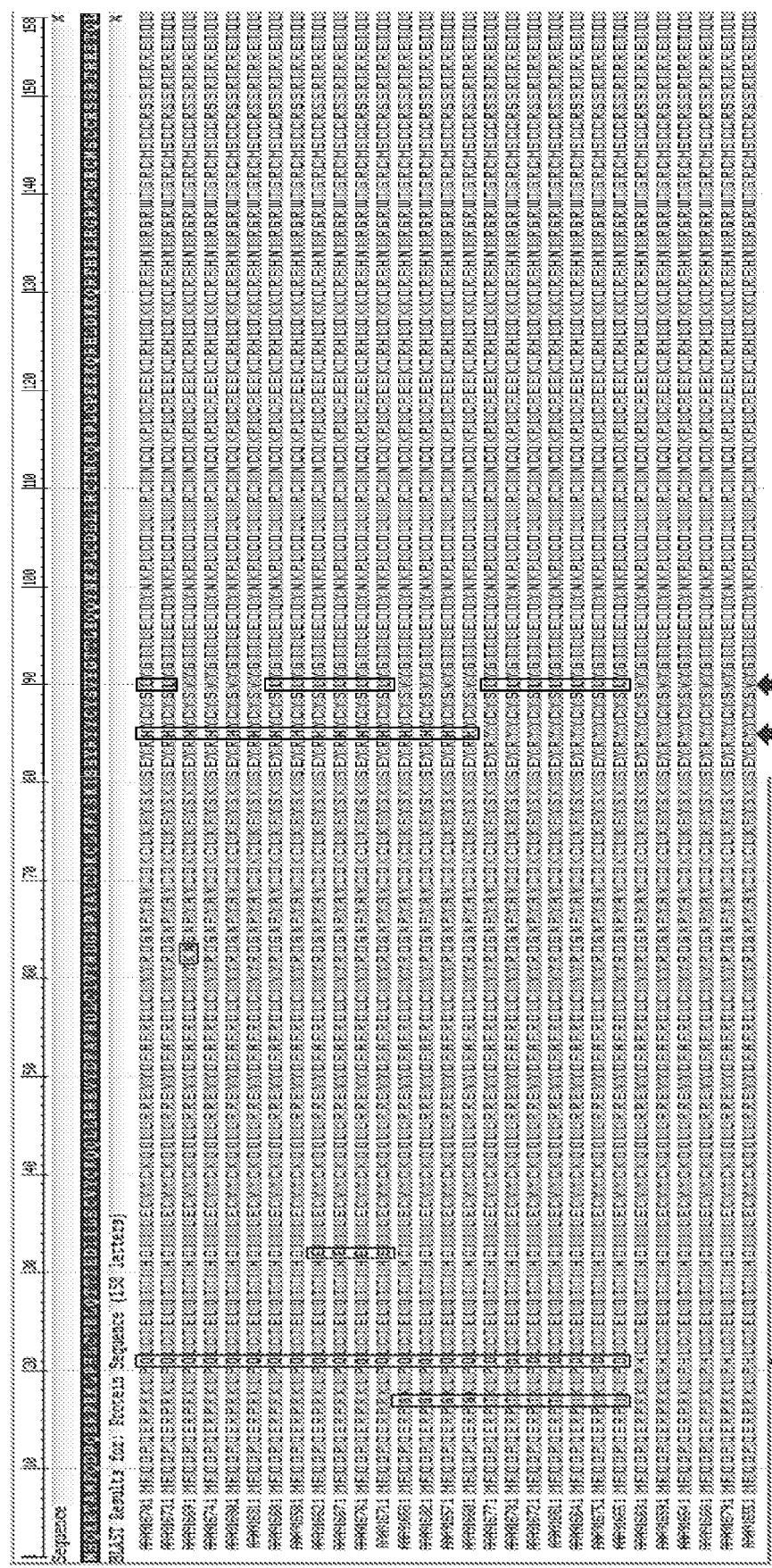
Figure 13B:
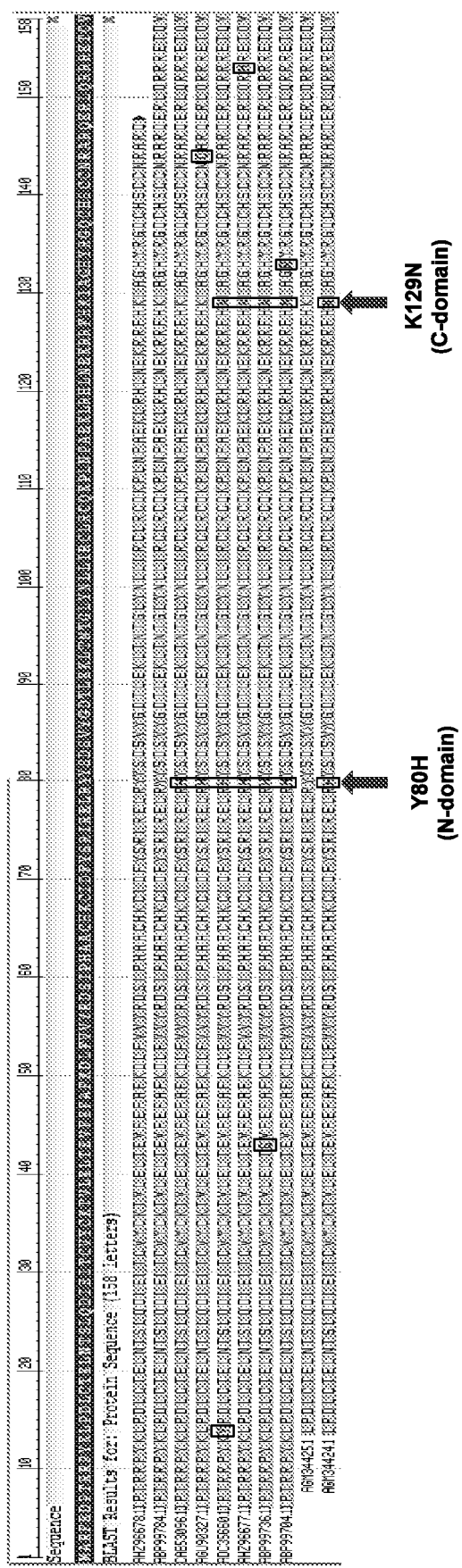
Figure 13C:
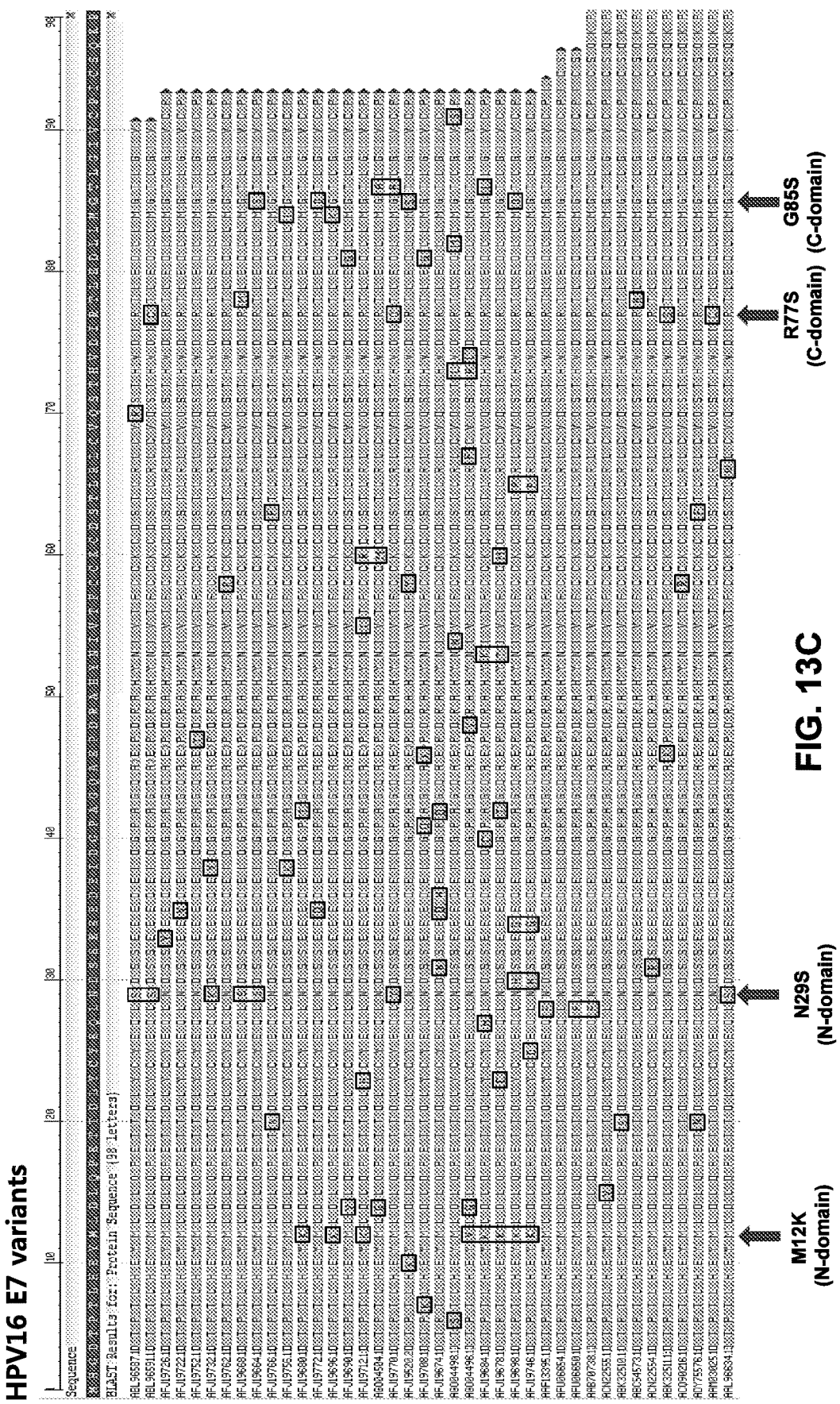
Figure 13D:
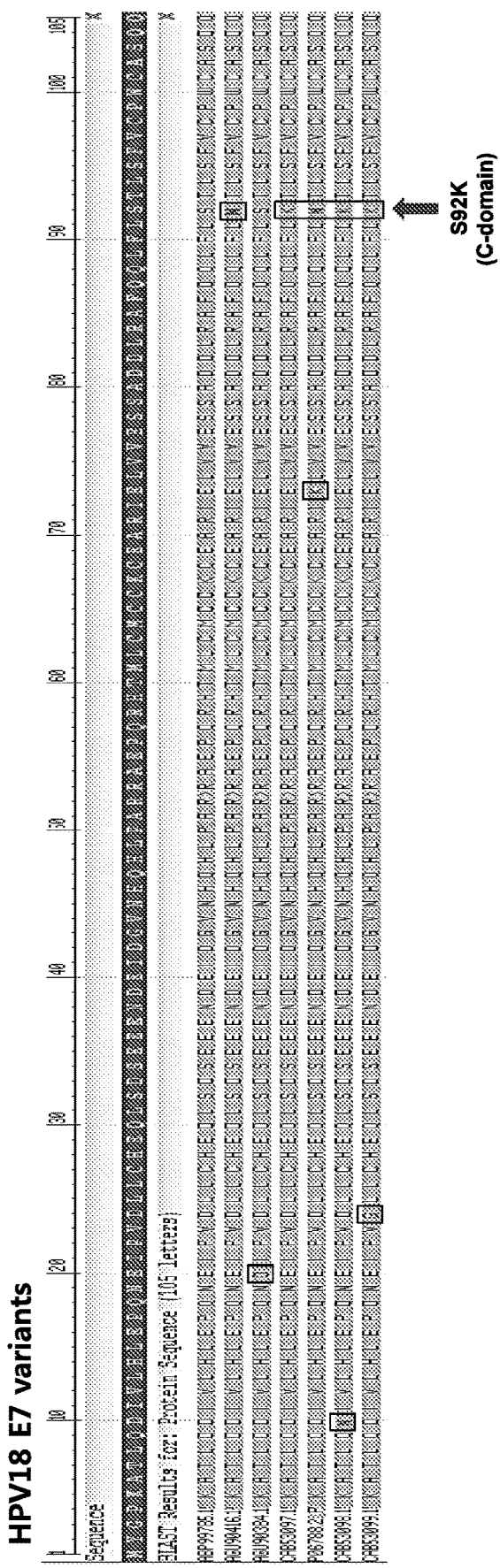

FIGS. 13A-13D show naturally occurring variants of E6 or E7 protein of HPV16 or HPV18. FIG. 13A shows the sequence comparison of the naturally occurring variants of E6 protein of HPV16: GenBank Accession Nos.: AAA91670.1 (SEQ ID NO: 19); AAA91673.1 (SEQ ID NO: 20); AAA91669.1 (SEQ ID NO: 21); AAA91674.1 (EQ ID NO: 22); AAA91680.1 (SEQ ID NO: 23); AAA91681.1 (SEQ ID NO: 24); AAA91668.1 (SEQ ID NO: 25); AAA91658.1 (SEQ ID NO: 26); AAA91662.1 (SEQ ID NO: 27); AAA91667.1 (SEQ ID NO: 28); AAA91676.1 (SEQ ID NO: 29); AAA91671.1 (SEQ ID NO: 30); AAA91656.1 (SEQ ID NO: 31); AAA91682.1 (SEQ ID NO: 32); AAA91657.1 (SEQ ID NO: 33); AAA91660.1 (SEQ ID NO: 34); AAA91677.1 (SEQ ID NO: 35); AAA91678.1 (SEQ ID NO: 36); AAA91672.1 (SEQ ID NO: 37); AAA91661.1 (SEQ ID NO: 38); AAA91664.1 (SEQ ID NO: 39); AAA91675.1 (SEQ ID NO: 40); AAA91665.1 (SEQ ID NO: 41); AAA91663.1 (SEQ ID NO: 42); AAA91659.1 (SEQ ID NO: 43); AAA91654.1 (SEQ ID NO: 44); AAA91666.1 (SEQ ID NO: 45); AAA91679.1 (SEQ ID NO: 46); and AAA91655.1 (SEQ ID NO: 47). FIG. 13B shows the sequence comparison of the naturally occurring variants of E6 protein of HPV18: GenBank Accession Nos.: AHZ96678.1 (SEQ ID NO: 48); ABP99784.1 (SEQ ID NO: 49); CAB53096.1 (SEQ ID NO: 50); AGU90327.1 (SEQ ID NO: 51); ADC35660.1 (SEQ ID NO: 52); AHZ96677.1 (SEQ ID NO: 53); ABP99736.1 (SEQ ID NO: 54); ABP99704.1 (SEQ ID NO: 55), AGM34425.1 (SEQ ID NO: 103), and AGM34423.1 (SEQ ID NO: 104). FIG. 13C shows the sequence comparison of the naturally occurring variants of E7 protein of HPV16: GenBank Accession Nos.: ABL96587.1 (SEQ ID NO: 56); ABL96591.1 (SEQ ID NO: 57); AFJ19726.1 (SEQ ID NO: 58); AFJ19722.1 (SEQ ID NO: 59); AFJ19752.1 (SEQ ID NO: 60); AFJ19732.1 (SEQ ID NO: 61); AFJ19762.1 (SEQ ID NO: 62); AFJ19668.1 (SEQ ID NO: 63); AFJ19664.1 (SEQ ID NO: 64); AFJ19766.1 (SEQ ID NO: 65); AFJ19756.1 (SEQ ID NO: 66); AFJ19680.1 (SEQ ID NO: 67); AFJ19772.1 (SEQ ID NO: 68); AFJ19696.1 (by SEQ ID NO: 69); AFJ19690.1 (SEQ ID NO: 70); AFJ19712.1 (by SEQ ID NO: 71); AGO04504.1 (SEQ ID NO: 72); AFJ19770.1 (SEQ ID NO: 73); AFJ19520.2 (SEQ ID NO: 74); AFJ19708.1 (SEQ ID NO: 75); AFJ19674.1 (SEQ ID NO: 76); AGO04498.1 (SEQ ID NO: 77); AGO04496.1 (SEQ ID NO: 78); AFJ19684.1 (SEQ ID NO: 79); AFJ19678.1 (SEQ ID NO: 80); AFJ19698.1 (SEQ ID NO: 81); AFJ19746.1 (SEQ ID NO: 82); AAF13395.1 (SEQ ID NO: 83); AFU06654.1 (SEQ ID NO: 84); AFU06650.1 (SEQ ID NO: 85); AAB70738.1 (SEQ ID NO: 86); ACN22555.1 (SEQ ID NO: 87); ABK32510.1 (SEQ ID NO: 88); ABC54573.1 (SEQ ID NO: 89); ACN22554.1 (SEQ ID NO: 90); ABK32511.1 (SEQ ID NO: 91); ACQ90216.1 (SEQ ID NO: 92); ADY75576.1 (SEQ ID NO: 93); AAM03025.1 (SEQ ID NO: 94); and AAL96634.1 (SEQ ID NO: 95). FIG. 13D shows the sequence comparison of the naturally occurring variants of E7 protein of HPV18: GenBank Accession Nos.: ABP99785.1 (SEQ ID NO: 96); AGU90416.1 (SEQ ID NO: 97); AGU90384.1 (SEQ ID NO: 98); CAB53097.1 (SEQ ID NO: 99); P06788.2.1 (SEQ ID NO: 100); CAB53098.1 (SEQ ID NO: 101); and CAB53099.1 (SEQ ID NO: 102).

FIG. 14 shows a diagram of GX-188 DNA vaccine variants. Lane 1 (A) represents a negative control: pGX27 vector only; Lane 2 (B) represents a GX-188 positive control: GX-188 DNA vaccine as shown in FIG. 1A; Lane 3 (C-1) represents an HPV16 E6 mutant: The C-1 construct contains mutations/substitutions at histidine (H) 21, tyrosine (Y) 85, and valine (V) 90 of HPV16 E6 by glutamine (Q), histidine (H), and leucine (L), respectively, compared to GX-188; Lane 4 (C-2) represents a HPV16 E7 mutant; The C-2 construct contains mutations/substitutions at methionine (M) 12 of HPV16 E7 by lysine (K) compared to GX-188, and at asparagine (N) 29, arginine (R) 77, and glycine (G) 85 of HPV16 E7 by serine (S) compared to GX-188; Lane 5 (D-1) represents a DNA vaccine variant in which sequences for $1^{st}$ to $78^{th}$ amino acids of the HPV16 E6, $1^{st}$ to $58^{th}$ amino acids of the HPV16 E7, $79^{th}$ to $158^{th}$ amino acids of HPV16 E6, $59^{th}$ to $98^{th}$ amino acids of HPV16 E7, $1^{st}$ to $85^{th}$ amino acids of the HPV18 E6, $1^{st}$ to $65^{th}$ amino acids of the HPV18 E7, $71^{st}$ to $158^{th}$ of the HPV18 E6, and $51^{st}$ to $105^{th}$ of the HPV18 E7; Lane 6 (D-2) represents a DNA vaccine variant in which sequences for $1^{st}$ to $130^{th}$ amino acids of the HPV16 E6, $1^{st}$ to $85^{th}$ amino acids of the HPV16 E7, $45^{th}$ to $158^{th}$ amino acids of HPV16 E6, $44^{th}$ to $98^{th}$ amino acids of HPV16 E7, $1^{st}$ to $85^{th}$ amino acids of the HPV18 E6, $1^{st}$ to $65^{th}$ amino acids of the HPV18 E7, $71^{st}$ to $158^{th}$ of the HPV18 E6, and $51^{st}$ to $105^{th}$ of the HPV18 E7; Lane 7 (E-1) represents a DNA vaccine variant having a different shuffling order (i.e., NCNCNCNC): The E-1 construct contains, from N terminus to C terminus, $1^{st}$ to $85^{th}$ amino acids of the HPV16 E6, $51^{st}$ to $98^{th}$ amino acids of the HPV16 E7, $1^{th}$ to $65^{th}$ amino acids of HPV16 E7, and $71^{th}$ to $158^{th}$ amino acids of the HPV16 E6, $1^{st}$ to $85^{th}$ amino acids of the HPV18 E6, $1^{st}$ to $65^{th}$ amino acids of the HPV18 E7, $71^{st}$ to $158^{th}$ of the HPV18 E6, and $51^{st}$ to $105^{th}$ of the HPV18 E7. The E-2 represents a DNA vaccine variant having a different shuffling order (i.e., CCNNCCNN): the E-2 construct contains, from N terminus to C terminus, $71^{st}$ to $158^{th}$ amino acids of the HPV16 E6, $51^{st}$ to $98^{th}$ amino acids of the HPV16 E7, $1^{th}$ to $85^{th}$ amino acids of the HPV16 E6, $1^{th}$ to $65^{th}$ amino acids of the HPV16 E7, $1^{st}$ to $85^{th}$ amino acids of the HPV18 E6, $1^{st}$ to $65^{th}$ amino acids of the HPV18 E7, $71^{st}$ to $158^{th}$ of the HPV18 E6, and $51^{st}$ to $105^{th}$ of the HPV18 E7.

Figure 15:
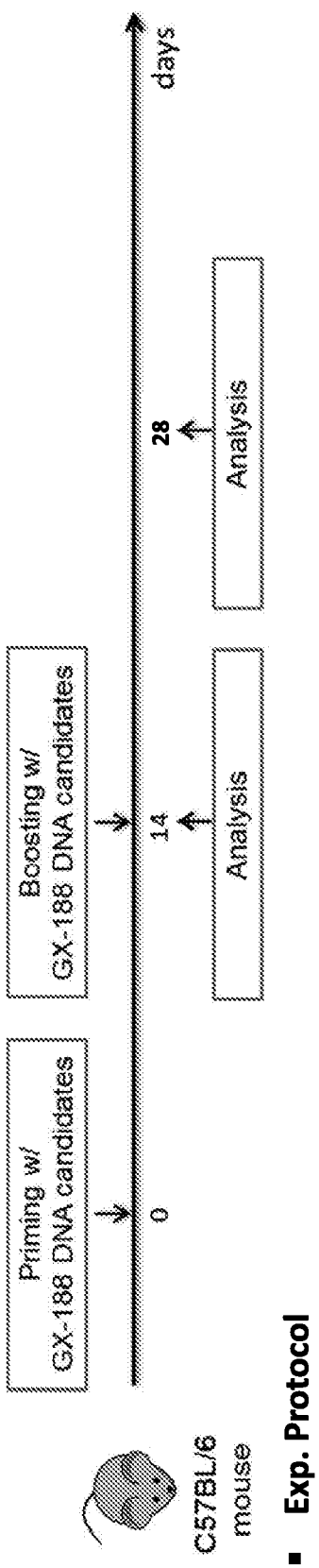

FIG. 15 shows a schematic diagram of the vaccine schedule for the GX-188 vaccine variants. C57/BL/6 mice were administered with each of the vaccine variants with electroporation delivery, A (negative control), B (positive control), C-1, C-2, D-1, D-2, E-1, and E-2. The mice were analyzed either at 2 weeks after single immunization or given a boost shot at 2 weeks after initial immunization. The mice received the boost shot were then analyzed at 2 weeks after last immunization.

Figure 16A:
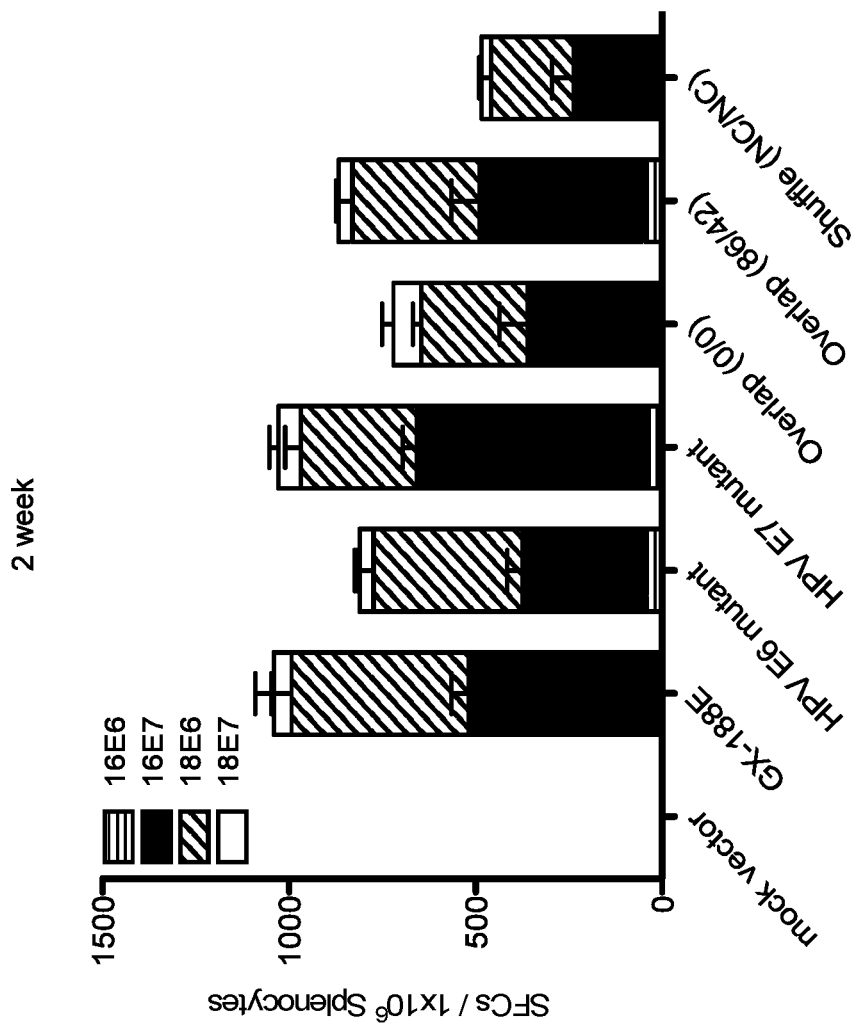
Figure 16B:
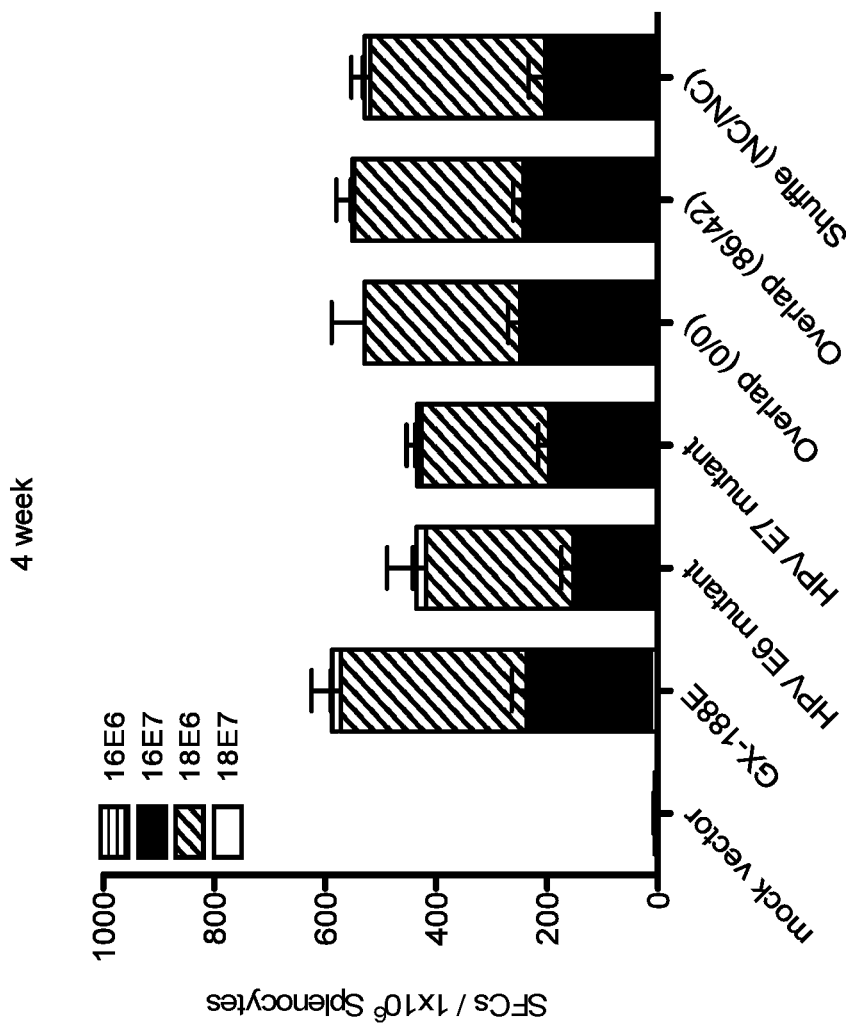

FIG. 16A demonstrates the results of the vaccine-induced immune responses after single vaccination as shown in FIG. 15. Y axis shows SFCs/1×10$^6$ splenocytes, while the X axis shows GX-188 vaccine variants. FIG. 16B shows the results of the vaccine-induced immune responses after boosting vaccination as shown in FIG. 15. Y-axis shows SFCs/1×10$^6$ splenocytes, while the X axis shows GX-188 vaccine variants.

DETAILED DESCRIPTION OF THE INVENTION

I. Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

It is to be noted that the term "a" or "an" entity, refers to one or more of that entity; for example, "a polypeptide," is understood to represent one or more polypeptides. As such, the terms "a" (or "an"), "one or more," and "at least one" can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

It is also understood that whenever embodiments are described herein as method of treatment format, otherwise analogous formats described as Swiss-type medical use format and/or pharmaceutical composition for use format are also provided.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. Examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a "coding region" or "coding sequence" is a portion of polynucleotide which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3'terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a first polypeptide chain and a second polypeptide chain of a chimeric molecule as described below. In addition, a vector, polynucleotide, or nucleic acid of the invention can encode heterologous coding regions, either fused or unfused to a nucleic acid encoding a chimeric molecule of the invention. Heterologous coding regions include without limitation specialized elements or motifs, such as a secretory signal peptide or a heterologous functional domain.

As used herein, the term "optimized," with regard to nucleotide sequences, refers to a polynucleotide sequence that encodes a polypeptide, wherein the polynucleotide sequence has been mutated to enhance a property of that polynucleotide sequence. In some embodiments, the optimization is done to increase transcription levels, increase translation levels, increase steady-state mRNA levels, increase or decrease the binding of regulatory proteins such as general transcription factors, increase or decrease splicing, or increase the yield of the polypeptide produced by the polynucleotide sequence. Examples of changes that can be made to a polynucleotide sequence to optimize it include codon optimization, G/C content optimization, removal of repeat sequences, removal of AT rich elements, removal of cryptic splice sites, removal of cis-acting elements that repress transcription or translation, adding or removing poly-T or poly-A sequences, adding sequences around the transcription start site that enhance transcription, such as Kozak consensus sequences, removal of sequences that could form stem loop structures, removal of destabilizing sequences, and two or more combinations thereof.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous signal peptide, e.g., tissue plasminogen activator (tPA), a signal peptide of Herpes Simplex Virus Glycoprotein D (HSV gDs), a signal peptide of a growth hormone, and any combinations thereof can be used. In some embodiments, the polynucleotide described herein further comprises a nucleic acid sequence encoding a signal peptide of tPA.

In certain embodiments, the polynucleotide described herein further comprises a nucleic acid sequence encoding the heterologous polypeptide which comprises an Fms-related tyrosine kinase 3 ligand ("FLT3L") or a portion thereof. The FLT3L is a factor for inducing proliferation and maturation of dendritic cells (DCs), which may enhance an immune response against an antigen and show an excellent effect to relieve a tumor when fused with a tumor antigen.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions which function in vertebrate cells, such as, but not limited to, promoter and enhancer segments from cytomegaloviruses (CMV) (the immediate early promoter, in conjunction with intron-A), simian virus 40 (SV40) (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins). In certain embodiments, the transcriptional control regions can be SV40 poly A, SV40 enhancer, pCMV early enhancer/promoter; rabbit β-globin intervening sequence (gIVS) or any combination thereof.

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors may be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), galactosidase (LacZ), glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus vectors, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

As known in the art, "sequence identity" between two polypeptides is determined by comparing the amino acid sequence of one polypeptide to the sequence of a second polypeptide. When discussed herein, whether any particular polypeptide is at least about 50%, 60%, 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

The term "GX-188 variants," "GX-188 analogues," "GX-188 variant constructs," "GX-188 analogue constructs" or any similar terms as used herein indicate that the construct, after administration of at least one dose of the construct, induces a cellular immune response in vivo similar to the cellular immune response induced after administration of GX-188 (FIG. 1A or SEQ ID NO: 9). The cellular immune response can be similar if the variant construct can induce a cellular immune response the same as or higher than the cellular immune response induced by GX-188. In other embodiments, the cellular immune response can be similar if the variant construct induces a cellular immune response at least about 0.9 fold (e.g., 90%), about 0.8 fold, about 0.7 fold, about 0.6 fold, about 0.5 fold, or about 0.4 fold higher than the immune response induced by GX-188. In one embodiment, the cellular immune response is a CD8 T cell response, CD4 T cell response, cytokine secretion, or any combination thereof. In another embodiment, the cellular immune response comprises an increased number of polyfunctional T cells. In certain embodiments, the poly-functional T cells exhibit at least three, at least four, or at least five markers selected from the group consisting of IFN-$\gamma$, IL-2, TNF-$\alpha$, MIP-$\beta$, CD107a/b, and any combination thereof, when measured by flow cytometry.

A "fusion" or "chimeric" molecule comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

The term "split," "splitting," or any similar terms, as used herein, is a conceptual term and refers to dividing an amino acid sequence into two amino acid sequences at the C-terminal end of an amino acid within the sequence. For example, an E6 protein of HPV16 can be split into two portions, an N terminal portion and a C-terminal portion. When an E6 protein of HPV16 is split into two portions at amino acid 85, the N-terminal portion can comprise amino acids 1 to amino acids 85 corresponding to SEQ ID NO: 2 while the C-terminal portion can comprise amino acids 86 to 158 corresponding SEQ ID NO: 2. The term "split" however, does not limit the boundaries of the N terminal portion (i.e., C-terminus of the N-terminal portion) and the C-terminal portion (N-terminus of C-terminal portion) to the exact amino acid site which splits the protein into two portions. For example, in one embodiment, when an E6 protein of HPV16 is split into two portions at amino acid 85, the N-terminal portion can comprise amino acids 1 to amino acids 85 corresponding to SEQ ID NO: 2, and the C-terminal portion can comprise amino acids 71 to 158 corresponding SEQ ID NO: 2. The amino acids 71 to 85 can be an overlapping sequence between the N-terminal portion and the C-terminal portion. In another embodiment, when an E6 protein of HPV16 is split into two portions at amino acid 70, the N-terminal portion comprises amino acids 1 to amino acids 70 corresponding to SEQ ID NO: 2 while the C-terminal portion comprises amino acids 71 to 158 corresponding SEQ ID NO: 2. In other embodiments, the N-terminal portion contains an overlapping sequence; thus the N-terminal portion can comprise amino acids 1 to amino acids 85 corresponding to SEQ ID NO: 2 while the C-terminal portion comprises amino acids 71 to 158 corresponding SEQ ID NO: 2. The fusion protein of the invention can be generated by constructing a fusion protein based on the sequences and then preparing a nucleotide sequence encoding the fusion protein synthetically, recombinantly, or by any other methods known in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

"Tumor" and "neoplasm" refer to any mass of tissue that result from excessive cell growth or proliferation, either benign (noncancerous) or malignant (cancerous) including pre-cancerous lesions. Tumor can be a cervical tumor. In specific embodiments, the cervical tumor is a benign tumor or a malignant tumor. In certain embodiments, the cervical tumor is squamous cell carcinoma (SCC), adenocarcinoma, adenosquamous carcinoma, small cell carcinoma, neuroendocrine tumor (NET), glassy cell carcinoma, villoglandular adenocarcinoma (VGA), non-carcinoma malignancies, melanoma, lymphoma, or cervical intraepithelial neoplasia (CIN). In some embodiments, the cervical tumor is CIN1, CIN2, CIN3, or cervical cancer.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells).

An "effective amount" of a polynucleotide encoding a fusion protein as disclosed herein is an amount sufficient to carry out a specifically stated purpose. An "effective amount" can be determined empirically and in a routine manner, in relation to the stated purpose.

As used herein, a "therapeutically effective amount" refers to an amount effective, at dosages and for periods of time necessary, to achieve a desired therapeutic result. A therapeutic result may be, e.g., lessening of symptoms, prolonged survival, and the like. A therapeutic result need not be a "cure".

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, the subjects in need of treatment include those already diagnosed with or suspected of having the disorder.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject.

II. Therapeutic Molecules

The present invention is directed to a therapeutic molecule or a use of the therapeutic molecule in a disease or condition related to human papillomavirus. As shown elsewhere herein, the therapeutic molecule can also be used as a diagnostic agent. In one aspect, the present therapeutic molecule is constructed by fusing more than one proteins in such a way that each of the proteins is split into two portions (the N-terminal portion and the C-terminal portion), but still comprises at least all epitopes of each of the proteins. The proteins that can be used in the present invention comprise at least two proteins, at least three proteins, at least four proteins, or more. In a particular embodiment, the therapeutic molecule comprises at least four proteins or one or more nucleotide sequences encoding the same. If the therapeutic molecule utilizes four proteins, the therapeutic molecule comprises eight polypeptide portions or eight nucleotide sequences thereof. The eight portions derived from the four proteins (each protein split into two portions) can be placed in any order such that the proteins do not bind to one or more tumor suppressors to which the full length proteins bind or do not form a dimer with any one of the four proteins.

The four proteins that are used for the therapeutic molecule of the invention can be an E6 protein of human papilloma virus type 16 (HPV16), an E6 protein of human papilloma virus type 18 (HPV18), and an E7 protein of HPV16, and an E7 protein of HPV18. However, any other combinations of one or more E6 proteins and one or more E7 proteins from HPV serotypes are possible, e.g., HPV serotypes 16, 18, 31, 33, 35, 39, 45, 51, 52, 56, 58, 59, 68, and 82 for high risk serotypes, HPV serotypes 6, 11, 40, 42, 43, 44, 54, 61, 72, 73, and 81 for low risk serotypes, or any combinations thereof. Therefore, when each of the four proteins is split or cut into two portions, the therapeutic molecule can comprises an N-terminal portion of an E6 protein of HPV16, a C-terminal portion of the E6 protein of HPV16, an N-terminal portion of an E6 protein of HPV18, and a C-terminal portion of the E6 protein of HPV18, an N-terminal portion of an E7 protein of HPV16, a C-terminal portion of the E7 protein of HPV16, an N-terminal portion of an E7 protein of HPV18, or any combination thereof. In a particular embodiment, the proteins used for the invention are derived only from HPV16 and/or HPV18.

II.A. E6 Protein of HPV16 and HPV18

E6 protein of HPV16 or HPV18 plays a major role in the induction and maintenance of cellular transformation. E6 protein acts mainly as an oncoprotein by stimulating the destruction of many host cell key regulatory proteins. E6 protein associates with host E6-AP ubiquitin-protein ligase, and inactivates tumor suppressors p53 and p73 by targeting them to the 26S proteasome for degradation. In turn, DNA damage and chromosomal instabilities increase and lead to cell proliferation and cancer development.

A number of sequences of naturally occurring E6 proteins of HPV16 and HPV18 is reported. For example, amino acid sequences of E6 proteins of HPV16 and HPV18 are reported as GenBank Accession Nos. AAL96630.1 and ABP99784.1, respectively. The wild-type nucleotide sequences encoding the E6 proteins of HPV16 and HPV18 are reported as GenBank Accession No. AF486325.1 and EF202153.1, respectively. The sequences are reproduced in Table 1.

TABLE 1

Sequences of E6 Protein of HPV16 and HPV18

| Description | Sequences |
|---|---|
| E6 of HPV16-<br>Nucleotide<br>sequence<br>(SEQ ID NO: 1) | ATGCACCAAAAGAGAACTGCAATGTTTCAGGACCCACAGGAGCGACCCAGAAGTTA<br>CCACATTTATGCACAGAGCTGCAAACAACTATACATGATATAATATTAGAATGTGTG<br>TACTGCAAGCAACAGTTACTGCGACGTGAGGTATATGACTTTGCTTTTCGGGATTTA<br>TGCATAGTATATAGAGATGGGAATCCATATGCAGTGTGTGATAAATGTTTAAAGTTT<br>TATTCTAAAATTAGTGAGTATAGATATTATTGTTATAGTGTGTATGGAACAACATTA<br>GAACAGCAATACAACAAACCGTTGTGTGATTTGTTAATTAGGTGTATTAACTGTCAA<br>AAGCCACTGTGTCCTGAAGAAAAGCAAAGACATCTGGACAAAAAGCAAAGATTCCAT<br>AATATAAGGGGTCGGTGGACCGGTCGATGTATGTCTTGTTGCAGATCATCAAGAACA<br>CGTAGAGAAACCCAGCTGTAA |
| E6 of HPV16-<br>Amino acid<br>sequence<br>(SEQ ID NO: 2) | MHQKRTAMFQDPQERPRKLPHLCTELQTTIHDIILECVYCKQQLLRREVYDFAFRDL<br>CIVYRDGNPYAVCDKCLKFYSKISEYRYYCYSVYGTTLEQQYNKPLCDLLIRCINCQ<br>KPLCPEEKQRHLDKKQRFHNIRGRWTGRCMSCCRSSRTRRETQL |
| E6 of HPV18-<br>Nucleotide<br>sequence<br>(SEQ ID NO: 3) | ATGGCGCGCTTTGAGGATCCAACACGGCGACCCTACAAGCTACCTGATCTGTGCACG<br>GAACTGAACACTTCACTGCAAGACATAGAAATAACCTGTGTATATTGCAAGACAGTA<br>TTGGAACTTACAGAGGTATTTGAATTTGCATTCAAAGATTTATTTGTAGTGTATAGA<br>GACAGTATACCGCATGCTGCATGCCATAAATGTATAGATTTCTATTCTAGAATTAGA<br>GAATTAAGATATTATTCAGACTCTGTGTATGGAGACACATTAGAAAAACTAACTAAC<br>ACTGGGTTATACAATTTATTAATAAGGTGCCTGCGGTGCCAGAAACCGTTGAATCCA<br>GCAGAAAAACTTAGACACCTTAATGAAAAACGACGATTCCACAAAATAGCTGGGCAC<br>TATAGAGGCCAGTGCCATTCGTGCTGCAACCGAGCACGACAGGAGAGACTCCAACGA<br>CGCAGAGAAACACAAGTATAA |
| E6 of HPV18-<br>Amino acid<br>sequence<br>(SEQ ID NO: 4) | MARFEDPTRRPYKLPDLCTELNTSLQDIEITCVYCKTVLELTEVFEFAFKDLFVVYR<br>DSIPHAACHKCIDFYSRIRELRYYSDSVYGDTLEKLTNTGLYNLLIRCLRCQKPLNP<br>AEKLRHLNEKRRFHKIAGHYRGQCHSCCNRARQERLQRRRETQV |

The term "E6 protein of HPV16 or HPV18" as used herein includes any naturally occurring variants or functional variants thereof. Examples of the naturally occurring variants of E6 protein of HPV16 include, but are not limited to, the sequences listed in FIG. 13A: GenBank Accession Nos. AGS42365.1, AGS42372.1, ABO15571.1, AGS42373.1, ABK32509.1, AHZ96692.1, AAL01368.1, AFS64243.1, AGS42377.1, AGS42352.1, AAD33252.1, AGS42313.1, BAN15947.1, ACK57853.1, NP 041325.1, AGS42269.1, AEV66122.1, AGS42267.1, ACL12310.1, ABO61749.1, AAL01351.1, AAV91676.1, AGS42341.1, AGS42314.1, BAN15937.1, ACS92692.1, AAM29170.1, AAQ10712.1, AAL96621.1, AAL96623.1, AGS42353.1, ADY75574.1, AAL96604.1, AEV66140.1, ACK57870.1, ACJ66712.1, AFS64227.1, AAL96619.1, AAL96620.1, ABO61747.1, ACK57855.1, ADH94042.1, AFS64252.1, AAL96612.1, AFS64257.1, AAL96614.1, ACJ66716.1, BAN15946.1, ADY75573.1, AGS42315.1, AAA91673.1, AAA91669.1, AAA91674.1, AAA91680.1, AAA91681.1, AAA91668.1, AAA91658.1, AAA91662.1, AAA91667.1, AAA91676.1, AAA91671.1, AAA91656.1, AAA91682.1, AAA91657.1, AAA91660.1, AAA91677.1, AAA91678.1, AAA91672.1, AAA91661.1 AAA91664.1, AAA91675.1, AAA91665.1, AAA91663.1, AAA91659.1, AAA91654.1, AAA91666.1, AAA91679.1, and AAA91655.1. In certain embodiments, an E6 protein of HPV16 includes one or more substitutions selected from D11E, E14D, R15P, R17I, R17T, R17G, L19V, H21Q, H21D, H21E, D32N, D32E, I34R, I34L, I34T, L35V, E36Q, V49L, R54W, I59V, R62K, N65S, A68G, D71E, I80V, Y85H, V90L, P102L, I108F, I108X, E120D, K122R, Q123E, R131T, I135M, Q157L, and any combination thereof.

Examples of H6 protein of HPV18 include, but are not limited to, the sequences listed in FIG. 13B: GenBank Accession Nos. CAB53096.1, AGU90327.1, ADC35660.1, AHZ96677.1, ABP99736.1, ABP99704.1, AHZ96678.1, AGM34425.1, AGM34424.1, and ABP99784.1. In certain embodiments, an E6 protein of HPV16 includes one or more substitutions selected from L14V, E43G, Y80H, K129N, H133R, R144Q, R153H, and any combination thereof.

II.A.1. E6 Protein of HPV16

In one embodiment, an E6 protein of HPV16 useful for the fusion protein does not bind to p53 or does not form a dimer with an E6 protein of HPV16. In order to prevent binding of an E6 protein of HPV16 to p53, the E6 protein is split into two portions, an N terminal portion of the E6 protein and a C-terminal portion of the E6 protein, each of which does not comprise one or more E6-associated protein biding sites. The resulting construct, while comprising all epitopes of the E6 protein, does not comprise the complete E6AP binding sites, and thus cannot form a complex with an E6-AP. In one embodiment, E6-AP binding sites of an E6 protein of HPV16 comprise L35 to Y39, L57 to R62, V69 to Y85, C87, Y88, Q98, Y99, L107, R109, Q114, and R136 corresponding to SEQ ID NO: 2. In another embodiment, E6-AP binding sites of an E6 protein of HPV16 comprise L35 to R136 corresponding to SEQ ID NO: 2. Therefore, in certain embodiments, an N terminal portion of an E6 protein of HPV16 has an amino acid sequence from a to b (16E6Na-b), and a C-terminal portion of the E6 protein of HPV16 has an amino acid sequence from c to d (16E6Cc-d), wherein a is amino acid 1 or 2 corresponding to SEQ ID NO: 2, b is an amino acid selected from amino acids 35 to 135 corresponding to SEQ ID NO: 2, c is an amino acid selected from amino acids equal to or higher than amino acid 36 and amino acids equal to or lower than amino acid b+1 corresponding to SEQ ID NO: 2, and d is amino acid 157 or 158 corresponding to SEQ ID NO: 2.

E6 protein of HPV16 can interact with p53 at amino acids 22LEU, 23CYS, 41LYS, 42GLN, 43GLN, 45LEU, 46ARG, 47ARG, 49VAL, 50TYR, 51ASP, 53ALA, 54PHE, 57LEU, 71ASP, 74LEU, 75LYS, 76PHE, 78SER, 79LYS, 80ILE, 82GLU, 83TYR, 84ARG, 85TYR, 86TYR, or 99TYR corresponding to SEQ ID NO: 2. The corresponding interaction sites on p53 can include 110ARG, 111LEU 112GLY, 113PHE, 114LEU, 115HIS, 116SER, 124CYS, 126TYR, 128PRO, 131ASN, 142PRO, 144GLN 146TRP, 229CYS, and 231THR of p53. Therefore, in certain embodiments, the N-terminal portion and the C-terminal portion of the E6 protein can be produced by splitting the E6 protein into two portions at the C-terminal end of an amino acid selected from amino acids 22 to 98 corresponding to SEQ ID NO: 2.

In some embodiments, the fusion protein of the invention does not form a dimer with an E6 protein of HPV16 by preventing an interaction with another E6 protein. Formation of a dimer with another E6 protein is required for the E6 protein to degrade p53. Therefore, by destroying the dimer formation site on the E6 protein, the E6 protein can no longer degrade p53. E6 protein of HPV16 forms a dimer with another E6 protein by directly interacting at Q42, K72, F76, and Y77 corresponding to SEQ ID NO: 2. In one embodiment, the N-terminal portion and the C-terminal portion of the E6 protein of HPV16 can be produced by splitting the E6 protein into two portions at the C-terminal end of an amino acid selected from amino acids 42 to 76 corresponding to SEQ ID NO: 2. In one embodiment, a fusion protein of the invention comprises an N-terminal portion of an E6 of HPV16 (16E6Na-b) and a C-terminal portion of an E6 protein of HPV16, wherein a is amino acid 1 or 2 corresponding to SEQ ID NO: 2, b is an amino acid selected from amino acids 42 to 76 corresponding to SEQ ID NO: 2, c is an amino acid selected from amino acids equal to or higher than amino acid 43 and amino acids equal to or lower than amino acid b+1 corresponding to SEQ ID NO: 2, and d is amino acid 157 or 158 corresponding to SEQ ID NO: 2.

In order for an E6 protein of HPV16 to form a dimer with another E6 protein, the E6 protein has to incorporate Zinc in its Zinc finger motif 1. When the Zinc finger motif 1 fails to incorporate Zinc, the E6 protein of HPV16 can no longer form a dimer. In particular, four cysteines of the Zinc finger motif 1, which are located at amino acids 37, 40, 70, and 73 corresponding to SEQ ID NO: 2, directly interact with Zinc. In one embodiment, the N-terminal portion of the E6 protein of HPV16 only contains one cysteine, two cysteines, or three cysteines within the Zinc finger motif 1 while the C-terminal portion of the E6 protein of HPV16 contains three cysteines, two cysteines, or one cysteine, respectively, within the Zinc finger motif 1. In another embodiment, the N-terminal portion and the C-terminal portion of the E6 protein can be produced by splitting the E6 protein into two portions at the C-terminal end of an amino acid selected from amino acids 37 to 72 corresponding to SEQ ID NO: 2. In one embodiment, a fusion protein of the invention comprises an N-terminal portion of an E6 of HPV16 (16E6Na-b) and a C-terminal portion of an E6 protein of HPV16, wherein a is amino acid 1 or 2 corresponding to SEQ ID NO: 2, b is an amino acid selected from amino acids 37 to 72 corresponding to SEQ ID NO: 2, c is an amino acid selected from amino acids equal to or higher than amino acid 38 and amino acids equal to or lower than amino acid b+1 corresponding to SEQ ID NO: 2, and d is amino acid 157 or 158 corresponding to SEQ ID NO: 2.

In some embodiments, the fusion protein comprises 16E6Na-b and 16E6Cc-d, wherein a is amino acid 1 or 2, d is amino acid 157 or 158, and b and c as follows: b is amino acid residue 35 and c is an amino acid residue 36; b is amino acid residue 36 and c is amino acid residue 36 or 37; b is amino acid residue 37 and c is amino acid residue 36, 37, or 38; b is amino acid residue 38 and c is amino acid residue 36, 37, 38, or 39; b is amino acid residue 39 and c is amino acid residue 36, 37, 38, 39, or 40; b is amino acid residue 40 and c is an amino acid selected from amino acid residue 36 to 41; b is amino acid residue 41 and c is an amino acid selected from amino acid residue 36 to 42; b is amino acid residue 42 and c is an amino acid selected from amino acid residue 36 to 43; b is amino acid residue 43 and c is an amino acid selected from amino acid residue 36 to 44; b is amino acid residue 44 and c is an amino acid selected from amino acid residue 36 to 45; b is amino acid residue 45 and c is an amino acid selected from amino acid residue 36 to 46; b is amino acid residue 46 and c is an amino acid selected from amino acid residue 36 to 47; b is amino acid residue 47 and c is an amino acid selected from amino acid residue 36 to 48; b is amino acid residue 48 and c is an amino acid selected from amino acid residue 36 to 49; b is amino acid residue 49 and c is an amino acid selected from amino acid residue 36 to 50; b is amino acid residue 50 and c is an amino acid selected from amino acid residue 36 to 51; b is amino acid residue 51 and c is an amino acid selected from amino acid residue 36 to 52; b is amino acid residue 52 and c is an amino acid selected from amino acid residue 36 to 53; b is amino acid residue 53 and c is an amino acid selected from amino acid residue 36 to 54; b is amino acid residue 54 and c is an amino acid selected from amino acid residue 36 to 55; b is amino acid residue 55 and c is an amino acid selected from amino acid residue 36 to 56; b is amino acid residue 56 and c is an amino acid selected from amino acid residue 36 to 57; b is amino acid residue 57 and c is an amino acid selected from amino acid residue 36 to 58; b is amino acid residue 58 and c is an amino acid selected from amino acid residues 36 to 59; b is amino acid residue 59 and c is an amino acid selected from amino acid residues 36 to 60; b is amino acid residue 60 and c is an amino acid selected from amino acid residues 36 to 61; b is amino acid residue 61 and c is an amino acid selected from amino acid residues 36 to 62; b is amino acid residue 62 and c is an amino acid selected from amino acid residues 36 to 63; b is amino acid residue 63 and c is an amino acid selected from amino acid residues 36 to 64; b is amino acid residue 64 and c is an amino acid selected from amino acid residues 36 to 65; b is amino acid residue 65 and c is an amino acid selected from amino acid residues 36 to 66; b is amino acid residue 66 and c is an amino acid selected from amino acid residues 36 to 67; b is amino acid residue 67 and c is an amino acid selected from amino acid residues 36 to 68; b is amino acid residue 68 and c is an amino acid selected from amino acid residues 36 to 69; b is amino acid residue 69 and c is an amino acid selected from amino acid residues 36 to 70; b is amino acid residue 70 and c is an amino acid selected from amino acid residues 36 to 71; b is amino acid residue 71 and c is an amino acid selected from amino acid residues 36 to 72; b is amino acid residue 72 and c is an amino acid selected from amino acid residues 36 to 73; b is amino acid residue 73 and c is an amino acid selected from amino acid residues 36 to 74; b is amino acid residue 74 and c is an amino acid selected from amino acid residues 36 to 75; b is amino acid residue 75 and c is an amino acid selected from amino acid residues 36 to 76; b is amino acid residue 76 and c is an amino acid selected from amino acid residues 36 to 77; b is amino acid residue 77 and c is an amino acid selected from amino acid residues 36 to 78; b is amino acid residue 78 and c is an amino acid selected from amino acid residues 36 to 79; b is amino acid residue 79 and c is an amino acid selected from amino acid residues 36 to 80; b is amino acid residue 80 and c is an amino acid selected from amino acid residues 36 to 81; b is amino acid residue 81 and c is an amino acid selected from amino acid residues 36 to 82; b is amino acid residue 82 and c is an amino acid selected from amino acid residues 36 to 83; b is amino acid residue 83 and c is an amino acid selected from amino acid residues 36 to 84; b is amino acid residue 84 and c is an amino acid selected from amino acid residues 36 to 85; b is amino acid residue 85 and c is an amino acid selected from amino acid residues 36 to 86; b is amino acid residue 86 and c is an amino acid selected from amino acid residues 36 to 87; b is amino acid residue 87 and c is an amino acid selected from amino acid residues 36 to 88; b is amino acid residue 88 and c is an amino acid selected from amino acid residues 36 to 89; b is amino acid residue 89 and c is an amino acid selected from amino acid residues 36 to 90; b is amino acid residue 90 and c is an amino acid selected from amino acid residues 36 to 91; b is amino acid residue 91 and c is an amino acid selected from amino acid residues 36 to 92; b is amino acid residue 92 and c is an amino acid selected from amino acid residues 36 to 93; b is amino acid residue 93 and c is an amino acid selected from amino acid residues 36 to 94; b is amino acid residue 94 and c is an amino acid selected from amino acid residues 36 to 95; b is amino acid residue 95 and c is an amino acid selected from amino acid residues 36 to 96; b is amino acid residue 96 and c is an amino acid selected from amino acid residues 36 to 97; b is amino acid residue 97 and c is an amino acid selected from amino acid residues 36 to 98; b is amino acid residue 98 and c is an amino acid selected from amino acid residues 36 to 99; b is amino acid residue 99 and c is an amino acid selected from amino acid residues 36 to 100; b is amino acid residue 100 and c is an amino acid selected from amino acid residues 36 to 101; b is amino acid residue 101 and c is an amino acid selected from amino acid residues 36 to 102; b is amino acid residue 102 and c is an amino acid selected from amino acid residues 36 to 103; b is amino acid residue 103 and c is an amino acid selected from amino acid residues 36 to 104; b is amino acid residue 104 and c is an amino acid selected from amino acid residues 36 to 105; b is amino acid residue 105 and c is an amino acid selected from amino acid residues 36 to 106; b is amino acid residue 106 and c is an amino acid selected from amino acid residues 36 to 107; b is amino acid residue 107 and c is an amino acid selected from amino acid residues 36 to 108; b is amino acid residue 108 and c is an amino acid selected from amino acid residues 36 to 109; b is amino acid residue 109 and c is an amino acid selected from amino acid residues 36 to 110; b is amino acid residue 110 and c is an amino acid selected from amino acid residues 36 to 111; b is amino acid residue 111 and c is an amino acid selected from amino acid residues 36 to 112; b is amino acid residue 112 and c is an amino acid selected from amino acid residues 36 to 113; b is amino acid residue 113 and c is an amino acid selected from amino acid residues 36 to 114; b is amino acid residue 114 and c is an amino acid selected from amino acid residues 36 to 115; b is amino acid residue 115 and c is an amino acid selected from amino acid residues 36 to 116; b is amino acid residue 116 and c is an amino acid selected from amino acid residues 36 to 117; b is amino acid residue 117 and c is an amino acid selected from amino acid residues 36 to 118; b is amino acid residue 118 and c is an amino acid selected from amino acid residues 36 to 119; b is amino acid residue 119 and c is an amino acid selected from amino acid residues 36 to 120; b is amino acid residue 120 and c is an amino acid selected from amino acid residues 36 to 121; b is amino acid residue 121 and c is an amino acid selected from amino acid residues 36 to 122; b is amino acid residue 122 and c is an amino acid selected from amino acid residues 36 to 123; b is amino acid residue 123 and c is an amino acid selected from amino acid residues 36 to 124; b is amino acid residue 124 and c is an amino acid selected from amino acid residues 36 to 125; b is amino acid residue 125 and c is an amino acid selected from amino acid residues 36 to 126; b is amino acid residue 126 and c is an amino acid selected from amino acid residues 36 to 127; b is amino acid residue 127 and c is an amino acid selected from amino acid residues 36 to 128; b is amino acid residue 128 and c is an amino acid selected from amino acid residues 36 to 129; b is amino acid residue 129 and c is an amino acid selected from amino acid residues 36 to 130; b is amino acid residue 130 and c is an amino acid selected from amino acid residues 36 to 131; b is amino acid residue 131 and c is an amino acid selected from amino acid residues 36 to 132; b is amino acid residue 132 and c is an amino acid selected from amino acid residues 36 to 133; b is amino acid residue 133 and c is an amino acid selected from amino acid residues 36 to 134; b is amino acid residue 134 and c is an amino acid selected from amino acid residues 36 to 135; or b is amino acid residue 135 and c is an amino acid selected from amino acid residues 36 to 136 corresponding to SEQ ID NO: 2.

In certain embodiment, the N-terminal portion of an E6 protein of HPV16 and the C-terminal portion of an E6 protein of HPV16, when aligned together, contain an overlapping sequence. The overlapping sequence can be at least 1, 5, 7, 10, 15, 20, 25, 30, 35, 40, 45, 50, 55, 60, 65, 70, 75, 80, 85, 90, 95, 100, 105, 110, 115, or 120 amino acids of the E6 protein of HPV16. While the N-terminal portion or the C-terminal portion can contain an overlapping sequence, however, neither the N-terminal portion nor the C-terminal portion comprises the complete E6AP binding domain, e.g., amino acids 35 to 136 corresponding to SEQ ID NO: 2.

The complex E6/E6-AP targets several other substrates to degradation via the proteasome including host NFX1-91, a repressor of human telomerase reverse transcriptase (hTERT). The resulting increased expression of hTERT prevents the shortening of telomere length leading to cell immortalization. Other cellular targets including Bak, Fas-associated death domain-containing protein (FADD) and procaspase 8, are degraded by E6/E6-AP causing inhibition of apoptosis. E6 protein also inhibits immune response by interacting with host IRF3 and TYK2. These interactions prevent IRF3 transcriptional activities and inhibit TYK2-mediated JAK-STAT activation by interferon alpha resulting in inhibition of the interferon signaling pathway. Therefore, an E6 protein of HPV16 can be split into an N-terminal portion of an E6 protein of HPV16 and a C-terminal portion of the E6 protein of HPV16 such that the fusion protein cannot bind to one or more substrates other than p53, e.g., a repressor of hTERT, Bak, FADD, procaspase 8 or cannot interact with host IRF3 and TYK2.

II.A.2. E6 Protein of HPV18

An E6 protein of HPV18 useful for the fusion protein does not bind to p53 or does not form a dimer with an E6 protein of HPV18. In order to prevent binding of an E6 protein of HPV18 to p53, the E6 protein is split into two portions, an N terminal portion of the E6 protein and a C-terminal portion of the E6 protein, each of which does not comprise one or more E6-associated protein binding sites. In one embodiment, E6-AP binding sites of an E6 protein of HPV18 comprise I30 to Y34, L52 to R57, A64 to Y80, S82, D83, L93, T94, L102, R104, Q109, and A131 corresponding to SEQ ID NO: 4. In another embodiment, E6-AP binding sites of an E6 protein of HPV18 comprise I30 to A131 corresponding to SEQ ID NO: 4. Therefore, in certain embodiments, an N terminal portion of an E6 protein of HPV18 has an amino acid sequence from a to b (18E6Ni-j), and a C-terminal portion of the E6 protein of HPV16 has an amino acid sequence from c to d (16E6Ck-l), wherein i is amino acid 1 or 2 corresponding to SEQ ID NO: 4, j is an amino acid selected from amino acids 30 to 130 corresponding to SEQ ID NO: 4, k is an amino acid selected from amino acids equal to or higher than amino acid 31 and amino acids equal to or lower than amino acid j+1 corresponding to SEQ ID NO: 4, and 1 is amino acid 157 or 158 corresponding to SEQ ID NO: 4.

E6 protein of HPV18 can interact with p53 at amino acids 17LEU, 18CYS, 36LYS, 44VAL, 45PHE, 46GLU, 48ALA, 49PHE, 52LEU, 66HIS, 69ILE, 70ASP, 71PHE, 73SER, 74ARG, 75ILE, 77GLU, 78LEU, 79ARG, 80TYR, or 81TYR corresponding to SEQ ID NO: 4. The corresponding interaction sites on p53 include 110ARG, 111LEU 112GLY, 113PHE, 114LEU, 115HIS, 116SER, 124CYS, 126TYR, 128PRO, 131ASN, 142PRO, 144GLN, 146TRP, 229CYS, and 231THR of p53. Therefore, in certain embodiments, the N-terminal portion and the C-terminal portion of the E6 protein of HPV18 can be produced by splitting the E6 protein into two portions at the C-terminal end of an amino acid selected from amino acids 17 to 80 corresponding to SEQ ID NO: 4.

In some embodiments, the fusion protein of the invention does not form a dimer with an E6 protein of HPV18 by preventing an interaction with another E6 protein. E6 protein of HPV18 forms a dimer with another E6 protein by directly interacting at T37, K67, F71, and Y72 corresponding to SEQ ID NO: 4. Therefore, the N-terminal portion and the C-terminal portion of the E6 protein of HPV18 can be produced by splitting the E6 protein of HPV18 into two portions at the C-terminal end of an amino acid selected from amino acids 37 to 71 corresponding to SEQ ID NO: 4. In one embodiment, a fusion protein of the invention comprises an N-terminal portion of an E6 of HPV18 (18E6Ni-j) and a C-terminal portion of an E6 protein of HPV18 (18E6Ck-l), wherein i is amino acid 1 or 2 corresponding to SEQ ID NO: 4, j is an amino acid selected from amino acids 37 to 71 corresponding to SEQ ID NO: 4, k is an amino acid selected from amino acids equal to or higher than amino acid 38 and amino acids equal to or lower than amino acid j+1 corresponding to SEQ ID NO: 4, and 1 is amino acid 157 or 158 corresponding to SEQ ID NO: 4.

In order for an E6 protein of HPV18 to form a dimer with another E6 protein to degrade p53, the E6 protein has to incorporate Zinc in its Zinc finger motif 1. Therefore, when the Zinc finger motif 1 fails to incorporate Zinc, the E6 protein of HPV18 can no longer form a dimer. In particular, four cysteines of the Zinc finger motif 1, which are located at amino acids 32, 35, 65, and 68 corresponding to SEQ ID NO: 4, directly interact with Zinc. In one embodiment, the N-terminal portion of the E6 protein of HPV18 only contains one cysteine, two cysteines, or three cysteines within the Zinc finger motif 1 while the C-terminal portion of the E6 protein of HPV18 contains three cysteines, two cysteines, or one cysteine, respectively, within the Zinc finger motif 1. In another embodiment, the N-terminal portion and the C-terminal portion of the E6 protein of HPV18 can be produced by splitting the E6 protein into two portions at the C-terminal end of an amino acid selected from amino acids 32 to 67 corresponding to SEQ ID NO: 4. In one embodiment, a fusion protein of the invention comprises an N-terminal portion of an E6 protein of HPV18 (18E6Ni-j) and a C-terminal portion of an E6 protein of HPV18, wherein i is amino acid 1 or 2 corresponding to SEQ ID NO: 4, j is an amino acid selected from amino acids 32 to 67 corresponding to SEQ ID NO: 4, k is an amino acid selected from amino acids equal to or higher than amino acid 33 and amino acids equal to or lower than amino acid j+1 corresponding to SEQ ID NO: 4, and 1 is amino acid 157 or 158 corresponding to SEQ ID NO: 4.

In some embodiments, the fusion protein comprises 18E6Ni-j and 18E6Ck-l, wherein i is amino acid 1 or 2, 1 is amino acid 157 or 158, and j and k as follows: j is amino acid residue 30 and k is an amino acid residue 31; j is amino acid residue 31 and k is amino acid residue 31 or 32; j is amino acid residue 32 and k is amino acid residue 31, 32, or 33; j is amino acid residue 33 and k is amino acid residue 31, 32, 33, or 34; j is amino acid residue 34 and k is amino acid residue 31, 32, 33, 34, or 35; j is amino acid residue 35 and k is an amino acid selected from amino acid residue 31 to 36; j is amino acid residue 36 and k is an amino acid selected from amino acid residue 31 to 37; j is amino acid residue 37 and k is an amino acid selected from amino acid residue 31 to 38; j is amino acid residue 38 and k is an amino acid selected from amino acid residue 31 to 39; j is amino acid residue 39 and k is an amino acid selected from amino acid residue 31 to 40; j is amino acid residue 40 and k is an amino acid selected from amino acid residue 31 to 41; j is amino acid residue 41 and k is an amino acid selected from amino acid residue 31 to 42; j is amino acid residue 42 and k is an amino acid selected from amino acid residue 31 to 43; j is amino acid residue 43 and k is an amino acid selected from amino acid residue 31 to 44; j is amino acid residue 44 and k is an amino acid selected from amino acid residue 31 to 45; j is amino acid residue 45 and k is an amino acid selected from amino acid residue 31 to 46; j is amino acid residue 46 and k is an amino acid selected from amino acid residue 31 to 47; j is amino acid residue 47 and k is an amino acid selected from amino acid residue 31 to 48; j is amino acid residue 48 and k is an amino acid selected from amino acid residue 31 to 49; j is amino acid residue 49 and k is an amino acid selected from amino acid residue 31 to 50; j is amino acid residue 50 and k is an amino acid selected from amino acid residue 31 to 51; j is amino acid residue 51 and k is an amino acid selected from amino acid residue 31 to 52; j is amino acid residue 52 and k is an amino acid selected from amino acid residue 31 to 53; j is amino acid residue 53 and k is an amino acid selected from amino acid residues 31 to 54; j is amino acid residue 54 and k is an amino acid selected from amino acid residues 31 to 55; j is amino acid residue 55 and k is an amino acid selected from amino acid residues 31 to 56; j is amino acid residue 56 and k is an amino acid selected from amino acid residues 31 to 57; j is amino acid residue 57 and k is an amino acid selected from amino acid residues 31 to 58; j is amino acid residue 58 and k is an amino acid selected from amino acid residues 31 to 59; j is amino acid residue 59 and k is an amino acid selected from amino acid residues 31 to 60; j is amino acid residue 60 and k is an amino acid selected from amino acid residues 31 to 61; j is amino acid residue 61 and k is an amino acid selected from amino acid residues 31 to 62; j is amino acid residue 62 and k is an amino acid selected from amino acid residues 31 to 63; j is amino acid residue 63 and k is an amino acid selected from amino acid residues 31 to 64; j is amino acid residue 64 and k is an amino acid selected from amino acid residues 31 to 65; j is amino acid residue 65 and k is an amino acid selected from amino acid residues 31 to 66; j is amino acid residue 66 and k is an amino acid selected from amino acid residues 31 to 67; j is amino acid residue 67 and k is an amino acid selected from amino acid residues 31 to 68; j is amino acid residue 68 and k is an amino acid selected from amino acid residues 31 to 69; j is amino acid residue 69 and k is an amino acid selected from amino acid residues 31 to 70; j is amino acid residue 70 and k is an amino acid selected from amino acid residues 31 to 71; j is amino acid residue 71 and k is an amino acid selected from amino acid residues 31 to 72; j is amino acid residue 72 and k is an amino acid selected from amino acid residues 31 to 73; j is amino acid residue 73 and k is an amino acid selected from amino acid residues 31 to 74; j is amino acid residue 74 and k is an amino acid selected from amino acid residues 31 to 75; j is amino acid residue 75 and k is an amino acid selected from amino acid residues 31 to 76; j is amino acid residue 76 and k is an amino acid selected from amino acid residues 31 to 77; j is amino acid residue 77 and k is an amino acid selected from amino acid residues 31 to 78; j is amino acid residue 78 and k is an amino acid selected from amino acid residues 31 to 79; j is amino acid residue 79 and k is an amino acid selected from amino acid residues 31 to 80; j is amino acid residue 80 and k is an amino acid selected from amino acid residues 31 to 81; j is amino acid residue 81 and k is an amino acid selected from amino acid residues 31 to 82; j is amino acid residue 82 and k is an amino acid selected from amino acid residues 31 to 83; j is amino acid residue 83 and k is an amino acid selected from amino acid residues 31 to 84; j is amino acid residue 84 and k is an amino acid selected from amino acid residues 31 to 85; j is amino acid residue 85 and k is an amino acid selected from amino acid residues 31 to 86; j is amino acid residue 86 and k is an amino acid selected from amino acid residues 31 to 87; j is amino acid residue 87 and k is an amino acid selected from amino acid residues 31 to 88; j is amino acid residue 88 and k is an amino acid selected from amino acid residues 31 to 89; j is amino acid residue 89 and k is an amino acid selected from amino acid residues 31 to 90; j is amino acid residue 90 and k is an amino acid selected from amino acid residues 31 to 91; j is amino acid residue 91 and k is an amino acid selected from amino acid residues 31 to 92; j is amino acid residue 92 and k is an amino acid selected from amino acid residues 31 to 93; j is amino acid residue 93 and k is an amino acid selected from amino acid residues 31 to 94; j is amino acid residue 94 and k is an amino acid selected from amino acid residues 31 to 95; j is amino acid residue 95 and k is an amino acid selected from amino acid residues 31 to 96; j is amino acid residue 96 and k is an amino acid selected from amino acid residues 31 to 97; j is amino acid residue 97 and k is an amino acid selected from amino acid residues 31 to 98; j is amino acid residue 98 and k is an amino acid selected from amino acid residues 31 to 99; j is amino acid residue 99 and k is an amino acid selected from amino acid residues 31 to 100; j is amino acid residue 100 and k is an amino acid selected from amino acid residues 31 to 101; j is amino acid residue 101 and k is an amino acid selected from amino acid residues 31 to 102; j is amino acid residue 102 and k is an amino acid selected from amino acid residues 31 to 103; j is amino acid residue 103 and k is an amino acid selected from amino acid residues 31 to 104; j is amino acid residue 104 and k is an amino acid selected from amino acid residues 31 to 105; j is amino acid residue 105 and k is an amino acid selected from amino acid residues 31 to 106; j is amino acid residue 106 and k is an amino acid selected from amino acid residues 31 to 107; j is amino acid residue 107 and k is an amino acid selected from amino acid residues 31 to 108; j is amino acid residue 108 and k is an amino acid selected from amino acid residues 31 to 109; j is amino acid residue 109 and k is an amino acid selected from amino acid residues 31 to 110; j is amino acid residue 110 and k is an amino acid selected from amino acid residues 31 to 111; j is amino acid residue 111 and k is an amino acid selected from amino acid residues 31 to 112; j is amino acid residue 112 and k is an amino acid selected from amino acid residues 31 to 113; j is amino acid residue 113 and k is an amino acid selected from amino acid residues 31 to 114; j is amino acid residue 114 and k is an amino acid selected from amino acid residues 31 to 115; j is amino acid residue 115 and k is an amino acid selected from amino acid residues 31 to 116; j is amino acid residue 116 and k is an amino acid selected from amino acid residues 31 to 117; j is amino acid residue 117 and k is an amino acid selected from amino acid residues 31 to 118; j is amino acid residue 118 and k is an amino acid selected from amino acid residues 31 to 119; j is amino acid residue 119 and k is an amino acid selected from amino acid residues 31 to 120; j is amino acid residue 120 and k is an amino acid selected from amino acid residues 31 to 121; j is amino acid residue 121 and k is an amino acid selected from amino acid residues 31 to 122; j is amino acid residue 122 and k is an amino acid selected from amino acid residues 31 to 123; j is amino acid residue 123 and k is an amino acid selected from amino acid residues 31 to 124; j is amino acid residue 124 and k is an amino acid selected from amino acid residues 31 to 125; j is amino acid residue 125 and k is an amino acid selected from amino acid residues 31 to 126; j is amino acid residue 126 and k is an amino acid selected from amino acid residues 31 to 127; j is amino acid residue 127 and k is an amino acid selected from amino acid residues 31 to 128; j is amino acid residue 128 and k is an amino acid selected from amino acid residues 31 to 129; j is amino acid residue 129 and k is an amino acid selected from amino acid residues 31 to 130; or j is amino acid residue 130 and k is an amino acid selected from amino acid residues 31 to 131 corresponding to SEQ ID NO: 4.

In certain embodiment, the N-terminal portion of an E6 protein of HPV18 and the C-terminal portion of an E6 protein of HPV18, when aligned together, contain an overlapping sequence. The overlapping sequence can be at least 1, 5, 7, 10, 15, 20, 25, 30, 35, 40, 45, 50, 55, 60, 65, 70, 75, 80, 85, 90, 95, 100, 105, 110, 115, or 120 amino acids of the E6 protein of HPV18. While the N-terminal portion or the C-terminal portion can contain an overlapping sequence, however, neither the N-terminal portion nor the C-terminal portion comprises the complete E6AP binding domain, e.g., amino acids 30 to 131 corresponding to SEQ ID NO: 4.

In addition, an E6 protein of HPV18 can be split into an N-terminal portion of and E6 protein of HPV18 and a C-terminal portion of the E6 protein of HPV18 such that the fusion protein cannot bind to one or more substrates other than p53, e.g., a repressor of hTERT, Bak, FADD, pro-caspase 8 or cannot interact with host IRF3 and TYK2.

II.B. E7 Protein of HPV16 and HPV18

E7 protein of HPV16 or HPV18 has both transforming and trans-activating activities. It disrupts the function of host retinoblastoma protein RB1/pRb, which is a key regulator of the cell cycle. E7 protein of HPV16 or HPV18 induces the disassembly of the E2F1 transcription factors from RB1, with subsequent transcriptional activation of E2F1-regulated S-phase genes. Inactivation of the ability of RB1 to arrest the cell cycle is critical for cellular transformation, uncontrolled cellular growth and proliferation induced by viral infection. Stimulation of progression from G1 to S phase allows the virus to efficiently use the cellular DNA replicating machinery to achieve viral genome replication. E7 protein of HPV16 or HPV18 interferes with histone deacetylation mediated by HDAC1 and HDAC2, leading to activation of transcription.

A number of sequences of naturally occurring E7 proteins of HPV16 and HPV18 is reported. For example, amino acid sequences of E7 proteins of HPV16 and HPV18 are reported as GenBank Accession Nos. NP_041326.1 (SEQ ID NO: 6) and ABP99785.1 (SEQ ID NO: 8), respectively. The wild-type nucleotide sequences encoding the E7 proteins of HPV16 and HPV18 are reported as GenBank Accession No. NC_001526.2 (SEQ ID NO: 5) and EF202153.1 (SEQ ID NO: 7), respectively. The sequences are reproduced in Table 2.

TABLE 2

Sequences of E7 Protein of HPV16 and HPV18

| Description | Sequences |
|---|---|
| E7 of HPV16-<br>Nucleotide<br>sequence<br>(SEQ ID NO: 5) | ATGCATGGAGATACACCTACATTGCATGAATATATGTTAGATTTGCAACCAGAGACA<br>ACTGATCTCTACTGTTATGAGCAATTAAATGACAGCTCAGAGGAGGAGGATGAAATA<br>GATGGTCCAGCTGGACAAGCAGAACCGGACAGAGCCCATTACAATATTGTAACCTTT<br>TGTTGCAAGTGTGACTCTACGCTTCGGTTGTGCGTACAAAGCACACACGTAGACATT<br>CGTACTTTGGAAGACCTGTTAATGGGCACACTAGGAATTGTGTGCCCCATCTGTTCT<br>CAGAAACCATAA |
| E7 of HPV16-<br>Amino acid<br>sequence<br>(SEQ ID NO: 6) | MHGDTPTLHEYMLDLQPETTDLYCYEQLNDSSEEEDEIDGPAGQAEPDRAHYNIVTF<br>CCKCDSTLRLCVQSTHVDIRTLEDLLMGTLGIVCPICSQKP |
| E7 of HPV18-<br>Nucleotide<br>sequence<br>(SEQ ID NO: 7) | ATGTATGGACCTAAGGCAACATTGCAAGACATTGTATTGCATTTAGAGCCTCAAAAT<br>GAAATTCCGGTTGACCTTCTATGTCACGAGCAATTAAGCGACTCAGAGGAAGAAAAC<br>GATGAAATAGATGGAGTTAATCATCAACATTTACCAGCCCGACGAGCCGAACCACAA<br>CGTCACACAATGTTGTGTATGTGTTGTAAGTGTGAAGCCAGAATTGAGCTAGTAGTA<br>GAAAGCTCAGCAGACGACCTTCGAGCATTCCAGCAGCTGTTTCTGAGCACCCTGTCC<br>TTTGTGTGTCCGTGGTGTGCATCCCAGCAGTAA |
| E7 of HPV 18-<br>Amino acid<br>sequence<br>(SEQ ID NO: 8) | MYGPKATLQDIVLHLEPQNEIPVDLLCHEQLSDSEEENDEIDGVNHQHLPARRAEPQ<br>RHTMLCMCCKCEARIELVVESSADDLRAFQQLFLSTLSFVCPWCASQQ |

The term "E7 protein of HPV16 or HPV18" as used herein includes any naturally occurring variants or functional variants thereof. Examples of the naturally occurring variants of E7 protein of HPV16 include, but are not limited to, the proteins listed in FIGS. 13C-D: GenBank Accession Nos. AAB70738.1, ACN22555.1, ABK32510.1, AAL96649.1, ABC54573.1, ACN22554.1, AAL96631.1, ABK32512.1, ACJ66713.1, AAL96650.1, ABK32511.1, ADY75576.1, AAM03025.1, AAL96634.1, AAL66736.1, AFU06654.1, AFU06650.1, ABL96585.1, ADH94043.1, AFU06662.1, AAO15692.1, AFU06676.1, AFU06594.1, AAF13395.1, AFJ19516.1, AFJ19720.1, AFJ19712.1, AGO04504.1, AFJ19770.1, AFJ19520.2, AFJ19778.1, ABL96586.1, AFJ19694.1, AFJ19686.1, AFJ19774.1, AFJ19708.1, ABL96587.1, AFJ19674.1, AFJ19704.1, AGO04488.1, ABL96591.1, AFJ19748.1, AGO04498.1, AGO04496.1, AFJ19684.1, AFJ19678.1, AGO04484.1, AFJ19698.1, AFJ19776.1, AFJ19746.1, AFJ19726.1, AFJ19722.1, AFJ19752.1, AFJ19732.1, AFJ19762.1, AFJ19668.1, AFJ19664.1, AFJ19766.1, AFJ19756.1, AFJ19680.1, AFJ19772.1, AFJ19696.1, AFJ19690.1, AGO04496.1, and ACQ90216.1. In certain embodiments, an E7 protein of HPV16 includes one or more substitutions selected from P6S, T7K, E10K, M12K, D14G, L15V, T20I, T20S, Y23H, Y23C, Y23N, C24S, Y25D, E26V, Q27H, L28S, L28F, N29S, N29Y, N29H, N29P, D30H, D30F, S31N, S31R, E33D, E34D, E34G, E35D, D36H, E37G, I38K, D39E, D39N, G40C, P41Q, A42D, A42T, G43E, E46K, D48V, R49G, A50V, H51L, N53K, N53T, I54N, V55I, T56I, C58Y, K60R, K60M, C61R, S63C, S63F, L65P, R66W, L67M, L67F, L67S, Q70R, H73L, H73R, V74L, R77C, R77Q, R77S, T78A, E80Y, D81G, L82P, L82M, M84T, M84I, G85D, G85S, G85A, T86A, T86I, V90M, C91S, Q96R, and any combination thereof.

Examples of E7 proteins of HPV18 include, but are not limited to, GenBank Accession Nos. AGU90416.1, AGU90384.1, CAB53097.1, P06788.2, ABP99745.1, CAB53098.1, CAB53099.1, ADC35661.1, ABP99785.1, and P06788.2.1. In some embodiments, an E7 protein of HPV18 includes one or more substitutions selected from D10N, E20D, D24G, E35K, E73K, R84G, S92N, S92K, and any combination thereof.

II.B.1. E7 Protein of HPV16

In one embodiment, an E7 protein of HPV16 useful for the fusion protein does not bind to pRb or does not form a dimer with an E7 protein of HPV16. In order to prevent binding of an E7 protein of HPV16 to pRb, the E7 protein can be split into two portions, an N terminal portion of the E7 protein and a C-terminal portion of the E7 protein, each of which does not comprise one or more pRb biding sites while the N-terminal portion and the C-terminal portion, when aligned, comprises the complete sequence of the E7 protein of HPV16. pRb binding sites on an E7 protein of HPV16 comprises a CR2 domain and a CR3 domain of the E7 protein. In one embodiment, the pRb binding sites of an E7 protein of HPV16 comprise E18 to D39, Q44 to P98, or E18 to P98 corresponding to SEQ ID NO: 6. Therefore, in certain embodiments, an N terminal portion of an E7 protein of HPV16 has an amino acid sequence from e to f (16E7Ne-f), and a C-terminal portion of the E7 protein of HPV16 has an amino acid sequence from g to h (16E6Cg-h), wherein e is amino acid 1 or 2 corresponding to SEQ ID NO: 6, f is an amino acid selected from amino acids 18 to 97 corresponding to SEQ ID NO: 6, g is an amino acid selected from amino acids equal to or higher than amino acid 19 and amino acids equal to or lower than amino acid f+1 corresponding to SEQ ID NO: 6, and h is amino acid 97 or 98 corresponding to SEQ ID NO: 6.

E7 protein of HPV16 can interact with pRb at amino acids 51HIS, 52TYR, 53ASN, 63SER, 64THR, 65LEU, 66ARG, 67LEU, 68CYS, 69VAL, 70GLN, 80GLU, 82LEU, 83LEU, 87LEU, 89ILE, 90VAL, 92PRO, 93ILE, 95SER, 97LYS, or 98PRO corresponding to SEQ ID NO: 6. The corresponding interaction sites on pRb include 378VAL, 379MET, 380ASN, 381THR, 382ILE, 383GLN, 384GLN, 387MET, 388ILE, 390ASN, 497 THR, 498TYR, 499SER, 500ARG, 501SER, 503 SER, and 531VAL of pRb. Therefore, in certain embodiments, the N-terminal portion and the C-terminal portion of the E7 protein can be produced by splitting the E7 protein into two portions at the C-terminal end of an amino acid selected from amino acids 51 to 97 corresponding to SEQ ID NO: 6.

In some embodiments, the fusion protein of the invention does not form a dimer with an E7 protein of HPV16 by preventing an interaction with another E7 protein. E7 protein of HPV16 forms a dimer with another E7 protein by directly interacting at the al helix ($^{73}$HVDIRTLEDLLM$^{84}$) (SEQ ID NO: 16), the β2 sheet ($^{64}$TLRLCVQS$^{71}$) (SEQ ID NO: 17), and/or the β1 sheet ($^{48}$DRAHYNIVTFC$^{58}$)(SEQ ID NO: 18). Therefore, the N-terminal portion and the C-terminal portion of the E6 protein can be split into two portions to destroy the al helix, the β2 sheet, or the β1 sheet of the E7 protein. In some embodiments, the N-terminal portion and the C-terminal portion of the E6 protein is produced by splitting the E7 protein at an amino acid that can destroy the CR3 domain, i.e., at the C-terminal end of an amino acid selected from amino acids 44 to 97 corresponding to SEQ ID NO: 6. In one embodiment, a fusion protein of the invention comprises an N-terminal portion of an E7 protein of HPV16 (16E6Ne-f) and a C-terminal portion of an E7 protein of HPV16, wherein e is amino acid 1 or 2 corresponding to SEQ ID NO: 6, f is an amino acid selected from amino acids 44 to 97 corresponding to SEQ ID NO: 6, g is an amino acid selected from amino acids equal to or higher than amino acid 45 and amino acids equal to or lower than amino acid f+1 corresponding to SEQ ID NO: 6, and h is amino acid 97 or 98 corresponding to SEQ ID NO: 6.

In some embodiments, the fusion protein comprises 16E7Ne-f and 16E7Cg-h, wherein e is amino acid 1 or 2, h is amino acid 97 or 98, and f and g as follows: f is amino acid residue 18 and g is an amino acid residue 19; f is amino acid residue 19 and g is amino acid residue 19 or 20; f is amino acid residue 20 and g is amino acid residue 19, 20, or 21; f is amino acid residue 21 and g is amino acid residue 19, 20, 21, or 22; f is amino acid residue 22 and g is amino acid residue 19, 20, 21, 22, or 23; f is amino acid residue 23 and g is an amino acid selected from amino acid residue 19 to 24; f is amino acid residue 24 and g is an amino acid selected from amino acid residue 19 to 25; f is amino acid residue 25 and g is an amino acid selected from amino acid residue 19 to 26; f is amino acid residue 26 and g is an amino acid selected from amino acid residue 19 to 27; f is amino acid residue 27 and g is an amino acid selected from amino acid residue 19 to 28; f is amino acid residue 28 and g is an amino acid selected from amino acid residue 19 to 29; f is amino acid residue 29 and g is an amino acid selected from amino acid residue 19 to 30; f is amino acid residue 30 and g is an amino acid selected from amino acid residue 19 to 31; f is amino acid residue 31 and g is an amino acid selected from amino acid residue 19 to 32; f is amino acid residue 32 and g is an amino acid selected from amino acid residue 19 to 33; f is amino acid residue 33 and g is an amino acid selected from amino acid residue 19 6 to 34; f is amino acid residue 34 and g is an amino acid selected from amino acid residue 19 to 35; f is amino acid residue 35 and g is an amino acid selected from amino acid residue 19 to 36; f is amino acid residue 36 and g is an amino acid selected from amino acid residue 19 to 37; f is amino acid residue 37 and g is an amino acid selected from amino acid residue 19 to 38; f is amino acid residue 38 and g is an amino acid selected from amino acid residue 19 to 39; f is amino acid residue 39 and g is an amino acid selected from amino acid residue 19 to 40; f is amino acid residue 40 and g is an amino acid selected from amino acid residue 19 to 41; f is amino acid residue 41 and g is an amino acid selected from amino acid residues 19 to 42; f is amino acid residue 42 and g is an amino acid selected from amino acid residues 19 to 43; f is amino acid residue 43 and g is an amino acid selected from amino acid residues 19 to 44; f is amino acid residue 44 and g is an amino acid selected from amino acid residues 19 to 45; f is amino acid residue 45 and g is an amino acid selected from amino acid residues 19 to 46; f is amino acid residue 46 and g is an amino acid selected from amino acid residues 19 to 47; f is amino acid residue 47 and g is an amino acid selected from amino acid residues 19 to 48; f is amino acid residue 48 and g is an amino acid selected from amino acid residues 19 to 49; f is amino acid residue 49 and g is an amino acid selected from amino acid residues 19 to 50; f is amino acid residue 50 and g is an amino acid selected from amino acid residues 19 to 51; f is amino acid residue 51 and g is an amino acid selected from amino acid residues 19 to 52; f is amino acid residue 52 and g is an amino acid selected from amino acid residues 19 to 53; f is amino acid residue 53 and g is an amino acid selected from amino acid residues 19 to 54; f is amino acid residue 54 and g is an amino acid selected from amino acid residues 19 to 55; f is amino acid residue 55 and g is an amino acid selected from amino acid residues 19 to 56; f is amino acid residue 56 and g is an amino acid selected from amino acid residues 19 to 57; f is amino acid residue 57 and g is an amino acid selected from amino acid residues 19 to 58; f is amino acid residue 58 and g is an amino acid selected from amino acid residues 19 to 59; f is amino acid residue 59 and g is an amino acid selected from amino acid residues 19 to 60; f is amino acid residue 60 and g is an amino acid selected from amino acid residues 19 to 61; f is amino acid residue 61 and g is an amino acid selected from amino acid residues 19 to 62; f is amino acid residue 62 and g is an amino acid selected from amino acid residues 19 to 63; f is amino acid residue 63 and g is an amino acid selected from amino acid residues 19 to 64; f is amino acid residue 64 and g is an amino acid selected from amino acid residues 19 to 65; f is amino acid residue 65 and g is an amino acid selected from amino acid residues 19 to 66; f is amino acid residue 66 and g is an amino acid selected from amino acid residues 19 to 67; f is amino acid residue 67 and g is an amino acid selected from amino acid residues 19 to 68; f is amino acid residue 68 and g is an amino acid selected from amino acid residues 19 to 69; f is amino acid residue 69 and g is an amino acid selected from amino acid residues 19 to 70; f is amino acid residue 70 and g is an amino acid selected from amino acid residues 19 to 71; f is amino acid residue 71 and g is an amino acid selected from amino acid residues 19 to 72; f is amino acid residue 72 and g is an amino acid selected from amino acid residues 19 to 73; f is amino acid residue 73 and g is an amino acid selected from amino acid residues 19 to 74; f is amino acid residue 74 and g is an amino acid selected from amino acid residues 19 to 75; f is amino acid residue 75 and g is an amino acid selected from amino acid residues 19 to 76; f is amino acid residue 76 and g is an amino acid selected from amino acid residues 19 to 77; f is amino acid residue 77 and g is an amino acid selected from amino acid residues 19 to 78; f is amino acid residue 78 and g is an amino acid selected from amino acid residues 19 to 79; f is amino acid residue 79 and g is an amino acid selected from amino acid residues 19 to 80; f is amino acid residue 80 and g is an amino acid selected from amino acid residues 19 to 81; f is amino acid residue 81 and g is an amino acid selected from amino acid residues 19 to 82; f is amino acid residue 82 and g is an amino acid selected from amino acid residues 19 to 83; f is amino acid residue 83 and g is an amino acid selected from amino acid residues 19 to 84; f is amino acid residue 84 and g is an amino acid selected from amino acid residues 19 to 85; f is amino acid residue 85 and g is an amino acid selected from amino acid residues 19 to 86; f is amino acid residue 86 and g is an amino acid selected from amino acid residues 19 to 87; f is amino acid residue 87 and g is an amino acid selected from amino acid residues 19 to 88; f is amino acid residue 88 and g is an amino acid selected from amino acid residues 19 to 89; f is amino acid residue 89 and g is an amino acid selected from amino acid residues 19 to 90; f is amino acid residue 90 and g is an amino acid selected from amino acid residues 19 to 91; f is amino acid residue 91 and g is an amino acid selected from amino acid residues 19 to 92; f is amino acid residue 92 and g is an amino acid selected from amino acid residues 19 to 93; f is amino acid residue 93 and g is an amino acid selected from amino acid residues 19 to 94; f is amino acid residue 94 and g is an amino acid selected from amino acid residues 19 to 95; f is amino acid residue 95 and g is an amino acid selected from amino acid residues 19 to 96; f is amino acid residue 96 and g is an amino acid selected from amino acid residues 19 to 97; or f is amino acid residue 97 and g is an amino acid selected from amino acid residues 19 to 98 corresponding to SEQ ID NO: 6.

In certain embodiment, the N-terminal portion of an E7 protein of HPV16 and the C-terminal portion of an E7 protein of HPV16, when aligned together, contain an overlapping sequence. The overlapping sequence can be at least 1, 5, 7, 10, 15, 20, 25, 30, 35, 40, 45, 50, 55, 60, 65, 70, 75, or 80 amino acids of the E7 protein of HPV16. While the N-terminal portion of the C-terminal portion can contain the overlapping sequence, however, neither the N-terminal portion nor the C-terminal portion comprises the complete pRb binding domain, e.g., amino acids 18 to 98 corresponding to SEQ ID NO: 6.

II.B.2. E7 Protein of HPV18

In certain embodiments, an E7 protein of HPV18 useful for the fusion protein does not bind to pRb or does not form a dimer with an E7 protein of HPV18. In order to prevent binding of an E7 protein of HPV18 to pRb, the E7 protein can be split into two portions, an N terminal portion of the E7 protein and a C-terminal portion of the E7 protein, each of which does not comprise one or more pRb binding sites while the N-terminal portion and the C-terminal portions, when aligned, comprise the complete sequence of the E7 protein of HPV18. PRb binding sites on an E7 protein of HPV18 comprise a CR2 domain and a CR3 domain of the E7 protein. In one embodiment, the pRb binding sites of an E7 protein of HPV18 comprise I21 to D42, Q47 to Q105, or I21 to Q105 corresponding to SEQ ID NO: 8. Therefore, in certain embodiments, an N terminal portion of an E7 protein of HPV18 has an amino acid sequence from m to n (16E7 Nm-n), and a C-terminal portion of the E7 protein of HPV18 has an amino acid sequence from o to p (16E6Co-p), wherein m is amino acid 1 or 2 corresponding to SEQ ID NO: 8, n is an amino acid selected from amino acids 21 to 104 corresponding to SEQ ID NO: 8, o is an amino acid selected from amino acids equal to or higher than amino acid 22 and amino acids equal to or lower than amino acid n+1 corresponding to SEQ ID NO: 8, and p is amino acid 104 or 105 corresponding to SEQ ID NO: 8.

E7 protein of HPV18 can interact with pRb at amino acids 58ARG, 59HIS, 60THR, 70ALA, 71ARG, 72ILE, 73GLU, 74LEU, 75VAL, 76VAL, 77GLU, 87GLN, 89LEU, 90PHE, 94LEU, 96PHE, 97VAL, 99PRO, 100TRP, 102ALA, 104GLN, and 105GLN corresponding to SEQ ID NO: 8. The corresponding interaction sites on pRb include 378VAL, 379MET, 380ASN, 381THR, 382ILE, 383GLN, 384GLN, 387MET, 388ILE, 390ASN, 497THR, 498TYR, 499SER, 500ARG, 501SER, 503 SER, and 531VAL of pRb. Therefore, in certain embodiments, the N-terminal portion and the C-terminal portion of the E7 protein of HPV18 are produced by splitting the E7 protein into two portions at the C-terminal end of an amino acid selected from amino acids 58 to 104 corresponding to SEQ ID NO: 8.

In some embodiments, the fusion protein of the invention does not form a dimer with an E7 protein of HPV18 by preventing an interaction with another E7 protein. E7 protein of HPV18 forms a dimer with another E7 protein by directly interacting at the α1 helix ($^{80}$ADDL-RAFQQLFL$^{91}$), the β2 sheet ($^{71}$RIELVVES$^{78}$), and/or the β1 sheet ($^{55}$EPQRHTMLCMC$^{65}$). Therefore, the N-terminal portion and the C-terminal portion of the E7 protein can be produced by splitting the E7 protein into two portions at an amino acid that destroys the al helix, the β2 sheet, or the β1 sheet of the E7 protein. In some embodiments, the N-terminal portion and the C-terminal portion of the E7 protein is produced by splitting the E7 protein at an amino acid that destroys the CR3 domain, i.e., at the C-terminal end of an amino acid selected from amino acids 47 to 104 corresponding to SEQ ID NO: 8. In one embodiment, a fusion protein of the invention comprises an N-terminal portion of an E7 protein of HPV18 (18E7 Nm-n) and a C-terminal portion of an E7 protein of HPV18 (18E7Co-p), wherein m is amino acid 1 or 2 corresponding to SEQ ID NO: 8, n is an amino acid selected from amino acids 21 to 104 corresponding to SEQ ID NO: 8, o is an amino acid selected from amino acids equal to or higher than amino acid 22 and amino acids equal to or lower than amino acid n+1 corresponding to SEQ ID NO: 8, and p is amino acid 104 or 105 corresponding to SEQ ID NO: 8.

In some embodiments, the fusion protein comprises 18E7 Nm-n and 18E7Co-p, wherein m is amino acid 1 or 2, p is amino acid 104 or 105, and n and o as follows: n is amino acid residue 21 and o is an amino acid residue 22; n is amino acid residue 22 and o is amino acid residue 22 or 23; n is amino acid residue 23 and o is amino acid residue 22, 23, or 24; n is amino acid residue 24 and o is amino acid residue 22, 23, 24, or 25; n is amino acid residue 25 and o is amino acid residue 22, 23, 24, 25, or 26; n is amino acid residue 26 and o is an amino acid selected from amino acid residue 22 to 27; n is amino acid residue 27 and o is an amino acid selected from amino acid residue 22 to 28; n is amino acid residue 28 and o is an amino acid selected from amino acid residue 22 to 29; n is amino acid residue 29 and o is an amino acid selected from amino acid residue 22 to 30; n is amino acid residue 30 and o is an amino acid selected from amino acid residue 22 to 31; n is amino acid residue 31 and o is an amino acid selected from amino acid residue 22 to 32; n is amino acid residue 32 and o is an amino acid selected from amino acid residue 22 to 33; n is amino acid residue 33 and o is an amino acid selected from amino acid residue 22 to 34; n is amino acid residue 34 and o is an amino acid selected from amino acid residue 22 to 35; n is amino acid residue 35 and o is an amino acid selected from amino acid residue 22 to 36; n is amino acid residue 36 and o is an amino acid selected from amino acid residue 22 to 37; n is amino acid residue 37 and o is an amino acid selected from amino acid residue 22 to 38; n is amino acid residue 38 and o is an amino acid selected from amino acid residue 22 to 39; n is amino acid residue 39 and o is an amino acid selected from amino acid residue 22 to 40; n is amino acid residue 40 and o is an amino acid selected from amino acid residue 22 to 41; n is amino acid residue 41 and o is an amino acid selected from amino acid residue 22 to 42; n is amino acid residue 42 and o is an amino acid selected from amino acid residue 22 to 43; n is amino acid residue 43 and o is an amino acid selected from amino acid residue 22 to 44; n is amino acid residue 44 and o is an amino acid selected from amino acid residues 22 to 45; n is amino acid residue 45 and o is an amino acid selected from amino acid residues 22 to 46; n is amino acid residue 46 and o is an amino acid selected from amino acid residues 22 to 47; n is amino acid residue 47 and o is an amino acid selected from amino acid residues 22 to 48; n is amino acid residue 48 and o is an amino acid selected from amino acid residues 22 to 49; n is amino acid residue 49 and o is an amino acid selected from amino acid residues 22 to 50; n is amino acid residue 50 and o is an amino acid selected from amino acid residues 22 to 51; n is amino acid residue 51 and o is an amino acid selected from amino acid residues 22 to 52; n is amino acid residue 52 and o is an amino acid selected from amino acid residues 22 to 53; n is amino acid residue 53 and o is an amino acid selected from amino acid residues 22 to 54; n is amino acid residue 54 and o is an amino acid selected from amino acid residues 22 to 55; n is amino acid residue 55 and o is an amino acid selected from amino acid residues 22 to 56; n is amino acid residue 56 and o is an amino acid selected from amino acid residues 22 to 57; n is amino acid residue 57 and o is an amino acid selected from amino acid residues 22 to 58; n is amino acid residue 58 and o is an amino acid selected from amino acid residues 22 to 59; n is amino acid residue 59 and o is an amino acid selected from amino acid residues 22 to 60; n is amino acid residue 60 and o is an amino acid selected from amino acid residues 22 to 61; n is amino acid residue 61 and o is an amino acid selected from amino acid residues 22 to 62; n is amino acid residue 62 and o is an amino acid selected from amino acid residues 22 to 63; n is amino acid residue 63 and o is an amino acid selected from amino acid residues 22 to 64; n is amino acid residue 64 and o is an amino acid selected from amino acid residues 22 to 65; n is amino acid residue 65 and o is an amino acid selected from amino acid residues 22 to 66; n is amino acid residue 66 and o is an amino acid selected from amino acid residues 22 to 67; n is amino acid residue 67 and o is an amino acid selected from amino acid residues 22 to 68; n is amino acid residue 68 and o is an amino acid selected from amino acid residues 22 to 69; n is amino acid residue 69 and o is an amino acid selected from amino acid residues 22 to 70; n is amino acid residue 70 and o is an amino acid selected from amino acid residues 22 to 71; n is amino acid residue 71 and o is an amino acid selected from amino acid residues 22 to 72; n is amino acid residue 72 and o is an amino acid selected from amino acid residues 22 to 73; n is amino acid residue 73 and o is an amino acid selected from amino acid residues 22 to 74; n is amino acid residue 74 and o is an amino acid selected from amino acid residues 22 to 75; n is amino acid residue 75 and o is an amino acid selected from amino acid residues 22 to 76; n is amino acid residue 76 and o is an amino acid selected from amino acid residues 22 to 77; n is amino acid residue 77 and o is an amino acid selected from amino acid residues 22 to 78; n is amino acid residue 78 and o is an amino acid selected from amino acid residues 22 to 79; n is amino acid residue 79 and o is an amino acid selected from amino acid residues 22 to 80; n is amino acid residue 80 and o is an amino acid selected from amino acid residues 22 to 81; n is amino acid residue 81 and o is an amino acid selected from amino acid residues 22 to 82; n is amino acid residue 82 and o is an amino acid selected from amino acid residues 22 to 83; n is amino acid residue 83 and o is an amino acid selected from amino acid residues 22 to 84; n is amino acid residue 84 and o is an amino acid selected from amino acid residues 22 to 85; n is amino acid residue 85 and o is an amino acid selected from amino acid residues 22 to 86; n is amino acid residue 86 and o is an amino acid selected from amino acid residues 22 to 87; n is amino acid residue 87 and o is an amino acid selected from amino acid residues 22 to 88; n is amino acid residue 88 and o is an amino acid selected from amino acid residues 22 to 89; n is amino acid residue 89 and o is an amino acid selected from amino acid residues 22 to 90; n is amino acid residue 90 and o is an amino acid selected from amino acid residues 22 to 91; n is amino acid residue 91 and o is an amino acid selected from amino acid residues 22 to 92; n is amino acid residue 92 and o is an amino acid selected from amino acid residues 22 to 93; n is amino acid residue 93 and o is an amino acid selected from amino acid residues 22 to 94; n is amino acid residue 94 and o is an amino acid selected from amino acid residues 22 to 95; n is amino acid residue 95 and o is an amino acid selected from amino acid residues 22 to 96; n is amino acid residue 96 and o is an amino acid selected from amino acid residues 22 to 97; n is amino acid residue 97 and o is an amino acid selected from amino acid residues 22 to 98; n is amino acid residue 98 and o is an amino acid selected from amino acid residues 22 to 99; n is amino acid residue 99 and o is an amino acid selected from amino acid residues 22 to 100; n is amino acid residue 100 and o is an amino acid selected from amino acid residues 22 to 101; n is amino acid residue 101 and o is an amino acid selected from amino acid residues 22 to 102; n is amino acid residue 102 and o is an amino acid selected from amino acid residues 22 to 103; n is amino acid residue 103 and o is an amino acid selected from amino acid residues 22 to 104; n is amino acid residue 104 and o is an amino acid selected from amino acid residues 22 to 105; corresponding to SEQ ID NO: 8.

In certain embodiment, the N-terminal portion of an E7 protein of HPV18 and the C-terminal portion of an E7 protein of HPV18, when aligned together, contain an overlapping sequence. The overlapping sequence can be at least 1, 5, 7, 10, 15, 20, 25, 30, 35, 40, 45, 50, 55, 60, 65, 70, 75, or 80 amino acids of the E7 protein of HPV18. While the N-terminal portion or the C-terminal portion can contain the overlapping sequence, however, neither the N-terminal portion nor the C-terminal portion comprises the complete pRb binding domain, e.g., amino acids 21 to 105 corresponding to SEQ ID NO: 8.

II.C. Fusion Protein

In one aspect, a therapeutic molecule of the invention is a fusion protein comprising at least two, at least three, at least four, at least five, at least six, at least seven, or at least eight portions of the E6 protein of HPV16, the E6 protein of HPV18, the E7 protein of HPV16, and the E7 protein of HPV18 or a nucleotide sequence encoding the fusion protein, wherein the fusion protein does not bind to p53 or does not form a dimer with the E6 protein of HPV16 or HPV18 and wherein the fusion protein does not bind to pRb or does not form a dimer with the E7 protein of HPV16 or HPV18.

In another aspect, a therapeutic molecule of the invention comprises more than one amino acid sequences. For example, a therapeutic molecule of the invention comprises eight amino acid sequences or eight nucleotide sequences encoding the eight amino acid sequences, wherein the eight amino acid sequences are an N-terminal portion of an E6 protein of HPV16, a C-terminal portion of the E6 protein of HPV16, an N-terminal portion of an E6 protein of HPV18, and a C-terminal portion of the E6 protein of HPV18, an N-terminal portion of an E7 protein of HPV16, a C-terminal portion of the E7 protein of HPV16, and an N-terminal portion of an E7 protein of HPV18.

In other aspects, a therapeutic molecule of the invention comprises (i) seven amino acid sequences or seven nucleotide sequences encoding the seven amino acid sequences, wherein seven amino acid sequences contain eight polypeptide portions; (ii) six amino acid sequences or six nucleotide sequences encoding the six amino acid sequences, wherein the six amino acid sequences contain eight polypeptide portions, (iii) five amino acid sequences or five nucleotide sequences encoding five amino acid sequences, wherein the five amino acid sequences contain eight polypeptide portions, (iv) four amino acid sequences or four nucleotide sequences encoding the four amino acid sequences, wherein the four amino acid sequences contain eight polypeptide portions, (v) three amino acid sequences or three nucleotide sequences encoding the three amino acid sequences, wherein the three amino acid sequences contain eight polypeptide portions, (vi) two amino acid sequences or three nucleotide sequences encoding the three amino acid sequences, wherein the two amino acid sequences contain eight polypeptide portions, or (vii) one amino acid sequence or a nucleotide sequence encoding the amino acid sequence, wherein the one amino acid sequence contains eight polypeptide portions, wherein the eight polypeptide portions are an N-terminal portion of an E6 protein of HPV16, a C-terminal portion of the E6 protein of HPV16, an N-terminal portion of an E6 protein of HPV18, a C-terminal portion of the E6 protein of HPV18, an N-terminal portion of an E7 protein of HPV16, a C-terminal portion of the E7 protein of HPV16, and an N-terminal portion of an E7 protein of HPV18.

In some embodiments, a fusion protein comprises at least four, at least five, at least six, at least seven or eight amino acid sequences selected from
  (1) an N-terminal portion of an E6 protein of HPV16,
  (2) a C-terminal portion of an E6 protein of HPV16,
  (3) an N-terminal portion of an E7 protein of HPV16,
  (4) a C-terminal portion of an E7 protein of HPV16,
  (5) an N-terminal portion of an E6 protein of HPV18,
  (6) a C-terminal portion of an E6 protein of HPV18,
  (7) an N-terminal portion of an E7 protein of HPV18, and
  (8) a C-terminal portion of an E7 protein of HPV18,
wherein the fusion protein does not bind to p53 or does not form a dimer with an E6 protein of HPV16 or HPV 18 and dose not bind to pRb or does not form a dimer with an E7 protein of HPV16 or HPV18. The fusion protein can further comprises the same number of the epitopes that are contained in the naturally occurring E6 protein of HPV16, the naturally occurring E6 protein of HPV18, the naturally occurring E7 protein of HPV18 and the naturally occurring E7 protein of HPV18, or more epitopes than the epitopes contained in the naturally occurring E6 protein of HPV16, the naturally occurring E6 protein of HPV18, the naturally occurring E7 protein of HPV18 and the naturally occurring E7 protein of HPV18.

In other embodiments, each of the N-terminal portion of an E6 protein of HPV16, the C-terminal portion of an E6 protein of HPV16, an N-terminal portion of an E6 protein of HPV18, and the C-terminal portion of an E6 protein of HPV18 in the fusion protein does not comprise the complete E6-associated protein (E6AP) binding site. In yet other embodiments, the fusion protein does not comprise the complete E6AP binding site, which comprises amino acids 35 to 136 corresponding to SEQ ID NO: 2 (E6 HPV16) or amino acids 30 to 131 corresponding to SEQ ID NO: 4 (E6 HPV18). For example, the fusion protein does not comprise the consecutive sequence of amino acids 35 to 136 corresponding to SEQ ID NO: 2 or amino acids 30 to 131 corresponding to SEQ ID NO: 4. In still other embodiments, each of the N-terminal portion of an E7 protein of HPV16, the C-terminal portion of an E7 protein of HPV16, the N-terminal portion of an E7 protein of HPV18, and the C-terminal portion of an E7 protein of HPV18 in the fusion protein does not comprise the complete CR2 domain or the complete CR3 domain or comprises either a CR2 domain or a CR3 domain, but not both. In some embodiments, the fusion protein does not comprise the consecutive sequence of amino acids 18 to 98 corresponding to SEQ ID NO: 6 or amino acids 21 to 105 corresponding to SEQ ID NO: 8 (E7 HPV18).

In certain embodiments, a fusion protein comprises (i) an N terminal portion of an E6 protein of HPV16, which comprises an amino acid sequence at least 80%, at least 85%, at least 90%, at least 95%, at least 96%, at least 97%, at least 98%, at least 99%, or 100% identical to the N terminal sequence of SEQ ID NO: 2 (16E6Na-b), wherein a is an amino acid selected from amino acid residue 1 or 2 corresponding to SEQ ID NO: 2 and b is an amino acid selected from amino acid residues 35 to 135 corresponding to SEQ ID NO: 2, (ii) a C-terminal portion of an E6 protein of HPV16, which comprises an amino acid sequence at least 80%, at least 85%, at least 90%, at least 95%, at least 96%, at least 97%, at least 98%, at least 99%, or 100% identical to the C-terminal sequence of SEQ ID NO: 2 (16E6Cc-d), wherein c is an amino acid selected from amino acid residues equal to or higher than 36 and amino acid residues equal to or lower than amino acid b+1 corresponding to SEQ ID NO: 2 and d is an amino acid selected from amino acid residue 157 or 158 corresponding to SEQ ID NO: 2, (iii) a N-terminal portion of an E6 protein of HPV18, which comprises an amino acid sequence at least 80%, at least 85%, at least 90%, at least 95%, at least 96%, at least 97%, at least 98%, at least 99%, or 100% identical to the N-terminal sequence of SEQ ID NO: 4 (18E6Ni-j), wherein i is an amino acid selected from amino acid residue 1 or 2 corresponding to SEQ ID NO: 4 and j is an amino acid selected from amino acid residues 30 to 130 corresponding to SEQ ID NO: 4, (iv) a C-terminal portion of an E6 protein of HPV18, which comprises an amino acid sequence at least 80%, at least 85%, at least 90%, at least 95%, at least 96%, at least 97%, at least 98%, at least 99%, or 100% identical to the C-terminal sequence of SEQ ID NO: 4 (18E6Ck-l), wherein k is an amino acid selected from amino acid residues equal to or higher than 31 and amino acid residues equal to or lower than j+1 corresponding to SEQ ID NO: 4 and l is an amino acid selected from amino acid residue 157 or 158 corresponding to SEQ ID NO: 4; (v) a N-terminal portion of an E7 protein of HPV16, which comprises an amino acid sequence at least 80%, at least 85%, at least 90%, at least 95%, at least 96%, at least 97%, at least 98%, at least 99%, or 100% identical to the N terminal sequence of SEQ ID NO: 6 (16E7Ne-f), wherein e is an amino acid selected from amino acid residue 1 or 2 corresponding to SEQ ID NO: 6 and f is an amino acid selected from amino acid residues 18 to 97 corresponding to SEQ ID NO: 6; (vi) a C-terminal portion of an E7 protein of HPV16, which comprises an amino acid sequence at least 80%, at least 85%, at least 90%, at least 95%, at least 96%, at least 97%, at least 98%, at least 99%, or 100% identical to the C-terminal sequence of SEQ ID NO: 6 (16E7Cg-h), wherein g is an amino acid selected from amino acid residues equal to or higher than 19 and amino acid residues equal to or lower than f+1 corresponding to SEQ ID NO: 6 and h is an amino acid selected from amino acid residue 97 or 98 corresponding to SEQ ID NO: 6; (vii) a N-terminal portion of an E7 protein of HPV18, which comprises an amino acid sequence at least 80%, at least 85%, at least 90%, at least 95%, at least 96%, at least 97%, at least 98%, at least 99%, or 100% identical to the N-terminal sequence of SEQ ID NO: 8 (18E7 Nm-n), wherein m is an amino acid selected from amino acid residue 1 or 2 corresponding to SEQ ID NO: 8 and n is an amino acid selected from amino acid residues 21 to 104 corresponding to SEQ ID NO: 8, and (viii) a C-terminal portion of an E7 protein of HPV18, which comprises an amino acid sequence at least 80%, at least 85%, at least 90%, at least 95%, at least 96%, at least 97%, at least 98%, at least 99%, or 100% identical to the C-terminal sequence of SEQ ID NO: 8 (18E7Co-p), wherein o is an amino acid selected from amino acid residues equal to or higher than 22 and amino acid residues equal to or lower than n+1 corresponding to SEQ ID NO: 8 and l is an amino acid selected from amino acid residue 104 or 105 corresponding to SEQ ID NO: 8, wherein the fusion protein does not bind to p53 or form a dimer with an E6 protein of HPV16 or HPV18, wherein the fusion protein does not bind to pRb or form a dimer with an E7 protein of HPV16 or HPV18, and wherein the fusion protein contains at least all epitopes of the naturally occurring E6 protein of HPV16 and HPV18 and the naturally occurring E7 protein of HPV16 and HPV18.

In other embodiments, a fusion protein comprises (i) an N terminal portion of an E6 protein of HPV16, which comprises an amino acid sequence at least 80%, at least 85%, at least 90%, at least 95%, at least 96%, at least 97%, at least 98%, at least 99%, or 100% identical to the N terminal sequence of SEQ ID NO: 2 (16E6Na-b), wherein a is an amino acid selected from amino acid residue 1 or 2 corresponding to SEQ ID NO: 2 and b is an amino acid selected from amino acid residues 35 to 39, 57 to 62, 69 to 85, 87 to 88, 98 to 99, 107, 109, 114, and 135 corresponding to SEQ ID NO: 2, (ii) a C-terminal portion of an E6 protein of HPV16, which comprises an amino acid sequence at least 80%, at least 85%, at least 90%, at least 95%, at least 96%, at least 97%, at least 98%, at least 99%, or 100% identical to the C-terminal sequence of SEQ ID NO: 2 (16E6Cc-d), wherein c is an amino acid selected from amino acid residues equal to or higher than 36 and amino acid residues equal to or lower than amino acid b+1 corresponding to SEQ ID NO: 2 and d is an amino acid selected from amino acid residue 157 or 158 corresponding to SEQ ID NO: 2, (iii) an N-terminal portion of an E6 protein of HPV18, which comprises an amino acid sequence at least 80%, at least 85%, at least 90%, at least 95%, at least 96%, at least 97%, at least 98%, at least 99%, or 100% identical to the N-terminal sequence of SEQ ID NO: 4 (18E6Ni-j), wherein i is an amino acid selected from amino acid residue 1 or 2 corresponding to SEQ ID NO: 4 and j is an amino acid selected from amino acid residues 30 to 34, 52 to 57, 64 to 80, 82 to 83, 93, 94, 102, 104, 109, and 130 corresponding to SEQ ID NO: 4, (iv) a C-terminal portion of an E6 protein of HPV18, which comprises an amino acid sequence at least 80%, at least 85%, at least 90%, at least 95%, at least 96%, at least 97%, at least 98%, at least 99%, or 100% identical to the C-terminal sequence of SEQ ID NO: 4 (18E6Ck-l), wherein k is an amino acid selected from amino acid residues equal to or higher than 31 and amino acid residues equal to or lower than j+1 corresponding to SEQ ID NO: 4 and l is an amino acid selected from amino acid residue 157 or 158 corresponding to SEQ ID NO: 4; (v) an N-terminal portion of an E7 protein of HPV16, which comprises an amino acid sequence at least 80%, at least 85%, at least 90%, at least 95%, at least 96%, at least 97%, at least 98%, at least 99%, or 100% identical to the N terminal sequence of SEQ ID NO: 6 (16E7Ne-f), wherein e is an amino acid selected from amino acid residue 1 or 2 corresponding to SEQ ID NO: 6 and f is an amino acid selected from amino acid residues 18 to 39 and 44 to 97 corresponding to SEQ ID NO: 6; (vi) a C-terminal portion of an E7 protein of HPV16, which comprises an amino acid sequence at least 80%, at least 85%, at least 90%, at least 95%, at least 96%, at least 97%, at least 98%, at least 99%, or 100% identical to the C-terminal sequence of SEQ ID NO: 6 (16E7Cg-h), wherein g is an amino acid selected from amino acid residues equal to or higher than 19 and amino acid residues equal to or lower than f+1 corresponding to SEQ ID NO: 6 and h is an amino acid selected from amino acid residue 97 or 98 corresponding to SEQ ID NO: 6; (vii) an N-terminal portion of an E7 protein of HPV18, which comprises an amino acid sequence at least 80%, at least 85%, at least 90%, at least 95%, at least 96%, at least 97%, at least 98%, at least 99%, or 100% identical to the N-terminal sequence of SEQ ID NO: 8 (18E7 Nm-n), wherein m is an amino acid selected from amino acid residue 1 or 2 corresponding to SEQ ID NO: 8 and n is an amino acid selected from amino acid residues 21 to 42 and 47 to 104 corresponding to SEQ ID NO: 8, and (viii) a C-terminal portion of an E7 protein of HPV18, which comprises an amino acid sequence at least 80%, at least 85%, at least 90%, at least 95%, at least 96%, at least 97%, at least 98%, at least 99%, or 100% identical to the C-terminal sequence of SEQ ID NO: 8 (18E7Co-p), wherein o is an amino acid selected from amino acid residues equal to or higher than 22 and amino acid residues equal to or lower than n+1 corresponding to SEQ ID NO: 8 and p is an amino acid selected from amino acid residue 104 or 105 corresponding to SEQ ID NO: 8, wherein the fusion protein does not bind to p53 or form a dimer with an E6 protein of HPV16 or HPV18, wherein the fusion protein does not bind to pRb or form a dimer with an E7 protein of HPV16 or HPV18, and wherein the fusion protein contains at least all epitopes of the naturally occurring E6 protein of HPV16 and HPV18 and the naturally occurring E7 protein of HPV16 and HPV18. In still other embodiments, f is an amino acid residue selected from 18 to 39 corresponding to SEQ ID NO: 6 and g is an amino acid selected from amino acid residues equal to or higher than 19 and amino acid residues equal to or lower than f+1 corresponding to SEQ ID NO: 6 or wherein f is an amino acid residue selected from amino acid residues 44 to 97 corresponding to SEQ ID NO: 6 and g is an amino acid selected from amino acid residues equal to or higher than 45 and amino acid residues equal to or lower than amino acid f+1 corresponding to SEQ ID NO: 6. In yet other embodiments, n is an amino acid residue selected from 21 to 41 and o is an amino acid selected from amino acid residues equal to or higher than 22 and amino acid residues equal to or lower than n+1 or wherein n is an amino acid residue selected from amino acid residues 47 to 104 and o is an amino acid selected from amino acid residues equal to or higher than 48 and amino acid residues equal to or lower than n+1 corresponding to SEQ ID NO: 8. In yet other embodiments, the fusion protein does not comprise the naturally occurring, full length E6 protein of HPV16, the naturally occurring, full length E7 protein of HPV16, the naturally occurring, full length E6 protein of HPV18, and the naturally occurring, full length E7 protein of HPV18.

The fusion protein can comprise the eight portions of the proteins in any order. All possible combinations of the eight portions include 33,600 possibilities, which are part of this application. In some embodiments, the fusion protein is constructed such that the N-terminal and the C-terminal portions from the same protein are not placed immediately next to each other. In other embodiments, the fusion protein is constructed such that the N-terminal or C-terminal portions from the same HPV serotypes are placed next to each other. In yet other embodiments, the N-terminal portions from different proteins (same HPV serotypes) are placed to next to each other, and the C-terminal portions from different proteins (same HPV serotypes) are placed next to each other. In certain embodiments, the fusion protein comprises, from N terminus to C terminus, (i) 16E6Na-b-16E7Ne-f-16E6Cc-d-16E7Cg-h-18E6Ni-j-18E7 Nm-n-18E6Ck-l-18E7Co-p; (ii) 18E6Ni-j-18E7 Nm-n-18E6Ck-l-18E7Co-p-16E6Na-b-16E7Ne-f-16E6Cc-d-16E7Cg-h; (iii) 16E7Ne-f-16E6Na-b-16E7Cg-h-16E6Cc-d-18E7 Nm-n-18E6Ni-j-18E7Co-p-18E6Ck-l; (iv) 18E7 Nm-n-18E6Ni-j-18E7Co-p-18E6Ck-l-16E7Ne-f-16E6Na-b-16E7Cg-h-16E6Cc-d; (v) 18E6Ni-j-16E7Ne-f-16E6Cc-d-18E6Ck-l-18E7 Nm-n-16E6Na-b-18E7Co-p-16E7Cg-h; (vi) 16E6Na-b-18E6Ni-j-18E7Co-p-16E6Cc-d-16E7Ne-f-18E7 Nm-n-16E7Cg-h-18E6Ck-l; (vii) 18E7 Nm-n-16E6Na-b-18E7Co-p-16E7Cg-h-16E7Ne-f-18E6Ni-j-16E6Cc-d-18E6Ck-l; or (viii) 16E7Ne-f-18E6Ni-j-16E7Cg-h-18E7Co-p-18E7 Nm-n-16E6Na-b-18E6Ck-l-16E6Cc-d. In some embodiments, (-) is a peptide bond. In certain embodiments, (-) is one or more amino acids.

In a particular embodiment, a fusion protein comprises, from N terminus to C terminus, 16E6Na-b-16E7Ne-f-16E6Cc-d-16E7Cg-h-18E6Ni-j-18E7 Nm-n-18E6Ck-l-18E7Co-p, a is amino acid residue 1 of SEQ ID NO: 2, b is amino acid residue 85 of SEQ ID NO: 2, c is amino acid residue 71 of SEQ ID NO: 2, d is amino acid residue 158 of SEQ ID NO: 2, e is amino acid residue 1 of SEQ ID NO: 6, f is amino acid residue 65 of SEQ ID NO: 6, g is amino acid residue 51 of SEQ ID NO: 6, h is amino acid residue 98 of SEQ ID NO: 6, i is amino acid residue 1 of SEQ ID NO: 4, j is amino acid residue 85 of SEQ ID NO: 4, k is amino acid residue 71 of SEQ ID NO: 4, l is amino acid residue 158 of SEQ ID NO: 4, m is amino acid residue 1 of SEQ ID NO: 8, n is amino acid residue 65 of SEQ ID NO: 8, o is amino acid residue 51 of SEQ ID NO: 8, and p is amino acid residue 105 of SEQ ID NO: 8. In some embodiments, a fusion protein comprises an amino acid sequence at least at least 80%, at least 85%, at least 90%, at least 95%, at least 96%, at least 97%, at least 98%, at least 99%, or 100% identical to SEQ ID NO: 10.

In other embodiments, the fusion protein comprises a heterologous moiety. The heterologous moiety can be a heterologous polypeptide or a non-polypeptide moiety.

Examples of heterologous polypeptides include, but are not limited to, a signal peptide, an immune enhancer peptide, or any other peptides that enhance a property of the fusion protein.

In one embodiment, a signal peptide that is fused to the fusion protein includes, but is not limited to, a signal peptide of tissue plasminogen activator (tPA), a signal peptide of Herpes Simplex Virus Glycoprotein D (HSV gDs), a signal peptide of a growth hormone, and any combinations thereof. In a particular embodiment, a signal peptide fused to the fusion protein comprises an amino acid sequence at least about 80%, 85%, 90%, 95%, 96%, 97%, 98%, 99%, or 100% identical to SEQ ID NO: 14.

In another embodiment, an immunity enhancer peptide includes, but is not limited to, a CD40 ligand, an fms-like tyrosine kinase-3 ligand (FLT3L), flagellin, OX40, or any combination thereof. In a specific embodiment, an immunity enhancer peptide is FLT3L. In another embodiment, the fusion protein is fused to an immunity enhancer peptide, which comprises an amino acid sequence at least about 80%, 85%, 90%, 95%, 96%, 97%, 98%, 99%, or 100% identical to SEQ ID NO: 12.

All of the description of the polynucleotide or the fusion protein in US 2013/0195905, published Aug. 1, 2013, are incorporated herein by reference in its entirety.

Examples of the fusion protein, the signal peptide, and the immunity enhancer peptide are shown in Table 3.

TABLE 3

| | Fusion proteins and the nucleotide sequences |
|---|---|
| Amino acid of Fusion Protein (SEQ ID NO: 10) | MHQKRTAMFQDPQERPRKLPHLCTELQTTIHDIILECVYCKQQLLRREVYDFAFRDLCI VYRDGNPYAVCDKCLKFYSKISEYRYMHGDTPTLHEYMLDLQPETTDLYCYEQLNDSSE EEDEIDGPAGQAEPDRAHYNIVTFCCKCDSTLDKCLKFYSKISEYRYYCYSVYGTTLEQ QYNKPLCDLLIRCINCQKPLCPEEKQRHLDKKQRFHNIRGRWTGRCMSCCRSSRTRRET QLHYNIVTFCCKCDSTLRLCVQSTHVDIRTLEDLLMGTLGIVCPICSQKPMARFEDPTR RPYKLPDLCTELNTSLQDIEITCVYCKTVLELTEVFEFAFKDLFVVYRDSIPHAACHKC IDFYSRIRELRYYSDSVMYGPKATLQDIVLHLEPQNEIPVDLLCHEQLSDSEEENDEID GVNHQHLPARRAEPQRHTMLCMCFYSRIRELRYYSDSVYGDTLEKLTNTGLYNLLIRCL RCQKPLNPAEKLRHLNEKRRFHKIAGHYRGQCHSCCNRARQERLQRRRETQVARRAEPQ RHTMLCMCCKCEARIELVVESSADDLRAFQQLFLSTLSFVCPWCASQQ |
| Codon-Optimized nucleotide sequence of Fusion Protein (SEQ ID NO: 9) | ATGCACCAGAAGAGAACCGCCATGTTCCAGGACCCTCAGGAGAGACCTAGGAAGCTGCC TCACCTGTGTACAGAGCTCCAGACAACCATCCACGACATCATCCTGGAGTGCGTGTACT GTAAGCAGCAGCTGCTGAGAAGAGAGGTGTACGACTTCGCCTTCAGAGACCTGTGCATC GTGTACAGAGACGGCAACCCTTACGCCGTGTGCGATAAGTGTCTGAAGTTCTATTCCAA AATCTCCGAATATAGGTACATGCACGGCGACACCCCTACCCTGCACGAGTACATGCTGG ACCTCCAGCCTGAGACCACAGACCTGTACTGCTACGAGCAGCTGAACGACAGCTCTGAG GAAGAGGACGAGATTGACGGACCTGCTGGCCAGGCCGAGCCTGACAGAGCCCACTACAA TATCGTGACATTCTGTTGCAAATGCGACTCCACACTGGACAAGTGCCTGAAGTTCTACA GCAAGATCTCTGAGTACAGATACTACTGCTACTCTGTGTACGGCACCACACTGGAGCAG CAGTACAACAAGCCTCTGTGCGACCTCCTGATCCGCTGCATCAACTGCCAGAAGCCTCT GTGCCCTGAGGAGAAGCAGAGACACCTGGACAAGAAGCAGCGGTTCCACAACATCAGAG GCAGATGGACCGGCAGGTGCATGTCCTGCTGTAGATCCTCCAGAACCAGACGGGAGACC CAGCTGCACTACAACATCGTGACCTTCTGCTGCAAGTGCGACTCTACCCTGAGACTGTG CGTGCAGTCTACCCACGTGGACATCAGAACCCTGGAGGACCTGCTGATGGGCACCCTGG GCATCGTGTGCCCTATCTGCTCTCAGAAGCCTATGGCCAGGTTCGAGGACCCTACCAGA AGACCCTACAAGCTGCCTGACCTGTGCACCGAGCTGAACACCTCTCTGCAAGACATCGA GATCACCTGCGTGTACTGCAAGACCGTGCTGGAGCTGACCGAGGTGTTCGAGTTCGCCT TCAAGGACCTGTTCGTGGTGTACAGAGACAGCATCCCTCACGCTGCCTGCCACAAGTGC ATCGACTTCTATTCCAGGATCAGGGAGCTGCGCTATTACTCCGACTCTGTGATGTACGG CCCCAAGGCCACCCTCCAGGACATCGTGCTGCACCTGGAGCCTCAGAACGAGATCCCCG TGGACCTGCTGTGCCACGAGCAGCTGTCTGACTCTGAAGAGGAGAACGACGAGATCGAC |

TABLE 3-continued

Fusion proteins and the nucleotide sequences

| | |
|---|---|
| | GGCGTGAACCACCAGCACCTGCCTGCCAGGAGAGCTGAACCCCAGCGGCATACCATGCT<br>GTGTATGTGCTTCTACTCTAGGATCAGAGAGCTGAGGTACTACTCTGACTCTGTGTACG<br>GCGACACCCTGGAGAAGCTGACCAACACCGGCCTGTACAACCTGCTGATCCGGTGCCTG<br>AGGTGCCAGAAGCCTCTGAACCCTGCCGAGAAGCTGAGACACCTGAACGAGAAGAGAAG<br>ATTCCACAAGATCGCTGGCCACTACAGAGGCCAGTGCCACTCTTGCTGCAACAGAGCCA<br>GACAGGAGAGACTCCAGCGGAGAAGGGAGACCCAGGTGGCCAGAAGAGCCGAGCCTCAG<br>AGACACACCATGCTGTGCATGTGCTGCAAGTGCGAGGCCAGAATCGAGCTGGTGGTGGA<br>GAGCTCTGCCGACGACCTGAGAGCCTTCCAGCAGCTGTTCCTGTCTACCCTGAGCTTCG<br>TGTGCCCTTGGTGCGCCTCTCAGCAG |
| Amino acid sequence of FLT3L (SEQ ID NO: 12) | ITQDCSFQHSPISSDFAVKIRELSDYLLQDYPVTVASNLQDEELCGGLWRLVLAQRWME<br>RLKTVAGSKMQGLLERVNTEIHFVTKCAFQPPPSCLRFVQTNISRLLQETSEQLVALKP<br>WITRQNFSRCLELQCQPDSSTLPPPWSPRPLEATAPTAPGGGSD |
| Nucleotide sequence of FLT3L (SEQ ID NO: 11) | ATCACCCAGGACTGCTCCTTCCAACACAGCCCCATCTCCTCCGACTTCGCTGTCAAAAT<br>CCGTGAGCTGTCTGACTACCTGCTTCAAGATTACCCAGTCACCGTGGCCTCCAACCTGC<br>AGGACGAGGAGCTCTGCGGGGGCCTCTGGCGGCTGGTCCTGGCACAGCGCTGGATGGAG<br>CGGCTCAAGACTGTCGCTGGGTCCAAGATGCAAGGCTTGCTGGAGCGCGTGAACACGGA<br>GATACACTTTGTCACCAAATGCCTTTCAGCCCCCCCCAGCTGTCTTCGCTTCGTCC<br>AGACCAACATCTCCCGCCTCCTGCAGGAGACCTCCGAGCAGCTGGTGGCGCTGAAGCCC<br>TGGATCACTCGCCAGAACTTCTCCCGGTGCCTGGAGCTGCAGTGTCAGCCCGACTCCTC<br>AACCCTGCCACCCCCATGGAGTCCCCGGCCCTGGAGGCCACAGCCCCGACAGCCCCGG<br>GCGGCGGCAGCGGCGAT |
| Amino acid sequence of signal peptide (SEQ ID NO: 14) | MDAMKRGLCCVLLLCGAVFVSPS |
| Nucleotide sequence of signal peptide (SEQ ID NO: 13) | ATGGATGCTATGAAACGGGGCCTGTGCTGCGTGCTGCTCCTGTGCGGCGCTGTGTTTGT<br>GAGCCCTAGC |
| Nucleotide sequence of GX-188 (SEQ ID NO: 15) | ACGCGTTGACATTGATTATTGACTAGTTATTAATAGTAATCAATTACGGGGTCATTAGT<br>TCATAGCCCATATATGGAGTTCCGCGTTACATAACTTACGGTAAATGGCCCGCCTGGCT<br>GACCGCCCAACGACCCCCGCCCATTGACGTCAATAATGACGTATGTTCCCATAGTAACG<br>CCAATAGGGACTTTCCATTGACGTCAATGGGTGGAGTATTTACGGTAAACTGCCCACTT<br>GGCAGTACATCAAGTGTATCATATGCCAAGTACGCCCCCTATTGACGTCAATGACGGTA<br>AATGGCCCGCCTGGCATTATGCCCAGTACATGACCTTATGGGACTTTCCTACTTGGCAG<br>TACATCTACGTATTAGTCATCGCTATTACCATGGTGATGCGGTTTTGGCAGTACATCAA<br>TGGGCGTGGATAGCGGTTTGACTCACGGGGATTTCCAAGTCTCCACCCCATTGACGTCA<br>ATGGGAGTTTGTTTTGGCACCAAAATCAACGGGACTTTCCAAAATGTCGTAACAACTCC<br>GCCCCATTGACGCAAATGGGCGGTAGGCGTGTACGGTGGGAGGTCTATATAAGCAGAGC<br>TCTCTGGCTAACTAGAGAACCCACTGCTTACTGGCTTATCGAAATTAATACGACTCACT<br>ATAGGGAGACCCAAGCTGGCTAGCGTGAGTTTGGGGACCCTTGATTGTTCTTTCTTTTT<br>CGCTATTGTAAAATTCATGTTATATGGAGGGGGCAAAGTTTTCAGGGTGTTGTTTAGAA<br>CGGGAAGATGTCCCTTGTATCACCATGGACCCTCATGATAATTTTGTTTCTTTCACTTT<br>CTACTCTGTTGACAACCATTGTCTCCTCTTATTTTCTTTTCATTTTCTGTAACTTTTTC<br>GTTAAACTTTAGCTTGCATTTGTAACGAATTTTTAAATTCACTTTTGTTTATTTGTCAG<br>ATTGTAAGTACTTTCTCTAATCACTTTTTTTTCAAGGCAATCAGGGTATATTATATTGT<br>ACTTCAGCACAGTTTTAGAGAACAATTGTTATAATTAAATGATAAGGTAGAATATTTCT<br>GCATATAAATTCTGGCTGGCGTGGAAATATTCTTATTGGTAGAAACAACTACATCCTGG<br>TCATCATCCTGCCTTTCTCTTTATGGTTACAATGATATACACTGTTTGAGATGAGGATA<br>AAATACTCTGAGTCCAAACCGGGCCCCTCTGCTAACCATGTTCATGCCTTCTTCTTTTT<br>CCTACAGCTCCTGGGCAACGTGCTGGTTATTGTGCTGTCTCATCATTTTGGCAAAGAAT<br>TGTAATACGACTCACTATAGGGCGAATTGAAGCTTGGTACCGCCACCATGGATGCTATG<br>AAACGGGGCCTGTGCTGCGTGCTGCTCCTGTGCGGCGCTGTGTTTGTGAGCCCTAGCAT<br>CACCCAGGACTGCTCCTTCCAACACAGCCCCATCTCCTCCGACTTCGCTGTCAAAATCC<br>GTGAGCTGTCTGACTACCTGCTTCAAGATTACCCAGTCACCGTGGCCTCCAACCTGCAG<br>GACGAGGAGCTCTGCGGGGCCTCTGGCGGCTGGTCCTGGCACAGCGCTGGATGGAGCG<br>GCTCAAGACTGTCGCTGGGTCCAAGATGCAAGGCTTGCTGGAGCGCGTGAACACGGAGA<br>TACACTTTGTCACCAAATGCCTTTCAGCCCCCCCCAGCTGTCTTCGCTTCGTCCAG<br>ACCAACATCTCCCGCCTCCTGCAGGAGACCTCCGAGCAGCTGGTGGCGCTGAAGCCCTG<br>GATCACTCGCCAGAACTTCTCCCGGTGCCTGGAGCTGCAGTGTCAGCCCGACTCCTCAA<br>CCCTGCCACCCCCATGGAGTCCCCGGCCCTGGAGGCCACAGCCCCGACAGCCCCGGGC<br>GGCGGCAGCGGCGATGCTAGCATGCACCAGAAGAGAACCGCCATGTTCCAGGACCCTCA<br>GGAGAGACCTAGGAAGCTGCCTCACCTGTGTACAGAGCTGCAGACAACCATCCACGACA<br>TCATCCTGGAGTGCGTGTACTGTAAGCAGCAGCTGCTGAGAAGAGAGGTGTACGACTTC<br>GCCTTCAGAGACCTGTGCATCGTGTACAGAGACGGCAACCCTTACGCCGTGTGCGATAA<br>GTGTCTGAAGTTCTATTCCAAAATCTCCGAATATAGGTACATGCACGGCGACACCCCTA<br>CCCTGCACGAGTACATGCTGGACCTCCAGCCTGAGACCACAGACCTGTACTGCTACGAG<br>CAGCTGAACGACAGCTCTGAGGAAGAGGACGAGATTGACGGACCTGCTGGCCAGGCCGA |

TABLE 3-continued

Fusion proteins and the nucleotide sequences

```
GCCTGACAGAGCCCACTACAATATCGTGACATTCTGTTGCAAATGCGACTCCACACTGG
ACAAGTGCCTGAAGTTCTACAGCAAGATCTCTGAGTACAGATACTACTGCTACTCTGTG
TACGGCACCACACTGGAGCAGCAGTACAACAAGCCTCTGTGCGACCTCCTGATCCGCTG
CATCAACTGCCAGAAGCCTCTGTGCCCTGAGGAGAAGCAGAGACACCTGGACAAGAAGC
AGCGGTTCCACAACATCAGAGGCAGATGGACCGGCAGGTGCATGTCCTGCTGTAGATCC
TCCAGAACCAGACGGGAGACCCAGCTGCACTACAACATCGTGACCTTCTGCTGCAAGTG
CGACTCTACCCTGAGACTGTGCGTGCAGTCTACCCACGTGGACATCAGAACCCTGGAGG
ACCTGCTGATGGGCACCCTGGGCATCGTGTGCCCTATCTGCTCTCAGAAGCCTATGGCC
AGGTTCGAGGACCCTACCAGAAGACCCTACAAGCTGCCTGACCTGTGCACCGAGCTGAA
CACCTCTCTGCAAGACATCGAGATCACCTGCGTGTACTGCAAGACCGTGCTGGAGCTGA
CCGAGGTGTTCGAGTTCGCCTTCAAGGACCTGTTCGTGGTGTACAGAGACAGCATCCCT
CACGCTGCCTGCCACAAGTGCATCGACTTCTATTCCAGGATCAGGGAGCTGCGCTATTA
CTCCGACTCTGTGATGTACGGCCCCAAGGCCACCCTCCAGGACATCGTGCTGCACCTGG
AGCCTCAGAACGAGATCCCCGTGGACCTGCTGTGCCACGAGCAGCTGTCTGACTCTGAA
GAGGAGAACGACGAGATCGACGGCGTGAACCACCAGCACCTGCCTGCCAGGAGAGCTGA
ACCCCAGCGGCATACCATGCTGTGTATGTGCTTCTACTCTAGGATCAGAGAGCTGAGGT
ACTACTCTGACTCTGTGTACGGCGACACCCTGGAGAAGCTGACCAACACCGGCCTGTAC
AACCTGCTGATCCGGTGCCTGAGGTGCCAGAAGCCTCTGAACCCTGCCGAGAAGCTGAG
ACACCTGAACGAGAAGAGAAGATTCCACAAGATCGCTGGCCACTACAGAGGCCAGTGCC
ACTCTTGCTGCAACAGAGCCAGACAGGAGAGACTCCAGCGGAGAAGGGAGACCCAGGTG
GCCAGAAGAGCCGAGCCTCAGAGACACACCATGCTGTGCATGTGCTGCAAGTGCGAGGC
CAGAATCGAGCTGGTGGTGGAGAGCTCTGCCGACGACCTGAGAGCCTTCCAGCAGCTGT
TCCTGTCTACCCTGAGCTTCGTGTGCCCTTGGTGCGCCTCTCAGCAGTAATCTAGAGTC
GGGGCGGCCGGCCGCTTCGAGCAGACATGATAAGATACATTGATGAGTTTGGACAAACC
ACAACTAGAATGCAGTGAAAAAAATGCTTTATTTGTGAAATTTGTGATGCTATTGCTTT
ATTTGTAACCATTATAAGCTGCAATAAACAAGTTAACAACAACAATTGCATTCATTTTA
TGTTTCAGGTTCAGGGGGAGGTGTGGGAGGTTTTTTAAAGCAAGTAAAACCTCTACAA
TGTGGTAAAATCGATAAGGATCTGAACGATGGAGCGGAGAATGGGCGGAACTGGGCGGA
GTTAGGGGCGGGATGGGCGGAGTTAGGGGCGGGACTATGGTTGCTGACTAATTGAGATG
CATGCTTTGCATACTTCTGCCTGCTGGGGAGCCTGGGGACTTTCCACACCTGGTTGCTG
ACTAATTGAGATGCATGCTTTGCATACTTCTGCCTGCTGGGGAGCCTGGGGACTTTCCA
CACCCTAACTGACACACATTCCACAGCGGATCCGTCGACTTCAGAAGAACTCGTCAAGA
AGGCGATAGAAGGCGATGCGCCGCGAATCGGGAGCGGCGATACCGTAGAGCACGAGGAA
GCGGTCAGCCCATTCGCCGCCAAGCTCTTCAGCAATATCACGGGTAGCCAACGCTATGT
CCTGATAGCGGTCCGCCACACCCAGCCGGCCACAGTCGATGAATCCAGAAAAGCGGCCA
TTTTCCACCATGATATTCGGCAAGCAGGCATCGCCATGGGTCACGACGAGATCCTCGCC
GTCGGGCATGCTCGCCTTGAGCCTGGCGAACAGTTCGGCTGGCGCGAGCCCCTGATGCT
CTTCGTCCAGATCATCCTGATCGACAAGACCGGCTTCCATCCGAGTACGTGCTCGCTCG
ATGCGATGTTTCGCTTGGTGGTCGAATGGGCAGGTAGCCGGATCAAGCGTATGCAGCCG
CCGCATTGCATCAGCCATGATGGATACTTTCTCGGCAGGAGCAAGGTGAGATGACAGGA
GATCCTGCCCCGGCACTTCGCCCAATAGCAGCCAGTCCCTTCCCGCTTCAGTGACAACG
TCGAGCACAGCTGCGCAAGGAACGCCCGTCGTGGCCAGCCACGATAGCCGCGCTGCCTC
GTCTTGCAGTTCATTCAGGGCACCGGACAGGTCGGTCTTGACAAAAAGAACCGGGCGCC
CCTGCGCTGACAGCCGGAACACGGCGGCATCAGAGCAGCCGATTGTCTGTTGTGCCCAG
TCATAGCCGAATAGCCTCTCCACCCAAGCGGCCGGAGAACCTGCGTGCAATCCATCTTG
TTCAATCATGCGAAACGATCCTCATCCTGTCTCTTGATCAGATCTTGATCCCCTGCGCC
ATCAGATCCTTGGCGGCAAGAAAGCCATCCAGTTTACTTTGCAGGGCTTCCCAACCTTA
CCAGAGGGCGCCCCAGCTGGCAATTCCGGTTCGCTTGCTGTCCATAAAACCGCCCAGTC
TAGCTATCGCCATGTAAGCCCACTGCAAGCTACCTGCTTTCTCTTTGCGCTTGCGTTTT
CCCTTGTCCAGATAGCCCAGTAGCTGACATTCATCCGGGGTCAGCACCGTTTCTGCGGA
CTGGCTTTCTACGTGAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTTTCCGAAGGT
AACTGGCTTCAGCAGAGCGCAGATACCAAATACTGTTCTTCTAGTGTAGCCGTAGTTAG
GCCACCACTTCAAGAACTCTGTAGCACCGCCTACATACCTCGCTCTGCTAATCCTGTTA
CCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCT
TGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGG
AGAGCGCACGAGGGAGCTTCCAGGGGGAAACGCCCGGTATCTTTATAGTCCTGTCGGGT
TTCGCCACCTCTGACTTGAGCGTCGATTTTTGTGATGCTCGTCAGGGGGCGGAGCCTA
TGGAAAAACGCCAGCAACGCGGCCTTTTTACGGTTCCTGGCCTTTTGCTGGCCTTTTGC
TCACATGTTCGGGCCCAATCGACCCGGGCGACGGCCAGTGAATTGTACCGATGTACGGG
CCAGATAT
```

II.D. Polynucleotide Encoding Fusion Protein

A therapeutic molecule of the invention can be one or more protein molecules described herein or a polynucleotide sequence encoding the protein molecule. In one aspect, a therapeutic molecule of the invention can include one or more DNA sequence, RNA sequence, or PNA sequence.

In another aspect, the polynucleotide sequence encoding the therapeutic molecule (e.g., fusion protein) is codon-optimized. The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 4. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at http://www.kazusa.or.jp/codon/(visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

In one embodiment, a nucleotide sequence encoding the therapeutic molecule (e.g., a fusion protein) is codon-optimized for human expression. In another embodiment, a nucleotide sequence encoding the therapeutic molecule (e.g., a fusion protein) is codon-optimized for prokaryotic or eukaryotic expression.

In other embodiments, a polynucleotide sequence encoding a fusion protein of the invention comprises codon-optimized sequences of an N-terminal portion of an E6 protein of HPV16, a C-terminal portion of an E6 protein of HPV16, an N-terminal portion of an E7 protein of HPV16, a C-terminal portion of an E7 protein of HPV16, an N-terminal portion of an E6 protein of HPV18, a C-terminal portion of an E6 protein of HPV18, an N-terminal portion of an E7 protein of HPV18, and a C-terminal portion of an E7 protein of HPV18, which are described elsewhere herein.

In some embodiments, the polynucleotide comprises a nucleotide sequence at least about 80%, 85%, 90%, 95%, 96%, 97%, 98%, 99%, or 100% identical to SEQ ID NO: 9. In other embodiments, the polynucleotide further comprises a nucleotide sequence encoding a heterologous moiety (e.g., a heterologous polypeptide or a non-peptide moiety) as

TABLE 4

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Stop | TGA Stop |
|   | TTG Leu (L) | TCG Ser (S) | TAG Stop | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) | described above. In some embodiments, the heterologous polypeptide comprises an Fms-related tyrosine kinase 3 ligand ("FLT3L") or a portion thereof, a signal peptide of tPA, or both. In yet other embodiments, the heterologous polynucleotide is codon-optimized.

In still other embodiments, a nucleotide sequence encoding the heterologous polypeptide encodes a signal peptide, wherein the nucleotide sequence comprises a nucleic acid sequence at least 80%, at least 85%, at least 90%, at least 95%, at least 96%, at least 97%, at least 98%, at least 99%, or 100% identical to SEQ ID NO: 13. In yet other embodiments, a nucleotide sequence encoding the heterologous polypeptide encodes an immunity enhancing peptide, wherein the nucleotide sequence comprises a nucleic acid sequence at least 80%, at least 85%, at least 90%, at least 95%, at least 96%, at least 97%, at least 98%, at least 99%, or 100% identical to SEQ ID NO: 11.

II.D.1. Transcription Control Sequences

In some embodiments, the polynucleotide molecules of the invention are operatively linked to at least one transcription control sequences. A transcription control sequences as used herein is any regulatory nucleotide sequence, such as a promoter sequence or promoter-enhancer combination, which facilitates the efficient transcription and translation of the coding nucleic acid to which it is operably linked. The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the transcription control sequences shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

II.D.2. Vectors

The invention also provides vectors comprising the polynucleotide molecules encoding a therapeutic molecules (e.g., a fusion protein) of the invention. Suitable vectors include expression vectors, viral vectors, and plasmid vectors.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include optimized polynucleotides encoding the fusion protein described herein. In one embodiment, the optimized coding sequence for the fusion protein is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

In some embodiments, a plasmid encoding a fusion protein of the invention is at least about 80%, 85%, 90%, 95%, 96%, 97%, 98%, 99%, or 100% identical to SEQ ID NO: 15.

II.D.3. Pharmaceutical Composition

Compositions containing the fusion protein of the present invention or the isolated polynucleotides of the present invention can contain a suitable pharmaceutically acceptable carrier. For example, they can contain excipients and/or auxiliaries that facilitate processing of the active compounds into preparations designed for delivery to the site of action.

The pharmaceutical composition can be formulated for parenteral administration (i.e. intravenous, subcutaneous, intradermal or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances, which increase the viscosity of the suspension, including, for example, sodium carboxymethyl cellulose, sorbitol and dextran. Optionally, the suspension can also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the invention can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the fusion protein of the invention or the polynucleotide encoding the protein is formulated with another HPV therapeutics.

In one embodiment, the polynucleotide encoding the fusion protein is formulated with a storage solution for injection (0.2 mg/ml potassium chloride, 1.44 mg/ml sodium phosphate monobasic, anhydrous, 0.24 mg/ml potassium phosphate monobasic, anhydrous, crystals, and 8 mg/ml sodium chloride at pH 7.5~7.9).

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition can take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a fusion protein, the optimized polynucleotide encoding the fusion protein, the vector comprising the polynucleotide, or the host cell comprising the vector, and a pharmaceutically acceptable carrier. In some embodiments, the composition is administered by a route selected from the group consisting of topical administration, intraocular administration, parenteral administration, intrathecal administration, subdural administration and oral administration. The parenteral administration can be intravenous or subcutaneous administration.

In certain embodiments, the pharmaceutical composition is formulated for electroporation.

III. Diagnostic and Treatment Methods

The present invention is directed to a method of identifying a responder from a non-responder to a therapeutic molecule described herein. The invention is further directed to a method of identifying a population of patients who will respond better to the therapeutic molecule of the invention or a method of improving a treatment regimen of the therapeutic molecule of the invention.

In one embodiment, the application is directed to the methods for identifying a subject who does not require a surgery for removal of a cervical tumor comprising administering an effective amount of a therapeutic molecule (e.g., a polynucleotide encoding a fusion protein) as described herein to the subject, where the subject exhibits an increased cellular immune response after the administration.

As used herein, the term "cellular immune response" or "cell-mediated immune response" is intended to encompass is an immune response that does not involve antibodies (humoral immunity), but rather involves the activation of phagocytes, antigen-specific cytotoxic T-lymphocytes (T-cells), and the release of various cytokines in response to an antigen. Cellular immunity protects the body by (i) activating antigen-specific cytotoxic T-lymphocytes that are able to induce apoptosis in body cells displaying epitopes of foreign antigen on their surface, such as virus-infected cells, cells with intracellular bacteria, and cancer cells displaying tumor antigens; (ii) activating macrophages and natural killer cells, enabling them to destroy pathogens; or (iii) stimulating cells to secrete a variety of cytokines that influence the function of other cells involved in adaptive immune responses and innate immune responses.

As a virus infection becomes established in the host, a series of molecular and cellular signals are initiated which activate cell-mediated immune responses. These signals include the production of interferons, other cytokines, and inflammatory mediators, in addition to the mobilization of local dendritic cells. Dendritic cells are thought to provide a critical cellular link for priming naive CD4 and CD8 T cells. Engagement of TCRs on the naive T cells with viral-peptide MHC complexes presented by the dendritic cells results in sequestration of the T cells and launches the antiviral T-cell response. The ensuing proliferation and differentiation of virus-specific T cells also occur in conjunction with inflammatory mediators such as interferons and other danger signals (Zajac A. J. and Harrington L. E., *Encyclopedia of Virology* 3(3):70-77, 2008).

CD8 T cells are potent antiviral effector cells due to their ability to produce both inflammatory mediators as well as cytotoxic effector molecules. CD8 T cells are commonly referred to as cytotoxic T lymphocytes (CTLs), due to their ability to kill virally infected target cells. As the effector T cell become activated following engagement with a virally infected target cell displaying an appropriate peptide-MHC complex, these killing functions are triggered, by subsequent release of perforin and granzyme molecules by T cells, which ensure the destruction of the infected cell. In addition to their direct killing of infected cells, CD8 T cells also produce a range of cytokines and chemokines (e.g., IFN-γ and TNF-α), which can help clear viral infections without causing death of infected cells (Zajac A. J. and Harrington L. E., *Encyclopedia of Virology* 3 (3): 70-77, 2008).

CD4 T cells are also critical constituents of the cell-mediated immune response to viral infections, as they are directly capable of antiviral functions, through IFN-γ production, and in some circumstances, by inducing lysis of virally infected cells. Following recognition of antigen in the context of MHC class II, a cascade of signaling events is initiated within the CD4 T cell which results in activation, proliferation, and differentiation into an effector CD4 T cells, which have been divided into two polarized subsets based on their cytokine production profile. T helper 1 (Th1) cells primarily produce IFN-γ, and are critical for the immune responses to various viral infections, and infections with intracellular bacteria. This subclass of effector cells is typically associated with antiviral cell-mediated immunity. On the contrary, T helper 2 (Th2) cells predominantly secrete the cytokines IL-4, IL-5, and IL-13, linked with the production of antibodies and humoral immune responses. The definition of CD4 T-cell subsets has expanded beyond Th1 and Th2 cells, with the importance of unique populations of regulatory CD4 T cells (which secrete IL-10) and also IL-17 producing 'Th17' cells (which secrete IL-17A) becoming evident (Zajac A. J. and Harrington L. E., *Encyclopedia of Virology* 3(3):70-77, 2008).

In some embodiments, the methods described herein further comprises measuring the increased cellular immune response of the subject after administration. In certain embodiments, the method described herein further comprises instructing a healthcare provider to measure the increased cellular immune response of the subject after administration.

As used herein, the term "healthcare provider" refers to individuals or institutions which directly interact with and/or administer a therapeutic molecule to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein the term "instructing a healthcare provider" includes orally directing a healthcare provider, or instructing a healthcare provider by using a written order, or both.

In some embodiments, the application is directed to the methods of treating a cervical tumor without a surgery comprising administering a polynucleotide encoding a fusion protein described herein, wherein the subject exhibits an increased cellular immune response after the administration, wherein the cellular immune response is increased at least about 2 fold after the administration, and wherein the cervical tumor is removed from the subject without a surgery.

As used herein, the term "increased cellular response" refers to increased CD8 T cell response, increased CD4 T cell response, increased cytokine secretion, or any combination thereof increased at least about 2 fold after the administration of a polynucleotide encoding a fusion protein described herein. For example, an increase in production/expression of common Th1 effector cytokines, e.g., IFN-γ, IL-2, and TNF-α, or any combination thereof, after at least one immunization (i.e., administration of at least one dose) with a polynucleotide encoding a fusion protein (e.g., HPV E6/E7 DNA therapeutic vaccine (GX-188)) described herein, compared to the baseline production of the common Th1 effector cytokines, e.g., IFN-γ, IL-2, and TNF-α, before vaccination.

In some embodiments, the increased CD4 T cell response comprises increased IFN-γ+ CD4 cells. In specific embodiments, the increased CD4 T cell response is at least about 1.5, 2.0, 2.5, 3.0, 3.5, or 4.0 fold increase in the number of IFN-γ+ CD4 cells.

In certain embodiments, the increased CD8 T cell response comprises increased expression of IFN-γ, IL-2, TNF-α, MIP-β, CD107a/b, or any combinations thereof. In some embodiments, the increased CD8 T cell response comprises increased CD38+ Ki67+ CD8 T cells. In specific embodiments, the increased CD8 T cell response is at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, at least about 15 fold, at least about 16 fold, at least about 17 fold, at least about 18 fold, at least about 19 fold, at least about 20 fold, at least about 21 fold, at least about 22 fold, at least about 23 fold, at least about 24 fold, or at least about 25 fold increase in the number of CD38+ Ki67+ CD8 T cells. In certain embodiments, the increased CD8 T cell response is measured by a flow cytometry.

In specific embodiments, the IFN-γ expression is increased at least 5 fold, at least 10 fold, at least 20 fold, at least 30 fold, at least 40 fold, at least 45 fold, at least 50 fold relative to the level prior to the administration.

In some embodiments, the IL-2 expression is increased at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, or at least about 15 fold relative to the level prior to the administration.

In specific embodiments, the TNF-α expression is increased at least about 2 fold, at least about 3 fold, at least about 4 fold, at least about 5 fold, at least about 10 fold, at least about 15 fold, at least about 16 fold, at least about 17 fold, at least about 18 fold, at least about 19 fold, at least about 20 fold, at least about 21 fold, at least about 22 fold, at least about 23 fold, at least about 24 fold, or at least about 25 fold relative to the level prior to the administration.

In certain embodiments, the increased cellular immune response comprises increased HPV16 and HPV18 E6 and E7 specific IFN-γ response. In some embodiments, the IFN-γ response is measured by IFN-γ ELISPOT assay.

In certain embodiments, increased cellular immune response is increased number of poly-functional T cells. As used herein, the term "poly-functional T cells" refer to polyfunctional HPV-specific CD8 T cells that show an increase in cytolytic activity, proliferative capacity, and secretion of effector molecules. In some embodiments, the poly-functional T cells show at least two, at least three, at least four, at least five, at least six or at least seven markers. In certain embodiments, the poly-functional T cells secrete at least IFN-γ and IL-2 and at least one additional markers. In specific embodiments, the poly-functional T cells exhibit at least three, at least four, or at least five markers selected from IFN-γ, IL-2, TNF-α, MIP-β, and CD107a/b when measured by flow cytometry.

In some embodiments, the application is directed to the methods described herein, wherein the number of the poly-functional T cells is increased at least about 5%, at least about 6%, at least about 7%, at least about 8%, at least about 9%, at least about 10%, at least about 15%, at least about 20%, or at least about 30% higher than the number of the poly-functional T cells prior to the administration of the polynucleotide encoding the fusion protein described herein.

In some embodiments, the application is directed to the methods of increasing systemic HPV-specific poly-functional CD8 T cell response in a subject in need thereof comprising administering a polynucleotide encoding a fusion protein described herein, wherein the poly-functional CD8 T cell response comprises increased expression of IFN-γ, IL-2, TNF-α, or any combination thereof. In specific embodiments, the administration comprises at least two doses or three doses.

In certain embodiments, the application is directed to the methods of treating a cervical tumor comprising (a) identifying a subject who does not exhibit an increased cellular immune response after administration of a polynucleotide encoding a fusion protein described herein and (b) determining the subject to be suitable for surgery to remove the cervical tumor.

As used herein, the term "determining the subject to be suitable for surgery to remove the cervical tumor" refers to providing general and/or specialized assessment, and/or advice relating to all, or any portion of, a patient's state of health to conclude that the patient is required to have a surgery to remove the cervical tumor.

In some embodiments, the application is directed to methods of treating a cervical tumor comprising (a) identifying a subject who does not exhibit an increased cellular immune response after administration of a polynucleotide encoding a fusion protein described herein and (b) instructing a healthcare provider to perform a surgery on the subject remove the cervical tumor.

In certain embodiments, the application is directed to the methods of treating a cervical tumor comprising (a) administering a polynucleotide encoding a fusion protein described herein to a subject in need thereof, (b) identifying the subject who does not exhibit an increased cellular immune response after administration of the fusion protein and (c) determining the subject to be suitable for surgery to remove the cervical tumor.

In certain embodiments, the application is directed to the methods of treating a cervical tumor in a population of subjects in need thereof comprising administering a polynucleotide encoding a fusion protein described herein to the population of subjects, wherein each of the subjects carries human leucocyte antigens (HLA)-A02.

In some embodiments, the application is directed to methods of treating a cervical tumor in a subject in need thereof comprising (a) identifying a subject who carries HLA-A02 and (b) administering to the subject a polynucleotide encoding a fusion protein as described herein.

In certain embodiments, the application is directed to the methods of improving cervical tumor treatment comprising administering a polynucleotide encoding a fusion protein described herein to a population of subjects, wherein each of the subjects carries human leucocyte antigens (HLA)-A02.

In some embodiments, the application is directed to the methods of improving cervical tumor treatment comprising (a) identifying a subject who carries HLA-A02 and (b) administering to the subject a polynucleotide encoding a fusion protein described herein.

In certain embodiments, the application is directed to the methods of improving cervical tumor treatment comprising (a) submitting a blood sample obtained from a subject in need thereof to identify the HLA type and (b) administering a polynucleotide encoding a fusion protein described herein to the subject who carries HLA-A02.

HLA-A is a group of human leukocyte antigens (HLA) that are coded for by the HLA-A locus, which is located at human chromosome 6p21.3 (HLA Nomenclature @ hla.alleles.org-Anthony Nolan Research Institute. 10 Nov. 2013. Retrieved 8 Dec. 2013). HLA is the major histocompatibility complex (MHC) specific to humans. HLA-A is one of three major types of human MHC class I cell surface receptors. The others are HLA-B and HLA-C. As of December 2013, there are 2432 known HLA-A alleles coding for 1740 active proteins and 117 null proteins (Allele Search Tool-European Molecular Biology Laboratory. 2013. Retrieved 20 Dec. 2013). (HLA)-A02 is a human leukocyte antigen serotype within the HLA-A serotype group. (HLA)-A02 also refers to HLA-A*02 (A*02), HLA-A2, HLA-A02, and HLA-A*2.

In certain embodiments, the application is directed to the methods of treating cervical tumor comprising (a) administering a first dose of a polynucleotide encoding a fusion protein to a subject in need thereof and (b) further administering a second dose of the polynucleotide to the subject who exhibits increased cellular immune response after administration of the first dose.

In certain embodiments, the application is directed to the methods of treating cervical tumor comprising (a) administering a first dose of a polynucleotide encoding a fusion protein described herein to a subject in need thereof, (b) measuring cellular immune response after the administration, and (c) administering a second dose of a polynucleotide to the subject who exhibits an increased cellular immune response after administration of the first dose. In some embodiments, the methods described herein further comprise measuring the cellular immune response after administration of the second dose. In certain embodiments, the methods described herein comprise administering a third dose of the polynucleotide described herein.

In some embodiments, the application is directed to the methods of treating cervical tumor comprising (a) administering a first dose and a second dose of a polynucleotide encoding a fusion protein described herein to a subject in need thereof and (b) further administering to the subject a third dose of a polynucleotide to the subject who exhibits increased cellular immune response after administration of the first dose or the second dose.

In certain embodiments, the application is directed to the methods of treating cervical tumor comprising (a) administering a first dose and a second dose of a polynucleotide encoding a fusion protein described herein to a subject in need thereof, (b) measuring cellular immune response after the administration of the first dose or the second dose, and (c) administering to the subject a third dose of a polynucleotide if the subject exhibits an increased cellular immune response after administration of the first or second dose.

According to the methods described herein, a polynucleotide encoding a fusion protein described herein can be administered at particular dosages. For example, in some embodiments the first dose is at least about 0.5 mg, at least about 1 mg, at least about 1.5 mg, at least about 2 mg, at least about 2.5 mg, at least about 3 mg, at least about 3.5 mg, at least about 4 mg, at least about 4.5 mg, or at least about 5 mg. In certain embodiments, the first dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg and the second dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg.

In certain embodiments, the second dose is at least about 0.5 mg, at least about 1 mg, at least about 1.5 mg, at least about 2 mg, at least about 2.5 mg, at least about 3 mg, at least about 3.5 mg, at least about 4 mg, at least about 4.5 mg, or at least about 5 mg.

In certain embodiments, the third dose is at least about 0.5 mg, at least about 1 mg, at least about 1.5 mg, at least about 2 mg, at least about 2.5 mg, at least about 3 mg, at least about 3.5 mg, at least about 4 mg, at least about 4.5 mg, or at least about 5 mg. In some embodiments, the third dose is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg.

In some embodiments, the second dose is administered at least about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks after the first dose. In certain embodiments, the third dose is administered at least about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks after the second dose.

Some embodiments of the invention include a method of inducing systemic HPV-specific poly-functional CD8 T cell response in a subject in need thereof comprising administering a polynucleotide encoding a fusion protein which comprises three or more amino acid sequences selected from:
  (1) an N-terminal portion of an E6 protein of HPV16,
  (2) a C-terminal portion of an E6 protein of HPV16,
  (3) an N-terminal portion of an E7 protein of HPV16,
  (4) a C-terminal portion of an E7 protein of HPV16,
  (5) an N-terminal portion of an E6 protein of HPV18,
  (6) a C-terminal portion of an E6 protein of HPV18,
  (7) an N-terminal portion of an E7 protein of HPV18, and
  (8) a C-terminal portion of an E7 protein of HPV18,
wherein the fusion protein does not bind to p53 or does not form a dimer with an E6 protein of HPV16 and HPV18 and wherein the fusion protein does not bind to pRb and does not form a dimer with an E7 protein of HPV16 and HPV18 and wherein the poly-functional CD8 T cell response comprises increased expression of IFN-γ and IL-2 and at least one, at least two, at least three, at least four, or at least five optional markers. In other embodiments, the optional marker is TNF-α.

In further embodiments, the administration of the method comprises at least two doses or three doses. In other embodiments, the IFN-γ expression is increased at least 5 fold, at least about 10 fold, at least about 20 fold, at least about 30 fold, at least about 40 fold, at least about 45 fold, at least about 50 fold relative to the level prior to the administration. In yet other embodiments, the IL-2 expression is increased at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, or at least about 15 fold relative to the level prior to the administration. In still other embodiments, the TNF-α expression is increased at least about 2 fold, at least about 3 fold, at least about 4 fold, at least about 5 fold, at least about 10 fold, at least about 15 fold, at least about 16 fold, at least about 17 fold, at least about 18 fold, at least about 19 fold, at least about 20 fold, at least about 21 fold, at least about 22 fold, at least about 23 fold, at least about 24 fold, or at least about 25 fold relative to the level prior to the administration.

In yet other embodiments, the administration does not increase IL-4 and IL17a expression.

In certain embodiments, a therapeutic molecule for the purpose of diagnostic methods includes other types of HPV vaccines. For example, examples of the HPV vaccines useful for the methods include, but are not limited to.

IV. Pharmaceutical Kits

The present invention also includes a pharmaceutical kit comprising a pharmaceutical composition which comprises a therapeutic molecule and instructions to use the composition. In one embodiment, the invention is directed to a kit comprising a pharmaceutical composition which comprises a polynucleotide encoding a fusion protein and instructions to perform a surgery to remove a cervical tumor if the cellular immune response after administration of an effective amount of the pharmaceutical composition is not increased, wherein the fusion protein comprises three or more amino acid sequences selected from:
  (1) an N-terminal portion of an E6 protein of HPV16,
  (2) a C-terminal portion of an E6 protein of HPV16,
  (3) an N-terminal portion of an E7 protein of HPV16,
  (4) a C-terminal portion of an E7 protein of HPV16,
  (5) an N-terminal portion of an E6 protein of HPV18,
  (6) a C-terminal portion of an E6 protein of HPV18,
  (7) an N-terminal portion of an E7 protein of HPV18, and
  (8) a C-terminal portion of an E7 protein of HPV18,
wherein the fusion protein does not bind to p53 or does not form a dimer with an E6 protein of HPV16 or HPV18 and wherein the fusion protein does not bind to a pRb or does not form a dimer with an E7 protein of HPV16 or HPV18.

In another embodiment, a pharmaceutical kit comprises a pharmaceutical composition comprising a polynucleotide encoding a fusion protein and instructions to administer an effective amount of the pharmaceutical composition to a subject who shows an increased number of poly-functional T cells after administration of an initial amount of the polynucleotide, wherein the fusion protein comprises three or more amino acid sequences selected from:
  (1) an N-terminal portion of an E6 protein of HPV16,
  (2) a C-terminal portion of an E6 protein of HPV16,
  (3) an N-terminal portion of an E7 protein of HPV16,
  (4) a C-terminal portion of an E7 protein of HPV16,
  (5) an N-terminal portion of an E6 protein of HPV18,
  (6) a C-terminal portion of an E6 protein of HPV18,
  (7) an N-terminal portion of an E7 protein of HPV18, and
  (8) a C-terminal portion of an E7 protein of HPV18,
wherein the fusion protein does not bind to p53 or does not form a dimer with an E6 protein of HPV16 or HPV18 and wherein the fusion protein does not bind to a pRb or does not form a dimer with an E7 protein of HPV16 or HPV18.

In other embodiments, a pharmaceutical kit comprises a pharmaceutical composition comprising a polynucleotide encoding a fusion protein and instructions to administer an effective amount of the pharmaceutical composition to a subject who shows an increased number of poly-functional T cells after administration of an initial amount of the polynucleotide, wherein the fusion protein comprises three or more amino acid sequences selected from:

(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to a pRb or does not form a dimer with an E7 protein of HPV16 or HPV18. In one embodiment, the poly-functional T cells secrete IFN-γ and IL-2.

In some embodiments, a pharmaceutical kit comprising a pharmaceutical composition which comprises a polynucleotide encoding a fusion protein and instructions to administer an effective amount of the pharmaceutical composition to a subject who carries HLA-A02, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to a pRb or does not form a dimer with an E7 protein of HPV16 or HPV18. In other embodiments, the kit comprises an effective amount of the therapeutic molecule, which is at least 1 mg, 2 mg, 3 mg, 4 mg, 5 mg, or 6 mg.

In some embodiments, a pharmaceutical kit comprises a pharmaceutical composition comprising a polynucleotide encoding a fusion protein and instructions to discontinue further administration of the pharmaceutical composition if a single dose or two doses of the pharmaceutical composition to a subject does not exhibit an increased cellular immune response, wherein the fusion protein comprises three or more amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to a pRb or does not form a dimer with an E7 protein of HPV16 or HPV18. In certain embodiments, the single dose is at least about 0.5 mg, 1 mg, 1.5 mg, 2 mg, 2.5 mg, 3 mg, 3.5 mg, 4 mg, 4.5 mg, or 5 mg. In other embodiments, the two doses comprises a first dose and a second dose, wherein the first dose is at least about 0.5 mg, 1 mg, 1.5 mg, 2 mg, 2.5 mg, 3 mg, 3.5 mg, 4 mg, 4.5 mg, or 5 mg and the second dose is at least about 0.5 mg, 1 mg, 1.5 mg, 2 mg, 2.5 mg, 3 mg, 3.5 mg, 4 mg, 4.5 mg, or 5 mg. In still other embodiments, the first dose and the second dose are identical. In yet other embodiments, the first dose and the second dose are different.

In certain embodiments, the first dose in the kit is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg, and the second dose in the kit is about 1 mg to about 5 mg, about 2 mg to about 4 mg, about 1 mg to about 4 mg, about 1 mg to about 10 mg, about 1 mg to about 9 mg, about 1 mg to about 8 mg, about 1 mg to about 7 mg, about 1 mg to about 6 mg. In a particular embodiment, the first dose in the kit is about 1 mg to 4 mg and the second dose in the kit is about 1 mg to about 4 mg. In some embodiments, the first dose is about 1 mg and the second dose is about 1 mg. In other embodiments, the first dose is about 2 mg and the second dose is about 2 mg. In yet other embodiments, the first dose is about 4 mg and the second dose is about 4 mg.

V. Methods of Making

The present invention is also directed to a method of making a therapeutic molecule for treatment of a disease or condition associated with human papillomavirus. In particular, the therapeutic molecule is constructed to contain all epitopes of several proteins from HPV, but does not contain a p53 binding domain and a pRb binding domain or does not form a dimer with the proteins from HPV.

One embodiment of the invention includes a method of making a polynucleotide encoding a fusion protein, which is effective in treating or preventing a cervical tumor caused by human papillomavirus infection comprising (i) constructing a polynucleotide that encodes a fusion protein comprising at least three amino acid sequences selected from:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the fusion protein does not bind to p53 or does not form a dimer with an E6 protein of HPV16 or HPV18 and wherein the fusion protein does not bind to pRb or does not form a dimer with an E7 protein of HPV16 or HPV18, and (ii) transfecting the polynucleotide in a host cell. In another embodiment, the fusion protein does not comprise a complete E6 associated protein (AP) binding site. In other embodiments, the fusion protein comprises at least all epitopes for immunogenicity contained in the naturally occurring E6 protein of HPV16 and HPV17 and the naturally occurring E7 protein of HPV16 and HPV17.

Some embodiments of the invention include a method of removing a p53 binding site and a pRb binding site in a fusion protein comprising the sequence of an E6 protein of HPV16, the sequence of an E7 protein of HPV16, the sequence of an E6 protein of HPV18, and the sequence of an E7 protein of HPV18, while comprising at least all of the epitopes for immunogenicity contained in the naturally occurring E6 protein of HPV16, the naturally occurring E7 protein of HPV16, the naturally occurring E6 protein of HPV18, and the naturally occurring E7 protein of HPV18 comprising (i) constructing a polynucleotide that encodes a fusion protein comprising:
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16, (5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein
(a) the E6 protein of HPV16 is split at the C-terminal end of amino acids 35 to 135 corresponding to SEQ ID NO: 2 into the N-terminal portion of the E6 protein of HPV16 (16E6Na-b) and the C-terminal portion of the E6 protein of HPV16 (16E6Cc-d), which when aligned together, comprise all of the sequences of the E6 protein of HPV16 and an optional overlapping sequence;
(b) the E7 protein of HPV16 is split at the C-terminal end of amino acids 18 to 97 corresponding to SEQ ID NO: 6 into the N-terminal portion of the E7 protein of HPV16 (16E7Ne-f) and the C-terminal portion of the E7 protein of HPV16 (16E7g-h), which when aligned together, comprise all of the sequences of the E7 protein of HPV16 and an optional overlapping sequence;
(c) the E6 protein of HPV18 is split at the C-terminal end of amino acids 30 to 130 corresponding to SEQ ID NO: 6 into the N-terminal portion of the E6 protein of HPV18 (18E6Ni-j) and the C-terminal portion of the E6 protein of HPV18 (18E6Nk-l), which when aligned together, comprise all of the sequences of the E6 protein of HPV18 and an optional overlapping sequence; and
(d) the E7 protein of HPV18 is split at the C-terminal end of amino acids 21 to 104 corresponding to SEQ ID NO: 8 into the N-terminal portion of the E7 protein of HPV18 (18E7Nm-n) and the C-terminal portion of the E7 protein of HPV18 (18E7Co-p), which when aligned together, comprise all of the sequences of the E7 protein of HPV18 and an optional overlapping sequence; and (ii) transfecting the polynucleotide in a host cell.

In certain embodiments, the overlapping sequence for the E6 protein of HPV16 in (a) comprises at least one amino acids, at least two amino acids, at least two amino acids, at least three amino acids, at least four amino acids, at least five amino acids, at least 10 amino acids, at least 15 amino acids, or at least 20 amino acids; the overlapping sequence for the E7 protein of HPV16 in (b) comprises at least one amino acids, at least two amino acids, at least two amino acids, at least three amino acids, at least four amino acids, at least five amino acids, at least 10 amino acids, at least 15 amino acids, or at least 20 amino acids; the overlapping sequence for the E6 protein of HPV18 in (c) comprises at least 1, 2, 5, 10, 15, 20, 25, 30, 35, or 40 amino acids; or the overlapping sequence for the E7 protein of HPV18 in (d) comprises at least 1, 2, 5, 10, 15, 20, 25, 30, 35, or 40 amino acids, wherein the overlapping sequences are sufficient to add or supplement any epitopes that were destroyed or deleted due to the cleavage of the E6 proteins or the E7 proteins into the N-terminal portion and the C-terminal portion.

In other embodiments, a method of preventing a formation of a dimer of an E6 protein of HPV16 and/or HPV18 and/or an E7 protein of HPV16 and/or HPV18 in a fusion protein comprising the sequence of an E6 protein of HPV16, the sequence of an E7 protein of HPV16, the sequence of an E6 protein of HPV18, and the sequence of an E7 protein of HPV18, while comprising all of the epitopes for immunogenicity of the E6 protein of HPV16, the E7 protein of HPV16, the E6 protein of HPV18, and the E7 protein of HPV18 comprising (i) constructing a polynucleotide that encodes a fusion protein comprising (1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein
(a) the E6 protein of HPV16 is split at the C-terminal end of amino acids 37 to 72 corresponding to SEQ ID NO: 2 into the N-terminal portion of the E6 protein of HPV16 (16E6Na-b) and the C-terminal portion of the E6 protein of HPV16 (16E6Cc-d), which when aligned together, comprise all of the sequences of the E6 protein of HPV16 and an optional overlapping sequence;
(b) the E7 protein of HPV16 is split at the C-terminal end of amino acids 44 to 97 corresponding to SEQ ID NO: 6 into the N-terminal portion of the E7 protein of HPV16 (16E7Ne-f) and the C-terminal portion of the E7 protein of HPV16 (16E7g-h), which when aligned together, comprise all of the sequences of the E7 protein of HPV16 and an optional overlapping sequence;
(c) the E6 protein of HPV18 is split at the C-terminal end of amino acids 32 to 67 corresponding to SEQ ID NO: 4 into the N-terminal portion of the E6 protein of HPV18 (18E6Ni-j) and the C-terminal portion of the E6 protein of HPV18 (18E6Nk-l), which when aligned together, comprise all of the sequences of the E6 protein of HPV18 and an optional overlapping sequence; and
(d) the E7 protein of HPV18 is split at the C-terminal end of amino acids 47 to 104 corresponding to SEQ ID NO: 8 into the N-terminal portion of the E7 protein of HPV18 (18E7Nm-n) and the C-terminal portion of the E7 protein of HPV18 (18E7Co-p), which when aligned together, comprise all of the sequences of the E7 protein of HPV18 and an optional overlapping sequence; and (ii) transfecting the polynucleotide in a host cell. In other embodiments, the overlapping sequence for the E6 protein of HPV16 in (a) comprises at least at least 1, 2, 5, 10, 15, 20, 25, 30, 35, or 40 amino acids; the overlapping sequence for the E7 protein of HPV16 in (b) comprises at least 1, 2, 5, 10, 15, 20, 25, 30, 35, or 40 amino acids; the overlapping sequence for the E6 protein of HPV18 in (c) comprises at least 1, 2, 5, 10, 15, 20, 25, 30, 35, or 40 amino acids; or the overlapping sequence for the E7 protein of HPV18 in (d) comprises at least 1, 2, 5, 10, 15, 20, 25, 30, 35, or 40 amino acids.

In some embodiments, the methods of making a polynucleotide encoding a fusion protein can result in any therapeutic molecule described herein. In other embodiments, the methods result in any polynucleotides described herein, but does not include SEQ ID NO: 9.

V.A.1. Host Cells

The invention also provides host cells comprising the polynucleotide molecules of the invention. As used herein, the term "transformation" shall be used in a broad sense to refer to the introduction of DNA into a recipient host cell that changes the genotype and consequently results in a change in the recipient cell.

"Host cells" refers to cells that have been transformed with vectors constructed using recombinant DNA techniques and encoding at least one heterologous gene. The host cells of the present invention are preferably of mammalian origin; most preferably of human or mouse origin. Those skilled in the art are credited with ability to preferentially determine particular host cell lines which are best suited for their purpose. Exemplary host cell lines include, but are not limited to, CHO, CAPTI, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte), PER.C6®, NS0, CAP, BHK21, and HEK 293 (human kidney). Host cell lines are typically available from commercial services, the American Tissue Culture Collection, or from published literature.

Introduction of the isolated nucleic acid molecules of the invention into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (MA), or flourescence-activated cell sorter analysis (FACS), immunohistochemistry and the like.

In certain embodiments, the nucleic acid molecules of the invention is administered to a subject by an electroporation. In vivo electroporation (EP) is a technique that significantly increases the immunogenicity of DNA vaccines via co-administration of small, localized electrical fields to increase the transfection efficiency of the injected DNA and the recruitment of immune cells such as dendritic cells, T and B lymphocytes to the site of immunization. Animal studies in animals have shown that in vivo EP increases the immunogenicity of DNA vaccines encoding a number of antigens. In humans, in vivo EP has been successful at delivering chemotherapeutic agents directly to tumors. More recently, DNA vaccines encoding tumor antigens have been administered to cancer patients by EP as potential immunotherapy (Vasan et al., *Plos One* 6(5): 1-10, 2011).

Host cells comprising the isolated nucleic acid molecules of the invention are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

V.A.2. Preparation of Polypeptides

The invention also provides a polynucleotide molecules or a polypeptide encoded by the polynucleotide molecules.

For recombinant protein production, a polynucleotide sequence of the invention encoding the fusion protein is inserted into an appropriate expression vehicle, i.e., a vector which contains the necessary elements for the transcription and translation of the inserted coding sequence, or in the case of an RNA viral vector, the necessary elements for replication and translation.

The polynucleotide sequence of the invention is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14: 725) and electroporation (Neumann et al. 1982, EMBO, J. 1: 841). A variety of host-expression vector systems can be utilized to express the fusion proteins described herein in eukaryotic cells. In one embodiment, the eukaryotic cell is an animal cell, including mammalian cells (e.g., HEK293 cells, CAPTI, PER.C6®, CHO, BHK, Cos, HeLa cells).

The fusion protein of the invention can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82:4438). Methods of producing transgenic animals are known in the art including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the fusion protein described herein coding sequence can be ligated into the vector in frame with the lac Z coding region so that a hybrid protein is produced; pGEX vectors can be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g., PreCission Protease (Pharmacia, Peapack, N.J.)) for easy removal of the tag after purification.

For the purposes of this invention, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art, as discussed above. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" can mean either from spun down whole cells, or from the cell culture containing both the medium and the suspended cells.

Genes encoding the polypeptides of the invention can also be multiplied in non-mammalian cells such as bacteria or yeast or plant cells to increase the gene numbers. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

Alternatively, optimized nucleotide sequences of the invention can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin. In vitro production allows scale-up to give large amounts of the desired polypeptides or polynucleotides.

EXAMPLES

Example 1

HPV E6/E7 DNA Therapeutic Vaccine (GX-188)

pGX-188 therapeutic HPV DNA vaccine (GX-188) as described herein, contains a plasmid DNA encoding E6 and E7 proteins of HPV serotypes 16 and 18 (HPV16 and HPV18) fused to extracellular domain of FLT3L and the signal sequence of tpa. (FIG. 1A).

Synthetic codon-optimized E6, or E7 genes were fragmented into two parts (C-terminal and N-terminal regions) with a small overlapping sequences (encoding 16 amino acids), and shuffled as shown in FIG. 1A. The fused DNA sequences including tpa, FLT3L, and shuffled E6/E7 genes were inserted in pGX27 vector (Park K. S., et al., *Vaccine*. 29:5481-5487, 2011) to generate pGX27-tFE6E7. GX-188 DNA vaccine was produced in *E. coli* DH5a under cGMP condition.

The 293T cells were transfected with pGX27 control vector only, GX-188, or pGX27 inserted with wild type E6 or E7 genes. Twenty-four hours post transfection, cell lysates were prepared and protein expressions were analyzed by immunoblotting. Nuclear and cytoplasmic fractions of cells were prepared as follows: cells were washed once with ice-cold phosphate-buffered saline (PBS) and collected at 3,000 rpm for 5 min. Cells were resuspended in buffer A (10 mM HEPES, pH 7.9, 10 mM KCl, 0.2 mM EDTA, 1 mM DTT, 0.25 mM PMSF, and proteinase inhibitor cocktail). After incubation on ice for 5 min, NP-40 was added to a final concentration of 0.25%. The mixtures were vortexed at high speed for 10 seconds. Extracts were collected by centrifugation at 13,000 rpm for 30 seconds. The supernatants were collected as cytoplasmic extracts. The pellet was resuspended in buffer B (20 mM HEPES, pH 7.9, 420 mM NaCl, 2 mM EDTA, 1 mM DTT, 0.25 mM PMSF, and PIC), followed by incubation at 4° C. for 30 min under gentle agitation. The mixtures were spun at 13,000 rpm for 15 min, and the supernatants were collected as nuclear extracts. For whole-cell protein lysates, cells were resuspended in lysis buffer (20 mM HEPES, pH 7.4, 150 mM NaCl, 5 mM EDTA, 10% glycerol, 0.5% Triton X-100, 1 mM DTT, 1 mM PMSF, 1 mM NaF, 1 mM Na3Vo4, and PIC). The following antibodies were used: anti-HPV16 E6 (N-17), anti-HPV16 E7 (ED17), anti-p53 (FL-393), anti-pRb (C-15) antibodies purchased from Santa Cruz Biotechnology, Inc., and anti-lamin B1 and anti-β-tubulin antibodies purchased from Abcam.

The purpose for inclusion of FLT3L and tpa is to promote antigen presentation and trafficking of the fused protein to the secretary pathway, respectively. The activity of tpa is evident, as GX-188-induced E6/E7 fusion protein was detected only in the cytoplasmic compartment of transfected cells, whereas E7 protein expressed by the same vector without tpa was found in both cytoplasmic and nuclear compartments as shown in FIG. 2A. The gene shuffling was done to prevent homodimerization of E6 and E7 regions of the fusion protein, which is crucial for their binding and degradation of p53 and pRb tumor suppressor proteins (Zanier K., et al., *Structure*. 20:604-617, 2012; Liu X., et al., *The Journal of Biological Chemistry*. 281:578-586, 2006). While E6/E7 fusion protein generated by GX-188 DNA vaccine was unable to degrade p53 and pRb proteins, wild type E6 and E7 proteins induced their degradation as shown in FIGS. 2B and 2C, respectively.

Study Design and Patients

This phase 1 clinical study was conducted as an open label, single center, dose-escalation study at Cheil General Hospital & Women's Healthcare Center, Seoul, Korea. The primary end-point was to evaluate safety and tolerability in patients with Cervical Intraepithelial Neoplasia 3 (CIN3). The secondary end-points included systemic induction of HPV E6- and E7-specific T cell immune responses measured by IFN-γ ELISPOT, as described herein, and changes of involved lesions and HPV infection status at the uterine cervix. Women aged between 20 and 50 years with histologically and virologically proven HPV16- or HPV18-associated CIN3 were enrolled in the study. The CIN3 was confirmed by colposcopy-directed biopsy and HPV16 or HPV18 positivity was determined by polymerase chain reaction. Subjects with hepatitis B virus, hepatitis C virus, or human immunodeficiency virus infections, abnormal electrocardiography (ECG) including arrhythmia, history of severe adverse drug events or severe allergic diseases were excluded. Females who were pregnant or planning to be pregnant were not recruited in the study. Vaccination consisted of a series of three vaccine injections administered intramuscularly to alternating deltoid muscles at weeks 0, 4, and 12. A standard 3+3 dose escalation scheme was followed and dose levels of 1 mg, 2 mg and 4 mg were tested. At the highest dose, 4 mg of GX-188 was split into 2 mg+2 mg and injected to the left and right deltoids muscles. For the intramuscular injector, an EP device (TriGrid Delivery System, Ichor medical systems, Inc.) was used to facilitate DNA uptake into cells.

According to the inclusion and exclusion criteria for this study, 9 out of 11 screened patients with only CIN3 were enrolled (Table 1). The screened patients were examined by multiple methods, including colposcopy, cytology, histology and HPV type test, at the visit for screening (VS) time point 2 weeks prior to the start of the trial. The assessments including colposcopy, histology, endocervical cytology, and HPV genotyping test were conducted by local laboratory at the trial site. The assessments were performed in compliance with the standardized method or the internal protocol of Cheil General Hospital and Women's Healthcare Center. Responses to treatment were evaluated using virology and histology results at weeks 20 and 36 post GX-188 vaccination.

Histological and cytological evaluation. For histological evaluation, biopsy samples were taken during screening and two follow-up visits at weeks 20 and 36. Samples were fixed with 10% formaldehyde and 4-5 μm sections were stained with hematoxylin and eosin (H&E). Endocervical samples were collected using cytobrush (Cytyc Corp., Boxborough, Mass.) during colposcopic examination. This endocervical cytology test was also used in addition to histology for the assessment of GX-188 vaccination. Data from histological and cytological analyses were reviewed independently by at least two pathologists and results were confirmed after discussion with by conference of all pathologists and investigators.

PCR for virological response. HPV typing was performed to determine whether subjects were infected by either HPV16 and/or HPV18. Samples were collected from the cervix by using a swab-type device, and total DNAs were extracted using the ACCUPREP® Genomic DNA Extraction kit (Bioneer Com. Seoul, Korea). HPV detection and genotyping was done by Multiplex-PCR system using the IVD CE marked SEEPLEX® HPV4A ACE Screening kit (Seegene Inc., Seoul, Korea) according to the manufacture's protocol. The SEEPLEX® HPV4A ACE Screening kit can identify HPV16, HPV18, other high-risk types (High risk common: 26, 31, 33, 35, 39, 45, 51, 52, 53, 56, 58, 59, 66, 68, 73, and/or 82), HPV6, and HPV11 types at the same time. PCR products were analyzed using an automatic MultiNA instrument (Shimadzu Co., Tokyo, Japan). HPV DNA genotyping was double checked in cervical cells using Cheil HPV DNA Chip with real time PCR to compensate the accuracy of HPV genotype as previously described (Hahn, H. S., et al., *European journal of obstetrics, gynecology, and reproductive biology* 169:202-206, 2013).

Sequence-based typing (SBT) of HLA was performed by heterozygous amplification followed by sequencing of the complete exons 2, 3 of HLA-A and -B. For locus-specific amplification primers were used in in-house method. After application by PCR, agarose gel electrophoresis of the PCR products was conducted to assess the quantity and quality. Cycle sequencing reactions using the ABI PRISM BigDye terminator kit (Applied Biosystems, CA, USA) and the automated ABI377 DNA Sequencer (Applied Biosystems, CA, USA) were performed. These data were analyzed by using SBT analysis program (Conexio Genomics, Assign SBT v3.5.1).

GX-188 vaccine achieved complete response in 7 out of 9 patients (78%). Among 7 responders, 6 patients carrying human leukocyte antigens (HLA)-A*02 exhibited high polyfunctional CD8 T cell responses as well as complete regression of CIN3 (Table 5).

All participating subjects received 3 injections of GX-188 DNA vaccine by electroporation, with the last 2 injections given at 4 and 12 weeks after the first injection (FIG. 1B). All subjects completed a total of 6 visits for treatment (VT) and follow-up (VF) at 2, 4, 8, and 16 week intervals without any dropouts (FIG. 1B).

TABLE 5

Baseline characteristics of the patients

| Group | Patient No. | Age at enrollment (yr) | HLA-A | HLA-DRB1 | Lesion grade |
|---|---|---|---|---|---|
| 1 mg Cohort | A01 | 44 | *02:06, *30:01 | *04:03, *07:01 | CIN3, severe dysplasia |
|  | A02 | 30 | *02:06, *02:07 | *08:03, *14:07 | CIN3, severe dysplasia |
|  | A03 | 44 | *02:01 | *01:01, *04:05 | CIN3, carcinoma in situ |
| 2 mg Cohort | A04 | 37 | *26:02, *30:01 | *09:01, *16:02 | CIN3, carcinoma in situ |
|  | A05 | 23 | *02:01, *30:01 | *08:03, *13:01 | CIN3, severe dysplasia |
|  | A06 | 25 | *02:01, *24:02 | *01:01, *09:01 | CIN3, severe dysplasia |
| 4 mg Cohort | A07 | 28 | *24:02, *26:02 | *09:01, *14:06 | CIN3, severe dysplasia |
|  | A08 | 23 | *02:01, *24:02 | *04:06, *15:01 | CIN3, severe dysplasia |
|  | A09 | 30 | *24:02, *26:01 | *08:03, *15:02 | CIN3, carcinoma in situ |

A total of 49 adverse events (AEs) were recorded during all visits. Twenty-three AEs, including eczema, ecchymosis, vaginal itching, sleepiness, anorexia, and dizziness were determined to be unrelated to the vaccination. Nineteen AEs including chills, injection site pain, swelling, and hypoaesthesia, were recorded to be associated with GX-188 vaccination (Table 2). Although the cause of the remaining 7 AEs, including headache, rhinitis and fatigue, were unknown, they were considered to be potentially associated with GX-188 vaccination. The incidence of GX-188 vaccine-related AEs became more frequent at higher doses (3 for 1 mg cohort, 9 for 2 mg cohort, and 14 for 4 mg cohort), presumably due to increased injection volume (0.5 ml for 1 mg cohort, 1 ml for 2 mg cohort, and 2 ml for 4 mg cohort). However, all these AEs were considered to be mild (grade 1) and all patients recovered completely within 3 days after GX-188 vaccination. Since neither severe AEs nor laboratory abnormalities were observed at any given dose (Table 6 and Table 7), the dose of GX-188 was elevated from 1 mg to 2 mg, and then to 4 mg (3 patients at each dose) without the enrollment of additional 3 subjects at each dose level according to 3+3 dose escalation design of this clinical trial protocol.

TABLE 6

Adverse drug reactions classified by MedDRA System Organ 2 Class (SOC) during the clinical study

| Adverse drug reactions | 1 mg (n = 3) | 2 mg (n = 3) | 4 mg (n = 3) |
|---|---|---|---|
| General disorders and administration site conditions | | | |
| Chills | 0 | 1 [1] | 0 |
| Fatigue | 0 | 0 | 2 [2] |
| Injection site erythema | 0 | 1 [1] | 1 [1] |

TABLE 6-continued

Adverse drug reactions classified by MedDRA System Organ 2 Class (SOC) during the clinical study

| Adverse drug reactions | 1 mg (n = 3) | 2 mg (n = 3) | 4 mg (n = 3) |
|---|---|---|---|
| Injection site pain | 1 [2] | 2 [5] | 2 [6] |
| Injection site paraesthesia | 1 [1] | 0 | 0 |
| Swelling | 0 | 1 [1] | 0 |
| Infections and infestations | | | |
| Rhinitis | 0 | 0 | 1 [1] |
| Nervous system disorders | | | |
| Headache | 0 | 0 | 2 [4] |
| Hypoaesthesia | 0 | 1 [1] | 0 |

$^a$Data are presented as a number of subjects and a number of incidences ([ ])
All adverse events possibly related to DNA vaccine plus electroporation, or unknown (fatigue, rhinitis, headache) were indicated. CTCAE grades of the events are 1 (mild), and all events recovered completely within 3 days after injection.

TABLE 7

Summary of Hematology test

| | | 1 mg (n = 3) | 2 mg (n = 3) | 4 mg (n = 3) | Total (n = 9) |
|---|---|---|---|---|---|
| WBC | VS | 5.2 ± 1.3 | 5.1 ± 0.6 | 4.5 ± 0.7 | 4.9 ± 0.9 |
| ($10^9$ $L^{-1}$) | VT2 | 5.7 ± 1.7 | 4.2 ± 0.1 | 4.4 ± 0.5 | 4.8 ± 1.1 |
| | VT4 | 5.6 ± 0.8 | 3.9 ± 0.3 | 4.3 ± 0.2 | 4.6 ± 1.0 |
| | VF1 | 6.0 ± 1.2 | 4.1 ± 0.7 | 5.8 ± 0.3 | 5.3 ± 1.1 |
| Neutrophils | VS | 51.3 ± 1.4 | 59.6 ± 13.2 | 55.7 ± 14.6 | 55.5 ± 10.5 |
| (%) | VT2 | 55.6 ± 5.1 | 55.7 ± 8.2 | 48.6 ± 9.1 | 53.3 ± 7.5 |
| | VT4 | 51.2 ± 5.0 | 54.4 ± 3.5 | 49.5 ± 9.6 | 51.7 ± 6.1 |
| | VF1 | 53.5 ± 8.1 | 52.5 ± 10.3 | 49.3 ± 12.6 | 51.7 ± 9.3 |
| Lymphocytes | VS | 38.2 ± 2.5 | 29.5 ± 11.2 | 35.8 ± 14.5 | 34.5 ± 10.0 |
| (%) | VT2 | 35.2 ± 4.4 | 30.9 ± 8.7 | 42.2 ± 8.9 | 36.1 ± 8.3 |
| | VT4 | 39.7 ± 3.7 | 31.2 ± 4.8 | 41.1 ± 10.5 | 37.3 ± 7.6 |
| | VF1 | 36.4 ± 5.6 | 33.3 ± 7.9 | 42.1 ± 11.7 | 37.3 ± 8.5 |
| Monocytes | VS | 5.0 ± 0.9 | 6.1 ± 1.1 | 4.7 ± 0.2 | 5.2 ± 1.0 |
| (%) | VT2 | 4.6 ± 0.5 | 7.3 ± 1.2 | 4.2 ± 1.2 | 5.4 ± 1.7 |
| | VT4 | 4.6 ± 0.3 | 8.0 ± 2.4 | 3.8 ± 0.2 | 5.5 ± 2.3 |
| | VF1 | 5.0 ± 1.1 | 8.3 ± 1.4 | 4.0 ± 0.4 | 5.8 ± 2.1 |
| Eosinophils | VS | 2.5 ± 0.7 | 2.1 ± 0.7 | 1.4 ± 0.4 | 2.0 ± 0.7 |
| (%) | VT2 | 2.1 ± 0.2 | 2.5 ± 1.0 | 2.0 ± 1.0 | 2.2 ± 0.7 |
| | VT4 | 2.1 ± 1.0 | 3.1 ± 0.8 | 2.6 ± 1.9 | 2.6 ± 1.2 |
| | VF1 | 2.2 ± 1.3 | 2.8 ± 0.4 | 1.6 ± 0.7 | 2.2 ± 0.9 |
| Basophils | VS | 0.6 ± 0.2 | 0.4 ± 0.1 | 0.4 ± 0.2 | 0.5 ± 0.2 |
| (%) | VT2 | 0.4 ± 0.1 | 0.4 ± 0.2 | 0.5 ± 0.1 | 0.4 ± 0.1 |
| | VT4 | 0.5 ± 0.3 | 0.6 ± 0.3 | 0.4 ± 0.1 | 0.5 ± 0.2 |
| | VF1 | 0.4 ± 0.1 | 0.3 ± 0.2 | 0.6 ± 0.2 | 0.4 ± 0.2 |
| RBC | VS | 4.0 ± 0.1 | 4.2 ± 0.2 | 4.2 ± 0.2 | 4.1 ± 0.2 |
| ($10^{12}$ $L^{-1}$) | VT2 | 4.0 ± 0.1 | 4.2 ± 0.1 | 4.3 ± 0.2 | 4.2 ± 0.2 |
| | VT4 | 4.0 ± 0.1 | 4.5 ± 0.0 | 4.3 ± 0.3 | 4.3 ± 0.3 |
| | VF1 | 4.0 ± 0.1 | 4.3 ± 0.2 | 4.2 ± 0.0 | 4.2 ± 0.2 |
| Hemoglobin | VS | 12.6 ± 0.4 | 12.7 ± 1.6 | 13.1 ± 0.4 | 12.8 ± 0.9 |
| (g $dL^{-1}$) | VT2 | 12.5 ± 0.2 | 12.4 ± 1.6 | 13.0 ± 0.7 | 12.7 ± 0.9 |
| | VT4 | 12.4 ± 0.8 | 12.6 ± 2.0 | 12.9 ± 0.6 | 12.6 ± 1.1 |
| | VF1 | 12.3 ± 1.1 | 12.2 ± 1.8 | 13.0 ± 0.1 | 12.5 ± 1.1 |

Data are presented as a mean value ± s.d.

Since it was reported that the administration of FLT3L protein could increase the frequency of white blood cells (WBCs) (Maraskovsky, E., et al., *Blood* 96:878-884, 2000; Evans, T. G., et al., *Vaccine* 21:322-329, 2002), the number of WBCs and the level of FLT3L were measured in the blood. A change in the number of WBCs was not observed (Table 6), which is likely due to little up-regulation of FLT3L level in the blood upon GX-188 vaccination (Table 8).

TABLE 8

Change of Flt3L concentration in blood

| Time points | 1 mg (n = 3) | 2 mg (n = 3) | 4 mg (n = 3) |
|---|---|---|---|
| VS  | 88.23 ± 26.93  | 63.70 ± 10.87 | 75.59 ± 19.29 |
| VT2 | 103.00 ± 43.08 | 62.32 ± 6.86  | 76.46 ± 5.97  |
| VT4 | 88.71 ± 17.80  | 66.52 ± 5.01  | 77.41 ± 19.90 |
| VF1 | 93.86 ± 38.59  | 72.38 ± 10.96 | 91.20 ± 4.80  |
| VF2 | 80.04 ± 29.15  | 71.71 ± 8.10  | 80.89 ± 16.00 |

Data are presented as a mean value ± s.d. (pg ml$^{-1}$)

To determine the immunological safety of the approach described herein, it was investigated whether the enhanced delivery of GX-188 DNA vaccine by EP generated anti-FLT3L and anti-DNA antibodies which are known to be associated with autoimmune disorders (Saade, F. and Petrovsky, N., *Expert review of vaccines* 11:189-209, 2012).

The level of FLT3L in the blood was measured using FLT3L ELISA kit (DFK00, R&D Systems) according to the manufacturer's instructions. Briefly, plasma samples and standards were added in microplate coated with a monoclonal antibody specific for human FLT3L. After washing away any unbound substances, an enzyme-linked polyclonal antibody specific for human Flt-3 Ligand was added to the wells. Following a wash to remove any unbound antibody-enzyme reagent, a substrate solution was added to the wells. The color development was stopped by adding 2N sulfuric acid and the intensity of the color was measured using microplate reader (Molecular devices, SpectraMax plus 384). Level of FLT3L in the blood (pg per ml) was calculated by creating standard curve using computer software capable of generating a log/log curve-fit (SoftMax Pro Software, v5.4.1). Data are presented as a mean value±s.d. of triplicate samples.

The level of anti-ds DNA antibody was determined by ELISA (CHORUS dsDNA-G, DIESSE, Italy). Briefly, the plasma (50 μl) was added into the microplate well coated with purified human DNA, and then, after washing, incubation was performed with anti-human IgG antibody conjugated with horse radish peroxidase. The unbound conjugate was eliminated, and the TMB substrate was added. To check the validity of the results, control samples supplied with the kit were used. If the signal for the control sample has a value outside the acceptable range, the calibration should be repeated. The calibration range was 10.0-150.0 IU ml$^{-1}$. The test sample can be interpreted as follows; positive when the result is >30.0 IU ml$^{-1}$, negative when the results is <20.0 IU ml$^{-1}$, doubtful for all values between 20.0 and 30.0 IU ml$^{-1}$. In the case of a doubtful result, the test should be repeated. Diagnostic sensitivity, cross-reactions, specificity, and precision of the test were described in the kit manual. The limit of detection was 10 IU ml−1.

Anti-FLT3L antibody levels were not significantly induced post vaccination compared to the control serum (data not shown), and the level of antibodies against DNA in the blood of patients with CIN3 was below the detection limit (Table 9), which is comparable to the previous results obtained from subjects immunized with DNA vaccine without EP (Le, T. P., et al., *Vaccine* 18:1893-1901, 2000; Yang, S. H., et al., *Gene Therapy* 13:1110-1117, 2006). Taken together, these results indicate that the incorporation of EP and genetic adjuvants is relatively tolerable in clinical trials of DNA vaccines and very similar to the safety profiles observed with the administration of a basic DNA vaccine without EP.

TABLE 9

Undetectable levels of anti-ds DNA antibody in subjects

|  | A01 | A02 | A03 | A04 | A05 | A06 | A07 | A08 | A09 |
|---|---|---|---|---|---|---|---|---|---|
| VS (IU ml$^{-1}$)  | <10.0 | <10.0 | <10.0 | <10.0 | <10.0 | <10.0 | <10.0 | <10.0 | <10.0 |
| VF1 (IU ml$^{-1}$) | <10.0 | <10.0 | <10.0 | <10.0 | <10.0 | <10.0 | <10.0 | <10.0 | <10.0 |

Detection limit, 10 IU ml$^{-1}$

Example 2

The Effect of GX-188 Vaccination on Cellular Immunity

To study the cellular immune response induced by GX-188, the number of HPV-specific IFN-γ-secreting T cells was determined by stimulating patients' peripheral blood mononuclear cells (PBMCs) with a mixture of overlapping peptides covering the entire length of HPV16 or HPV18 E6 and E7 proteins. An IFN-γ ELISPOT assay was performed before, at VS time point (−2 week), during, at VT2 (2 week) and VT4 time points (8 week), and after, at VF1 (20 week) and VF2 time points (36 week), GX-188 vaccination.

Cryopreserved and thawed PBMCs were adapted with OPTMIZER™ CTS™ medium (Life technologies) for more than 6 hours at 37° C., 5% $CO_2$, and subsequently PBMCs ($2\times10^5$ cells per well) were stimulated with 2 μg ml$^{-1}$ of four different pools of HPV16 and HPV18 E6- or E7-derived peptides (20-mer with 10 amino acids overlapping) for 48 hours. Phytohaemagglutinin (PHA) and the medium only served as positive and negative controls, respectively. After stimulation, spots indicating IFN-γ secreting cells were developed according to manufacturer's instructions (BD Bioscience). The number of spots was analyzed with an automated IMMUNOSPOT® Analyzer (Cellular Technology Ltd.). The HPV-specific responses were calculated by subtracting the mean number of spots in the medium only control from the mean number of spots in experimental wells, which were expressed as SFCs per $10^6$ PBMCs (Urbani, S. et al., J Exp Med., 201(5):675-80, 2005). The assay was performed in triplicate, and the background number of spots was 5.7±2.2 (mean±s.d.). Antigen-specific T-cell responses were considered to be positive when the mean number of antigen wells minus background was 3-fold higher than that of the medium control or to be greater than 55 SFCs per $10^6$ PBMCs (Barnes, E. et al., Sci Transl Med. 4(115):115ra1, 2012; Streeck, H. et al., Nat Protoc., 4(4): 461-9, 2009). In addition, a post-analyzed vaccine-induced response was defined as at least a 3-fold increase in T-cell frequency after vaccination compared to the results before vaccination (de Vos van Steenwijk, P. J. et al., Cancer Immunol Immunother., 61(9):1485-92, 2012).

Relatively high pre-existing IFN-γ ELISPOT response was detected in one patient (A03), whereas other 8 patients displayed weak pre-existing HPV-specific cellular immunity prior to vaccination. Based on the criteria described above, all subjects exhibited a marked increase in the vaccine-induced E6- and E7-specific IFN-γ ELISPOT response compared to the background level prior to vaccination as shown in FIGS. 3A-3I. Two out of nine patients (A06 and A08) developed a considerably enhanced IFN-γ response even after a single immunization (VT2), and additional 4 patients exhibited such an elevated response after two vaccinations (VT4). Two patients (A01 and A03) in the 1 mg dose group (FIGS. 3A and 3D) displayed an increased IFN-γ response after 3 shots of the GX-188 vaccine (VF1), suggesting that vaccine-induced cellular immune responses became progressively stronger in all patients during GX-188 vaccination. In particular, patient A08 (FIG. 3H) exhibited the highest magnitude of IFN-γ ELISPOT response with reactivity up to 3,500 spot forming unit (SFU) per $10^6$ PBMCs. It is likely that T-cell responses against the E6 antigen was more vigorous than those against E7 antigen in all patients (69~89% against E6 vs. 11~31% against E7 at VF1) as shown in FIGS. 3A-3I.

The establishment of memory T cells, normally starting to form about 4 weeks after immunization, is usually one of the indispensable factors for protective efficacy of a vaccine (Wherry, E. J. and Ahmed, R., Journal of Virology 78:5535-5545, 2004; Kaech, S. M., et al., Nature reviews Immunology 2:251-262, 2002). A relatively high level of IFN-γ ELISPOT response was observed in 8 out of 9 patients at 24 weeks (VF2) following the last vaccination, which, when compared to the responses at 8 weeks (VF1) post vaccination, is decreased for one patient (A03), comparable for three patients (A01, A06, and A09) and increased for four patients (A02, A05, A07, and A08) (FIGS. 3B, 3E, 3G, and 3H). Overall, this finding indicates that GX-188 vaccination-induced E6/E7-specific memory T cell response can be maintained for at least 24 weeks post last vaccination.

To address whether the IFN-γ response to E6/E7 antigens measured by ELISPOT assay was generated mainly by T cells and to determine which subset of T cells played a predominant role, intracellular cytokine staining (ICS) assays were performed for IFN-γ at pre- and post-vaccination time points (VS and VF1). Specifically, cryopreserved and thawed PBMCs of patients harvested before (VS) and after (VF1) GX-188 vaccination were resuspended in OPTI-MIZER™ CTS™, and rested for more than 6 hours at 37° C., 5% $CO_2$. PBMCs were plated in duplicate and stimulated with a combined mixture of HPV16 E6 and E7 peptides in one pool (15-mer with 8 amino acid overlapping) at a concentration 2 μg/ml, α-CD3 mAb (positive control) or the medium alone (negative control) in the presence of 1 μg $ml^{-1}$ of α-CD28 (L293, BD Bioscience) and α-CD49d (L25, BD Bioscience) for 13 hours. Secretion inhibitors (monensin/brefeldin A, BD Bioscience) were added 90 minutes after initial stimulation. After stimulation, cells were washed with PBS for subsequent immunostaining and polychromatic flow cytometric analysis. Antibodies for staining cells were CD19-APCCy7 (HIB19, Biolegend), CD4-PerCPCy5.5 (RPA-T4, Biolegend), CD8-PECy7 (RPA-T8, BD Bioscience), CD3-BV605 (Bright Violet 605) (UCHT1, Biolegend), CD3-BV500 (UCHT1, BD Horizon), Live/dead-APCCy7 (Life technologies), MIP-1β-PE (D21-1351, BD Bioscience), IFN-γ-APC (4S.B3, Biolegend), TNF-α-BV421 (MAb11, Biolegend), IL-2-BV711 (5344.111, BD Horizon), CD107a-FITC (H4A3, BD Bioscience), and CD107b-FITC (H4B4, BD Bioscience). FACS analysis was accomplished by Fortessa flow cytomer (BD Bioscience), and the data was analyzed using FlowJo software (Tree Star). Boolean gating was used to determine simultaneous cytokine production from CD8 T cells. Analysis of polyfunctionality was performed with SPICE (Roederer, M. et al., Cytometry A., 79(2):167-74, 2011). A positive response was defined as at least twice the percentage of cytokine-producing T cells than in the medium only control, and the response should be visible as a clearly distinguishable population of cytokine-producing cells separated from the nonproducing cells. A vaccine-induced response was defined as at least a 3-fold increase in the percentage of antigen-specific cytokine-producing T cells of the baseline sample (pre-vaccination) (Welters, M. J. et al., Clin Cancer Res., 1; 14(1):178-87, 2008).

As shown in FIGS. 4A-4E, the vaccination with GX-188 resulted in an increase in HPV16-specific IFN-γ$^+$ CD4 T cell responses in all 9 patients (FIGS. 4B and 4C), while IFN-γ$^+$ CD8 T cell response was enhanced in 8 out of 9 patients, all except for patient A04 (FIGS. 4D and 4E). Thus, with the exception of one patient, GX-188 vaccine elicited activation of both HPV16-specific CD4 and CD8 T cells.

Since persistent HPV infection impairs T helper (Th) 1-type cellular response to HPV, leading to cervical cancer progression (Deligeoroglou, E., et al., Infectious diseases in obstetrics and gynecology 2013:540850, 2013; Bais, A. G., et al., Journal of clinical pathology 58:1096-1100, 2005; Clerici, M., et al., Journal of the National Cancer Institute 89:245-250, 1997; Peghini, B. C., et al., Human immunology 73:920-926, 2012), it was investigated whether GX-188 DNA vaccine could drive differentiation of HPV-specific CD4 T cells into Th1 effector cells. Cryopreserved and thawed PBMCs ($2\times10^5$ per well) were resuspended in OPTI-MIZER™ CTS™, and rested for more than 6 hours at 37° C., 5% $CO_2$, and subsequently PBMCs were plated in duplicate and were stimulated in RPMI 1640 containing 10% FBS, 100 U $ml^{-1}$ penicillin and 100 μg $ml^{-1}$ streptomycin with a combined mixture of HPV16 E6 and E7 peptides in one pool (15-mer with 8 amino acids overlapping) at a concentration 2 μg $ml^{-1}$ or the medium only as negative control in 96-well plates. Culture supernatants were harvested 48 hours after the stimulation and cytokines were quantitated by Th1/Th2/Th17 cytometric bead array (CBA) kit (BD Biosciences). According to manufacturer's instructions, the proposed detection limit was 2.5~5 pg $ml^{-1}$ (IL-2, IL-4, IL-10, TNF-α, and IFN-γ) or 19 pg $ml^{-1}$ (IL-17A), and the cut-off value was set to 5 pg $ml^{-1}$ because the standard curve of each cytokine showed linearity starting at a concentration of 5 pg $ml^{-1}$ as shown in FIG. 12. Positive antigen-specific reaction was defined as a cytokine concentration above the cut-off value and >2×the concentration of the medium control (Welters, M. J. et al., Clin Cancer Res., 1; 14(1):178-87, 2008). A vaccine-induced response was defined as at least a 3-fold increase in the antigen-specific cytokine production over the baseline sample (Welters, M. J. et al., Clin Cancer Res., 1; 14(1):178-87, 2008).

The baseline production of common Th1 effector cytokines, such as IFN-γ, IL-2, and TNF-α, before vaccination was remarkably low upon stimulation with E6/E7 peptides. However, the amounts of these cytokines markedly increased after vaccination in most of the patients (median 49.9-, 13-, and 22.9-fold increases for IFN-γ, IL-2, and TNF-α, respectively) as shown in FIG. 5A-C, respectively. Consistent with the IFN-γ ELISPOT and ICS data, A08 patient also showed the greatest increase of Th1 cytokine production. Given that the level of IL-2 production increases progressively during functional memory T-cell differentiation (Wherry, E. J., et al., *Nature immunology* 4:225-234, 2003), this substantial increase in IL-2 production may indicate efficient generation of HPV-specific memory T cells upon GX-188 vaccination. On the other hand, Th2 (IL-4 and IL-10) (FIG. 5D-E, respectively) and Th17 (IL-17A) (FIG. 5F) cytokines were not significantly increased by vaccination, although patient A04 had a slightly increased level in production of an immunosuppressive cytokine, IL-10. Taken together with above IFN-γ ELISPOT and ICS analyses, these results suggest that GX-188 vaccination leads to the induction of a strong Th1-polarized HPV-specific cellular immune response.

Example 3

GX-188 Vaccine-Induced Polyfunctional CD8 T Cells

During persistent viral infection, virus-specific CD8 T cells become unresponsive to viral antigens and show progressive loss of effector functions (Wherry, E. J., *Journal of virology* 77:4911-4927, 2003; Wherry, E. J., et al., *Immunity* 27:670-684, 2007). To determine whether GX-188 vaccination induced multiple aspects of HPV-specific CD8 T-cell functionality, the ability of HPV-specific CD8 T cells to co-produce effector cytokines; IFN-γ, IL-2, TNF-α, and MIP-1β was assessed. Similar to the results obtained by ICS for IFN-γ (FIGS. 4A-4E), 8 out of 9 patients, with the exception of A04, displayed an increase in proportions of HPV-specific CD8 T cells co-producing IFN-γ and IL-2, TNF-α or MIP-1β post-vaccination (VF1) compared to pre-vaccination (VS) (FIG. 6A-C and FIG. 7B-D).

Cytolytic activity of virus-specific CD8 T cells is another major indicator in evaluating vaccine efficacy against viral infection (Pantaleo, G. and Harari, A., *Nature Reviews Immunology* 6:417-423, 2006; Seder, R. A., *Nature reviews Immunology* 8:247-258, 2008). Since the expression of CD107a/b is exclusively found during degranulation by cytotoxic T cells (Betts, M. R., et al., *Journal of immunological methods* 281:65-78, 2003), the ability of HPV-specific CD8 T cells to concurrently produce IFN-γ and up-regulate CD107a/b expression was also evaluated. As reflected in FIG. 6D and FIG. 7E, the frequency of IFN-γ$^+$ CD107a/b$^+$ CD8 T cells escalated in all patients except A04 post vaccination. To determine the polyfunctionality of HPV16-specific CD8 T cells induced by vaccination in these 8 patients, IFN-γ, IL-2, TNF-α, MIP-1β, and CD107a/b were simultaneously assessed using Boolean gating. Patient A08 exhibited the highest polyfunctional profile in which 87.6% of HPV16-specific CD8 T cells were at least triple-positive and 15% of them had all 5 functions (FIG. 6E-F). In other 6 patients (A01, A02. A03, A05, A06 and A07), 7.8%~46.3% of HPV-specific CD8 T cells had 3 or more functions (FIG. 6F). However, HPV16-specific CD8 T cells from patient A09 were not polyfunctional (FIG. 6F). Overall, these results indicate that GX-188 vaccination could induce antigen-specific CD8 T cells with various polyfunctional profiles in most patients.

Optimal expansion of responding T cells upon antigen stimulation has been known to be essential for providing effective protective immunity by therapeutic vaccination (Wherry, E. J., *Journal of virology* 77:4911-4927, 2003; Wherry, E. J., et al., *Journal of virology* 79:8960-8968, 2005). Therefore, activation-induced proliferation of CD8 T cells responding to HPV16 E6/E7 peptides pre- (VS) and post- (VF1) vaccination was examined by measuring the levels of Ki67 and CD38 expression, which serve as a marker of proliferation and activation, respectively (Gerdes, J., et al., *Journal of immunology* 133:1710-1715, 1984; Sandoval-Montes, C., and Santos-Argumedo, L., *Journal of leukocyte biology* 77:513-521, 2005). Ki-67 was demonstrated to be a valid tool for measuring antigen-specific cellular proliferation ex vivo and could be used as an alternative to the standard proliferation assay, such as carboxyfluorescein succinimidyl ester (CFSE)-labeling and 5-bromo-2-deoxyuridine (BrdU) incorporation (Soares, A. et al., J Immunol Methods., 362(1-2):43-50, 2010; Shedlock, D. J. et al., Cytometry A., 77(3):275-84, 2010).

Cryopreserved and thawed PBMCs (1×10$^6$ cells per well) were adapted with OPTMIZER™ CTS™ medium (Life technologies) for more than 6 hours at 37° C., 5% $CO_2$. PBMCs were plated in duplicate and stimulated with a combined mixture of HPV16 E6 and E7 peptides in one pool (15-mer with 8 amino acids overlapping) at a concentration 2 μg ml$^{-1}$ in RPMI 1640 containing 10% FBS, 100 U ml$^{-1}$ penicillin and 100 μg ml$^{-1}$ streptomycin for 5 days. α-CD3 mAb and the medium alone served as positive and negative controls, respectively. After 3 days, cell cultures were replaced with 100 μl of fresh R10 medium. At the end of culture, cells were washed with PBS for subsequent immunostaining and polychromatic flow cytometric analysis. The cells were stained with CD19-FITC, CD4-PerCPCy5.5, CD8-PECy7, CD38-BV421 (HIT2, BD Bioscience), CD3-BV605, Ki-67-PE (B56, BD Bioscience), and Live/Dead-APCCy7. Responses at least 3-fold greater than those of the medium control were considered to be positive. A vaccine-induced response was defined as at least a 3-fold increase in the percentage of antigen-specific proliferating CD8 T cells of the baseline sample.

Although one patient (A01) displayed a relatively high pre-existing level pre-vaccination (VS), the rest of the patients demonstrated low levels of Ki67$^+$CD38$^+$ CD8 T cells as shown in FIG. 8. After vaccination, all patients exhibited meaningful improvement in proliferative activity of HPV-specific CD8 T cells. In accordance with the pattern of functional CD8 T cell response as shown in FIG. 6, 2 patients (A04 and A09) displayed only a minor increase in proliferating CD8 T cell population, whereas the other 7 patients displayed a much greater increase of Ki67$^+$CD38$^+$ CD8 T cell population, within a range of 3.1- to 21.2-fold increase. Herein, the background level of Ki67 expression from the non-stimulated cells was quite low (0.011±0.015%), and thus peptide-stimulated Ki67$^+$ CD38$^+$ CD8 T cells might be considered as antigen-specific proliferating CD8 T cells as shown in FIG. 8. Collectively, these results indicate that GX-188 vaccination in CIN3 patients substantially augmented both the expansion and polyfunctionality of HPV-specific CD8 T cells.

Example 4

The Measure of Antibody Response to E7 and E6 Proteins Following GX-188 Vaccination Plasma samples were evaluated for total IgG antibody responses to E6 and E7 by an endpoint dilution enzyme-linked immunosorbent assay (ELISA). Specifically, plasma samples were collected and frozen at −70° C. A binding ELISA was performed to measure the anti-HPV16/18 E6 or E7 antibody response induced by GX-188 vaccination. Endpoint titers of antibodies were determined by coating 96-well enzyme immunoassay plates (THERMO SCIENTIFIC™) with HPV16/HPV18 E6 or E7 proteins (1 μg ml$^{-1}$) (recombinant HPV16 E6, HPV16 E7, and HPV18 E7 were purchased from ProteinX Lab; recombinant HPV18 E6 was purchased from MyBioSource). The plate was blocked with PBS, 5% skim milk for 1 hour at room temperature. Test plasma were serially diluted in PBS containing 5% skimmed milk and 0.1% Tween 20, and added to the plate wells in triplicate. After 1 hour incubation at room temperature, E6- or E7-specific antibodies were detected by incubating the plates for 1 hour at room temperature with goat anti-human IgG antibody conjugated to HRP (Bethyl, A80-104P). After a last wash (Tablet, Fluka), specific binding was detected with TMB substrate (SurModics). The reaction was stopped with $0.5N_{H2SO4}$ (Sigma-Aldrich), and the absorbance read at 450 nm in a microplate reader (Molecular devices, Spectra-Max plus 384). Negative cut-off (NCO) values were defined as the mean optical density plus 1.645x s.d. of 12 healthy control plasma (Biochemed) (Mire-Sluis, A. R. et al., J Immunol Methods., 289(1-2):1-16, 2004). Positivity was considered if the average optical density of a sample was greater than NCO values (0.173 for HPV16 E6, 0.213 for HPV16 E7, 0.214 for HPV18 E6, and 0.227 for HPV18 E7). To account for non-specific binding of samples to the plate, each plasma was tested in a well coated with an irrelevant protein, EPO-BRP (EDQM, batch 3, ph. Eur. Reference standard).

All patients had barely detectable or undetectable IgG titer to both E6 and E7 proteins at baseline (VS), as shown in FIGS. 9A-9L indicating no meaningful pre-existing E6- and E7-specific IgG antibody responses. Interestingly, the antibody titers to E6 were not developed or boosted at all in any dose cohort after vaccination. Three out of nine patients (A05, A07, and A09) generated weak anti-E7 antibody responses following vaccination with antibody titers ranging from 1:8 to 1:256 (FIGS. 9A-9L). It is worth noting that T-cell responses to E7 antigens were lower than those against E6 antigens and that measurable antibody titers to E7 proteins were not associated with CD8 T cell responses to E7 antigens in PBMC.

Example 5

The Effect of GX-188 Vaccination on HPV Infections and Lesions

GX-188-induced clinical responses were determined by evaluating the patients' HPV infection status as well as the cytological and histological changes of their high-grade cervical lesions over the 36-week period of the clinical trial (Table 10 and FIG. 1B). At baseline (VS), all 9 patients had CIN3 with either severe dysplasia (A01, A02, A05, A06, A07, and A08) or carcinoma in situ (A03, A04, and A09) according to histological evaluation of colposcopic-directed biopsy specimens (Tables 5 and 10). At 8 weeks post last vaccination (VF1), 6 out of 9 patients were free of lesions—2 patients from each cohort (A01 and A03 from 1 mg cohort, A05 and A06 from 2 mg cohort, A07 and A08 from 4 mg cohort)—indicating dose-independency of the response presumably due to saturation dose at 1 mg (Table 10). Three of these responder patients (A03, A06, and A08) were negative for intraepithelial lesion based on cytological analysis after the second immunization at week 12 (VT4), while 3 other patients (A01, A05, and A07) displayed such responses after the third vaccination at week 20 (VF1) and the last responder patient (A02) cleared the lesion at the end of the 36 week trial (VF2). Notably, none of the 6 early responders displayed any recurrent cervical dysplasia during the remaining duration of the trial. In cases of 2 non-responders, patient A04 was treated by cervical conization at week 24, while patient A09 was monitored without surgery until the end of study, per patient's request, and remained stably at CIN3 without progressing to invasive carcinoma.

Colposcopic, cytological, and histological image analysis before vaccination (VS) and at the end of the trial (VF2) more clearly demonstrated the difference in clinical responses to GX-188 between responders and non-responders, as shown by the photographs from representative responder A05 and non-responder A09 patients in FIG. 10. In colposcopic evaluation of cervix, patient A05 displayed significantly reduced dense acetowhite epithelium and disappearance of coarse punctuation in transformation zone after vaccination, whereas patient A09 still had dense lesions in the cervix as shown in FIG. 10A. The endocervical cytology test demonstrated that GX-188 vaccination induced the normalization of a high-grade squamous intraepithelial lesion (HSIL) with spidery cytoplasmic process and normochromic nuclei in patient A05, but no change in cytological appearance in patient A09 as shown in FIG. 10B. In histological features, the biopsy revealed that abnormal thick epithelium of CIN3 with marked nuclear variation regressed to normal squamous epithelium without atypical epithelium in patient A05 after vaccination, but was still present in patient A09 as shown in FIG. 10C.

HPV16 was identified in the lesions of all 9 subjects at the start of the trial, and one patient (A05) was found to also be co-infected with HPV18. At week 12 (VT4), 4 patients (A01, A03, A06, and A08) and patient A05 showed clearance of HPV16 and HPV18 viruses, respectively (Table 10), indicating viral clearance after the second immunization. At week 20 (VF1), HPV DNAs in cervical lesions were cleared in 6 out of 9 patients (A01, A03, A05, A06, A07, and A08) and one more patient (A02) cleared the virus at week 36 (VF2). Since these 7 patients also cleared their lesions with the identical kinetics, there was perfect correlation between the clinical and virological responses (Table 10). Beside HPV16 and HPV18, two patients (A06 and A07) were found to be co-infected with other high-risk common types of HPV at baseline (VS). One patient (A05) became infected with the common HPV type in the midst of the trial (VT4). In contrast to A07 patient, A05 and A06 patients cleared co-infected common types of HPV at VF2 and VT4, respectively, presumably due to a bystander effect caused by the elimination of HPV16-infected intraepithelial neoplastic cells. Another reason for clearance of these viruses is by the cross-reactivity of the HPV16 E6/E7-specific CD8 T cells generated upon vaccination, since there is approximately 50-60% homology in E6 and E7 amino acid sequences between HPV16 or HPV18 and other high-risk type strains.

It is notable that the 3 patients (A03, A06, and A08) who cleared their lesions and HPV infection at the early time point (VT4) promptly displayed a relatively high magnitude of HPV-specific polyfunctional CD8 T cell response (Table 10, FIGS. 6 and 8). In addition, the other 4 patients (A01, A02, A05, and A07) with a meaningful polyfunctional CD8 T cell response exhibited the complete resolutions of their lesions and HPV infections after the third vaccination either at week 20 (VF1) or at the end of the trial (VF2 at week 36) (Table 10, FIGS. 6 and 8). In contrast, 2 non-responder patients (A04 and A09) had almost no polyfunctional CD8 T cell response. The correlation between induction of polyfunctional T cell response and clinical outcome is readily apparent when the individual data from the patients were grouped into non-responders (A04 and A09) and responders (A01, A02, A03, A05, A06, A07 and A08) to generate the polyfunctional profile with 3 or more functions (FIG. 11). Hence, the results as presented herein indicate the clinical efficacy of GX-188 vaccine strongly correlates with the extent of systemic HPV-specific polyfunctional CD8 T cell response. Overall, GX-188 vaccination led to the clinically and virologically meaningful complete response rate of 78% (7 out of 9 patients) (Table 10).

GX-188 and C-1, C-2, D-1, D-2, E-1, and E-2 fragments were digested with BstXI and AleI restriction enzymes and then ligated to generate each plasmid of C-1, C-2, D-1, D-2, E-1, and E-2, respectively. In particular, for the C-1 construct, histidine (H) 21, tyrosine (Y) 85, and valine (V) 90

TABLE 10

Virological and clinical responses during and after immunization with GX-188 DNA vaccine by electroporation

| Patient No. | Dose | At week 0 (VT1) | | | At week 12 (VT4) | | | At week 20 (VF1) | | | At week 36 (VF2) | | |
|---|---|---|---|---|---|---|---|---|---|---|---|---|---|
| | | HPV status[a] | Cytology | Histology | HPV status[a] | Cytology | Histology | HPV status[a] | Cytology | Histology | HPV status[a] | Cytology | Histology |
| A01 | 1 mg | 16 | ASC-H | CIN3 | Negative | ASC-US | Negative | NIL | Normal | Negative | NIL | Normal |
| A02 | 1 mg | 16 | HSIL | CIN3 | 16 | HSIL | 16 | HSIL | CIN3 | Negative | NIL | Normal |
| A03 | 1 mg | 16 | HSIL | CIN3 | Negative | NIL | Negative | NIL | Normal | Negative | NIL | Normal |
| A04 | 2 mg | 16 | HSIL | CIN3 | 16 | HSIL | 16 | HSIL | CIN3 | N.D.[b] | N.D.[b] | N.D.[b] |
| A05 | 2 mg | 16 & 18 | HSIL | CIN3 | 16 & Common | ASC-US | Negative, Common | NIL | Normal | Negative | NIL | Normal |
| A06 | 2 mg | 16 & Common | ASC-H | CIN3 | Negative | NIL | Negative | NIL | Normal | Negative | NIL | Normal |
| A07 | 4 mg | 16 & Common | HSIL | CIN3 | 16 & Common | ASC-US | Negative, Common | NIL | Normal | Negative[c], Common | NIL[c] | Normal[c] |
| A08 | 4 mg | 16 | ASC-US | CIN3 | Negative | NIL | Negative | NIL | Normal | Negative | NIL | Normal |
| A09 | 4 mg | 16 | HSIL | CIN3 | 16 | HSIL | 16 | HSIL | CIN3 | 16 | HSIL | CIN3 |

[a]PCR results for the detection of HPV (Negative, both HPV 16 and 18 negative; 16, HPV 16 positive; Common, other high risk HPV 26, 31, 33, 35, 39, 45, 51, 52, 53, 56, 58, 59, 66, 68, 73 and/or 82 positive)
[b]not done. A04 patient were treated by cervical conization at week 24
[c]A07 patient has visited and undergone examinations for colposcopy and cervical biopsy at week 42 instead of week 36 due to her personal situations.
CIN3; cervical intraepithelial neoplasia grade III,
ASC-H; atypical squamous cells-cannot exclude high-grade squamous intraepithelial lesion,
ASC-US; atypical squamous cells of undetermined significance,
HSIL; high grade squamous intraepithelial lesion,
NIL; no intraepithelial lesion Statistical analysis used herein: Descriptive statistics of the safety, pharmacodynamics and pharmacokinetic outcomes was performed using SAS® (V9.1) software. Standard and two-tailed paired Student's t test was performed to analyze statistical significance of all quantitative data using Prism 5.0 software (GraphPad).

Example 6

Construction of GX-188 Variants and their Immunogenicity

Many variants of the GX-188 construct have been constructed as described. The constructed GX-188 variants include C-1, C-2, D-1, D-2, E-1, and E-2. See FIG. 14. Some constructs (C-1 and C-2) contain one or more mutations or substitutions in the E6 or E7 protein portions (i.e., H21Q in 16E6N and Y85H and V90L in 16E6C for C-1 and M12K and N29S in 16E7N and R77S and G85S in 16E7C for C-2, respectively); some constructs (D-1 and D-2) contain shorter or longer overlapping sequences (i.e., 0+0+0+0 and 86+42+15+15, respectively); and some constructs (E-1 and E2) contain different antigen shuffling order of the E6 and E7 protein portions (NCNCNCNC and CCNNCCNN, respectively). The mutation/substitution variants (C-1 and C-2) are based on the naturally occurring mutation and/or substitutions as shown in FIGS. 13A-13D.

In order to construct the variants from GX-188, each gene fragment containing the substitution/mutation, variation in the overlapping sequences, and changes in antigen shuffling was chemically synthesized with BstXI (5') and AleI (3') restriction sites in its terminus to facilitate insertion into GX-188.

of HPV16 E6 were substituted by glutamine (Q), histidine (H), and leucine (L), respectively. The entire plasmid sequence comprising the nucleotide sequence encoding the C-1 construct is shown as SEQ ID NO: 105. The amino acid sequence of the C-1 construct is shown as SEQ ID NO: 106. For the C-2 construct, methionine (M) 12 of HPV16 E7 was substituted by lysine (K), and asparagine (N) 29, arginine (R) 77, and glycine (G) 85 of HPV16 E7 were substituted by serine (S). The entire plasmid sequence comprising the nucleotide sequence encoding the C-2 construct is shown as SEQ ID NO: 107. The amino acid sequence of the C-2 construct is shown as SEQ ID NO: 108. The D-1 construct contains $1^{st}$ to $78^{th}$ amino acids of the HPV16 E6, $1^{st}$ to $58^{th}$ amino acids of the HPV16 E7, $79^{th}$ to $158^{th}$ amino acids of HPV16 E6, $59^{th}$ to $98^{th}$ amino acids of HPV16 E7, $1^{st}$ to $85^{th}$ amino acids of HPV18 E6, $1^{st}$ to $65^{th}$ of HPV18 E7, $71^{st}$ to $158^{th}$ of HPV18 E6, and $51^{st}$ to 105 of HPV18 E7. The entire plasmid sequence comprising the nucleotide sequence encoding the D1 construct is shown as SEQ ID NO: 109. The amino acid sequence of the D-1 construct is shown as SEQ ID NO: 110. The D-2 construct contains $1^{st}$ to $130^{th}$ amino acids of the HPV16 E6, $1^{st}$ to $85^{th}$ amino acids of the HPV16 E7, $45^{th}$ to $158^{th}$ amino acids of HPV16 E6, and $44^{th}$ to $98^{th}$ amino acids of HPV16 E7, $1^{st}$ to $85^{th}$ amino acids of HPV18 E6, $1^{st}$ to $65^{th}$ of HPV18 E7, $71^{st}$ to $158^{th}$ of HPV18 E6, and $51^{st}$ to 105 of HPV18 E7. The entire plasmid sequence comprising the nucleotide sequence encoding the D-2 construct is shown as SEQ ID NO: 111. The amino acid sequence of the D-2 construct is shown as SEQ ID NO: 112. The E-1 construct contains, from the N terminus to C terminus, $1^{st}$ to $85^{th}$ amino acids of the HPV16 E6, $51^{st}$ to $98^{th}$ amino acids of the HPV16 E7, $1^{st}$ to $65^{th}$ amino acids of HPV16 E7, $71^{st}$ to $158^{th}$ amino acids of HPV16 E6, $1^{st}$ to 85th amino acids of HPV18 E6, 1st to 65th of HPV18 E7, 71st to 158th of HPV18 E6, and 51st to 105 of HPV18 E7. The entire plasmid sequence comprising the nucleotide sequence encoding the E-1 construct is shown as SEQ ID NO: 113. The amino acid sequence of the E-1 construct is shown as SEQ ID NO: 114. The E-2 construct contains, from the N terminus to C terminus, 71st to 158th amino acids of the HPV16 E6, 51st to 98th amino acids of the HPV16 E7, 1st to 85th amino acids of HPV16 E6, 1st to 65th amino acids of HPV16 E6, 1st to 85th amino acids of HPV18 E6, 1st to 65th of HPV18 E7, 71st to 158th of HPV18 E6, and 51st to 105 of HPV18 E7. The entire plasmid sequence comprising the nucleotide sequence encoding the E-2 construct is shown as SEQ ID NO: 115. The amino acid sequence of the E-2 construct is shown as SEQ ID NO: 116.

To investigate the cellular immune response induced by GX-188 and the GX-188 variants, mice were vaccinated one or twice with 8 μg of GX-188 and the GX-188 variant plasmid DNA with electroporation delivery. FIG. 15 summarizes the vaccination schedule for each construct. The vaccinated mice were analyzed at 2 weeks after each vaccination. IFN-γ ELISPOT assays were performed to measure the vaccine-induced T cell responses. Splenocytes were prepared in a single cell level and were stimulated with 2 μg ml$^{-1}$ of four different peptide pools for 24 hours as described in Example 2. Concanavalin A (ConA) and the medium only served as positive and negative controls, respectively. After stimulation, spot forming cells (SFCs) were developed according to manufacturer's instructions (BD Bioscience). The number of responsive cells was calculated by subtracting the mean number of spots induced in the absence of the stimulants from the number of spots in the presence of the stimulants. The number of responsive cells is expressed as SFCs per $10^6$ splenocytes.

Mice immunized with the vaccine variants exhibited significantly augmented IFN-γ ELISPOT response at both single and multiple vaccination compared to the mice vaccinated with mock vector (See FIGS. 16A and 16B). Most of the GX-188 variants exhibited comparable IFN-γELISPOT response to GX-188 after multiple vaccination. These results indicate that the vaccine GX-188 variants can also induce sufficient cell-mediated immune response, e.g., IFN-γ ELISPOT response, after vaccination. Especially, although the IFN-γ ELISPOT responses were lowest after the single vaccination of E1 and E2 (antigen shuffling), the vaccine-induced T cell responses were enhanced after boosting vaccination, and are comparable to the other GX-188 variants This result suggests that substitutions/mutations and antigen shuffling would retain the ability to induce vaccine induced T cell responses to the multiple vaccination.

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

The present application claims benefit to U.S. Provisional Application No. 62/038,134, filed Aug. 15, 2014 and U.S. Provisional Application No. 62/039,270, filed Aug. 19, 2014, which are incorporated by reference in their entireties.

What is claimed is:

1. A method of treating a cervical tumor in a subject in need thereof, comprising
administering to the subject a first dose of a pharmaceutical composition comprising a polynucleotide encoding a fusion protein,
measuring a cellular immune response in the subject after the administration of the first dose,
administering to the subject a second dose of the composition, and
administering to the subject a third dose of the composition,
wherein the subject exhibits an increased cellular immune response after administration of the first dose and wherein said increased cellular immune response is an increase in a number of poly-functional T cells,
wherein the fusion protein comprises the amino acid sequences (1)-(8):
(1) an N-terminal portion of an E6 protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the first dose is about 1 mg to about 4 mg;
wherein the second dose is about 1 mg to about 4 mg and administered about 1 week after administering the first dose;
wherein the third dose is about 1 mg to about 4 mg and administered about 2 weeks after administering the second dose; and
wherein the method does not include a surgery for removal of the cervical tumor.

2. A method for identifying a subject who does not require a surgery for removal of a cervical tumor, said method comprising administering to the subject an effective amount of a first dose of a pharmaceutical composition comprising a polynucleotide encoding a fusion protein, administering to the subject an effective amount of a second dose of the composition and administering to the subject an effective amount of a third dose of the composition, wherein the subject exhibits an increased cellular immune response after the administration of the first dose,
measuring a cellular immune response in the subject after the administration of the first dose, wherein the subject who does not require a surgery for removal of a cervical tumor exhibits an increased cellular immune response compared to before the administration of the first dose, wherein said increased cellular immune response is an increase in a number of poly-functional T cells,
wherein the fusion protein comprises the amino acid sequences (1)-(8):
(1) an N-terminal portion of an Ed protein of HPV16,
(2) a C-terminal portion of an E6 protein of HPV16,
(3) an N-terminal portion of an E7 protein of HPV16,
(4) a C-terminal portion of an E7 protein of HPV16,
(5) an N-terminal portion of an E6 protein of HPV18,
(6) a C-terminal portion of an E6 protein of HPV18,
(7) an N-terminal portion of an E7 protein of HPV18, and
(8) a C-terminal portion of an E7 protein of HPV18,
wherein the first dose is about 1 mg to about 4 mg;
wherein the second dose is about 1 mg to about 4 mg and administered about 1 week after administering the first dose; and
wherein the third dose is about 1 mg to about 4 mg and administered about 2 weeks after administering the second dose.

3. The method of claim 2, wherein the poly-functional T cells exhibit three or more markers selected from the group consisting of IFN-γ, IL-2, TNF-a, MIP-P, CD107a/b, and any combination thereof, measured by flow cytometry.

4. The method of claim 2, wherein the number of the polyfunctional T cells is increased at least about 5% higher than the number of the poly-functional T cells prior to the administration of the polynucleotide.

5. The method of claim 2, wherein the increase in number of poly-functional T cells comprises increased expression of IFN-γ, IL-2, TNF-a, MIP-p, CD107a/b, or a combination thereof or increased CD38+Ki67+CDS T cells.

6. The method of claim 2, wherein the increase in number of poly-functional T cells is at least about 2 fold increase in the number of CD38+Ki67+CDS T cells.

7. The method of claim 2, wherein the administration of the third dose does not increase IL-4 or IL-17a expression.

8. The method of claim 2, wherein the cervical tumor is squamous cell carcinoma (SCC), adenocarcinoma, adenosquamous carcinoma, small cell carcinoma, neuroendocrine tumor (NET), glassy cell carcinoma, villoglandular adenocarcinoma (VGA), non-carcinoma malignancies, melanoma, lymphoma, or cervical intraepithelial neoplasia (CIN).

9. The method of claim 2, wherein the fusion protein comprises the amino acid sequence of SEQ ID NO: 10.

10. The method of claim 2, wherein the polynucleotide comprises the nucleotide sequence of SEQ ID NO: 9.

11. The method of claim 10, wherein the polynucleotide further comprises a nucleic acid sequence encoding a heterologous polypeptide, wherein the heterologous polypeptide comprises an Fms-related tyrosine kinase 3 ligand (FLT3L) or a portion thereof.

12. The method of claim 11, wherein the polynucleotide further comprises a signal peptide of tPA.

13. The method of claim 1, wherein the first dose is about 2 mg; wherein the second dose is about 2 mg and administered about 1 week after administering the first dose; and wherein the third dose is about 2 mg and administered at about 2 weeks after administering the second dose.

14. The method of claim 1, wherein the first dose is about 3 mg; wherein the second dose is about 3 mg and administered at about 1 week after administering the first dose; and wherein the third dose is about 3 mg and administered about 2 weeks after administering the second dose.

15. The method of claim 2, wherein the first dose is about 2 mg; wherein the second dose is about 2 mg and administered about 1 week after administering the first dose; and wherein the third dose is about 2 mg and administered about 2 weeks after administering the second dose.

16. The method of claim 2, wherein the first dose is about 3 mg; wherein the second dose is about 3 mg and administered about 1 week after administering the first dose; and wherein the third dose is about 3 mg and administered about 2 weeks after administering the second dose.

17. The method of claim 1, wherein the poly-functional T cells exhibit three or more markers selected from the group consisting of IFN-γ, IL-2, TNF-a, MIP-P, CD107a/b, and any combination thereof, measured by flow cytometry.

18. The method of claim 1, wherein the number of the polyfunctional T cells is increased at least about 5% higher than the number of the poly-functional T cells prior to the administration of the polynucleotide.

19. The method of claim 1, wherein the increase in number of poly-functional T cells comprises an increased expression of IFN-γ, IL-2, TNF-a, MIP-p, CD107a/b, or a combination thereof or increased CD38+Ki67+CDS T cells.

20. The method of claim 1, wherein the increase in number of poly-functional T cells is at least about 2 fold increase in number of CD38+Ki67+CDS T cells.

21. The method of claim 1, wherein the administration of the third dose does not increase IL-4 or IL-17a expression.

22. The method of claim 1, wherein the cervical tumor is squamous cell carcinoma (SCC), adenocarcinoma, adenosquamous carcinoma, small cell carcinoma, neuroendocrine tumor (NET), glassy cell carcinoma, villoglandular adenocarcinoma (VGA), non-carcinoma malignancies, melanoma, lymphoma, or cervical intraepithelial neoplasia (CIN).

23. The method of claim 1, wherein the fusion protein comprises the amino acid sequence of SEQ ID NO: 10.

24. The method of claim 1, wherein the polynucleotide comprises the nucleotide sequence of SEQ ID NO: 9.

25. The method of claim 24, wherein the polynucleotide further comprises a nucleic acid sequence encoding a heterologous polypeptide, wherein the heterologous polypeptide comprises an Fms-related tyrosine kinase 3 ligand (FLT3L) or a portion thereof.

26. The method of claim 25, wherein the polynucleotide further comprises a signal peptide of tPA.

\* \* \* \* \*